(12) United States Patent
Dimarchi et al.

(10) Patent No.: US 9,573,987 B2
(45) Date of Patent: Feb. 21, 2017

(54) CTP-BASED INSULIN ANALOGS FOR TREATMENT OF DIABETES

(71) Applicant: INDIANA UNIVERSITY RESEARCH AND TECHNOLOGY CORPORATION, Indianapolis, IN (US)

(72) Inventors: Richard D. Dimarchi, Carmel, IN (US); Pengyun Li, Bloomington, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 4 days.

(21) Appl. No.: 14/366,187

(22) PCT Filed: Dec. 19, 2012

(86) PCT No.: PCT/US2012/070503
§ 371 (c)(1),
(2) Date: Jun. 17, 2014

(87) PCT Pub. No.: WO2013/096386
PCT Pub. Date: Jun. 27, 2013

(65) Prior Publication Data
US 2015/0299285 A1 Oct. 22, 2015

Related U.S. Application Data

(60) Provisional application No. 61/578,052, filed on Dec. 20, 2011.

(51) Int. Cl.
| | |
|---|---|
| *A61K 38/28* | (2006.01) |
| *C07K 14/62* | (2006.01) |
| *A61K 47/48* | (2006.01) |
| *C07K 14/00* | (2006.01) |
| *A61K 38/00* | (2006.01) |

(52) U.S. Cl.
CPC ............ *C07K 14/62* (2013.01); *A61K 38/28* (2013.01); *A61K 47/48215* (2013.01); *A61K 47/48246* (2013.01); *C07K 14/00* (2013.01); *A61K 38/00* (2013.01); *C07K 2319/31* (2013.01); *C07K 2319/91* (2013.01)

(58) Field of Classification Search
CPC ....................................................... A61K 38/28
See application file for complete search history.

(56) References Cited

U.S. PATENT DOCUMENTS

| | | | |
|---|---|---|---|
| 3,740,385 A | 6/1973 | Ondetti | |
| 4,275,152 A | 6/1981 | Esders et al. | |
| 4,741,897 A | 5/1988 | Andrews et al. | |
| 4,876,242 A | 10/1989 | Applebaum et al. | |
| 4,985,407 A | 1/1991 | Foxton et al. | |
| 5,028,586 A | 7/1991 | Balschmidt et al. | |
| 5,359,030 A | 10/1994 | Ekwuribe | |
| 5,451,527 A * | 9/1995 | Sarin ..................... | C07K 14/59 436/518 |
| 5,514,646 A | 5/1996 | Chance et al. | |
| 5,759,818 A | 6/1998 | Boime | |
| 5,843,634 A | 12/1998 | Brate et al. | |
| 6,180,767 B1 | 1/2001 | Wickstrom et al. | |
| 6,197,926 B1 | 3/2001 | Gaur et al. | |
| 6,476,290 B1 | 11/2002 | Wright et al. | |
| 6,630,348 B1 | 10/2003 | Lee et al. | |
| 6,746,853 B1 | 6/2004 | Dahiyat et al. | |
| 7,045,337 B2 | 5/2006 | Schultz et al. | |
| 7,326,688 B2 | 2/2008 | O'Harte | |
| 7,521,422 B2 | 4/2009 | Bernard | |
| 2002/0038026 A1 | 3/2002 | Rao et al. | |
| 2002/0137134 A1 | 9/2002 | Gerngross | |
| 2002/0160938 A1 | 10/2002 | Brandenburg et al. | |
| 2003/0195147 A1 | 10/2003 | Pillutla et al. | |
| 2003/0204063 A1 | 10/2003 | Gravel et al. | |
| 2004/0018590 A1 | 1/2004 | Gerngross | |
| 2004/0054130 A1 | 3/2004 | Ng et al. | |
| 2004/0121940 A1 | 6/2004 | DeGroot et al. | |
| 2005/0014679 A1 | 1/2005 | Beals et al. | |
| 2005/0187147 A1 | 8/2005 | Newman et al. | |
| 2006/0171920 A1 | 8/2006 | Shechter et al. | |
| 2006/0210534 A1 | 9/2006 | Lee et al. | |
| 2006/0223753 A1 | 10/2006 | Glass | |
| 2007/0129284 A1 | 6/2007 | Kjeldsen et al. | |
| 2007/0173452 A1 | 7/2007 | DiMarchi et al. | |
| 2007/0203058 A1 | 8/2007 | Lau et al. | |
| 2007/0224119 A1 | 9/2007 | McTavish | |

(Continued)

FOREIGN PATENT DOCUMENTS

| | | |
|---|---|---|
| EP | 0220958 | 5/1987 |
| EP | 741188 | 11/1996 |

(Continued)

OTHER PUBLICATIONS

"Peptides: Frontiers of Peptide Science," Proceedings of the Fifteenth American Peptide Symposium, Jun. 14-19, 1997, Nashville, Tennessee, USA; ed. James P. Tam and Praven T.P. Kaumaya.
De et al., Synthesis and characterization of ester-based prodrugs of glucagon-like peptide 1, Biopolymers, 94(4): 448-56 (2010).
Harris, J. Milton, Final Word: PEGylation—A "Sunset" Technology? <http://licence.icopyright.net/user/viewFreeUse.act?fuid= OTU1NjY3OA%3D%3D>, BioPharm International, Jun. 1, 2004.
M.J. Roberts et al., "Chemistry for Peptide and Protein PEGylation," Advance Drug Delivery Reviews, Elsevier BV, Amsterdam, NL, vol. 54, No. 4, Jun. 17, 2002, pp. 459-476.

(Continued)

*Primary Examiner* — Gyan Chandra
(74) *Attorney, Agent, or Firm* — Barnes & Thornburg LLP

(57) ABSTRACT

Insulin analogs comprising a non-native glycosylation site sequence are provided having high potency and specificity for the insulin receptor. In one embodiment a peptide sequence of greater than 18 amino acids is used as a linking moiety to link human insulin A and B chains, or analogs or derivatives thereof, to provide high potency single chain insulin analogs. In one embodiment the linking moiety comprises one or more glycosylation sites. Also disclosed are prodrug and conjugate derivatives of the insulin analogs.

7 Claims, 51 Drawing Sheets

(56) References Cited

U.S. PATENT DOCUMENTS

| | | | |
|---|---|---|---|
| 2008/0113411 A1 | 5/2008 | Sheffer | |
| 2008/0113905 A1 | 5/2008 | DiMarchi et al. | |
| 2008/0125574 A1 | 5/2008 | Sheffer et al. | |
| 2008/0280814 A1* | 11/2008 | Ludvigsen | A61K 38/28 514/1.1 |
| 2009/0054305 A1 | 2/2009 | Schlein et al. | |
| 2009/0176964 A1 | 7/2009 | Walensky et al. | |
| 2009/0192072 A1 | 7/2009 | Pillutla et al. | |
| 2009/0209453 A1 | 8/2009 | Moyle | |
| 2009/0221037 A1 | 9/2009 | Lee et al. | |
| 2010/0081614 A1 | 4/2010 | Fares et al. | |
| 2011/0065633 A1 | 3/2011 | DiMarchi et al. | |
| 2011/0257091 A1 | 10/2011 | DiMarchi | |
| 2011/0288003 A1 | 11/2011 | DiMarchi et al. | |
| 2012/0010134 A1 | 1/2012 | Zion et al. | |
| 2012/0184489 A1 | 7/2012 | Rau et al. | |

FOREIGN PATENT DOCUMENTS

| | | |
|---|---|---|
| EP | 1161452 | 2/2000 |
| EP | 1193272 | 6/2004 |
| EP | 2036539 A1 | 3/2009 |
| EP | 2036923 A1 | 3/2009 |
| WO | 90/12814 | 11/1990 |
| WO | 93/03174 | 2/1993 |
| WO | 93/06844 | 4/1993 |
| WO | 96/34882 | 11/1996 |
| WO | 98/11126 | 3/1998 |
| WO | 99/46283 | 9/1999 |
| WO | 00/50456 | 8/2000 |
| WO | 02/10195 | 2/2002 |
| WO | 2004/067548 | 8/2004 |
| WO | 2004/078777 | 9/2004 |
| WO | 2005/054291 | 6/2005 |
| WO | 2006/047214 | 5/2006 |
| WO | 2006/097521 | 9/2006 |
| WO | 2007/096332 | 8/2007 |
| WO | 2008/019368 | 2/2008 |
| WO | 2008/021560 | 2/2008 |
| WO | 2008/025528 | 3/2008 |
| WO | 2008/081418 | 7/2008 |
| WO | WO2009034118 A1 | 3/2009 |
| WO | WO2009034119 A1 | 3/2009 |
| WO | 2009/067636 | 5/2009 |
| WO | 2009/095479 | 8/2009 |
| WO | 2009/099763 | 8/2009 |
| WO | 2010/011313 | 1/2010 |
| WO | 2010/071807 | 6/2010 |
| WO | 2010/080605 | 7/2010 |
| WO | 2010/080606 | 7/2010 |
| WO | 2010/080609 | 7/2010 |
| WO | 20100080607 | 7/2010 |
| WO | 2011/159895 | 12/2011 |
| WO | 2011/163012 | 12/2011 |
| WO | 2011/163460 | 12/2011 |
| WO | 2011/163462 | 12/2011 |
| WO | 2014/088836 | 6/2014 |

OTHER PUBLICATIONS

De, A. and DiMarchi, R. Synthesis & Analysis of Peptide Hormone-based prodrugs, (2009) Proceedings of the 21st American Peptide Society 160-161.

Battersby et al., "Diketopiperazine Formation and N-Terminal Degradation in Recombinant Human Growth Hormone", *International Journal of Peptide & Protein Research* 44: 215-222, (1994).

Eriksson et al., "hPEPT1 Affinity and Translocation of Selected Gln-Sar and Glu-Sar Dipeptide Derivatives", *Molecular Pharmaceutics* vol. 2, No. 3: 242-249 (May 10, 2005).

Garcia-Aparicio et al., "Design and Discovery of a Novel Dipeptidyl-peptidase IV (CD26)-Based Prodrug Approach", *J. Med. Chem.* 49: 5339-5351 (2006).

Goolcharran et al., "Comparison of the Rates of Deamidation, Diketopiperazine Formation, and Oxidation in Recombinant Human Vascular Endothelial Growth Factor and Model Peptides", *AAPS Pharmsci 2000* 2(1) article 5: 1-6 (Mar. 17, 2000).

Santos et al., Cyclization-Activated Prodrugs. Synthesis, Reactivity and Toxicity of Dipeptide Esters of Paracetamol, *Bioorganic & Medicinal Chemistry Letters* 15: 1595-1598 (2005).

Sato, H., "Enzymatic procedure for site-specific pegylation of proteins," Advanced Drug Delivery Reviews 54, pp. 487-504 (2002).

Ward, "Fatty Acid Acylation of Peptides: Developing strategies to enhance medicines for treating metabolic disorders," Jan. 14, 2009.

DiMarchi, "Peptides—Development of Prodrug Chemistry," RBF Symposium Feb. 1-4, 2011 India.

Yang et al., "A Novel Approach to Resin-Based Cysteine Alkylation," American Peptide Society, 2005.

PCT International Search Report for PCT/US2009/068745 completed by the US Searching Authority on Feb. 1, 2010.

PCT International Search Report for PCT/US2009/031593 completed by the US Searching Authority on Jul. 16, 2009.

Schuttler, A. and D. Brandenburg, Preparation and Properties of Covalently Linked Insulin Dimers. Hoppe-Seylers Zeitschrift Fur Physiologische Chemie, 1982. 363(3): p. 317-330.

Tatnell, M.A., et al., Evidence Concerning the Mechanism of Insulin-Receptor Interaction and the Structure of the Insulin-Receptor from Biological Properties of Covalently Linked Insulin Dimers. Biochemical Journal, 1983. 216(3): p. 687-694.

Roth, R.A., et al., Effects of Covalently Linked Insulin Dimers on Receptor Kinase-Activity and Receptor down Regulation. Febs Letters, 1984. 170(2): p. 360-364.

Tatnell, M.A., R.H. Jones, and P.H. Sonksen, Covalently-Linked Insulin Dimers—Their Metabolism and Biological Effects Invivo as Partial Competitive Antagonists of Insulin-Clearance. Diabetologia, 1984. 27(1): p. 27-31.

Joost, H.G., et al., Quantitative Dissociation of Glucose-Transport Stimulation and Insulin-Receptor Tyrosine Kinase Activation in Isolated Adipocytes with a Covalent Insulin Dimer (B29,B29'-Sunberoyl-Insulin). Biochemical Pharmacology, 1989. 38(14): p. 2269-2277.

Breiner, M., et al., Heterogeneity of Insulin-Receptors in Rat-Tissues as Detected with the Partial Agonist B29,B29'-Suberoyl-Insulin. Molecular Pharmacology, 1993. 44(2): p. 271-276.

Deppe, C., et al., Structure-Activity Relationship of Covalently Dimerized Insulin Derivatives—Correlation of Partial Agonist Efficacy with Cross-Linkage at Lysine B29. Naunyn-Schmiedebergs Archives of Pharmacology, 1994. 350(2): p. 213-217.

Shojaee-Moradie, F., et al., Demonstration of a Relatively Hepatoselective Effect of Covalent Insulin Dimers on Glucose-Metabolism in Dogs. Diabetologia, 1995. 38(9): p. 1007-1013.

Du X et al, Hydroxyl group of insulin A19Tyris essential for receptor binding: studies on (A9Phe) insulin, BioChem and Mol Biology International, Academic Press, Lindon, GB vol. 45, No. 2, Jun. 1, 1998, pp. 255-260. found in extended EP search report 09837982.9 (08055; 216442).

PCT International Search Report for PCT/US2009/068716 completed by the US Searching Authority on May 3, 2010.

European supplemental search report for EP 09837983.7 completed by the EPO on Mar. 15, 2012.

Cheng et al., "The Development of an Insulin-based Prodrug," APS poster presentation, 2011.

Coffman et al., "Insulin-metal ion interactions: the binding of divalent cations to insulin hexamers and tetramers and the assembly of insulin-hexamers," Biochemistry, Aug. 9, 1988, vol. 27, No. 16, pp. 6179-6187.

De, Design of peptide-based prodrug chemistry and its application to glucagon-like Thesis Aug. 2007. [Retrieved from the Internet on Jun. 16, 2009: <https://scholarworksiu.edu/dspace/browse?value=De%2C+ArnabBtype=author>]; p. 8, para 2; p. 16, para 3; p. 40, para 1; p. 66, para 2; p. 77, para 1-2; p. 79, para 1.

De, et al., "Investigation of the feasibily of an amide-based prodrug under physiological conditions," Int. J. Pept. Res. Ther., 14, pp. 255-262 (2008).

(56) References Cited

OTHER PUBLICATIONS

Du et al., "Biochemistry and Molecular Biology International," vol. 45, No. 2, Jun. 1, 1998, pp. 255-260 XP008147747.
GenBank entry AAH05278, Jul. 15, 2006 [http:www/ncbi.nim.nih.gov/protein/13528972>].
Han et al., "IGF-based Insulin Analogs with an A-Chain Lactam," APS poster presentation, May 12, 2011.
Kaur et al., "Novel Single Chain Insulin Analogs Consisting of a Non-Peptide Based Connection," APS poster presentation, May 12, 2011.
Han et al., "Structure-Activity Relationship of Insulin at Position $A^{19}$," APS poster presentation, Jun. 7, 2009.
Han et al., "Insulin Chemical Synthesis Using a Two-Step Orthogonal Formation of the Disulfides," APS poster presentation, Jun. 7, 2009.
Kaur et al., "Chemical Synthesis of Insulin and Related Analogs," APS poster presentation, Jun. 7, 2009.
Kristensen et al., "Alanine Scanning Mutagenesis of Insulin," The Journal of Biological Chemistry, 1997, 272(20):12978-12983.
Madsen et al., "Structure—Activity and Protraction Relationship of Long-Acting Glucagon-like Peptide-1 Derivatives: Importance of Fatty acid Length, Polarity, and Bulkiness," J. Med. Chem. 2007, 50, pp. 6126-6132.
Mayer et al., Insulin Structure and Function, Peptide Science 2007, 88(5):687-713.
Mroz, Piotr et al., "Bioactivity of Insulin Analogs with Altered B-Chain Secondary Structure," APS poster presentation, Jun. 7, 2009.
O'Brien, Assay for DPPIV Activity using a Homogenous, Luminescent Method, Cell Notes, 2005, 11:8-11 (http://www.promega.com/resources/articles/pubhub/cellnotes/assay-for-dppiv-activity-using-a-homogeneous-luminescent-method/).
PCT International Search Report for PCT/US2009/068711 completed by the US Searching Authority on Feb. 4, 2010.
PCT International Search Report for PCT/US2009/068712 completed by the US Searching Authority on Mar. 24, 2010.
PCT International Search Report for PCT/US2009/068713.
PCT International Search Report for PCT/US2011/041601 completed by the US Searching Authority on Nov. 10, 2011.
Phillips et al., "Supramolecular protein engineering: design of zinc-stapled insulin hexamers as a long acting depot," J. Biol. Chem., Apr. 16, 2010, vol. 285, No. 16, pp. 11755-11759.
Schilling et al., "Degradation of Insulin by Trypsin and Alphachymotrypsin," Pharmaceutical Research 1991, 8(6):721-727 (abstract).
Quan et al., "Coordinated Interaction of the Insulin B-chain Helical Domain with the aromatic Active Site," APS poster presentation, Jun. 7, 2009.
Wang et al., "Identification of Site(s) of Insulin Nitration by Peroxynitrite and Characterization of its Structural Change," Protein & Peptide Letters 2008, 15:1063-1067.
Zhao et al., "Improved Pharmacokinetics through Site-Specific PEGylation of Insulin Analogs," APS poster presentation, May 12, 2011.
Gershonov et al, A Novel Approach for a Watter-Soluble long Acting Insulin Prodrug . . . , J. Med. Chem (2000) vol. 43, pp. 2530-2537.
Evans et al., "Effect of Î-Endorphin C-Terminal Peptides on Glucose Uptake in Isolated Skeletal Muscles of the Mouse", Peptides, vol. 18, No. 1, pp. 165-167, (1997).
Kurapkat et al "Inactive conformation of an insulin despite its wild-type sequence", Protein Science, vol. 6, No. 3, pp. 580-587 (Mar. 1997).
Hamel et al "Cyclosporin a prodrugs: Design, systhesis and biophysical properties", J. Peptide Research, vol. 63 No. 2 pp. 147-154 (Feb. 2004).
Coy et al, J of Medicinal Chemistry, 1973, vol. 16, No. 7, 827-829.
Yang et al, "Relationship between insulin A chain regions and insulin biological activities," World J. of Gastroentero, 2000: 6(3): 371-373 (Jun. 2000).
Hinds et al, Advancec Drug Delivery Reviews 2002, (54) 505-530 (Jun. 17, 2002).
Hua et al, J of Bilogical Chemistry, Mar. 2008, vol. 283, No. 21, 14703-14716 (May 23, 2008).
Weiland et al, "Antagonistic effects of a covalenly dimerized insulin derivatized insulin derivative on insulin receptors in 3T3-L1 adipocytes", PNAS, vol. 87, pp. 1154-1158, Feb. 1990.
Cloutier, et al, "Low-energy (3-24eV) electron damage to the peptide backbone" J Phys Chem B. 111(7), p. 1620-1624 (Feb. 22, 2007).
G. Rajpal et al, "Single Chain Insulins as Receptor Agonists", Molecular Endocrinology, vol. 23, No. 5, Feb. 19, 2009 p. 679-688.
Suaifan et al, "Effects of steric bulk and stereochemistry on the rates of diketopiperazine formation from N-aminoacyl-2,2-dimethylthiazolidine-4-carboxamides (Dmt dipeptide amides)—a model for a new prodrug linker system," Tetrahedron 62, pp. 11245-11266, (Nov. 2006).
Shechter et al , "Reversible pegylation of insulin facilitates its prolonged action in vitro", Eur. J. Pharm. and Biopharm. 70 (Apr. 7, 2008) p. 19-28.
Hiroshi Ogawa et al "N-Methylation of sleeted peptide bonds on the biological activity of insulin", International J of Peptide and Protein Research, vol. 30, No. 4, p. 460-473 (Oct. 1987).
Shechter et al , "Albumin-insulin conjugate releasing insulin slowly under physiogiacal conditions: a new concept for long-acting insulin", Bioconjugate Chemistry vol. 16, No. 4, p. 913-920 (Jul.-Aug. 2005).
Worrall et al "Synthesis of an organoinsulin molecule tha tcan be activated by antibody catalysis", PNAS vol. 98, No. 24, p. 13514-13518 (Nov. 20, 2001).
PCT International Search Report and Written Opinion completed by the ISA/US on Apr. 5, 2013 and issued in connection with PCT/US2012/070503, 2013.
Peavy et al, JBC, vol. 260 (6), p. 13989-13994 (1985).

* cited by examiner

| A-Chain | |
|---|---|
| | 1                    21 |
| Insulin | GIVEQCCTSICSLYQLENYCN |
| IGF I | ---DE--FRS-D-RR--M--A |
| IGF II | ----E--FRS-D-AL--T---A |

| B-Chain | |
|---|---|
| | 1                               30 |
| Insulin | FVNQHLCGSHLVEALYLVCGERGFFYTPKT |
| IGF I | *GPET---AE--D--QF---D---YFNKP- |
| IGF II | AYRPSET---GE--DT-QF----D---YFSRPA |

| C-Chain | |
|---|---|
| | 1                                    35 |
| Proinsulin | RREAEDLQVGQVELGGGPGAGSLQPLALEGSLQKR |
| IGF I | GYGSSSRRAPQT |
| IGF II | SRVSRRSR |

| D-Chain | |
|---|---|
| | 1           8 |
| | ********* |
| | PLKPAKSA |
| | *T*PAKSE |

Fig. 5

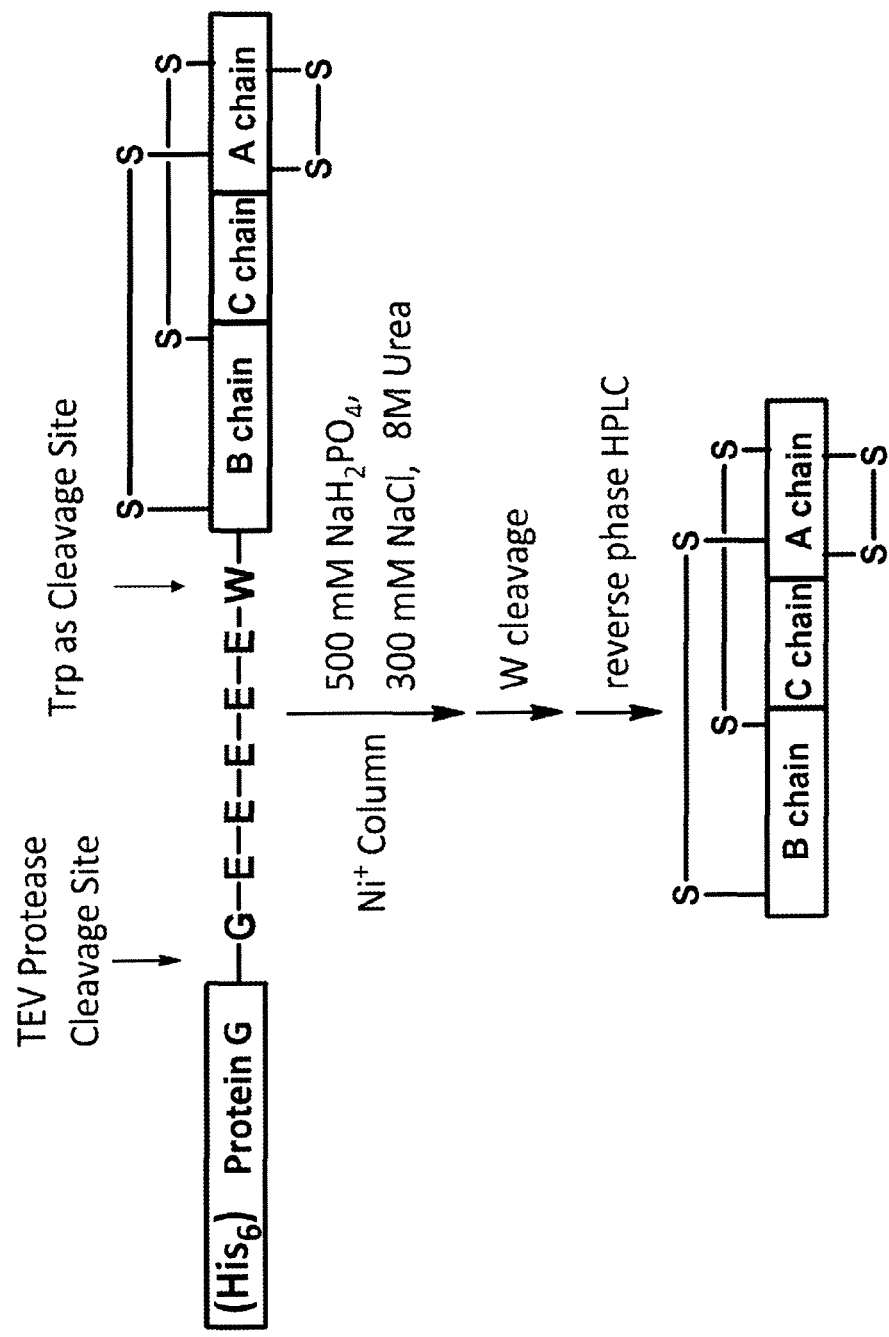
Fig. 17: Scheme of Biosynthesis (Insulin Analogs)

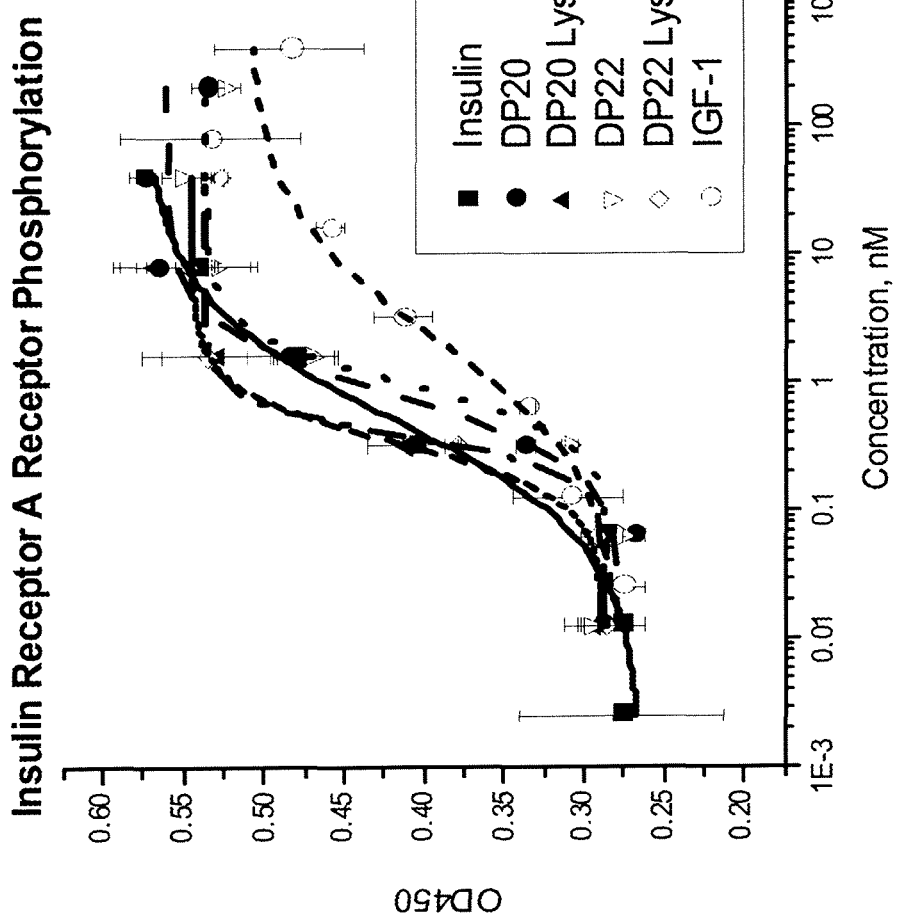
Fig 18A. DP20-CTP Analog Activity: *in vitro* insulin receptor A phosphorylation.

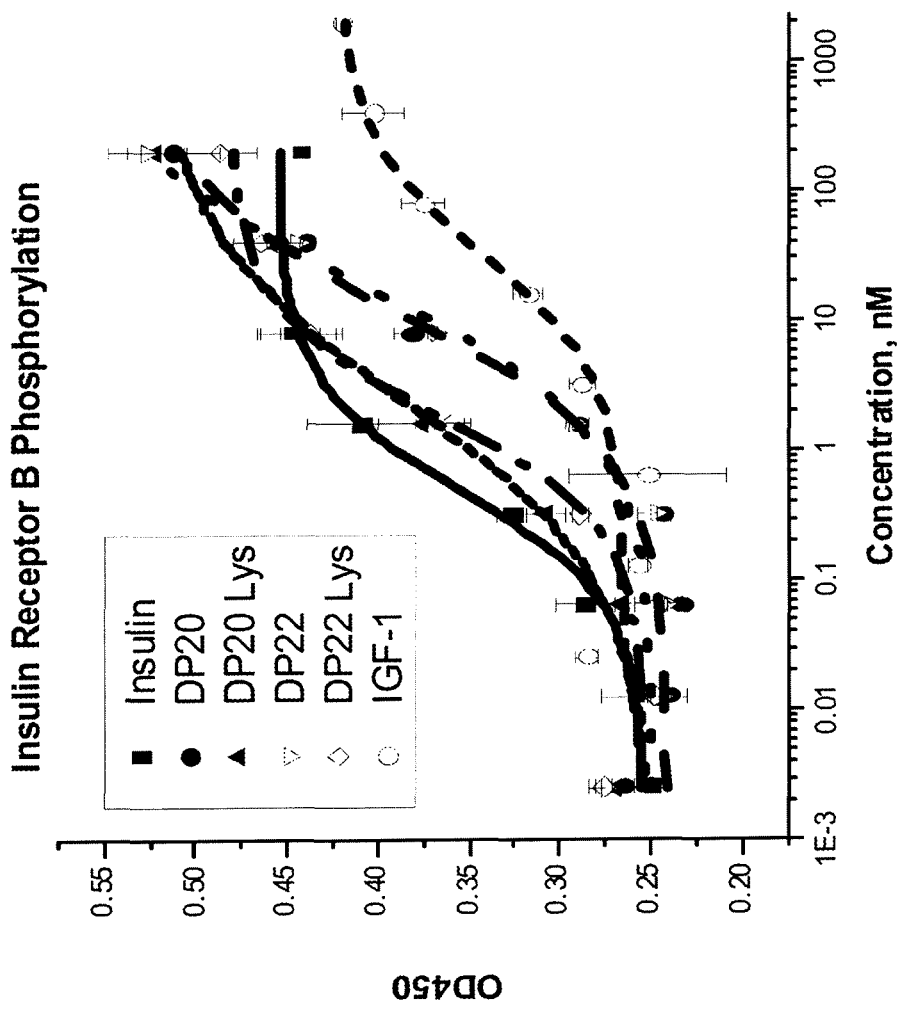
Fig 18B. DP20-CTP Analog Activity: *in vitro* insulin receptor B phosphorylation.

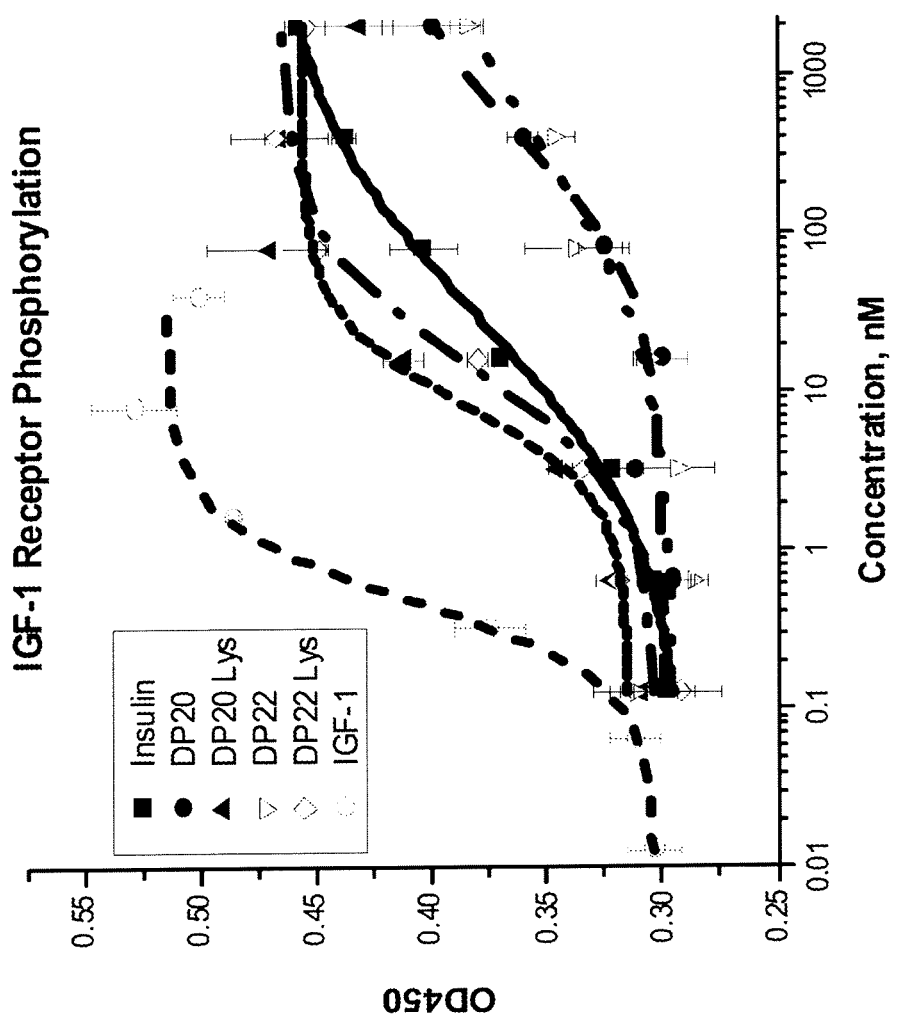
Fig 18C. DP20-CTP Analog Activity: *in vitro* IGF-1 receptor phosphorylation.

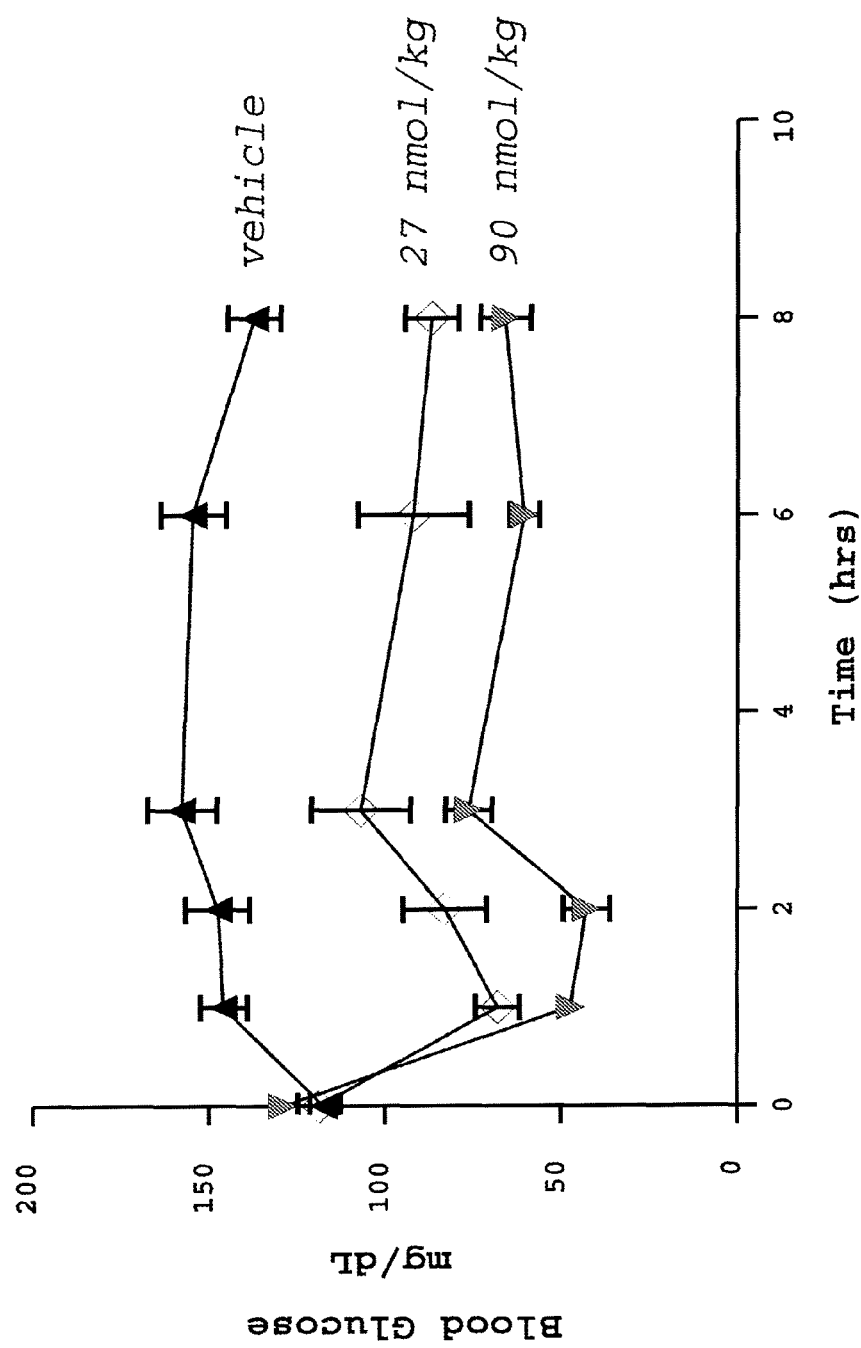

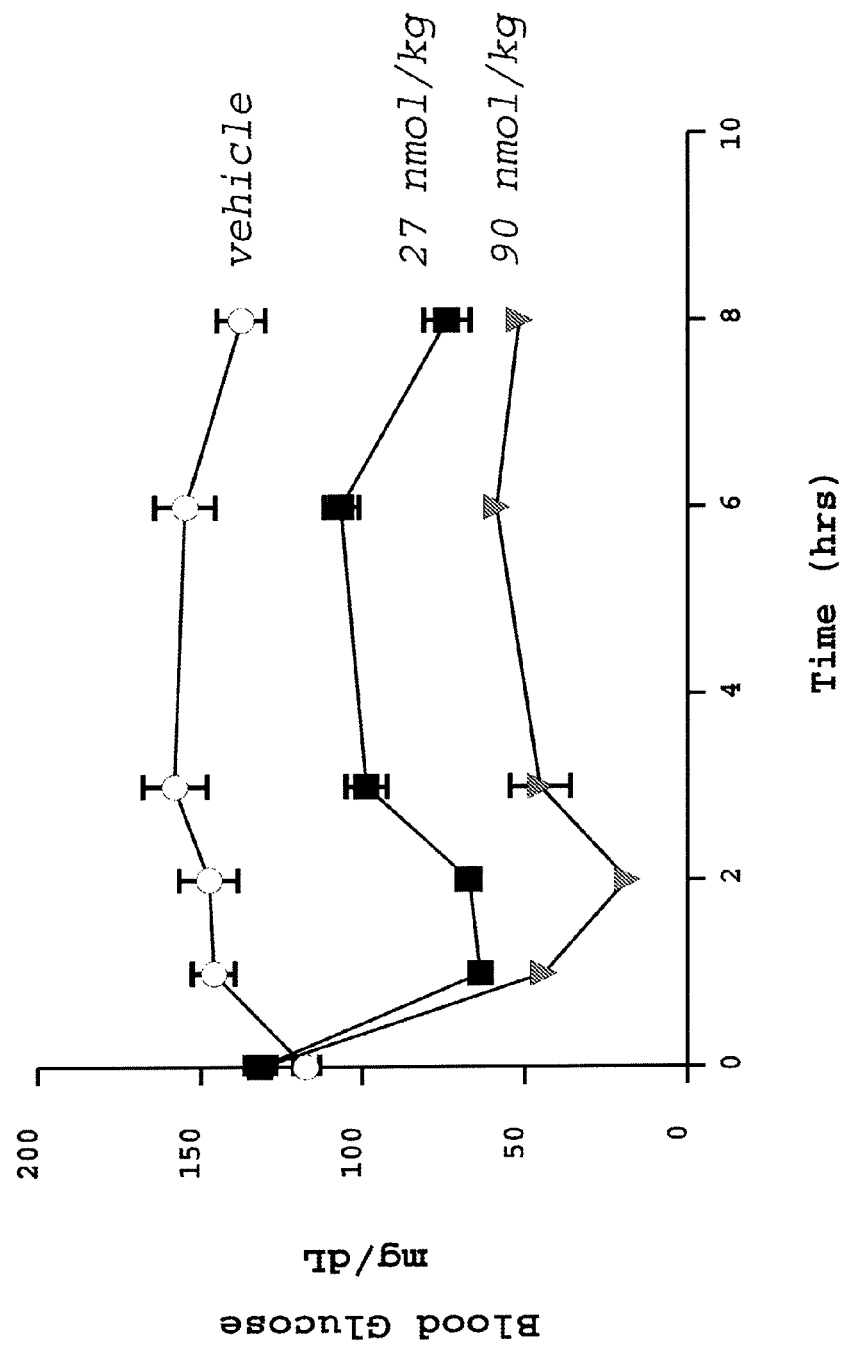
Figure 19C. Comparative Insulin Dose Titration. $B^1$(H5,H10,Y16,L17)25-CTP-$A^1$(H8,N18,N21)

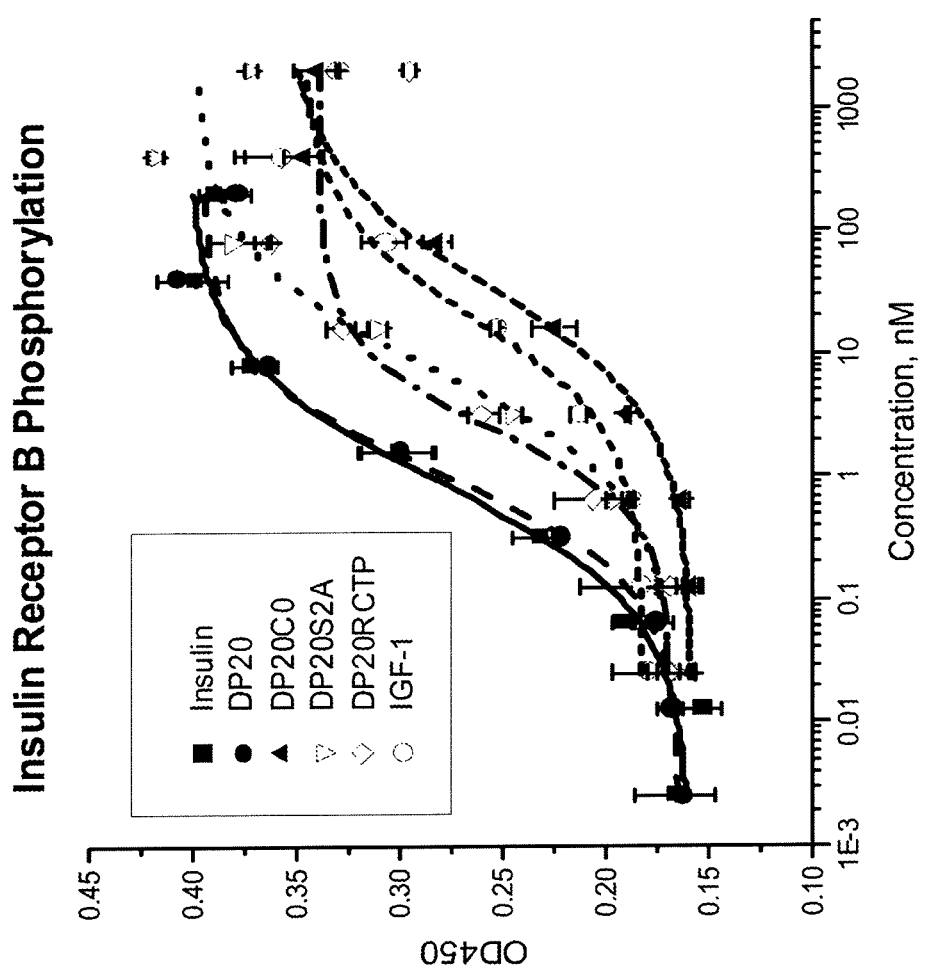
Fig 20A. DP20-CTP Analog Activity: *in vitro* insulin receptor B phosphorylation.

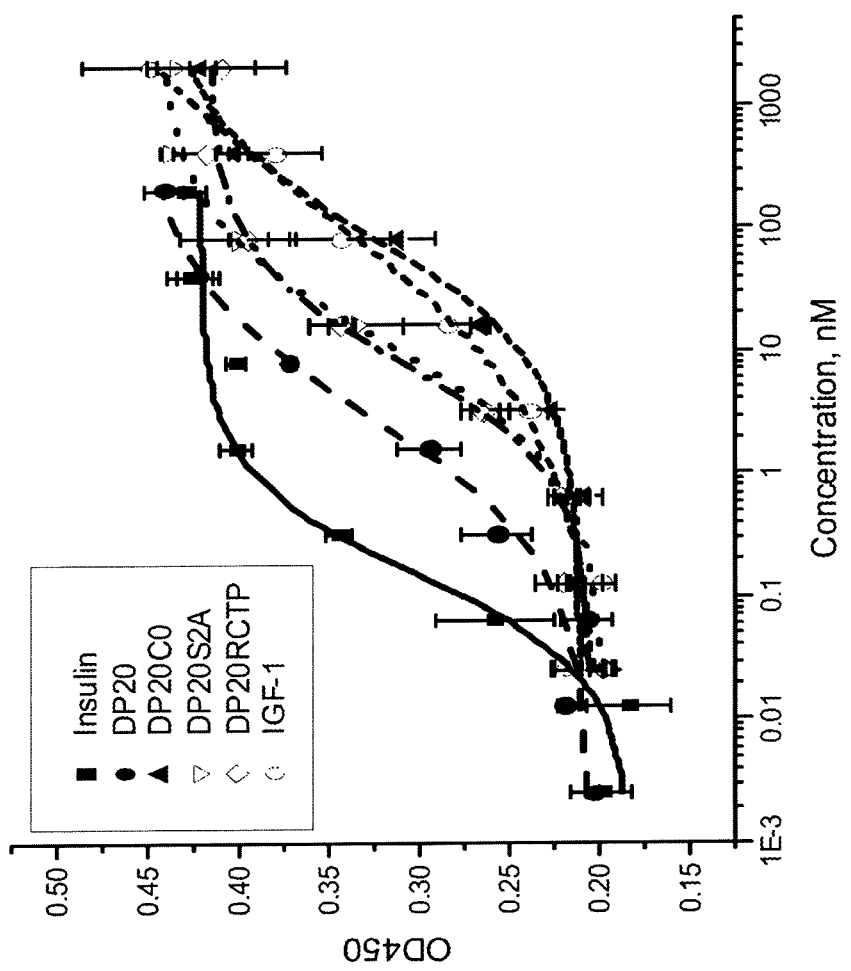
Fig 20B. DP20-CTP Analog Activity: *in vitro* insulin receptor A phosphorylation.

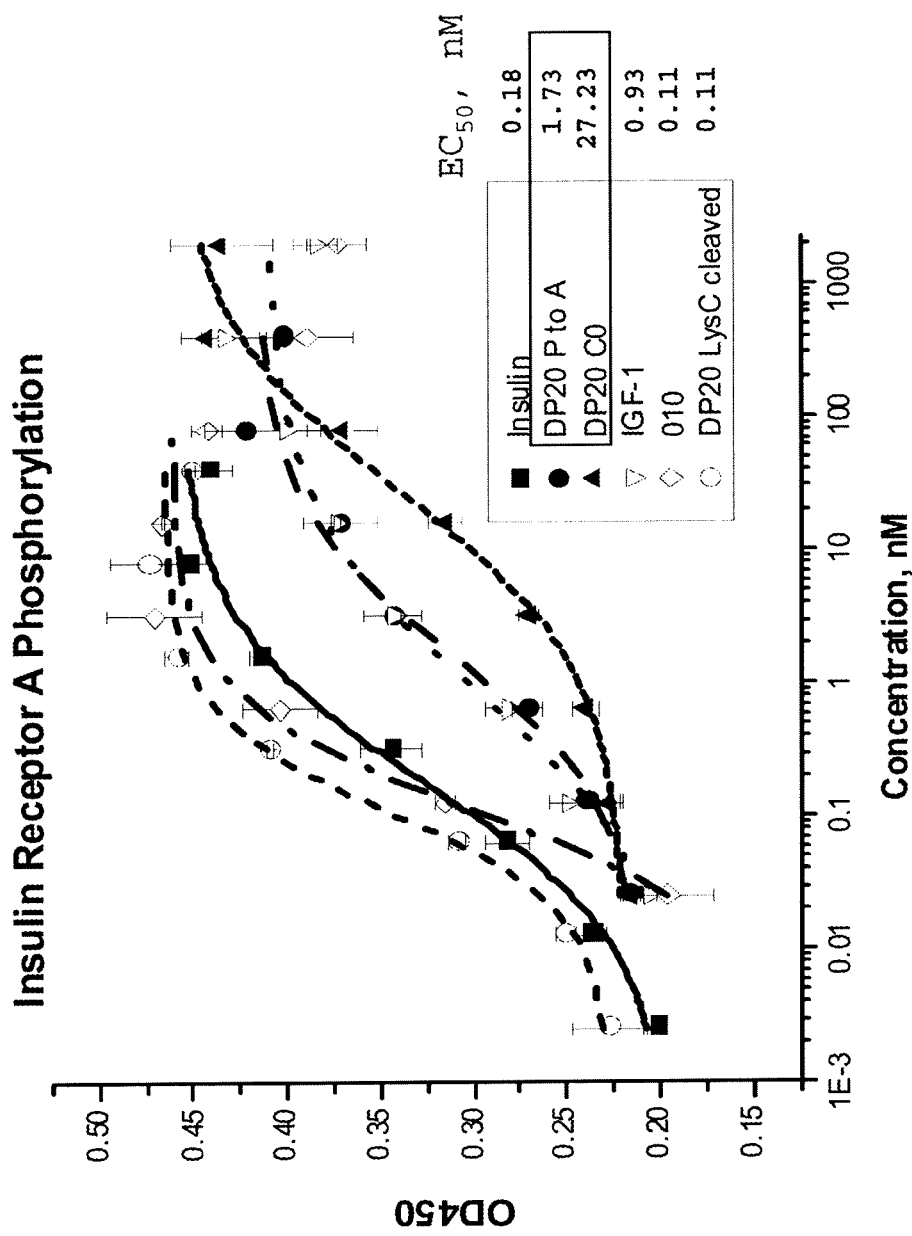
Fig 21. DP20 C-Peptide Analogs Activity: *in vitro* insulin receptor A phosphorylation.

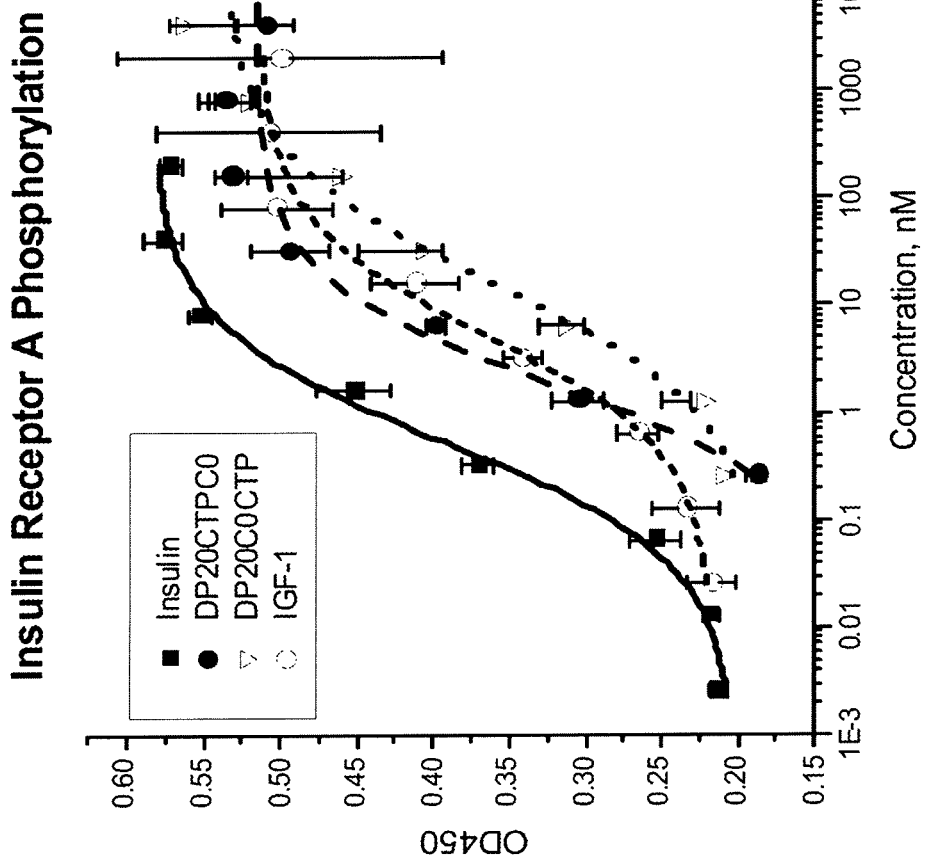
Fig 22A. DP20-CTP Multimer Activity: *in vitro* insulin receptor A phosphorylation.

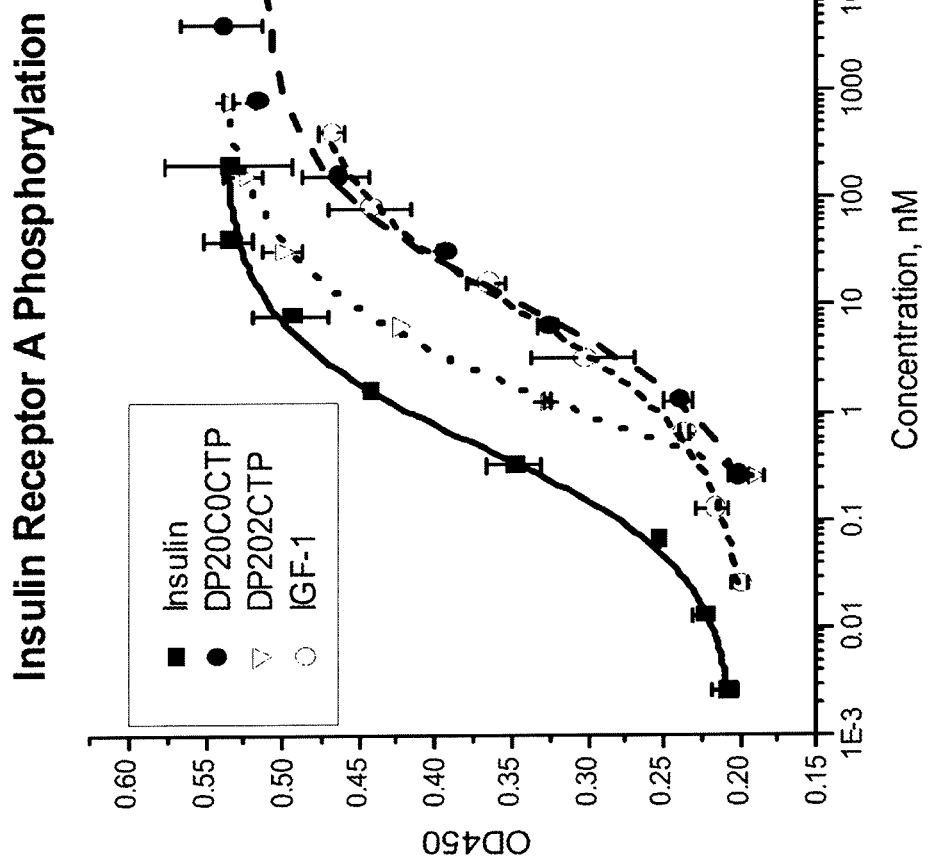
Fig 22B. DP20-CTP Multimer Activity: *in vitro* insulin receptor A phosphorylation.

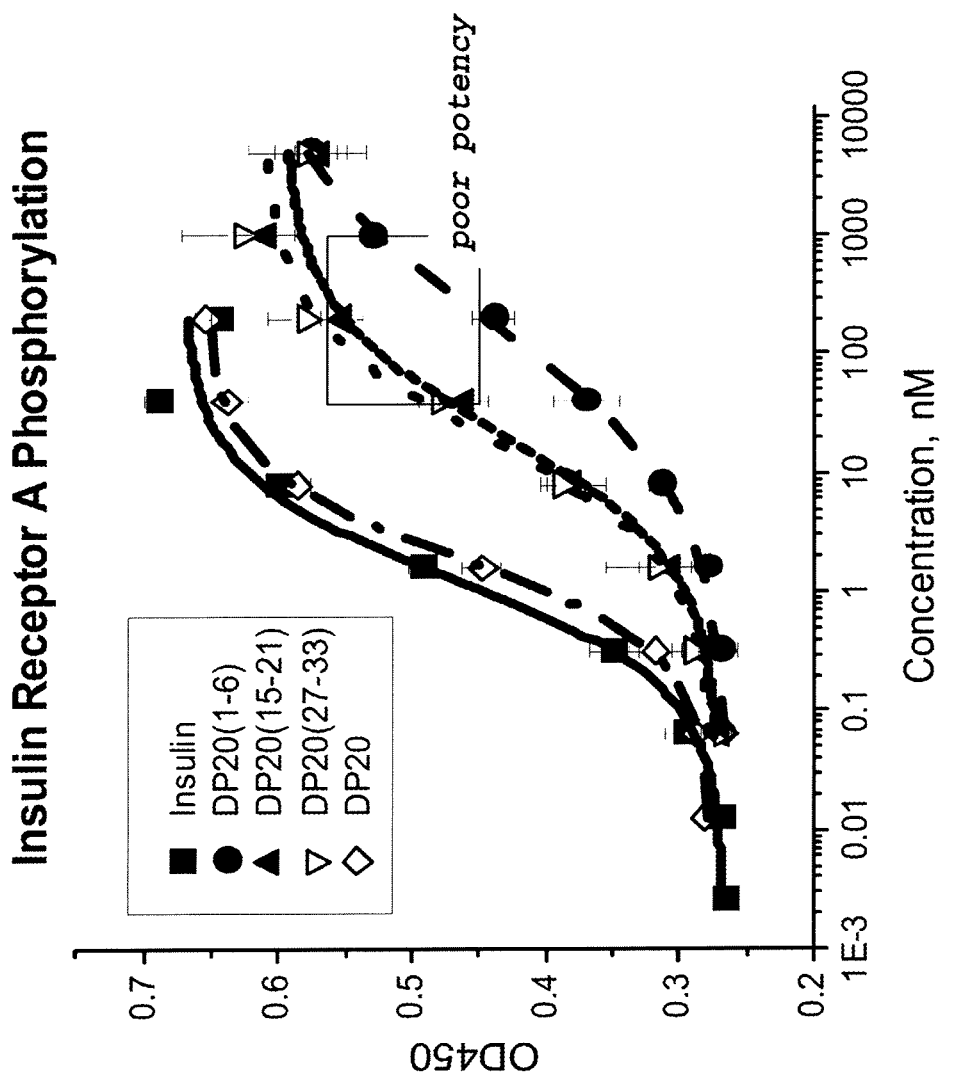
Fig 23. DP20-based Proinsulin Analog Activity: *in vitro* insulin receptor A phosphorylation.

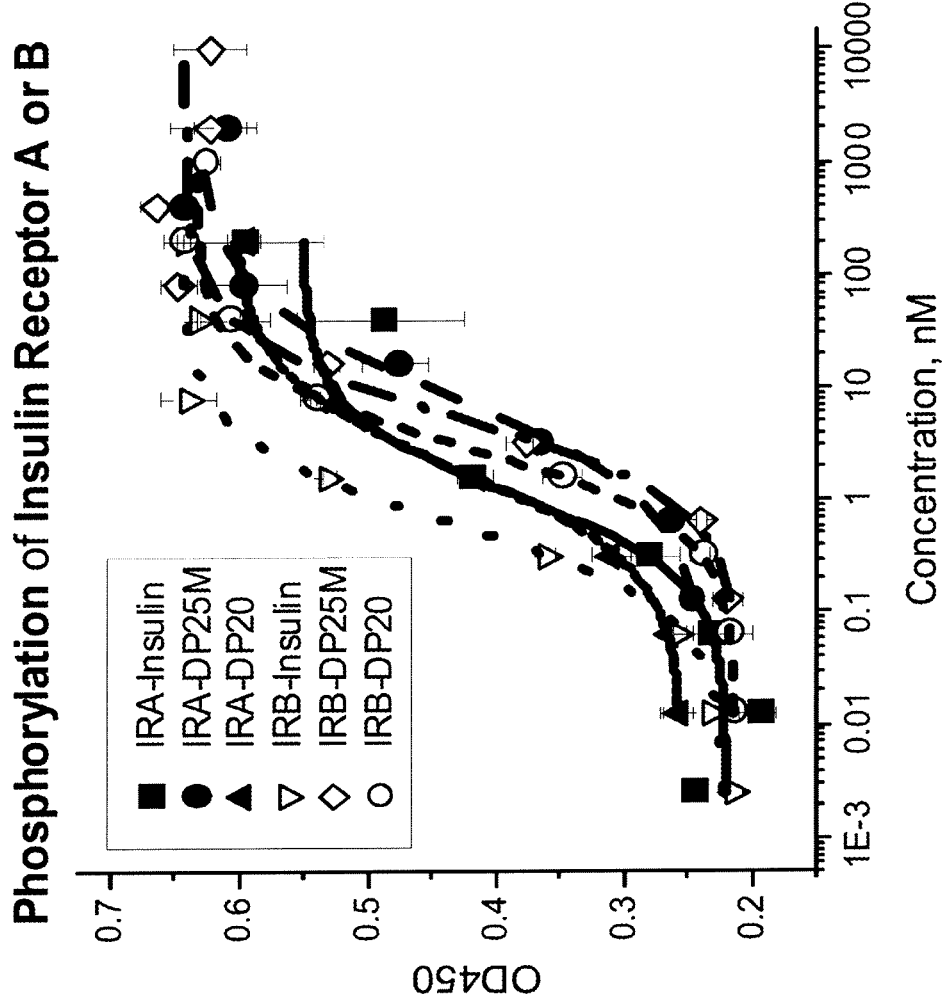
Fig 24. "Insulinized" DP20 (DP25M).

Comparative Insulin Tolerance Tests Acylated Analogs

Comparative Insulin Tolerance Test for Detimir & MIU-55

Comparative Insulin Tolerance Test for MIU-49

$B^1$(C16-rE0,H5,Aib9,H10,E13-K17,Y16)25a : $A^1$(N18,N21)

Comparative Insulin Tolerance Test for Detimer & MIU-56
MIU-56: C8-20k, PEGylated monomer B$^1$(H5,Y16,L17)25-a-PEG8-K-PEG4-A$^1$(N18,21)

Comparative Insulin Tolerance Test for MIU-56 & MIU-57

Comparative Insulin Tolerance Test for MIU-56 & MIU-57

Blood Glucose AUC Over 24hrs

Comparative Insulin Dose Titration MIU-56 & 57

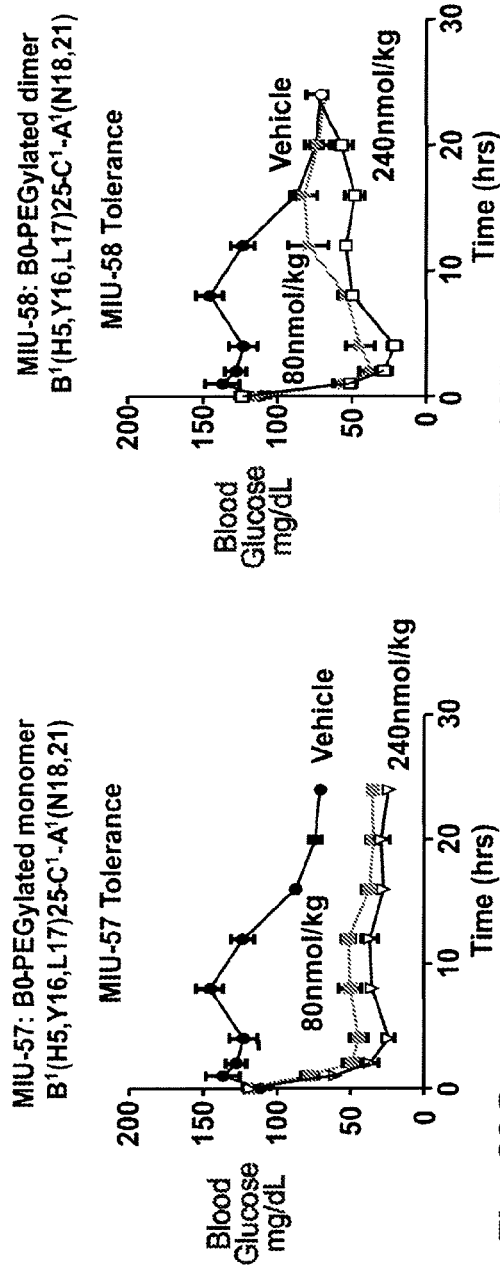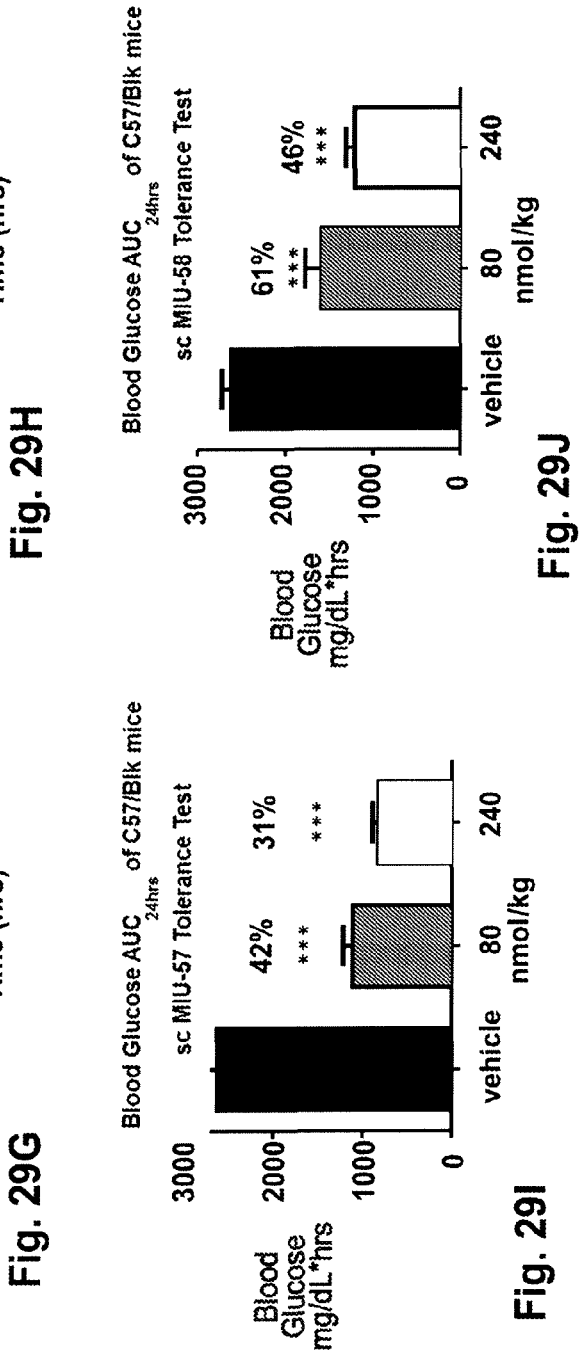
Fig. 29G, Fig. 29H, Fig. 29I, Fig. 29J

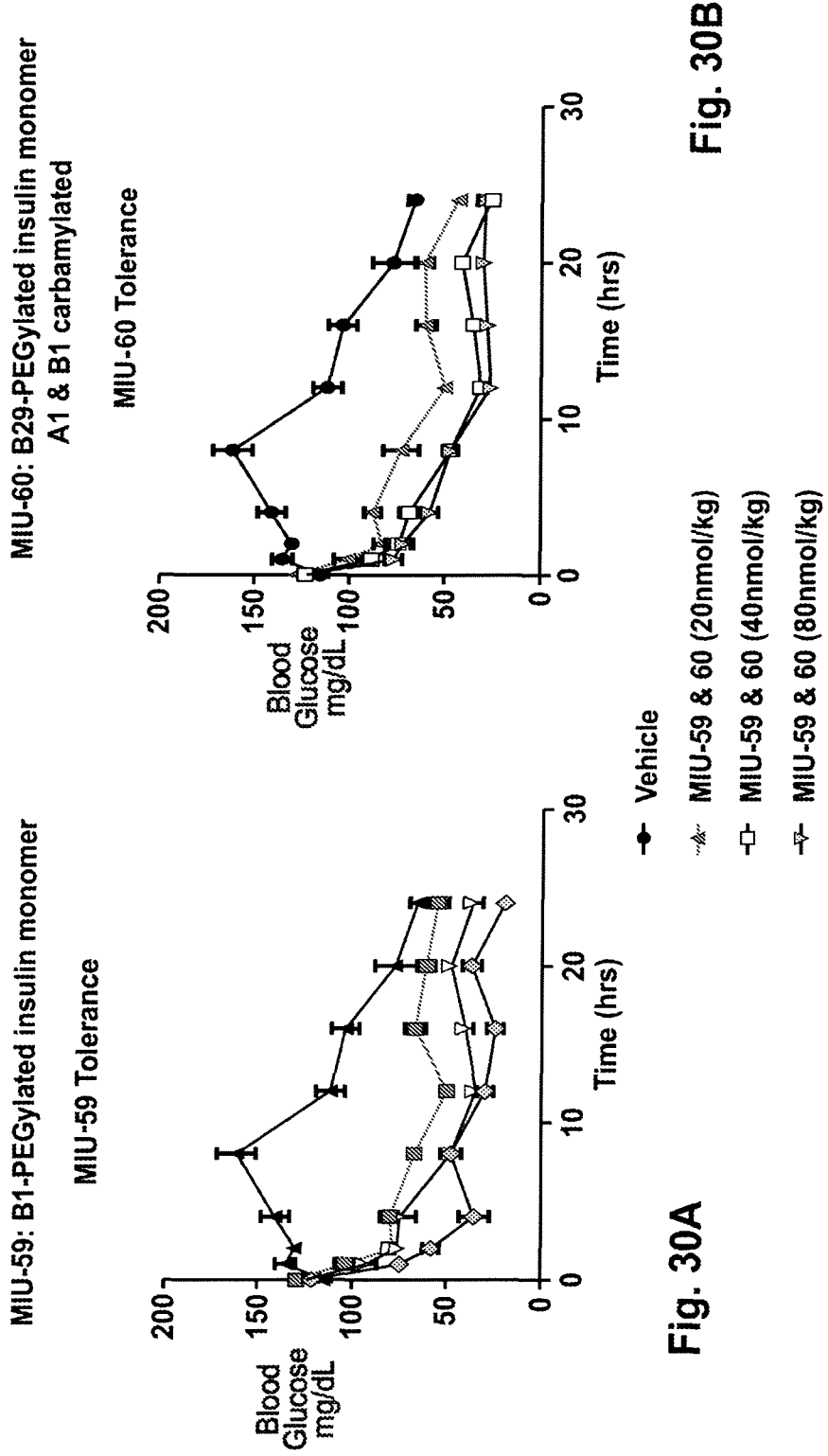

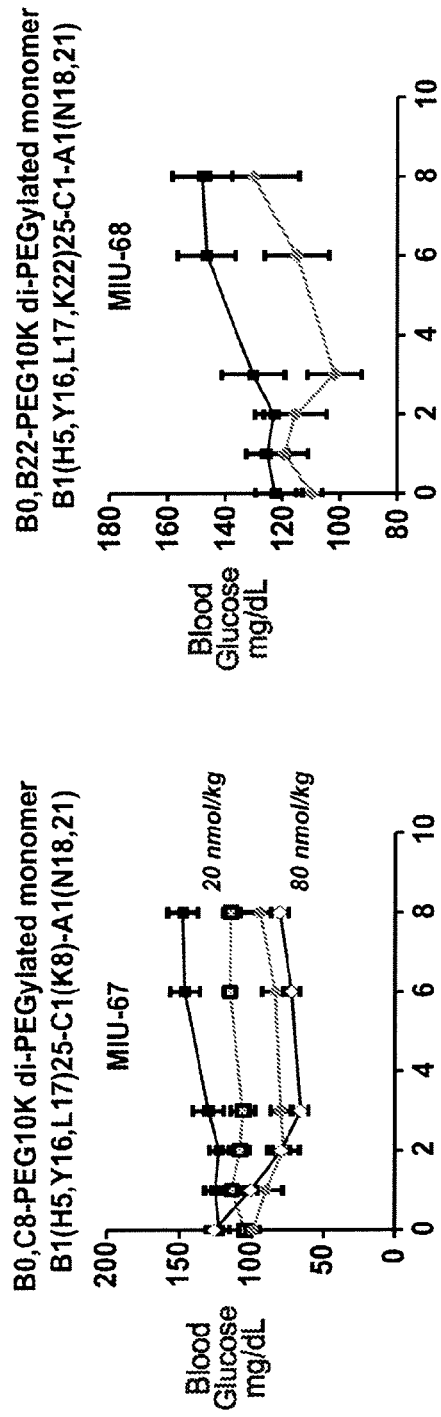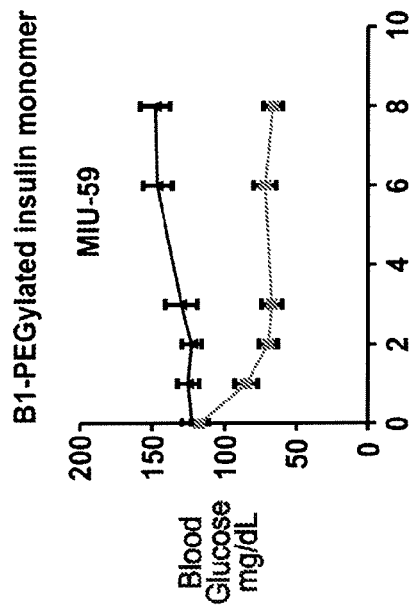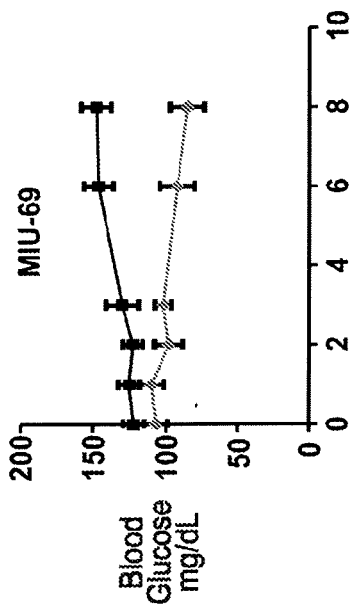
Fig. 31A / Fig. 31B / Fig. 31C / Fig. 31D

Glucose at 12 & 24 h in db/db mice

CTP-BASED INSULIN ANALOGS FOR TREATMENT OF DIABETES

CROSS REFERENCE TO RELATED APPLICATIONS

This application is a U.S. national counterpart application of international application serial No. PCT/US2012/070503 filed Dec. 19, 2012, which claims priority to U.S. Provisional Patent Application No. 61/578,052 filed on Dec. 20, 2011, the disclosures of which are expressly incorporated by reference in their entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: One 61 KB ACII (Text) file named "CTPSeqList_ST25.txt" created on Dec. 11, 2012.

BACKGROUND

Insulin is a proven therapy for the treatment of juvenile-onset diabetes and later stage adult-onset diabetes. The peptide is biosynthesized as a larger linear precursor of low potency (approximately 2% to 9% of native insulin), named proinsulin. Proinsulin is proteolytically converted to insulin by the selective removal of a 35-residue connecting peptide (C peptide). The resultant heteroduplex formed by disulfide links between the insulin "A chain" (SEQ ID NO: 1) and "B chain" (SEQ ID NO: 2) chain, representing a total of 51 amino acids, has high potency for the insulin receptor (nM range). Native insulin has approximately one hundredfold selective affinity for the insulin receptor relative to the related insulin-like growth factor 1 receptor, but demonstrates little selectively for the two different insulin receptor isoforms, named A & B.

The insulin-like growth factors 1 and 2 are single chain liner peptide hormones that are highly homologous in their A and B chain sequences, sharing approximately fifty percent homology with native insulin. The IGF A and B chains are linked by a "C-peptide", wherein the C-peptides of the two IGFs differ in size and amino acid sequence, the first being twelve and the second being eight amino acids in length. Human IGF-1 is a 70 aa basic peptide having the protein sequence shown in SEQ ID NO: 3, and has a 43% homology with proinsulin (Rinderknecht et al. (1978) J. Biol. Chem. 253:2769-2776). Human IGF-2 is a 67 amino acid basic peptide having the protein sequence shown in SEQ ID NO: 4. The IGFs demonstrate considerably less activity at the insulin B receptor isoform than the A-receptor isoform.

Applicants have previously identified IGF-1 based insulin peptides analogs, (wherein the native Gln-Phe dipeptide of the B-chain is replaced by Tyr-Leu) that display high activity at the insulin receptor (see PCT/US2009/068713, the disclosure of which is incorporated herein). Such analogs (referred to herein as IGF YL analog peptides) are more readily synthesized than insulin and enable the development of co-agonist analogs for insulin and IGF-1 receptors, and selective insulin receptor specific analogs. Furthermore, these insulin analogs can also be formulated as single chain insulin agonists in accordance with the present disclosure.

Insulin is a proven therapy for the treatment of juvenile-onset diabetes and later stage adult-onset diabetes, but one of relatively narrow therapeutic index. The ideal insulin therapy is an insulin formulation capable of providing once-a-day time action (qd). Nature uses glycosylation to inhibit renal clearance of a number of native proteins, and as disclosed herein insulin analogs are provided that can be glycosylated during biosynthesis. More particularly, one aspect of the present disclosure describes insulin analogs that have been modified to include a peptide sequence that is prone to O-linked hyperglycosylation when the protein is expressed in a eukaryotic cellular expression system.

In addition, these insulin agonists analogs can be further modified to yield analogs having an improved therapeutic index (e.g., through the use of prodrug chemistry); an extended duration of action (e.g., by linkage of plasma proteins such as albumin, or other modifications, including pegylation and acylation); and preferred tissue targeting (e.g., through the use of chemical modification with cholesterol or vitamin-like substituents). The preparation of single chain insulin analogs using a peptide linker sequence, including for example a peptide linker sequence that comprises glycosylation sites, also provides a novel structural location for where many of these chemical modifications can be successfully deployed. The primary use of such optimized insulin-agonists would be in the treatment of insulin-dependent diabetes.

SUMMARY

As disclosed herein insulin analogs are provided that have been modified to comprise a peptide sequence that is glycosylated by eukaryotic cell expression systems. In one embodiment the insulin analogs are modified to comprise a peptide sequence named C-terminal peptide (CTP: SSSSKAPPPSLPSPSRLPGPSDTPILPQR; SEQ ID NO: 64), which is prone to O-linked hyperglycosylation when the protein is expressed in a eukaryotic cellular expression system. The CTP peptide can be covalently linked to the N-terminus and/or the carboxy terminus of the B-chain of a two chain insulin analog without undermining the inherent in vitro activity of the insulin analog. Of even greater surprise is the fact that the CTP peptide can also be used to connect the B and A chains of insulin to form a single chain insulin analog while still maintaining high in vitro potency in a manner that the native proinsulin C-peptide can not.

In accordance with one embodiment an insulin analog is provided comprising an A chain and a B chain and a CTP peptide. In one embodiment the A chain comprises the sequence GIVEQCCTSICSLYQLENYCN (SEQ ID NO: 1) and the B chain comprises the sequence FVNQHLCG-SHLVEALYLVCGERGFF (SEQ ID NO: 96). More particularly, the A and B chain are linked to one another via disulfide bonds and said CTP peptide is covalently bound to the amino and/or carboxy terminus of the B chain. In one embodiment the CTP peptide comprises the sequence SSSSX$_{50}$APPPSLPSPSRLPGPSDTPILPQX$_{51}$ (SEQ ID NO: 66), wherein X$_{50}$ and X$_{51}$ are independently selected from arginine and lysine. In one embodiment a single chain insulin analog is prepared wherein the carboxy terminus of the B chain is linked to the amino terminus of the A chain via a CTP peptide, and in a further embodiment the single chain insulin analog optionally comprises a CTP peptide linked to the amino terminus of the B chain. In another embodiment an insulin analog is provided as a two-chain construct with the CTP peptide covalently linked to the C-terminus of the B-chain optionally with a second CTP linked to the amino terminus of the B chain. When two or more sequences comprising a CTP peptide are linked to an insulin analog disclosed herein, the sequence comprising the CTP peptides can be the same or different. In vitro and in vivo characterization reveals the CTP modified insulin analogs have high potency in the absence of glycosylation. Thus modification of insulin analog by linking a CTP peptide provides a mechanism to extend insulin action that is based on glycosylation, a natural approach to longer duration proteins.

Even more surprising, applicants have found that when a single chain insulin analog is prepared using a peptide as the linking moiety to join the A and B chain, the exact sequence of the CTP peptide does not need to be maintained. Accordingly, in one embodiment a single chain insulin analog comprising an A chain, a B chain and a linking moiety is provided wherein the linking moiety comprises a peptide of at least 18 amino acids, (including for example peptides of 18 to 158, 29 to 87 or 29 to 58 amino acids) that covalently links the carboxy terminus of the B chain to the amino terminus of the A chain to form a contiguous amino acid chain, with the proviso that the linking moiety does not comprises an 18 amino acid sequence that is identical to an 18 amino acid sequence fragment of SEQ ID NO: 53 directly linked to the carboxy terminus of the B chain. In one embodiment the linking moiety comprises a 29 contiguous amino acid sequence, directly linked to the carboxy terminal amino acid of the B chain, wherein at least 58% of the amino acids comprising said 29 contiguous amino acid sequence are either serine or proline. In another embodiment the linking moiety comprises a 29 contiguous amino acid sequence, directly linked to the carboxy terminal amino acid of the B chain, wherein the 29 contiguous amino acid sequence has greater than 55, 60, 65, 75, 80, 85, 90, 92, or 95% sequence identity to SEQ ID NO: 64), with the proviso that the linking moiety does not comprises an 18 amino acid sequence that is identical to an 18 amino acid sequence fragment of SEQ ID NO: 53. In another embodiment the linking moiety comprises the sequence of SEQ ID NO: 66. In one embodiment the A chain comprises the sequence GIVEQCCTSICSLYQLENYCN (SEQ ID NO: 1) and the B chain comprises the sequence FVNQHLCGSHLVEALYL-VCGERGFF (SEQ ID NO: 96).

In a further embodiment nucleic acid sequences encoding the insulin analogs disclosed herein are also encompassed by the present invention, as well as prokaryotic and eukaryotic cells comprising such nucleic acid sequences. In accordance with one embodiment eukaryotic host cells comprising nucleic acid sequences encoding the modified insulin analogs disclosed herein are used to produce hyperglycosylated insulin analogs.

The insulin agonists disclosed herein may comprise the native insulin B and A chain sequences or any of the known analogs or derivatives thereof that exhibit insulin agonist activity when linked to one another in a heteroduplex. As disclosed herein such A chain and B chain peptides can be linked to one another by the CTP peptide, or a derivative peptide thereof, to form a single chain insulin agonist, or the CTP peptide can be linked to the amino or carboxy terminus of the A or B chain of a two chain insulin heteroduplex. In accordance with one embodiment the B chain comprises the sequence $R_{22}$-$X_{25}LCGX_{29}X_{30}LVX_{33}X_{34}LX_{36}LVCGX_{41}X_{42}GFX_{45}$ (SEQ ID NO: 16), and the A chain comprises the sequence $GIVX_4X_5CCX_8X_9X_{10}CX_{12}LX_{14}X_{15}LX_{17}X_{18}X_{19}CX_{21}$-$R_{13}$ (SEQ ID NO: 18), wherein $X_4$ is glutamic acid or aspartic acid;
$X_5$ is glutamine or glutamic acid
$X_8$ is histidine or phenylalanine;
$X_9$ is serine, arginine, lysine, ornithine or alanine;
$X_{10}$ is isoleucine or serine;
$X_{12}$ is serine or aspartic acid;
$X_{14}$ is tyrosine, arginine, lysine, ornithine or alanine;
$X_{15}$ is glutamine, glutamic acid, arginine, alanine, lysine, ornithine or leucine;
$X_{17}$ is glutamic acid, aspartic acid, asparagine, lysine, ornithine or glutamine;
$X_{18}$ is methionine, asparagine, glutamine, aspartic acid, glutamic acid or threonine;
$X_{19}$ is tyrosine, 4-methoxy-phenylalanine or 4-amino phenylalanine;
$X_{21}$ is selected from the group consisting of alanine, glycine, serine, valine, threonine, isoleucine, leucine, glutamine, glutamic acid, asparagine, aspartic acid, histidine, tryptophan, tyrosine, and methionine;
$X_{25}$ is histidine or threonine;
$X_{29}$ is selected from the group consisting of alanine, glycine and serine;
$X_{30}$ is selected from the group consisting of histidine, aspartic acid, glutamic acid, homocysteic acid and cysteic acid;
$X_{33}$ is selected from the group consisting of aspartic acid and glutamic acid;
$X_{34}$ is selected from the group consisting of alanine and threonine;
$X_{36}$ is tyrosine;
$X_{41}$ is selected from the group consisting of glutamic acid, aspartic acid or asparagine;
$X_{42}$ is selected from the group consisting of alanine, ornithine, lysine and arginine;
$X_{45}$ is tyrosine;
$R_{22}$ is selected from the group consisting of AYRPSE (SEQ ID NO: 11), FVNQ (SEQ ID NO: 10), PGPE (SEQ ID NO: 9), a tripeptide glycine-proline-glutamic acid, a tripeptide valine-asparagine-glutamine, a dipeptide proline-glutamic acid, a dipeptide asparagine-glutamine, glutamine, glutamic acid and an N-terminal amine; and
$R_{13}$ is COOH or $CONH_2$. In one embodiment $X_8$, $X_{25}$ and $X_{30}$ are each histidine.

Additional derivatives of the insulin agonists are encompassed by the present disclosure including modifications that improve the solubility of the underlying insulin agonist. In one embodiment the solubility of the insulin agonist peptide is enhanced by the covalent linkage of a hydrophilic moiety to the peptide. In one embodiment the hydrophilic moiety is linked to either the N-terminal amino acid of the B chain or to the side chain of an amino acid located at the terminal end of the B chain (e.g. a lysine present at any of positions B26-30) or to the side chain of any amino acid comprising the linking moiety binding the B chain to the A chain in a single chain insulin analog. In one embodiment the hydrophilic moiety is albumin, including for example, albumins such as human serum albumin (HSA) and recombinant human albumin (rHA). In one embodiment the hydrophilic moiety is a polyethylene glycol (PEG) chain, having a molecular weight selected from the range of about 500 to about 40,000 Daltons. In one embodiment the polyethylene glycol chain has a molecular weight selected from the range of about 500 to about 5,000 Daltons. In another embodiment the polyethylene glycol chain has a molecular weight of about 10,000 to about 20,000 Daltons.

Acylation or alkylation can increase the half-life of insulin analog peptides, and prodrug derivatives thereof, in circulation. Acylation or alkylation can advantageously delay the onset of action and/or extend the duration of action at the insulin receptors. The insulin analogs disclosed herein can be further modified by acylation or alkylation at the same amino acid position where a hydrophilic moiety is linked, or at a different amino acid position.

Also encompassed by the present disclosure are pharmaceutical compositions comprising the insulin analog, and a pharmaceutically acceptable carrier. In accordance with one embodiment a pharmaceutical composition is provided comprising any of the insulin analogs disclosed herein, or derivative thereof, preferably at a purity level of at least 90%, 91%, 92%, 93%, 94%, 95%, 96%, 97%, 98% or 99%, and a pharmaceutically acceptable diluent, carrier or excipient. Such compositions may contain an insulin agonist peptide as disclosed herein at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored within various package containers. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

In accordance with one embodiment a method of producing a hyperglycosylated insulin analog is provided. In one embodiment the method comprises providing a eukaryotic host cell (e.g., yeast, mouse or human), that comprises a gene encoding an insulin analog that comprises a CTP peptide, and culturing the cell under conditions that allow expression of the insulin analog gene. In one embodiment the host cell expresses human glycosylation enzymes such that glycosylated proteins (glycoproteins) produced in the host cell exhibit protein glycosylation identical to that of human cells (see US Patent Application Publication Nos. 2004/0018590 and 2002/0137134, the disclosures of which are incorporated herein by reference).

In accordance with one embodiment an improved method of regulating blood glucose levels in insulin dependent patients is provided. The method comprises the steps of administering to a patient an insulin agonist peptide disclosed herein, or pharmaceutical salt or other derivative thereof, in an amount therapeutically effective for the control of diabetes.

BRIEF DESCRIPTION OF THE DRAWINGS

FIG. 5 is an alignment of the human proinsulin (A chain, SEQ ID NO: 1; B chain, SEQ ID NO: 2 and the C chain, SEQ ID NO: 53) and insulin-like growth factors I and II (IGF I; SEQ ID NO: 3 and IGF II; SEQ ID NO: 4) amino acid sequences. The alignment demonstrates that these three peptides share a high level of sequence identity (* indicates a space with no corresponding amino acid and a dash (-) indicates the identical amino acid as present in insulin).

FIG. 8A shows the structure of an IGF-1 single chain dimer that comprises two single chain IGF$^{B16B17}$ analog peptides (IGF-1B chain [$C^0H^5Y^{16}L^{17}O^{22}P^{28}R^{29}$]-A chain[$O^{9,14,15}N^{18,21}$]; SEQ ID NO: 54) linked together by a disulfide bond between the side chains of the amino terminus of the B chains. The native insulin disulfides ($A^6$-$A^{11}$, $A^7$-$B^7$, $A^{20}$-$B^{19}$) are not shown but are resident in the dimer form. The single chain form of the disulfide dimer can be converted to a two-chain form by selective proteolytic digestion of the two Arg-Gly (B29 A1) bonds as denoted by the arrows. FIG. 8B is a graph demonstrating the relative insulin receptor binding of insulin, a single chain IGF$^{B16B17}$ analog peptide dimer and a two chain IGF$^{B16B17}$ analog peptide dimer. FIG. 8C is a graph demonstrating the relative activity of insulin, and a two chain IGF$^{B16B17}$ analog peptide dimer to induce insulin receptor phosphorylation.

FIG. 10A is a graph comparing relative insulin receptor binding of native insulin (measured at 1 hour at 4° C.) and the A19 IGF prodrug derivative (Aib,dPro-IGF1YL) over time (0 hours, 2.5 hours and 10.6 hours) incubated in PBS. FIG. 10B is a graph comparing relative insulin receptor binding of native insulin and the A19 IGF prodrug derivative (Aib,dPro-IGF1YL) over time (0 hours, 1.5 hours and 24.8 hours) incubated in 20% plasma/PBS at 37° C. As indicated by the data presented in the graph, increased activity is recovered from the A19 IGF prodrug derivative sample as the prodrug form is converted to the active IGF1YL peptide.

FIG. 11A is a graph comparing relative insulin receptor binding of native insulin and the A19 IGF prodrug derivative (IGF1YL: dK,(N-isobutylG) over time (0 hours, 5 hours and 52 hours) incubated in PBS. FIG. 11B is a graph comparing relative insulin receptor binding of native insulin and the A19 IGF prodrug derivative (IGF1YL: dK,(N-isobutylG) over time (0 hours, 3.6 hours and 24.8 hours) incubated in 20% plasma/PBS at 37° C. As indicated by the data presented in the graph, increased activity is recovered from the A19 IGF prodrug derivative sample as the prodrug form is converted to the active IGF1YL peptide.

FIG. 12A is a graph comparing relative insulin receptor binding of native insulin (measured at 1 hour at 4° C.) and the A19 IGF prodrug derivative (IGF1YL: dK(e-acetyl),Sar) over time (0 hours, 7.2 hours and 91.6 hours) incubated in PBS. FIG. 12B is a graph comparing relative insulin receptor binding of native insulin and the A19 IGF prodrug derivative (IGF1YL: dK(e-acetyl),Sar) over time (0 hours, 9 hours and 95 hours) incubated in 20% plasma/PBS at 37° C. As indicated by the data presented in the graph, increased activity is recovered from the A19 IGF prodrug derivative sample as the prodrug form is converted to the active IGF1YL peptide.

FIG. 17. is a schematic overview of the biosynthesis of single chain insulin analogs in E. coli and purification under denaturing conditions. Details of the procedure are provided in Example 15.

FIGS. 18A-18C are graphs demonstrating the activity of single chain insulin analogs DP20 (GEEEEEKGPEHLC-GAHLVDALYLVCGDRGFYSSSSRAPPPSLPSPSR-LPGPSD TPILPQKGIVDECCHRSCDLRRLENYCN; SEQ ID NO: 68) and DP19 (MGSSSSKAPPPSLPSPSR-LPGPSDTPILPQGEEEEEKGPEHLCG AHLVDALYL-VCGDRGFYGYGSSSRRAPQTGIVDECCHRSCDLR-RLENYCN; SEQ ID NO: 67) at the insulin subtype A and B receptors and the IGF receptor. FIGS. 18A and 18B are graphs demonstrating the in vitro phosphorylation activity of single chain insulin analogs at the insulin subtype A receptor (FIG. 18A) and the insulin subtype B receptor (FIG. 18B). The single chain insulin analogs tested comprise a CTP peptide as the linking peptide (DP20; ●), a CTP peptide (SEQ ID NO: 64) is used as the linking peptide, wherein the single chain analog is cleaved at the lysine of CTP to produce a two chain insulin (DP20 Lys C; ▲); a CTP peptide (SEQ ID NO: 64) located at the N-terminus and used as the linking peptide (DP22; ∇), wherein the single chain analog is cleaved at the lysine of CTP to produce a two chain insulin (DP20 Lys C; ◊); relative to a two chain native insulin (■). The full length sequence of DP19 (CTP-GE₅K-B chain-C¹ peptide-A Chain) and DP20 (GE₅K-B chain-CTP(K)-A Chain are provided as SEQ ID NO: 67 and SEQ ID NO: 68, respectively. FIG. 18C demonstrates the surprisingly low in vitro phosphorylation activity of the single chain analogs at the IGF receptor (lower than native insulin), wherein cleavage of the single chain analogs into two chain analogs substantially increases their activity at the IGF receptor. Thus the single chain analog (DP20) has a higher selectivity for the insulin receptor compared to the IGF receptor than the two chain version of DP20.

FIGS. 19A-19C are graphs demonstrating the comparative insulin dose titration in normal mice of DP19 (FIG. 19B) and DP20 (FIG. 19C) relative to native insulin (FIG. 19A). The insulin and insulin analogs were administered either at 27 or 90 nmol/kg.

FIGS. 20A and 20B are graphs demonstrating the in vitro phosphorylation activity of single chain insulin analogs comprising a CTP peptide as the linking peptide (DP20; ●); a CTP peptide as the linking peptide wherein the serines have been replaced with alanine (DP20 S2A (SEQ ID NO: 80); ∇); a CTP peptide as the linking peptide wherein the amino acid content remains the same but the sequence has been randomized (DP20R CTP; ◊, wherein, the linking peptide is PPRPPQSASPPDLSPLSGTPSRPSLS; SEQ ID NO: 69); and the native proinsulin C peptide as the linking peptide (DP20 C⁰ (SEQ ID NO: 76); ▲), relative to a two chain native insulin (■) peptide and native IGF (○). Activity of each peptide was tested at both the insulin A subtype receptor and at the insulin B subtype receptor. As indicated by the data, single chain insulin analogs using the CTP peptide or the modified derivatives of that sequence produce potent insulin agonists relative to the native proinsulin or IGF peptides at both insulin receptor subtypes.

FIG. 21 is a graph demonstrating the in vitro phosphorylation activity of single chain insulin analogs at the insulin subtype A receptor. The activity of single chain analogs comprising a CTP peptide as the linking peptide, wherein the prolines have been replaced with alanine (DP20 P to A (SEQ ID NO: 70); ●); the native proinsulin C peptide is used as the linking peptide (DP20 C⁰ (SEQ ID NO: 71); ▲); the native IGF-1 C peptide is used as the linking peptide (i.e., 010: (SEQ ID NO: 72); ◇); a CTP peptide (SEQ ID NO: 64) is used as the linking peptide, wherein the single chain analog is cleaved at the lysine of CTP to produce a two chain insulin (DP20 Lys C; ○); relative to a two chain native insulin (■) and native IGF (▽). As indicated by the data single chain insulin analogs using the CTP peptide wherein the proline residues have been replaced with alanine retain activity as insulin agonists relative to the native proinsulin peptides at the insulin receptor. Cleavage of the DP20 single chain analog with Lys C produces a two chain insulin bearing a CTP peptide on the B chain carboxy terminus that has potency similar to native insulin.

FIGS. 22A and 22B are graphs demonstrating the in vitro phosphorylation activity of single chain insulin analogs comprising a CTP peptide as the linking peptide. FIG. 22A is a graph comparing the activity of single chain analogs comprising a CTP peptide linked to the native proinsulin C peptide as the linking peptide (DP20 CTPC⁰ (SEQ ID NO: 73); ●); a native proinsulin C peptide linked to a CTP peptide the as the linking peptide (DP20 C⁰CTP (SEQ ID NO: 74); ▽) relative to a two chain native insulin (■) peptide and native IGF (○). FIG. 22B is a graph comparing single chain analogs comprising a native proinsulin C peptide linked to a CTP peptide the as the linking peptide (DP20 C⁰CTP (SEQ ID NO: 74); ●); two end to end linked CTP peptides the as the linking peptide (DP20 2CTP (SEQ ID NO: 75); ▽) relative to a two chain native insulin (■) peptide and native IGF (○).

FIG. 23 is a graph demonstrating the in vitro phosphorylation activity at the insulin subtype A receptor of single chain insulin analogs comprising a truncated native proinsulin C peptide as the linking peptide. The activity of single chain insulin analogs comprising the native proinsulin C peptide having either the first 6 amino acids removed (DP20 C⁰ (desC1-6) (SEQ ID NO: 76); ●), amino acids 15-21 removed (DP20 C⁰ (desC15-21) (SEQ ID NO: 77); ▲), or amino acids 27-33 removed (DP20 C⁰ (desC27-33) (SEQ ID NO: 78); ▽) relative to a two chain native insulin (■) peptide and an insulin analog having CTP as the linking peptide (◇) is shown (DP20).

FIG. 24 is a graph demonstrating the in vitro phosphorylation activity at the insulin subtype A and B receptors (IRA and IRB) comparing the activity of an derivative of DP20 (DP25M; modified to be more insulin like) to insulin and DP20.

FIGS. 26C and 26D provide data on blood glucose AUC values after administration of the listed analogs.

FIGS. 27C and 27D provide data on blood glucose AUC values after administration of the listed analogs.

FIGS. 28A and 28B are graphs showing the results of insulin tolerance tests comparing the ability of the acylated insulin analog Detemir relative to the pegylated single chain insulin analog MIU-56 to reduce and maintain low blood glucose levels. FIGS. 28C and 28D show the blood glucose $AUC_{24\ hrs}$ in mice administered Detemir and MIU-56, respectively.

FIGS. 29A and 29B are graphs showing the results of insulin tolerance tests comparing MIU-56 and MIU-57. FIGS. 29C and 29D show the blood glucose $AUC_{24\ hrs}$ in mice administered MIU-56 and MIU-57, respectively. Results from comparative insulin dose titrations of MIU-56 and MIU-57 reveal that a similar profile is obtained in mice for dosages ranging from 20 nmol/kg through 80 nmol/kg (see FIGS. 29E and 29F). A dimer (MIU 58) was prepared comprising two insulin single chain analogs (B¹(H5,Y16,L17)25-C¹-A¹ (N18,21) linked head to head via a 20 kDa PEG chain. FIGS. 29G-29J represents the results obtained from a comparative insulin tolerance test for MIU-57 and MIU-58 using C57/Blk mice. FIGS. 29G and 29H are graphs showing the results of insulin tolerance tests comparing MIU-57 and MIU-58. FIGS. 29I and 29J show the blood glucose $AUC_{24\ hrs}$ in mice administered MIU-57 and MIU-58, respectively.

FIGS. 30A & 30B provide data from a comparative insulin dose titration of two pegylated insulin derivatives. The insulin derivatives differ based on the placement of a 20 kDa PEG which is linked to the N-terminus (FIG. 30A) of MIU-59, or to the side chain of amino acid B29, of an insulin analog MIU-60, wherein the A1 and B1 amino acids have been carbamylated (FIG. 30B).

FIGS. 31A-31D provide data from a comparative insulin dose titration of the three single chain insulin analogs MIU-67, MIU-68 and MIU-69, each comprising two PEG chains of 10 kDa each relative to the single pegylated (20K PEG) native insulin derivative (MIU-59). More particularly, the activities of single chain insulin analogs MIU-67 ($B^1$(H5,Y16,L17)25-$C^1$(K8)-$A^1$(N18,21)) having two PEG chains (10K each) one linked at the N-terminus and the other at amino acid 8 of the linking moiety (position C8), MIU-68 ($B^1$(H5,Y16,L17, K22)25-$C^1$(K8)-$A^1$(N18,21)) having two PEG chains (10K each) one linked at the N-terminus and the other at amino acid B22 and MIU-69 ($B^1$(H5,Y16,L17)25-$C^1$(K8)-$A^1$(K14, N18,21)) having two PEG chains (10K each) one linked at the N-terminus and the other at amino acid A14 were compared. Each compound was administered at two dosages (20 and 80 nmol/kg).

As shown in FIG. 33 the two compounds performed almost identically.

DETAILED DESCRIPTION

Definitions

Figure 1:
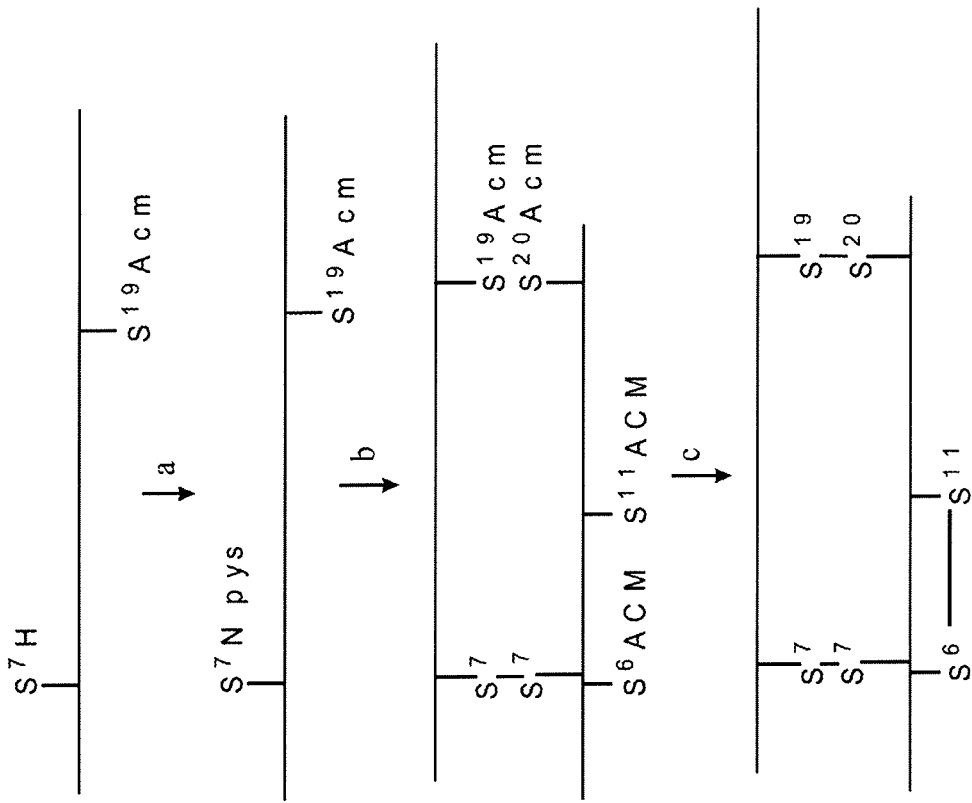
FIG. 1. is a schematic overview of the two step synthetic strategy for preparing human insulin. Details of the procedure are provided in Example 1.

In describing and claiming the invention, the following terminology will be used in accordance with the definitions set forth below.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein, the term "prodrug" is defined as any compound that undergoes chemical modification before exhibiting its pharmacological effects.

As used herein the term "amino acid" encompasses any molecule containing both amino and carboxyl functional groups, wherein the amino and carboxylate groups are attached to the same carbon (the alpha carbon). The alpha carbon optionally may have one or two further organic substituents. For the purposes of the present disclosure designation of an amino acid without specifying its stereochemistry is intended to encompass either the L or D form of the amino acid, or a racemic mixture. However, in the instance where an amino acid is designated by its three letter code and includes a superscript number, the D form of the amino acid is specified by inclusion of a lower case d before the three letter code and superscript number (e.g., $dLys^{-1}$), wherein the designation lacking the lower case d (e.g., $Lys^{-1}$) is intended to specify the native L form of the amino acid. In this nomenclature, the inclusion of the superscript number designates the position of the amino acid in the insulin analog sequence, wherein amino acids that are located within the insulin analog sequence are designated by positive superscript numbers numbered consecutively from the N-terminus. Additional amino acids linked to the insulin analog peptide either at the N-terminus or through a side chain are numbered starting with 0 and increasing in negative integer value as they are further removed from the insulin analog sequence. For example, the position of an amino acid within a dipeptide prodrug linked to the N-terminus of an insulin analog is designated $aa^{-1}$-$aa^{0}$-insulin analog, wherein $aa^0$ represents the carboxy terminal amino acid of the dipeptide and $aa^{-1}$ designates the amino terminal amino acid of the dipeptide.

As used herein the term "hydroxyl acid" refers to amino acids that have been modified to replace the alpha carbon amino group with a hydroxyl group.

As used herein the term "non-coded amino acid" encompasses any amino acid that is not an L-isomer of any of the following 20 amino acids: Ala, Cys, Asp, Glu, Phe, Gly, His, Ile, Lys, Leu, Met, Asn, Pro, Gln, Arg, Ser, Thr, Val, Trp, Tyr.

A "dipeptide" is a compound formed by linkage of an alpha amino acid or an alpha hydroxyl acid to another amino acid, through a peptide bond.

As used herein the term "chemical cleavage" absent any further designation encompasses a non-enzymatic reaction that results in the breakage of a covalent chemical bond.

A "bioactive polypeptide" refers to polypeptides which are capable of exerting a biological effect in vitro and/or in vivo.

As used herein a general reference to a peptide is intended to encompass peptides that have modified amino and carboxy termini. For example, an amino acid sequence designating the standard amino acids is intended to encompass standard amino acids at the N- and C-terminus as well as a corresponding hydroxyl acid at the N-terminus and/or a corresponding C-terminal amino acid modified to comprise an amide group in place of the terminal carboxylic acid.

As used herein an "acylated" amino acid is an amino acid comprising an acyl group which is non-native to a naturally-occurring amino acid, regardless by the means by which it is produced. Exemplary methods of producing acylated amino acids and acylated peptides are known in the art and include acylating an amino acid before inclusion in the peptide or peptide synthesis followed by chemical acylation of the peptide. In some embodiments, the acyl group causes the peptide to have one or more of (i) a prolonged half-life in circulation, (ii) a delayed onset of action, (iii) an extended duration of action, (iv) an improved resistance to proteases, and (v) increased potency at the IGF and/or insulin peptide receptors.

As used herein, an "alkylated" amino acid is an amino acid comprising an alkyl group which is non-native to a naturally-occurring amino acid, regardless of the means by which it is produced. Exemplary methods of producing alkylated amino acids and alkylated peptides are known in the art and including alkylating an amino acid before inclusion in the peptide or peptide synthesis followed by chemical alkylation of the peptide. Without being held to any particular theory, it is believed that alkylation of peptides will achieve similar, if not the same, effects as acylation of the peptides, e.g., a prolonged half-life in circulation, a delayed onset of action, an extended duration of action, an improved resistance to proteases and increased potency at the IGF and/or insulin receptors.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, the term "hydrophilic moiety" refers to any compound that is readily water-soluble or readily absorbs water, and which are tolerated in vivo by mammalian species without toxic effects (i.e. are biocompatible). Examples of hydrophilic moieties include polyethylene glycol (PEG), polylactic acid, polyglycolic acid, a polylactic-polyglycolic acid copolymer, polyvinyl alcohol, polyvinylpyrrolidone, polymethoxazoline, polyethyloxazoline, polyhydroxyethyl methacrylate, polyhydroxypropyl methacrylamide, polymethacrylamide, polydimethylacrylamide, and derivatised celluloses such as hydroxymethylcellulose or hydroxyethylcellulose and co-polymers thereof, as well as natural polymers including, for example, albumin, heparin and dextran.

As used herein, the term "treating" includes prophylaxis of the specific disorder or condition, or alleviation of the symptoms associated with a specific disorder or condition and/or preventing or eliminating said symptoms. For example, as used herein the term "treating diabetes" will refer in general to maintaining glucose blood levels near normal levels and may include increasing or decreasing blood glucose levels depending on a given situation.

As used herein an "effective" amount or a "therapeutically effective amount" of an insulin analog refers to a nontoxic but sufficient amount of an insulin analog to provide the desired effect. For example one desired effect would be the prevention or treatment of hyperglycemia. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route such as intranasal, inhalation, subcutaneous, intramuscular, intraspinal, or intravenous.

Throughout the application, all references to a particular amino acid position by letter and number (e.g. position A5) refer to the amino acid at that position of either the A chain (e.g. position A5) or the B chain (e.g. position B5) in the respective native human insulin A chain (SEQ ID NO: 1) or B chain (SEQ ID NO: 2), or the corresponding amino acid position in any analogs thereof. For example, a reference herein to "position B28" absent any further elaboration would mean the corresponding position B27 of the B chain of an insulin analog in which the first amino acid of SEQ ID NO: 2 has been deleted. Similarly, amino acids added to the N-terminus of the native B chain are numbered starting with B0, followed by numbers of increasing negative value (e.g., B–1, B–2 . . . ) as amino acids are added to the N-terminus.

As used herein the term "native insulin peptide" is intended to designate the 51 amino acid heteroduplex comprising the A chain of SEQ ID NO: 1 and the B chain of SEQ ID NO: 2, as well as single-chain insulin analogs that comprise SEQ ID NOS: 1 and 2. The term "insulin peptide" as used herein, absent further descriptive language is intended to encompass the 51 amino acid heteroduplex comprising the A chain of SEQ ID NO: 1 and the B chain of SEQ ID NO: 2, as well as single-chain insulin analogs thereof (including for example those disclosed in published international application WO96/34882 and U.S. Pat. No. 6,630,348, the disclosures of which are incorporated herein by reference), including heteroduplexes and single-chain analogs that comprise modified analogs of the native A chain and/or B chain and derivatives thereof. Such modified analogs include modification of the amino acid at position A19, B16 or B25 to a 4-amino phenylalanine or one or more amino acid substitutions at positions selected from A5, A8, A9, A10, A12, A14, A15, A17, A18, A21, B1, B2, B3, B4, B5, B9, B10, B13, B14, B17, B20, B21, B22, B23, B26, B27, B28, B29 and B30 or deletions of any or all of positions B1-4 and B26-30. Insulin peptides as defined herein can also be analogs derived from a naturally occurring insulin by insertion or substitution of a non-peptide moiety, e.g. a retroinverso fragment, or incorporation of non-peptide bonds such as an azapeptide bond (CO substituted by NH) or pseudo-peptide bond (e.g. NH substituted with $CH_2$) or an ester bond (e.g., a depsipeptide, wherein one or more of the amide (—CONHR—) bonds are replaced by ester (COOR) bonds).

An "A19 insulin analog" is an insulin peptide that has a substitution of 4-amino phenylalanine or 4-methoxy phenylalanine for the native tyrosine residue at position 19 of the A chain of native insulin.

As used herein an "IGF$^{B61317}$ analog peptide" is a generic term that comprising an A chain and B chain heteroduplex, as well as single-chain insulin analogs thereof, wherein the A chain comprises the peptide sequence of SEQ ID NO: 15 and the B chain comprises the sequence of SEQ ID NO: 17 as well as analogs of those sequences wherein the analog of the A chain and/or B chain comprise 1-3 further amino acid substitutions, with the proviso that the B chain does not comprise the sequence of SEQ ID NO: 2 and comprises a tyrosine at position B16 and a leucine at position B17.

An "IGF YL analog" is a peptide comprising an IGF A chain of SEQ ID NO: 15 and an IGF B chain of SEQ ID NO: 28.

As used herein, the term "single-chain insulin analog" encompasses a group of structurally-related proteins wherein insulin or IGF A and B chains, or analogs or derivatives thereof, are covalently linked to one another to form a linear polypeptide chain. As disclosed herein the single-chain insulin analog comprises the covalent linkage of the carboxy terminus of the B chain to the amino terminus of the A chain via a linking moiety.

As used herein the term "insulin A chain", absent further descriptive language is intended to encompass the 21 amino acid sequence of SEQ ID NO: 1 as well as functional analogs and derivatives thereof that when combined with an insulin B chain have activity at the insulin receptor. For example, functional analogs and derivatives include the A chain of A19 insulin analogs as well as other analogs known to those skilled in the art, that comprise modification of the sequence of SEQ ID NO: 1 by one or more amino acid insertions, deletions or substitutions at positions selected from A4, A5, A8, A9, A10, A12, A14, A15, A17, A18, A21.

As used herein the term "insulin B chain", absent further descriptive language is intended to encompass the 30 amino acid sequence of SEQ ID NO: 2, as well as modified functional analogs of the native B chain that when combined with an insulin A chain have activity at the insulin receptor. For example, functional analogs and derivatives, including modification of the amino acid at position B16 or B25 to a 4-amino phenylalanine or one or more amino acid insertions, deletions or substitutions at positions selected from B1, B2, B3, B4, B5, B9, B10, B13, B14, B17, B20, B21, B22, B23, B25, B26, B27, B28, B29 and B30 or deletions of any or all of positions B1-4 and B26-30.

A "glycosylation site" designates any amino acid residue or region in a polypeptide which is subject to glycosylation, i.e., the attachment of a carbohydrate structure. Such sites are typically N-glycosylation sites (i.e., any amino acid residue or region in a polypeptide which allows the attachment of a carbohydrate structure through N-linkage) or O-glycosylation sites (i.e., any amino acid residue or region in a polypeptide which allows the attachment of a carbohydrate structure through O-linkage).

As used herein a "non-native glycosylation site" is a glycosylation site that is not present in the native peptide. Specifically, either the native sequence of the peptide has been modified to introduce a glycosylation site at a position where there was previous not such a site, or additional amino acid(s) are added to the native peptide wherein the added sequences together with the native sequence introduce a glycosylation site, or the added amino acid(s) comprise a glycosylation site.

As used herein the term "hyperglycosylated peptide" refers to an amino acid sequence comprising two or more non-native glycosylation sites that have been glycosylated. The glycosylation sites of the hyperglycosylation peptide may include N-linked glycosylation sites, and/or O-linked glycosylation sites.

As used herein a CTP peptide is an amino acid sequence comprising the sequence SSSSKAPPPSLPSPSRLPGPSDT-PILPQR (SEQ ID NO: 64), a sequence comprising 18-28 amino acid fragment of SEQ ID NO: 64, or a sequence comprising an 18 to 29 amino acid sequence that shares at least 50% sequence identity with an 18 to 29 amino acid sequence of (SEQ ID NO: 64), with the proviso that the CTP peptide does not comprise an 18 amino acid sequence that is identical to an 18 amino acid sequence contained within the native proinsulin C-peptide (SEQ ID NO: 53).

As used herein the term "derivative" is intended to encompass chemical modification to a compound (e.g., an amino acid), including chemical modification in vitro, e.g. by introducing a group in a side chain in one or more positions of a polypeptide, e.g. a nitro group in a tyrosine residue, or iodine in a tyrosine residue, or by conversion of a free carboxylic group to an ester group or to an amide group, or by converting an amino group to an amide by acylation, or by acylating a hydroxy group rendering an ester, or by alkylation of a primary amine rendering a secondary amine or linkage of a hydrophilic moiety to an amino acid side chain. Other derivatives are obtained by oxidation or reduction of the side-chains of the amino acid residues in the polypeptide.

As used herein the term IGF A chain, absent further descriptive language is intended to encompass the 21 amino acid sequence of native IGF 1 or IGF 2 (SEQ ID NOs: 5 and 7 respectively), as well as functional analogs thereof known to those skilled in the art, including modification of the sequence of SEQ ID NO: 5 and 7 by one or more amino acid substitutions at positions selected from A5, A8, A9, A10, A12, A14, A15, A17, A18, A21.

As used herein the term "IGF YL B chain", absent further descriptive language is intended to encompass an amino acid sequence comprising SEQ ID NO: 17, including for example the sequence of SEQ ID NO: 6, as well as analogs of the IGF YL B chain and derivatives thereof, including modification of the amino acid at position B16 or B25 to a 4-amino phenylalanine or one or more amino acid substitutions at positions selected from B1, B2, B3, B4, B5, B9, B10, B13, B14, B17, B20, B21, B22, B23, B26, B27, B28, B29 and B30 or deletions of any or all of positions B1-4 and B26-30.

The term "identity" as used herein relates to the similarity between two or more sequences. Identity is measured by dividing the number of identical residues by the total number of residues and multiplying the product by 100 to achieve a percentage. Thus, two copies of exactly the same sequence have 100% identity, whereas two sequences that have amino acid deletions, additions, or substitutions relative to one another have a lower degree of identity. Those skilled in the art will recognize that several computer programs, such as those that employ algorithms such as BLAST (Basic Local Alignment Search Tool, Altschul et al. (1993) J. Mol. Biol. 215:403-410) are available for determining sequence identity.

As used herein, the term "selectivity" of a molecule for a first receptor relative to a second receptor refers to the following ratio: $EC_{50}$ of the molecule at the second receptor divided by the $EC_{50}$ of the molecule at the first receptor. For example, a molecule that has an $EC_{50}$ of 1 nM at a first receptor and an $EC_{50}$ of 100 nM at a second receptor has 100-fold selectivity for the first receptor relative to the second receptor.

As used herein an amino acid "modification" refers to a substitution of an amino acid, or the derivation of an amino acid by the addition and/or removal of chemical groups to/from the amino acid, and includes substitution with any of the 20 amino acids commonly found in human proteins, as well as atypical or non-naturally occurring amino acids. Commercial sources of atypical amino acids include Sigma-Aldrich (Milwaukee, Wis.), ChemPep Inc. (Miami, Fla.), and Genzyme Pharmaceuticals (Cambridge, Mass.). Atypical amino acids may be purchased from commercial suppliers, synthesized de novo, or chemically modified or derivatized from naturally occurring amino acids.

As used herein an amino acid "substitution" refers to the replacement of one amino acid residue by a different amino acid residue.

As used herein, the term "conservative amino acid substitution" is defined herein as exchanges within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln, cysteic acid and homocysteic acid;
III. Polar, positively charged residues:
His, Arg, Lys; Ornithine (Orn)
IV. Large, aliphatic, nonpolar residues:
Met, Leu, Ile, Val, Cys, Norleucine (Nle), homocysteine
V. Large, aromatic residues:
Phe, Tyr, Trp, acetyl phenylalanine As used herein the general term "polyethylene glycol chain" or "PEG chain", refers to mixtures of condensation polymers of ethylene oxide and water, in a branched or straight chain, represented by the general formula $H(OCH_2CH_2)$—OH, wherein n is at least 2. "Polyethylene glycol chain" or "PEG chain" is used in combination with a numeric suffix to indicate the approximate average molecular weight thereof. For example, PEG-5,000 refers to polyethylene glycol chain having a total molecular weight average of about 5,000 Daltons.

As used herein the term "pegylated" and like terms refers to a compound that has been modified from its native state by linking a polyethylene glycol chain to the compound. A "pegylated polypeptide" is a polypeptide that has a PEG chain covalently bound to the polypeptide.

As used herein a "linker" is a bond, molecule or group of molecules that binds two separate entities to one another. Linkers may provide for optimal spacing of the two entities or may further supply a labile linkage that allows the two entities to be separated from each other. Labile linkages include photocleavable groups, acid-labile moieties, base-labile moieties and enzyme-cleavable groups.

As used herein an "IGF dimer" is a complex comprising two IGF YL analog peptides (each itself comprising an A chain and a B chain) covalently bound to one another via a linker. The term IGF dimer, when used absent any qualifying language, encompasses both IGF homodimers and IGF heterodimers. An IGF homodimer comprises two identical subunits, whereas an IGF heterodimer comprises two subunits that differ, although the two subunits are substantially similar to one another.

The term "$C_1$-$C_n$ alkyl" wherein n can be from 1 through 6, as used herein, represents a branched or linear alkyl group having from one to the specified number of carbon atoms. Typical $C_1$-$C_6$ alkyl groups include, but are not limited to, methyl, ethyl, n-propyl, iso-propyl, butyl, iso-Butyl, sec-butyl, tert-butyl, pentyl, hexyl and the like.

The terms "$C_2$-$C_n$ alkenyl" wherein n can be from 2 through 6, as used herein, represents an olefinically unsaturated branched or linear group having from 2 to the specified number of carbon atoms and at least one double bond. Examples of such groups include, but are not limited to, 1-propenyl, 2-propenyl (—$CH_2$—CH=$CH_2$), 1,3-butadienyl, (—CH=CHCH=$CH_2$), 1-butenyl (—CH=$CHCH_2CH_3$), hexenyl, pentenyl, and the like.

The term "$C_2$-$C_n$ alkynyl" wherein n can be from 2 to 6, refers to an unsaturated branched or linear group having from 2 to n carbon atoms and at least one triple bond. Examples of such groups include, but are not limited to, 1-propynyl, 2-propynyl, 1-butynyl, 2-butynyl, 1-pentynyl, and the like.

As used herein the term "aryl" refers to a mono- or bicyclic carbocyclic ring system having one or two aromatic rings including, but not limited to, phenyl, naphthyl, tetrahydronaphthyl, indanyl, indenyl, and the like. The size of the aryl ring and the presence of substituents or linking groups are indicated by designating the number of carbons present. For example, the term "($C_1$-$C_3$ alkyl)($C_6$-$C_{10}$ aryl)" refers to a 5 to 10 membered aryl that is attached to a parent moiety via a one to three membered alkyl chain.

The term "heteroaryl" as used herein refers to a mono- or bi-cyclic ring system containing one or two aromatic rings and containing at least one nitrogen, oxygen, or sulfur atom in an aromatic ring. The size of the heteroaryl ring and the presence of substituents or linking groups are indicated by designating the number of carbons present. For example, the term "($C_1$-$C_n$ alkyl)($C_5$-$C_6$ heteroaryl)" refers to a 5 or 6 membered heteroaryl that is attached to a parent moiety via a one to "n" membered alkyl chain.

As used herein, the term "halo" refers to one or more members of the group consisting of fluorine, chlorine, bromine, and iodine.

As used herein the term "patient" without further designation is intended to encompass any warm blooded vertebrate domesticated animal (including for example, but not limited to livestock, horses, cats, dogs and other pets) and humans.

The term "isolated" as used herein means having been removed from its natural environment. In some embodiments, the analog is made through recombinant methods and the analog is isolated from the host cell.

The term "purified," as used herein relates to the isolation of a molecule or compound in a form that is substantially free of contaminants normally associated with the molecule or compound in a native or natural environment and means having been increased in purity as a result of being separated from other components of the original composition. The term "purified polypeptide" is used herein to describe a polypeptide which has been separated from other compounds including, but not limited to nucleic acid molecules, lipids and carbohydrates.

A "peptidomimetic" refers to a chemical compound having a structure that is different from the general structure of an existing peptide, but that functions in a manner similar to the existing peptide, e.g., by mimicking the biological activity of that peptide. Peptidomimetics typically comprise naturally-occurring amino acids and/or unnatural amino acids, but can also comprise modifications to the peptide backbone. For example a peptidomimetic may include a sequence of naturally-occurring amino acids with the insertion or substitution of a non-peptide moiety, e.g. a retroinverso fragment, or incorporation of non-peptide bonds such as an azapeptide bond (CO substituted by NH) or pseudopeptide bond (e.g. NH substituted with $CH_2$), or an ester bond (e.g., depsipeptides, wherein one or more of the amide (—CONHR—) bonds are replaced by ester (COOR) bonds). Alternatively the peptidomimetic may be devoid of any naturally-occurring amino acids.

As used herein the term "charged amino acid" or "charged residue" refers to an amino acid that comprises a side chain that is negatively charged (i.e., de-protonated) or positively charged (i.e., protonated) in aqueous solution at physiological pH. For example, negatively charged amino acids include aspartic acid, glutamic acid, cysteic acid, homocysteic acid, and homoglutamic acid, whereas positively charged amino acids include arginine, lysine and histidine. Charged amino acids include the charged amino acids among the 20 amino acids commonly found in human proteins, as well as atypical or non-naturally occurring amino acids.

As used herein the term "acidic amino acid" refers to an amino acid that comprises a second acidic moiety (other than the alpha carboxylic acid of the amino acid), including for example, a side chain carboxylic acid or sulfonic acid group.

ABBREVIATIONS

Insulin analogs will be abbreviated as follows:

The insulin A and B chains will be designated by a capital A for the A chain and a capital B for the B chain wherein a superscript 0 (e.g., $A^0$ or $B^0$) will designate the base sequence is an insulin sequence (A chain: SEQ ID NO: 1, B chain SEQ ID NO: 2) and a superscript 1 (e.g., $A^1$ or $B^1$) will designate the base sequence is an IGF-1 sequence (A chain: SEQ ID NO: 5, B chain SEQ ID NO: 62). Modifications that deviate from the native insulin and IGF sequence are indicated in parenthesis following the designation of the A or B chain (e.g., [$B^1$(H5,H10,Y16,L17): $A^1$(H8,N18,N21)]) with the single letter amino acid abbreviation indicating the substitution and the number indicating the position of the substitution in the respective A or B chain, using native insulin numbering. A colon between the A and B chain indicates a two chain insulin whereas a dash will indicate a covalent bond and thus a single chain analog. In single chain analogs a linking moiety will be included between the A and B chains and the designation $C^1$ refers to the native IGF 1 C peptide, SEQ ID NO: 13.

EMBODIMENTS

In accordance with one embodiment insulin analogs are provided herein that have been modified to introduce one or more glycosylation sites. Glycosylation of peptide based pharmaceuticals can confer additional benefits to the base peptide including increased serum half-life; increased functional in vivo half-life; and reduced degradation. Introducing glycosylation sites into insulin analogs provides locations for attachment of a carbohydrate moiety on the insulin agonist, such that when the insulin agonist is produced in a eukaryotic cell capable of glycosylation, the insulin agonist is glycosylated. In one embodiment an insulin analog is provided wherein the peptide sequence has been modified, either by the addition and/or the substitution of amino acids to add new glycosylation sites not present in native insulin. In one embodiment the glycosylation site is introduced at the amino or carboxy terminus of the B chain, or in the case of a single chain analog the glycosylation site can be introduced to the linking peptide of the single chain analog. In a further embodiment, a single chain analog is provided wherein at least one glycosylation site is introduced to both the amino terminus of the B chain and to the linking moiety of the single chain analog.

Applicants have discovered that high potency single chain insulin analogs can be prepared where the linking moiety joining the carboxy terminus of the B chain to the amino terminus of the A chain can be greater than 18 amino acids, provided the linking moiety doe not have the native proinsulin C peptide directly linked to the B chain carboxy terminus. In accordance with this discovery single chain insulin analogs are provided that comprise an insulin A chain, an insulin B chain and a linking moiety, wherein the linking moiety comprises a peptide of at least 18 amino acids, including for example, 18 to 87, 29 to 87, or 29 to 58 amino acids, wherein the linking moiety covalently links the carboxy terminus of the B chain to the amino terminus of the A chain to form a contiguous amino acid chain. More particularly the linking moiety does not comprise the sequence of the native proinsulin C peptide (SEQ ID NO: 53), or a contiguous 18, 20, 25 or 30 amino acid fragment of SEQ ID NO: 53 directly linked to the carboxy terminus of the B chain. In one embodiment a single chain insulin analog is provided wherein the linking moiety comprises a sequence of at least 18 amino acids wherein the linking moiety comprises a contiguous 4, 8, 16, 18, 20, 25 or 30 amino acid fragment of the native proinsulin C peptide (SEQ ID NO: 53), with the proviso that the linking moiety also comprises a non-$C^0$ peptide of at least 8, 16, 18, 24 or 29 amino acids that is linked to the carboxy terminus of the B chain. As used herein a non-$C^0$ peptide is any peptide that has less than 90% sequence identity with a sequence contained within the native proinsulin C peptide (SEQ ID NO: 53) and/or does not comprise a 15 amino acid sequence identical to a 15 amino acid sequence contained within SEQ ID NO 53. In one embodiment the non-$C^0$ peptide comprises one or more N-linked and/or O-linked glycosylation sites.

In one embodiment the linking moiety comprises a peptide of 18 to 145, 18 to 87, 29 to 87, or 29 to 58 amino acids wherein said linking moiety lacks a contiguous sequence of at least 18 amino acids that has greater than 80% sequence identity with SEQ ID NO: 53. The linking moiety in some embodiments includes other polymer materials in addition to, or substituting for, amino acid residues, include for example polyethylene glycol.

In one embodiment the linking moiety comprises a 29 contiguous amino acid sequence, directly linked to the carboxy terminal amino acid of the B chain, wherein said 29 contiguous amino acid sequence has greater than 60, 80 or 90% sequence identity to SEQ ID NO: 66), with the proviso that the sequence does not comprise a 15 amino acid sequence identical to a 15 amino acid sequence contained within SEQ ID NO 53. In another embodiment the linking moiety comprises a 29 contiguous amino acid sequence, directly linked to the carboxy terminal amino acid of the B chain, wherein at least 58% of the amino acids comprising the 29 contiguous amino acid sequence are selected from the group consisting of serine and proline.

In another embodiment the linking moiety comprises a 29 contiguous amino acid sequence, directly linked to the carboxy terminal amino acid of the B chain, wherein said 29 contiguous amino acid sequence has greater than 70%, 80%, 90% sequence identity to $SSSSX_{50}APPPSLPSPSRLPGPSDTPILPQX_{51}$ (SEQ ID NO: 66), wherein $X_{50}$ and $X_{51}$ are independently selected from arginine and lysine, with the proviso that the sequence does not comprise a 15 amino acid sequence identical to a 15 amino acid sequence contained within SEQ ID NO 53. In another embodiment the linking moiety comprises a 29 contiguous amino acid sequence, directly linked to the carboxy terminal amino acid of the B chain, wherein said 29 contiguous amino acid sequence is an analog of SEQ ID NO: 64, wherein said analog differs from SEQ ID NO: 64 only by 1, 2, 3, 4, 5 or 6 amino acid modification (wherein said modification are selected from amino acid substitutions, deletions or insertions), and in a further embodiment the amino acid modifications are conservative amino acid substitutions. In another embodiment the linking moiety comprises a 29 contiguous amino acid sequence, directly linked to the carboxy terminal amino acid of the B chain, wherein said 29 contiguous amino acid sequence is an analog of (SEQ ID NO: 64), wherein said analog differs from (SEQ ID NO: 64) only by 1, 2 or 3 amino acid substitutions.

Glycosylation

During nascent in vivo protein production insulin analogs comprising glycosylation sites may undergo further processing, known as post-translational modification, wherein sugar (glycosyl) residues may be added enzymatically in a process known as glycosylation. The resulting proteins bearing covalently linked oligosaccharide side chains are known as glycosylated proteins or glycoproteins. Accordingly, a protein that bears a glycosylation site is not necessarily glycosylated. In accordance with one embodiment insulin agonists analogs are provided that have been modified to comprise a peptide sequence that is prone to hyperglycosylation when expressed in a eukaryotic expression system.

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. In one embodiment the insulin analog comprises glycosyl residues such that the glycosylation pattern is human.

It is known to those skilled in the art that differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line or HEK293 cells. Such glycoproteins may also be immunogenic in humans and show reduced half-life in vivo after administration. Specific receptors in humans and other animals may recognize specific glycosyl residues and promote the rapid clearance of the protein from the bloodstream. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. For example, yeast strains have been genetically modified to express non-naturally occurring glycosylation enzymes such that glycosylated proteins (glycoproteins) produced in these yeast strains exhibit protein glycosylation identical to that of animal cells, especially human cells (see US Patent Application Publication Nos. 2004/0018590 and 2002/0137134, the disclosures of which are incorporated herein by reference).

Non-native and native glycosylation sequences are known to those skilled in the art and include N-linked glycosylation sites, and O-linked glycosylation sites. N-linked glycosylation sites are peptide sequences that serve as recognition sites for enzymatic attachment of a carbohydrate moiety to the side chain of an asparagine residue. The tripeptide O-linked glycosylation sequences include asparagine-X-serine and asparagine-X-threonine, where X is any amino acid except proline. Thus, the presence of either of these tripeptide sequences in a polypeptide creates a potential glycosylation site. O-linked glycosylation are peptide sequences that serve as recognition sites for enzymatic attachment of a carbohydrate moiety to the side chain of a hydroxyamino acid, most commonly serine or threonine, although 5-hydroxyproline or 5-hydroxylysine may also be used. In one embodiment the O-linked glycosylation sugar is N-aceylgalactosamine, galactose, or xylose. A number of O-linked glycosylation sites are known in the art and have been reported in the literature. See, e.g., Ten Hagen et al. (11029) J. Biol. Chem. 274(39):27867-74; Hanisch et al. (2001) Glycobiology 11:731-740; and Ten Hagen et al. (2003) Glycobiology 13:1R-16R.

In accordance with one embodiment a method of producing a hyperglycosylated insulin analog is provided. The method comprises providing a eukaryotic host cell that comprises a gene encoding an insulin analog that has been modified to include a non-native glycosylation site (e.g., a CTP peptide sequence) and culturing the cell under conditions that allow expression of the insulin analog gene. In one embodiment the host cell expresses human glycosylation enzymes such that glycosylated proteins (glycoproteins) produced in the host cell exhibit protein glycosylation identical to that of human cells (see US Patent Application Publication Nos. 2004/0018590 and 2002/0137134, the disclosures of which are incorporated herein by reference). In accordance with one embodiment the eukaryotic host cell is selected from yeast (e.g., *Pichia pastoris*) or mammalian (CHO or HEK293) cells.

Another means of increasing the number of carbohydrate moieties on the insulin analog is by chemical or enzymatic coupling of glycosides to the insulin analog. These procedures are advantageous in that they do not require production of the insulin analog in a host cell that has glycosylation capabilities for N- or O-linked glycosylation. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. Methods for coupling glycosides to peptides are described in WO 87/05330 published 11 Sep. 1987, and in Aplin and Wriston (1981) CRC Crit. Rev. Biochem., pp. 259-306, both of which are incorporated herein by reference.

In accordance with one embodiment an insulin analog is provided wherein a glycosylation site has been introduced into the insulin peptide. One or more glycosylations sites can be added either by modifying the native insulin sequence by amino acid substitutions, deletions or additions. In one embodiment the insulin analog comprises a modification of one or more of the B25-B30 amino acids, or the addition of a peptide sequence to the N terminus or C-terminus of the A or B chain to introduce one or more non-native glycosylation sites into the insulin analog. In one embodiment an insulin analog, either a two chain or single chain analog, is provided wherein a peptide comprising a glycosylation site has been linked to the carboxy terminus of the insulin B chain. In one embodiment a single chain insulin analog is provided comprising a linking moiety that covalently joins the carboxy terminus of an insulin B chain to the amino terminus of an insulin A chain, wherein the linking moiety comprises an amino acid sequence of greater than 18 residues and comprises one or more glycosylation sites. In a further embodiment an insulin analog is provided comprising two peptide sequences that each contain at least one glycosylation site (either the same or different). In one embodiment, a first peptide sequence containing a glycosylation site is linked to the N terminus of the B chain and the second peptide sequence containing a glycosylation site is linked to the C-terminus of the A or B chain. In one embodiment the insulin analog is a single chain analog wherein the linking moiety joining the B and A chains comprises the second peptide sequence.

Oligosaccharide Units

The structure and number of oligosaccharide units attached to a particular glycosylation site in a hyperglycosylated insulin analog can be variable. These may be, for instance, N-acetyl glucosamine, N-acetyl galactosamine, mannose, galactose, glucose, fucose, xylose, glucuronic acid, iduronic acid and/or sialic acids. In one embodiment, hyperglycosylated insulin analogs comprise non-native N-linked and/or O-linked carbohydrate chain(s) selected from:

a) a mammalian type sugar chain, preferably of the type expressed by CHO cells;

b) a sugar chain comprising a complex N-carbohydrate chain (e.g., a triantenary or biantenary structure), including for example carbohydrates containing high mannose and acetylglucosamine molecules and high terminal sialic acid residues;

c) a sugar chain comprising an O-carbohydrate chain optionally with a terminal sialic acid residue;

d) a sugar chain sialylated by alpha-2,6-sialyltransferase or alpha-2,3-sialyltransferase; and/or e) a sialylated sugar chain displaying between 3 to 30 or 7 to 23 sialyl-N-acetylgalactosamine. In one embodiment, the hyperglycosylated insulin analog is produced by a mammalian glycosylation mutant that stably expresses alpha 2,6 sialyltransferase and presents a deficiency in CMP-Neu5Ac Hydrolase activity, and in a further embodiment the mammalian glycosylation mutant is a CHO glycosylation mutant. Such glycosylation typically includes N-acetyl glucosamine, N-acetyl galactosamine, mannose, galactose, glucose, fucose, xylose, glucuronic acid, iduronic acid and/or sialic acids.

Glycosylated insulin analogs as disclosed herein comprises at least one carbohydrate moiety covalently linked to a non-native glycosylation site and may include one or more carbohydrate moieties covalently linked to a native glycoyslation site. In some embodiments, the hyperglycosylated insulin analog comprises O-linked glycosylation. In other embodiments, the hyperglycosylated insulin analog comprises N-linked glycosylation. In other embodiments, the hyperglycosylated insulin analog comprises both O-linked and N-linked glycosylation.

The CTP Peptide

In one embodiment a glycosylation site is introduced by the addition of amino acid sequences to the base insulin analog. More particularly, applicants have discovered that peptide sequence named C-terminal peptide (CTP: SSSSKAPPPSLPSPSRLPGPSDTPILPQR; SEQ ID NO: 64), which is prone to 0-linked hyperglycosylation when the protein is expressed in a eukaryotic cellular expression system can be covalently linked to an insulin analog without undermining the inherent in vitro activity of the insulin analog.

In accordance with one embodiment a two chain insulin analog is provided wherein the insulin B chain and A chain are linked by disulfide bonds, wherein the insulin analog has the general structure of (CTP peptide1)$_m$-(insulin B-chain)-(CTP peptide2)$_n$: (insulin A-chain) wherein m is an integer selected from 0 to 4, n is an integer selected from 0 to 4, and CTP peptide1 and CTP peptide2 represent amino acids sequences comprising a CTP peptide wherein CTP peptide1 and CTP peptide2 can be the same or different amino acid sequences. The CTP peptide can be any CTP peptide as disclosed herein and the insulin B chain and insulin A chain can be any sequence disclosed herein or any sequence known to function as an insulin receptor agonist. Accordingly, the CTP peptides can be linked to the amino and/or carboxy terminus of the B chain of a two chain insulin analog or to the amino terminus of the B chain and/or as the linking peptide in single chain analogs. The CTP peptide can also be linked to the amino or carboxy terminus of the A chain in a two chain insulin analog or to the carboxy terminus of the A chain in a single chain insulin analog.

In accordance with one embodiment an insulin analog is provided comprising A chain and a B chain and a CTP peptide, wherein the CTP peptide is a peptide having at least 60, 70, 80, 85, 90, or 95% sequence identity with (SEQ ID NO: 64). In one embodiment the CTP peptide is a peptide comprising a 18 to 29 amino acid sequence that shares at least 80, 82, 84, 86, 88, 90, 92, 94, 96 or 98% sequence identity with a 18 to 29 amino acid region of (SEQ ID NO: 64). In one embodiment the CTP peptide comprises an analog of (SEQ ID NO: 64), wherein said analog differs from (SEQ ID NO: 64) by 1, 1 to 2, 3 to 4, 4 to 6 or up to 8 amino acid modification wherein the modification is an amino acid substitution, deletion or insertion. In one embodiment the analog differs from (SEQ ID NO: 64) by 1, 1 to 2, 3 to 4, 4 to 6 or up to 8 amino acid substitutions wherein the amino acid substitutions are at one or more positions selected from 1-4, 7-15, 18, 20, 21, 24 and 27 of (SEQ ID NO: 64). In one embodiment the amino acid substitution are at one or more positions selected from 1, 2, 3, 4, 10, 13, 15, and 21 of (SEQ ID NO: 64). In one embodiment the amino acid substitution are at one or more positions selected from 7, 8, 9, 12, 14, 18, 20, 24 and 27 of (SEQ ID NO: 64). In one embodiment the CTP peptide comprises a 29 amino acid sequence that differs from SEQ ID NO: 66 by 1 to 2 amino acid substitutions. In a further embodiment the CTP peptide comprises a fragment of SEQ ID NO: 64 wherein the fragment represents a 18 to 28 contiguous amino acid sequence identical to an amino acid sequence contained within SEQ ID NO: 64. In one embodiment the CTP peptide consists of SEQ ID NO: 66, SEQ ID NO: 64 or SEQ ID NO: 79.

In accordance with one embodiment the CTP peptide comprises a peptide of the sequence SSSSX$_{50}$APPPSLPSPSRLPGPSDTPILPQX$_{51}$ (SEQ ID NO: 66), wherein X$_{50}$ and X$_{51}$ are independently arginine or lysine, or a peptide that differs from SSSSX$_{50}$APPPSLPSP-SRLPGPSDTPILPQX$_{51}$ (SEQ ID NO: 66) by one or two amino acid modifications. In one embodiment the CTP peptide is a 29 amino acid sequence comprising a sequence selected from the group consisting of SSSSRAP- PPSLPSPSRLPGPSDTPILPQK (SEQ ID NO: 79), SSSSKAPPPSLPSPSRLPGPSDTPILPQR (SEQ ID NO: 64) and SSSSRAPPPSLPSPSRLPGPSDTPILPQ (SEQ ID NO: 65). In one embodiment the CTP peptide comprises the sequence (SSSSX$_{50}$APPPSLPSPSRLPGPSDTPILPQX$_{51}$)$_n$ (SEQ ID NO: 66), wherein n is an integer selected from the group consisting of 1, 2, 3 and 4, and in a further embodiment n is 1 or 2. In a further embodiment a first CTP peptide is linked to the N-terminus of the B chain and a second CTP peptide is linked to the carboxy terminus of the B chain, wherein the first and second CTP peptides comprise sequences independently selected from the group consisting of SEQ ID NO: 79, SEQ ID NO: 64, SEQ ID NO: 66 and SEQ ID NO: 65.

Surprisingly, applicants have discovered that the CTP peptide can be used to connect the B and A chains of insulin to form a single chain insulin analog while still maintaining high in vitro potency in a manner that the native proinsulin C-peptide can not. In one embodiment a single chain insulin analog is prepared wherein the carboxy terminus of the B chain is linked to the amino terminus of the A chain via a CTP peptide. In another embodiment an insulin analog is provided as a two-chain construct with the CTP covalently linked to the C-terminus of the B-chain and/or the amino terminus of the B chain. In vitro and in vivo characterization reveals the CTP modified insulin analogs have high potency in the absence of glycosylation, thus providing a mechanism to extend insulin action that is based on glycosylation, a natural approach to longer duration proteins.

In accordance with one embodiment two chain insulin analogs are provide wherein the A and B chain are linked to one another via disulfide bonds and the CTP peptide is covalently bound to the amino and/or carboxy terminus of the B chain.

Single Chain Analogs

Proinsulin is a low potency precursor polypeptide that is proteolytically converted to insulin by the selective removal of a 35-residue connecting peptide (C peptide; SEQ ID NO: 53). Single chain insulin analogs have been prepared wherein the carboxy terminus of the insulin B chain is linked to the amino terminus of the A chain via a peptide linker. The conventional wisdom is that the linking peptide joining the A and B chains must be no larger than 11 to 12 amino acids to maintain potency. Surprisingly, applicants have discovered that so long as the native proinsulin C peptide is not directly linked to the B chain carboxy terminus, peptides of lengths much greater than 18 amino acids can be used as linking peptides with minimal loss of potency at the insulin receptor.

In one embodiment a single chain insulin agonist analog is provided that comprises the general structure B-LM-A wherein B represents an insulin B chain, A represents an insulin A chain, and LM represents a linking moiety linking the carboxy terminus of the B chain to the amino terminus of the A chain. The insulin A and B chains can be any known insulin sequence, including those disclosed herein, that when linked together as a heteroduplex form a functional insulin (i.e. capable of binding and activating an insulin receptor).

In one embodiment a single chain insulin analog is provided comprising an A chain, a B chain and a linking moiety, wherein the linking moiety comprises a peptide of 18 amino acids that covalently links the carboxy terminus of the B chain to the amino terminus of the A chain to form a contiguous amino acid chain, with the proviso that the linking moiety does not comprise the sequence of SEQ ID NO: 53, or any fragment thereof, directly linked to the carboxy terminus of the B chain. Applicants have found that the native proinsulin C peptide appears to have a negative impact on the potency of insulin single chain analogs when the peptide is attached to the carboxy terminus of the B chain. Inserting a CTP peptide between the B chain and the native proinsulin C peptide produces a more potent single chain insulin analog relative to proinsulin itself (See FIG. 22).

Accordingly, single chain insulin analogs can be prepared having surprisingly long linking peptides while retaining the potency of the underlying insulin analog. More particularly, in one embodiment the linking moiety comprises a peptide sequence of at least 18 amino acids that does not comprise the sequence of the native proinsulin C peptide (SEQ ID NO: 53), or a contiguous 18, 20, 25 or 30 amino acid fragment of SEQ ID NO: 53 directly linked to the carboxy terminus of the B chain. In one embodiment a single chain insulin analog is provided that comprises the sequence of the native proinsulin C peptide (SEQ ID NO: 53), or a contiguous 18, 20, 25 or 30 amino acid fragment of SEQ ID NO: 53 with the proviso that the linking moiety also comprises a non-C$^o$ peptide of at least 4, 8, 16, 20, 24 or 28 amino acids directly linked to the carboxy terminus of the B chain. In this context reference to an insulin analog comprising a non-C$^o$ peptide being "directly linked" is intended to mean that the carboxy terminal amino acid of the B chain is covalently linked to the amino terminal amino acid of the non-C$^o$ peptide. As used herein a non-C$^o$ peptide is any peptide that has less than 90% sequence identity with a sequence contained within the native proinsulin C peptide (SEQ ID NO: 53) and/or does not comprise a 15 amino acid sequence identical to a 15 amino acid sequence contained within SEQ ID NO 53. In one embodiment the non-C$^o$ peptide comprises one or more N-linked and/or O-linked glycosylation sites. In one embodiment the non-C$^o$ peptide comprises a CTP peptide, and in one further embodiment the non-C$^o$ peptide is CTP (SEQ ID NO: 64). In one embodiment a single chain insulin analog is provided wherein the linking peptide comprises a first CTP peptide (e.g., a sequence comprising SEQ ID NO: 66) directly linked to the carboxy terminus of the B chain and a second peptide linking the first CTP peptide to the amino terminus of the A chain. The second peptide can be any amino acid sequence ranging from 1 to 58 amino acids, and in one embodiment the second peptide is approximately 1 to 29 amino acids in length. In one embodiment the second peptide comprises one or more N-linked and/or O-linked glycosylation sites. In another embodiment the second peptide comprises either a second CTP peptide or comprises the native C peptide of proinsulin, IGF-1 or IFG-2. In any of these embodiments a further sequence comprising a CTP peptide can be linked to the amino terminus of the B chain.

In one embodiment a single chain insulin analog is provided wherein the linking moiety is a peptide of 18 to 174, 18 to 145, 18 to 116, 18 to 97, 29 to 145, 29 to 145, 29 to 116, 29 to 97, 29 to 58 amino acids residues, and in a further embodiment the linking moiety comprises a total of 29 to 58 amino acids. In one embodiment the linking moiety is a peptide of 18 to 174, 18 to 145, 18 to 116, 18 to 97, 29 to 145, 29 to 145, 29 to 116, 29 to 97, 29 to 58 amino acids residues, wherein the linking moiety comprises the sequence (SSSSX$_{50}$APPPSLPSPSRLPGPSDTPILPQX$_{51}$)$_n$ (SEQ ID NO: 66) wherein n is 1, 2 or 3 and X$_{50}$ and X$_{51}$ are independently selected from arginine and lysine. The linking moiety in some embodiments includes other polymers (e.g., polyethylene glycol) in addition to, or substituting for, amino acid residues of the linking moiety.

In accordance with one embodiment a single chain insulin analog is provided having the general structure of (CTP peptide1)$_m$-(insulin B-chain)-(CTP peptide2)$_n$-(insulin A-chain) wherein m is an integer selected from 0 to 4, n is an integer selected from 1 to 4, and CTP peptide1 and CTP peptide2 represent amino acids sequences comprising a CTP peptide wherein CTP peptide1 and CTP peptide2 can be the same or difference amino acid sequences. The CTP peptide can be any CTP peptide as disclosed herein and the insulin B chain and insulin A chain can be any sequence disclosed herein or any sequence known to function as an insulin receptor agonist. In one embodiment the linking moiety comprises a 29 contiguous amino acid sequence, directly linked to the carboxy terminal amino acid of the B chain, wherein said 28 contiguous amino acid sequence has greater than 95% sequence identity to SEQ ID NO: 66. In one embodiment the CTP peptide comprises the sequence SSSSX$_{50}$APPPSLPSPSRLPGPSDTPILPQX$_{52}$ (SEQ ID NO: 66), wherein X$_{50}$ and X$_{51}$ are independently selected from arginine and lysine. In another embodiment the CTP peptide comprises a sequence selected from the group consisting of SSSSRAPPPSLPSPSRLPGPSDTPILPQK (SEQ ID NO: 75), SSSSKAPPPSLPSPSRLPGPSDTPIL-PQR (SEQ ID NO: 64) or SSSSRAPPPSLPSPSRLPGPS-DTPILPQ (SEQ ID NO: 65), and in a further embodiment the CTP peptide comprises the sequence SSSSRAP-PPSLPSPSRLPGPSDTPILPQK (SEQ ID NO: 75).

Alternatively, applicants have discovered that the primary sequence of the CTP peptide does not appear to be critical (see data presented in FIG. 20). Accordingly, in one embodiment the linking moiety comprises a peptide having a length of at least 18 amino acids that shares a similar amino acid content. For example, in one embodiment the linking moiety comprises a 29 contiguous amino acid sequence, directly linked to the carboxy terminal amino acid of the B chain, wherein at least 58% of the amino acids comprising said 29 contiguous amino acid sequence are selected from the group consisting of serine and proline. In a further embodiment the linking moiety comprises at least one glycosylation site. In one embodiment the linking moiety comprises an analog of (SEQ ID NO: 66), wherein said analog differs from (SEQ ID NO: 66) by 1, 2, 3, 4, 5 or 6 amino acid substitutions. In one embodiment the linking peptide comprises a CTP peptide wherein amino acid substitutions are made at one or more positions selected from positions 1, 2, 3, 4, 10, 13, 15, and 21 of (SEQ ID NO: 66).

Applicants have also found that multiple copies of the CTP peptide can be used as the linking peptide in single chain analogs and/or linked to the amino terminus of the B chain in single chain or two chain insulin analogs. The multiple copies of the CTP peptide can be identical or can differ in sequence and can be arranged in a head to tail or head to head orientation. In accordance with one embodiment an insulin analog is provided comprising a CTP peptide having the sequence (SSSSX$_{50}$APPPSLP-SPSRLPGPSDTPILPQX$_{51}$)$_n$(SEQ ID NO: 66), wherein n is an integer selected from the group consisting of 1, 2, 3 and 4 and X$_{50}$ and X$_{51}$ are independently selected from arginine and lysine. In one embodiment an insulin analog is provided as either a two chain or single chain analog wherein the sequence (SSSSX$_{50}$APPPSLPSPSRLPGPSDTPILPQX$_{51}$)$_n$ (SEQ ID NO: 66), wherein n is independently selected from the group consisting of 1, 2, 3 and 4, and X$_{50}$ and X$_{51}$ are independently selected from arginine and lysine, is linked to both the amino and carboxy terminus of the B chain, with n being the same or different for the CTP peptide located at the amino and carboxy terminus of the B chain.

In one embodiment a single chain insulin agonist analog is provided that comprises the general structure B-LM-A wherein B represents an insulin B chain, A represents an insulin A chain, and LM represents a peptide linking moiety of at least 18 amino acids linking the carboxy terminus of the B chain to the amino terminus of the A chain. The insulin A and B chains can be any known insulin sequence, including those disclosed herein, that when linked together as a heteroduplex form a functional insulin. In one embodiment the B chain comprises the sequence R$_{22}$-X$_{25}$LCGX$_{29}$X$_{30}$LVX$_{33}$X$_{34}$LYLVCGX$_{41}$X$_{42}$GFX$_{45}$ (SEQ ID NO: 17) and the A chain comprises the sequence GIVX$_4$X$_5$CCX$_8$X$_9$X$_{10}$CX$_{12}$LX$_{14}$X$_{15}$LX$_{17}$X$_{18}$X$_{19}$CX$_{21}$-R$_{13}$ (SEQ ID NO: 18) wherein X$_4$ is glutamic acid or aspartic acid;
X$_5$ is glutamine or glutamic acid
X$_8$ is histidine, threonine or phenylalanine;
X$_9$ is serine, arginine, lysine, ornithine or alanine;
X$_{10}$ is isoleucine or serine;
X$_{12}$ is serine or aspartic acid
X$_{14}$ is tyrosine, arginine, lysine, ornithine or alanine;
X$_{15}$ is glutamine, glutamic acid, arginine, alanine, lysine, ornithine or leucine;
X$_{17}$ is glutamine, glutamic acid, arginine, aspartic acid, ornithine or lysine;
X$_{18}$ is methionine, asparagine, glutamine, aspartic acid, glutamic acid or threonine;
X$_{19}$ is tyrosine, 4-methoxy-phenylalanine or 4-amino phenylalanine;
X$_{21}$ is selected from the group consisting of alanine, glycine, serine, valine, threonine, isoleucine, leucine, glutamine, glutamic acid, asparagine, aspartic acid, histidine, tryptophan, tyrosine, and methionine;
X$_{25}$ is histidine or threonine;
X$_{29}$ is selected from the group consisting of alanine, glycine and serine;
X$_{30}$ is selected from the group consisting of histidine, aspartic acid, glutamic acid, homocysteic acid and cysteic acid;
X$_{33}$ is selected from the group consisting of aspartic acid, glutamine and glutamic acid;
X$_{34}$ is selected from the group consisting of alanine and threonine;
X$_{41}$ is selected from the group consisting of glutamic acid, aspartic acid or asparagine;
X$_{42}$ is selected from the group consisting of alanine, lysine, ornithine and arginine;
X$_{45}$ is tyrosine or phenylalanine;
R$_{22}$ is selected from the group consisting of AYRPSE (SEQ ID NO: 11), FVNQ (SEQ ID NO: 10), PGPE (SEQ ID NO: 9), a tripeptide glycine-proline-glutamic acid, a tripeptide valine-asparagine-glutamine, a dipeptide proline-glutamic acid, a dipeptide asparagine-glutamine, glutamine, glutamic acid and a bond; and
R$_{13}$ is COOH or CONH$_2$. In one embodiment the B chain further comprises an amino terminal extension comprising 1 to 6 charged amino acids.

In one embodiment a single chain insulin analog is provided comprising the general formula B chain-LM-A chain wherein the B chain comprises the sequence R$_{25}$-HLCGSX$_{30}$LVEALYLVCGERGFF (SEQ ID NO: 56), LM is a linking moiety comprising the sequence SSSSX$_{50}$APPPSLPSPSRLPGPSDTPILPQX$_{51}$ (SEQ ID NO 66) and the A chain comprises the sequence of GIVEQCCX$_8$SICSLYQLENX$_{19}$CX$_{21}$-R$_{13}$ (SEQ ID NO: 26), wherein $X_{30}$ is selected from the group consisting of histidine, aspartic acid, glutamic acid, homocysteic acid and cysteic acid;

$X_8$ is histidine, threonine or phenylalanine;

$X_{19}$ is tyrosine, 4-methoxy-phenylalanine or 4-amino phenylalanine;

$X_{21}$ is alanine, glycine or asparagine;

$X_{22}$ is selected from the group consisting of phenylalanine and desamino-phenylalanine;

$X_{50}$ and $X_{51}$ are independently selected from arginine and lysine; and $R_{25}$ is selected from the group consisting of $X_{22}$VNQ (SEQ ID NO: 50), a tripeptide valine-asparagine-glutamine, a dipeptide asparagine-glutamine, glutamine, AYRPSE (SEQ ID NO: 11), PGPE (SEQ ID NO: 9), a tripeptide glycine-proline-glutamic acid, a dipeptide proline-glutamic acid, glutamic acid. In one embodiment $X_8$ and $X_{30}$ are each histidine, $X_{21}$ is asparagine and $R_{25}$ is selected from the group consisting of $X_{22}$VNQ (SEQ ID NO: 50), and a tripeptide glycine-proline-glutamic acid. In a further embodiment the single chain insulin analog also comprises a CTP peptide linked to the N-terminus of the B chain. In one embodiment the linking moiety consists of the peptide (SSSSKAPPPSLPSPSRLPGPSDTPILPQR)$_n$, wherein n is 1 or 2. In one embodiment a single chain insulin agonist is provided comprising the general formula B chain-LM-A chain wherein the B chain comprises the sequence FVNQHLCGSHLVEALYLVCGERGFF (SEQ ID NO: 104) or an amino acid differing from SEQ ID NO: 104 by 1 to three amino acids selected independently from positions B1, B2, B3, B4, B5, B9, B10, B13, B14, B17, B20, B21, B22, and B23, the A chain comprises the sequence GIVEQCCTSICSLYQLENYCN (SEQ ID NO: 1) or an amino acid differing from SEQ ID NO: 1 by 1 to three amino acids selected independently from positions, A5, A8, A9, A10, A12, A14, A15, A17, A18, A21, and the linking moiety (LM) comprises the sequence (SSSSX$_{50}$APPPSLPSPSRLPGPSDTPILPQX$_{51}$)$_n$ (SEQ ID NO: 66), wherein $X_{50}$ and $X_{51}$ are independently selected from arginine and lysine; and n is 1 or 2, with the proviso that B24 is linked directly to the first serine of SEQ ID NO: 66 without any intervening amino acids.

In one embodiment the single chain insulin analog comprises the sequence of GEEEEEKFVNQHLCGSHLVEALYLVCGERGFFSSSSRAPPPSLPSPSRLPGPSDTPILPQRGIVEQCCTSICSLYQLENYCN (DP30; SEQ ID NO: 83), GEEEEEKFVNQHLCGSHLVEALYLVCGERGFFSSSSRAPPPSLPSPSRLPGPSD TPILPQKGIVEQCCTSICSLYQLENYCN (DP31; SEQ ID NO: 84), GEEEEEKGPEHLCGSHLVEALYLVCGERGFFSSSSRAPPPSLPSPSRLPGPSDTP ILPQKGIVEQCCTSICSLYQLENYCN (DP33; SEQ ID NO: 85), FVNQHLCGSHLVEALYLVCGERGFFSSSSRAPPPSLPSPSRLPGPSDTPILPQRG IVEQCCTSICSLYQLENYCN (DP30; SEQ ID NO: 88), FVNQHLCGSHLVEALYLVCGERGFFSSSSRAPPPSLPSPSRLPGPSDTPILPQKG IVEQCCTSICSLYQLENYCN (DP31; SEQ ID NO: 89) or GPEHLCGSHLVEALYLVCGERGFFSSSSRAPPPSLPSPSRLPGPSDTPILPQKGI VEQCCTSICSLYQLENYCN (DP33; SEQ ID NO: 90). In one embodiment a dimer of the single chain insulin analog is provided, including for example homodimers or heterodimers comprising SEQ ID NO: 88 and SEQ ID NO: 90.

Insulin A and B Chains

The single chain insulin agonists of the present invention may comprise the native B and A chain sequences of human insulin (SEQ ID NOs: 1 and 2, respectively) or any of the known analogs or derivatives thereof that exhibit insulin agonist activity when linked to one another in a heteroduplex. Such analogs include, for example, proteins having an A-chain and a B-chain that differ from the A-chain and B-chain of human insulin by having one or more amino acid deletions, one or more amino acid substitutions, and/or one or more amino acid insertions that do not destroy the insulin activity of the insulin analog.

One type of insulin analog, "monomeric insulin analog," is well known in the art. These are fast-acting analogs of human insulin, including, for example, insulin analogs wherein:

(a) the amino acyl residue at position B28 is substituted with Asp, Lys, Leu, Val, or Ala, and the amino acyl residue at position B29 is Lys or Pro;

(b) the amino acyl residues at any of positions B27, B28, B29, and B30 are deleted or substituted with a nonnative amino acid. In one embodiment an insulin analog is provided comprising an Asp substituted at position B28 or a Lys substituted at position 28 and a proline substituted at position B29. Additional monomeric insulin analogs are disclosed in Chance, et al., U.S. Pat. No. 5,514,646; Chance, et al., U.S. patent application Ser. No. 08/255,297; Brems, et al., Protein Engineering, 5:527-533 (1992); Brange, et al., EPO Publication No. 214,826 (published Mar. 18, 1987); and Brange, et al., Current Opinion in Structural Biology, 1:934-940 (1991). These disclosures are expressly incorporated herein by reference for describing monomeric insulin analogs.

Insulin analogs may also have replacements of the amidated amino acids with acidic forms. For example, Asn may be replaced with Asp or Glu. Likewise, Gln may be replaced with Asp or Glu. In particular, Asn(A18), Asn(A21), or Asp(B3), or any combination of those residues, may be replaced by Asp or Glu. Also, Gln(A15) or Gln(B4), or both, may be replaced by either Asp or Glu.

As disclosed herein single chain insulin agonists are provided comprising a B chain and an A chain of human insulin, or analogs or derivative thereof, wherein the carboxy terminus of the B chain is linked to the amino terminus of the A chain via a linking moiety. In one embodiment the A chain is an amino acid sequence selected from the group consisting of GIVEQCCTSICSLYQLENYCN (SEQ ID NO: 1), GIVDECCFRSCDLRRLEMYCA (SEQ ID NO: 5) or GIVEECCFRSCDLALLETYCA (SEQ ID NO: 7) and the B chain comprises the sequence FVNQHLCGSHLVEALYLVCGERGFFYTPKT (SEQ ID NO: 2), GPETLCGAELVDALYLVCGDRGFYFNKPT (SEQ ID NO: 6) or AYRPSETLCGGELVDTLYLVCGDRGFYFSRPA (SEQ ID NO: 8), or a carboxy shortened sequence thereof having one to five amino acids corresponding to B26, B27, B28, B29 and B30 deleted, and analogs of those sequences wherein each sequence is modified to comprise one to five amino acid substitutions at positions corresponding to native insulin positions (see peptide alignment shown in FIG. 5) selected from A5, A8, A9, A10, A14, A15, A17, A18, A21, B1, B2, B3, B4, B5, B9, B10, B13, B14, B20, B22, B23, B26, B27, B28, B29 and B30. In one embodiment the amino acid substitutions are conservative amino acid substitutions. Suitable amino acid substitutions at these positions that do not adversely impact insulin's desired activities are known to those skilled in the art, as demonstrated, for example, in Mayer, et al., Insulin Structure and Function, Biopolymers. 2007; 88(5):687-713, the disclosure of which is incorporated herein by reference.

In accordance with one embodiment the single chain insulin analog peptides may comprise an insulin A chain and an insulin B chain or analogs thereof, wherein the A chain comprises an amino acid sequence that shares at least 70% sequence identity (e.g., 70%, 75%, 80%, 85%, 90%, 95%) over the length of the native peptide, with at least one of GIVEQCCTSICSLYQLENYCN (SEQ ID NO: 1), GIVDECCFRSCDLRRLEMYCA (SEQ ID NO: 5) or GIVEECCFRSCDLALLETYCA (SEQ ID NO: 7) and the B chain comprises an amino acid sequence that shares at least 60% sequence identity (e.g., 60%, 65%, 70%, 75%, 80%, 85%, 90%, 95%) over the length of the native peptide, with at least one of the sequence FVNQHLCGSHLVEALYLVCGERGFFYTPKT (SEQ ID NO: 2), GPETLCGAELVDALYLVCGDRGFYFNKPT (SEQ ID NO: 6) or AYRPSETLCGGELVDTLYLVCGDRGFYFSRPA (SEQ ID NO: 8) or a carboxy shortened sequence thereof having one to four amino acids corresponding to B27, B28, B29 and B30 deleted.

Additional amino acid sequences can be added to the amino terminus of the B chain or to the carboxy terminus of the A chain of the single chain insulin agonists of the present invention. For example, a series of negatively charged amino acids can be added to the amino terminus of the B chain, including for example a peptide of 1 to 12, 1 to 10, 1 to 8 or 1 to 6 amino acids in length and comprising one or more negatively charged amino acids including for example glutamic acid and aspartic acid. In one embodiment the B chain amino terminal extension comprises 1 to 6 charged amino acids. In one embodiment the single chain insulin analog comprises a B chain amino terminal extension that comprises the sequence $X_{60}X_{61}X_{62}X_{63}X_{64}X_{65}K$ (SEQ ID NO: 19), wherein $X_{60}$ is selected from the group consisting of glycine, glutamic acid and aspartic acid, and $X_{61}$, $X_{62}$, $X_{63}$ $X_{64}$ and $X_{65}$ are independently glutamic acid or aspartic acid. In one embodiment the B chain amino terminal extension comprises the sequence $GX_{61}X_{62}X_{63}X_{64}X_{65}K$ (SEQ ID NO: 20) or $X_{61}X_{62}X_{63}X_{64}X_{65}RK$ (SEQ ID NO: 21), wherein $X_{61}$, $X_{62}$, $X_{63}$ $X_{64}$ and $X_{65}$ are independently glutamic acid or aspartic acid. In one embodiment the B chain comprises the sequence GEEEEEKGPEHLCGAHLVDALYLVCGDX$_{42}$GFY (SEQ ID NO: 22), wherein $X_{42}$ is selected from the group consisting of alanine lysine, ornithine and arginine. In accordance with one embodiment the single chain insulin analogs disclosed comprise a C-terminal amide or ester in place of a C-terminal carboxylate on the A chain.

High potency single chain insulin analogs can also be prepared based on modified IGF I and IGF II sequences, as described in International application PCT/2009/068713, the disclosure of which is expressly incorporated herein by reference. More particularly, analogs of IGF I and IGF II that comprise a substitution of a tyrosine leucine dipeptide for the native IGF amino acids at positions corresponding to B16 and B17 of native insulin have a tenfold increase in potency at the insulin receptor. Accordingly, the single chain insulin analogs disclosed herein may include an A chain of IGF I (SEQ ID NO: 5) or IGF II (SEQ ID NO: 7) and a modified B chain of IGF I (SEQ ID NO: 6) or IGF II (SEQ ID NO: 8) or the B chain of native insulin (SEQ ID NO: 2). In addition, the single chain insulin analogs disclosed herein may include a native insulin A chain, or analog thereof, and a modified B chain of IGF I (SEQ ID NO: 6) or IGF II (SEQ ID NO: 8), as well as analogs of said B chains. In one embodiment the single chain insulin analog comprises an IGF I (SEQ ID NO: 5) A chain, or analog or derivative thereof and a modified B chain of IGF I (SEQ ID NO: 6), IGF II (SEQ ID NO: 8) or native insulin (SEQ ID NO: 2), or analogs or derivatives thereof.

Additional modifications to the single chain IGF or insulin A and B chains include, for example, modification of the amino acids at one or more of positions A19, B16 or B25 (relative to the native insulin A and B chains) to a 4-amino phenylalanine or one or more amino acid substitutions at positions selected from A5, A8, A9, A10, A14, A15, A17, A18, A21, B1, B2, B3, B4, B5, B9, B10, B13, B14, B20, B21, B22, B23, B26, B27, B28, B29 and B30 (relative to the native A and B chains of insulin) or deletions of any or all of positions B1-4 and B26-30. In one embodiment the substitutions at positions selected from A5, A8, A9, A10, A14, A15, A17, A18, A21, B1, B2, B3, B4, B5, B9, B10, B13, B14, B20, B21, B22, B23, B26, B27, B28, B29 and B30 are conservative amino acid substitutions relative to the native insulin sequence.

In accordance with one embodiment the B chain comprises the sequence $R_{22}$-$X_{25}$LCG$X_{29}$$X_{30}$LV$X_{33}$$X_{34}$LYLVCG$X_{41}$$X_{42}$GF$X_{45}$ (SEQ ID NO: 17), and the A chain comprises the sequence GIV$X_{4}$$X_{5}$CC$X_{8}$$X_{9}$$X_{10}$C$X_{12}$LX$_{14}$$X_{15}$L$X_{17}$$X_{18}$$X_{19}$C$X_{21}$-$R_{13}$ (SEQ ID NO: 18), wherein $X_4$ is glutamic acid or aspartic acid;

$X_5$ is glutamine or glutamic acid $X_8$ is histidine, threonine or phenylalanine;

$X_9$ is serine, arginine, lysine, ornithine or alanine;

$X_{10}$ is isoleucine or serine;

$X_{12}$ is serine or aspartic acid $X_{14}$ is tyrosine, arginine, lysine, ornithine or alanine;

$X_{15}$ is glutamine, glutamic acid, arginine, alanine, lysine, ornithine or leucine;

$X_{17}$ is glutamic acid, aspartic acid, asparagine, lysine, ornithine or glutamine;

$X_{18}$ is methionine, asparagine, glutamine, aspartic acid, glutamic acid or threonine;

$X_{19}$ is tyrosine, 4-methoxy-phenylalanine or 4-amino phenylalanine;

$X_{21}$ is selected from the group consisting of alanine, glycine, serine, valine, threonine, isoleucine, leucine, glutamine, glutamic acid, asparagine, aspartic acid, histidine, tryptophan, tyrosine, and methionine;

$X_{25}$ is histidine or threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid, glutamine and glutamic acid;

$X_{34}$ is selected from the group consisting of alanine and threonine;

$X_{41}$ is selected from the group consisting of glutamic acid, aspartic acid or asparagine;

$X_{42}$ is selected from the group consisting of alanine, lysine, ornithine and arginine;

$X_{45}$ is tyrosine or phenylalanine;

$R_{22}$ is selected from the group consisting of AYRPSE (SEQ ID NO: 11), FVNQ (SEQ ID NO: 10), PGPE (SEQ ID NO: 9), a tripeptide glycine-proline-glutamic acid, a tripeptide valine-asparagine-glutamine, a dipeptide proline-glutamic acid, a dipeptide asparagine-glutamine, glutamine, glutamic acid and an N-terminal amine; and $R_{13}$ is COOH or CONH$_2$. In one embodiment $X_8$, $X_{25}$ and $X_{30}$ are each histidine. In a further embodiment the single chain insulin analog peptide comprises an analog of the A chain peptide sequence of SEQ ID NO: 15 and/or a B chain peptide sequence of SEQ ID NO: 16 wherein the analog of the A chain and B chain each comprise 1-3 further amino acid substitutions.

In one embodiment a single chain insulin analog is provided that comprises the structure: IB-LM-IA, wherein IB comprises the sequence $R_{22}$-$X_{25}$LCG$X_{29}X_{30}$LV$X_{33}X_{34}$LYLVCG$X_{41}X_{42}$GF$X_{45}$ (SEQ ID NO: 17), LM is a linking moiety as disclosed herein and having at least 18 amino acids that covalently links IB to IA, and IA comprises the sequence GIV$X_4X_5$CC$X_8X_9X_{10}$C$X_{12}$L$X_{14}X_{15}$L$X_{17}X_{18}X_{19}$C$X_{21}$-$R_{13}$ (SEQ ID NO: 18), wherein $X_4$ is glutamic acid or aspartic acid;

$X_5$ is glutamine or glutamic acid;

$X_8$ is histidine or phenylalanine;

$X_9$ and $X_{14}$ are independently selected from arginine, lysine, ornithine or alanine;

$X_{10}$ is isoleucine or serine;

$X_{12}$ is serine or aspartic acid;

$X_{14}$ is tyrosine, arginine, lysine, ornithine or alanine;

$X_{15}$ is arginine, lysine, ornithine or leucine;

$X_{17}$ is glutamic acid or glutamine;

$X_{18}$ is methionine, asparagine or threonine;

$X_{19}$ is tyrosine, 4-methoxy-phenylalanine or 4-amino phenylalanine;

$X_{21}$ is alanine, glycine or asparagine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid and glutamic acid;

$X_{34}$ is selected from the group consisting of alanine and threonine;

$X_{41}$ is selected from the group consisting of glutamic acid, aspartic acid or asparagine;

$X_{42}$ is selected from the group consisting of alanine, lysine, ornithine and arginine;

$R_{22}$ is selected from the group consisting of AYRPSE (SEQ ID NO: 11), FVNQ (SEQ ID NO: 10), PGPE (SEQ ID NO: 9), a tripeptide glycine-proline-glutamic acid, a tripeptide valine-asparagine-glutamine, a dipeptide proline-glutamic acid, a dipeptide asparagine-glutamine, glutamine, glutamic acid and an N-terminal amine; and $R_{13}$ is COOH or $CONH_2$, further wherein the amino acid at the designation $X_{45}$ is directly bound to the linking moiety, LM (i.e., the designation IB-LM-IA as used herein is intended to represent that the B chain carboxyl terminus and the amino terminus of the A chain are directly linked to the linking moiety LM without any further intervening amino acids). The linking moiety can be any of the structures described herein.

In accordance with one embodiment an insulin analog is provided wherein the A chain of the insulin peptide comprises the sequence GIVEQCC$X_8$SICSLYQL$X_{17}$N$X_{19}$C$X_{23}$ (SEQ ID NO: 23) and the B chain comprising the sequence $X_{24}$LCG$X_{29}X_{30}$LVEALYLVCGERGFF (SEQ ID NO: 24) wherein $X_8$ is selected from the group consisting of threonine and histidine;

$X_{17}$ is glutamic acid or glutamine;

$X_{19}$ is tyrosine, 4-methoxy-phenylalanine or 4-amino phenylalanine;

$X_{23}$ is asparagine or glycine;

$X_{24}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid. In a further embodiment the B chain comprises the sequence $X_{22}$VNQ$X_{25}$LCG$X_{29}X_{30}$LVEALYLVCGERGFFYT-$Z_1$-$B_1$ (SEQ ID NO: 25) wherein $X_{22}$ is selected from the group consisting of phenylalanine and desamino-phenylalanine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$Z_1$ is a dipeptide selected from the group consisting of aspartate-lysine, lysine-proline, and proline-lysine; and $B_1$ is selected from the group consisting of threonine, alanine or a threonine-arginine-arginine tripeptide.

In accordance with one embodiment a single chain insulin analog is provided that comprises the structure: IB-LM-IA, wherein IB comprises the sequence $X_{25}$LCG$X_{29}X_{30}$LVEALYLVCG ERGFF (SEQ ID NO: 24), LM is a linking moiety as disclosed herein that covalently links IB to IA, and IA comprises the sequence GIVEQCC$X_8$SICSLYQLEN$X_{19}$C$X_{21}$ (SEQ ID NO: 26). In accordance with one embodiment the A chain comprises the sequence GIVEQCC$X_8$SICSLYQL$X_{17}$N$X_{19}$C$X_{23}$ (SEQ ID NO: 23) or GIVDECC$X_8X_9$SCDL$X_{14}X_{15}$L$X_{17}X_{18}X_{19}$C$X_{21}$-$R_{13}$ (SEQ ID NO: 27), and the B chain comprises the sequence $X_{25}$LCG$X_{29}X_{30}$LV$X_{33}X_{34}$LYLVCGD$X_{42}$GF$X_{45}$ (SEQ ID NO: 28) wherein $X_8$ is histidine or phenylalanine;

$X_9$ and $X_{14}$ are independently selected from arginine, lysine, ornithine or alanine;

$X_{15}$ is arginine, lysine, ornithine or leucine;

$X_{17}$ is glutamic acid or glutamine;

$X_{18}$ is methionine, asparagine or threonine;

$X_{19}$ is tyrosine, 4-methoxy-phenylalanine or 4-amino phenylalanine;

$X_{21}$ is alanine, glycine or asparagine;

$X_{23}$ is asparagine or glycine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid and glutamic acid;

$X_{34}$ is selected from the group consisting of alanine and threonine;

$X_{42}$ is selected from the group consisting of alanine, lysine, ornithine and arginine;

$X_{45}$ is tyrosine; and $R_{13}$ is COOH or $CONH_2$. In one embodiment at least one of n and k is 1.

In a further embodiment the A chain comprises the sequence GIVDECCH$X_9$SCDL$X_{14}X_{15}$L$X_{17}X_{18}$ $X_{19}$C$X_{21}$-

$R_{13}$ (SEQ ID NO: 27), and the B chain comprises the sequence $X_{25}LCGX_{29}X_{30}LVX_{33}X_{34}LYLVCGDX_{42}GFX_{45}$ (SEQ ID NO: 28) wherein $X_9$ and $X_{14}$ are independently selected from arginine, lysine, ornithine or alanine;

$X_{15}$ is arginine, lysine, ornithine or leucine;

$X_{17}$ is glutamic acid, aspartic acid, asparagine, lysine, ornithine or glutamine;

$X_{18}$ is methionine, asparagine or threonine;

$X_{19}$ is tyrosine, 4-methoxy-phenylalanine or 4-amino phenylalanine;

$X_{21}$ is alanine, glycine or asparagine;

$X_{23}$ is asparagine or glycine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid and glutamic acid;

$X_{34}$ is selected from the group consisting of alanine and threonine;

$X_{42}$ is selected from the group consisting of alanine, lysine, ornithine and arginine;

$X_{45}$ is tyrosine or phenylalanine and $R_{13}$ is COOH or $CONH_2$. In a further embodiment the A chain comprises the sequence $GIVDECCHX_9SCDLX_{14}X_{15}LX_{17}MX_{19}CX_{21}$-$R_{13}$ (SEQ ID NO: 29), and the B chain comprises the sequence $X_{25}LCGAX_{30}LVDALYLVCGDX_{42}GFX_{45}$ (SEQ ID NO: 30) wherein $X_9$, $X_{14}$ and $X_{15}$ are independently ornithine, lysine or arginine;

$X_{17}$ is glutamic acid or glutamine;

$X_{19}$ is tyrosine, 4-methoxy-phenylalanine or 4-amino phenylalanine;

$X_{21}$ is alanine, glycine or asparagine;

$X_{25}$ is selected from the group consisting of histidine and threonine;

$X_{30}$ is selected from the group consisting of histidine, aspartic acid and glutamic acid;

$X_{42}$ is selected from the group consisting of alanine, lysine, ornithine and arginine;

$X_{45}$ is tyrosine or phenylalanine and $R_{13}$ is COOH or $CONH_2$. In one embodiment the B chain is selected from the group consisting of $HLCGAELVDALYLVCGDX_{42}GFY$ (SEQ ID NO: 31), $GPEHLCGAELVDALYLVCGDX_{42}GFY$ (SEQ ID NO: 32), $GPEHLCGAELVDALYLVCGDX_{42}GFYFNPKT$ (SEQ ID NO: 33) and $GPEHLCGAELVDALYLVCGDX_{42}GFYFNKPT$ (SEQ ID NO: 34), wherein $X_{42}$ is selected from the group consisting of ornithine, lysine and arginine. In a further embodiment the A chain comprises the sequence $GIVDECCHX_9SCDLX_{14}X_{15}LQMYCN$-$R_{13}$ (SEQ ID NO: 36), wherein $X_9$, $X_{14}$ and $X_{15}$ are independently ornithine, lysine or arginine.

In one embodiment a single chain insulin analog is provided comprising the general formula IB-LM-IA wherein IB is an amino acid sequence selected from the group consisting of $HLCGAELVDALYLVCGDX_{42}GFY$ (SEQ ID NO: 31), $GPEHLCGAELVDALYLVCGDX_{42}GFY$ (SEQ ID NO: 32), $GPEHLCGAELVDALYLVCGDX_{42}GFYFNPKT$ (SEQ ID NO: 33) and $GPEHLCGAELVDALYLVCGDX_{42}GFYFNKPT$ (SEQ ID NO: 34), LM is a linking moiety as disclosed herein.

In accordance with one embodiment a single chain insulin analog is provided that comprises the structure: IB-LM-IA, wherein IB comprises the sequence $X_{25}LCGX_{29}X_{30}LVX_{33}X_{34}LYLVCGDX_{42}GFX_{45}$ (SEQ ID NO: 28), LM is a linking moiety as disclosed herein that covalently links IB to IA, and IA comprises the sequence $GIVEQCCHSICSLYQLENX_{19}CX_{21}$-$R_{13}$ (SEQ ID NO: 37) or $GIVDECCX_8X_9SCDLX_{14}X_{15}LX_{17}X_{18}X_{19}CX_{21}$-$R_{13}$ (SEQ ID NO: 38), wherein the C-terminal phenylalanine residue of SEQ ID NO: 58 is directly covalently bound to the linking moiety, LM, in the absence of any intervening amino acids. In accordance with one embodiment a single chain insulin analog is provided that comprises the sequence $X_{25}LCGX_{29}X_{30}LVX_{33}X_{34}LYLVCGDX_{42}GFX_{45}$ (SEQ ID NO: 28)-$(SSSSX_{50}APPPSLPSPSRLPGPSDTPILPQX_{51})_n$ (SEQ ID NO: 66)-$GIVDECCX_8X_9SCDLX_{14}X_{15}LX_{17}X_{18}X_{19}CX_{21}$-$R_{13}$ (SEQ ID NO: 27) or $X_{25}LCGX_{29}X_{30}LVX_{33}X_{34}LYLVCGDX_{42}GFX_{45}(Y_1)_k$ (SEQ ID NO: 28)-$(SSSSX_{50}APPPSLPSPSRLPGPSDTPILPQX_{51})_n$(SEQ ID NO: 66)-$GIVEQCCHSICSLYQLENX_{19}CX_{21}$-$R_{13}$ (SEQ ID NO: 37), wherein $X_8$ is histidine, threonine or phenylalanine;

$X_9$ is serine, arginine, lysine, ornithine or alanine;

$X_{14}$ is tyrosine, arginine, lysine, ornithine or alanine;

$X_{15}$ is glutamine, glutamic acid, arginine, alanine, lysine, ornithine or leucine;

$X_{17}$ is glutamic acid, aspartic acid, asparagine, lysine, ornithine or glutamine;

$X_{18}$ is methionine, asparagine, glutamine, aspartic acid, glutamic acid or threonine;

$X_{19}$ is tyrosine, 4-methoxy phenylalanine or 4-amino-phenylalanine;

$X_{21}$ is alanine, glycine or asparagine;

$X_{25}$ is histidine or threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid, glutamine and glutamic acid;

$X_{34}$ is selected from the group consisting of alanine and threonine;

$X_{42}$ is selected from the group consisting of alanine, lysine, ornithine and arginine;

$X_{45}$ is tyrosine or phenylalanine; and $X_{50}$ and $X_{51}$ are independently arginine or lysine and n is 1 or 2.

In accordance with one embodiment a single chain insulin analog is provided that comprises the structure: IB-LM-IA, wherein IB comprises the sequence $X_{25}LCGX_{29}X_{30}LVX_{33}X_{34}LYLVCGDX_{42}GFX_{45}$ (SEQ ID NO: 28), LM is a linking moiety as disclosed herein and the A chain comprises the sequence $GIVDECCHX_9SCDLX_{14}X_{15}LQMYCN$-$R_{13}$ (SEQ ID NO: 36), wherein $X_9$, $X_{14}$ and $X_{15}$ are independently ornithine, lysine or arginine and $R_{13}$ is COOH or $CONH_2$.

In one embodiment the B chain is selected from the group consisting of FVNQHLCGSHLVEALYLVCGERGFF (SEQ ID NO: 104), HLCGAELVDALYLVCGDOGFY (SEQ ID NO: 39), GPEHLCGAELVDALYLVCGDOGFY (SEQ ID NO: 40), GPEHLCGAELVDALYLVCGDOGFYFNPKT (SEQ ID NO: 41) and GPEHLCGAELVDALYLVCGDOG-FYFNKPT (SEQ ID NO: 42) and the A chain is $GIVDECCHOSCDLOOLQMX_{19}CN$-$R_{13}$ (SEQ ID NO: 43) or SEQ ID NO: 1, wherein $X_{19}$ is tyrosine, 4-methoxy-phenylalanine or 4-amino phenylalanine.

In one embodiment the single chain insulin further comprises a polyethylene glycol chain covalently linked to the side chain of an amino acid of the linking moiety and/or at a position selected from the group consisting of A9, A14 and A15 of the A chain or positions B0, B1, B10, B22, B28 or B29 of the B chain. In one embodiment the polyethylene glycol chain is covalently linked to the amino terminal amino acid of the B chain.

Synthesis of Insulin Analogs

The present disclosure is also directed to nucleic acid sequence encoding any of the insulin analogs disclosed herein as well as host cells comprising such nucleic acid sequences. Single chain insulin analogs disclosed herein can be expressed using standard techniques and expression vectors known to those skilled in the art. The insulin analogs disclosed herein can be expressed in prokaryotic (e.g., E coli) or eukaryotic (yeast, mammalian cells) host cells. In accordance with one embodiment hyperglycosylated insulin analogs are synthesized using recombinant eukaryotic host cells comprising a nucleic acid sequence that encodes an insulin analog disclosed herein that comprises a CTP peptide. In one embodiment the eukaryotic host cell is a yeast cell, more typically a yeast cell (e.g., P. pastoris) that has been modified to express human glycosylation genes. Alternatively, the host cell in one embodiment is a mammalian host cell (e.g., CHO cells), optionally modified to express human glycosylation genes.

In accordance with one embodiment a method of producing a hyperglycosylated insulin analog is provided, wherein the method comprises culturing a host cell comprising a CTP modified insulin analog encoding gene under conditions wherein the CTP modified insulin analog protein is produced. The expressed protein can then be recovered from the culture. In one embodiment the host cell expresses an insulin B chain of the general formula (CTP peptide1)$_m$-(insulin B-chain)-(CTP peptide2)$_n$ wherein m is an integer selected from 0 to 4, n is an integer selected from 0 to 4, and CTP peptide1 and CTP peptide2 represent amino acids sequences comprising a CTP peptide wherein CTP peptide1 and CTP peptide2 can be the same or difference amino acid sequences. The same cell may also express the insulin A chain wherein the B chain and A chain are recovered from the cell and reconstituted as a two chain insulin. Alternatively, the A chain can be expressed in a separate host cell that is either co-cultured with the first recombinant cell or cultured separately.

In one embodiment a host cell is provided comprising a gene that encodes a single chain insulin analog wherein the linking moiety that links the carboxy terminus of the insulin B chain to the amino terminus of the A chain comprises a CTP peptide. In an alternative embodiment the gene encodes a single chain insulin analog comprising a CTP peptide linked to the N-terminus of the B chain. In one embodiment the gene encodes a single chain analog comprising a first CTP peptide linked to the N-terminus of the B chain and a linking moiety that comprises a second CTP peptide, wherein the first and second CTP peptide are the same or different. In one embodiment the CTP peptide comprises a sequence selected from SEQ ID NO: 66, SEQ ID NO: 64 or SEQ ID NO: 75.

In one embodiment the host cell expresses a single chain insulin analog of the general formula (CTP peptide1)$_m$-(insulin B-chain)-(CTP peptide2)$_n$-(insulin A-chain) wherein m is an integer selected from 0 to 4, n is an integer selected from 1 to 4, and CTP peptide1 and CTP peptide2 represent amino acids sequences comprising a CTP peptide wherein CTP peptide1 and CTP peptide2 can be the same or difference amino acid sequences. The method comprises the steps of culturing the host cells comprising the gene encoding a CTP insulin analog under conditions wherein said protein is produced and recovering the protein from the culture.

In one embodiment the insulin analog is expressed as a single chain analog wherein the linking moiety comprises a unique peptide cleavage site at the junction of the linking moiety and the insulin A chain, and the method further comprising the step of cleaving the recovered protein to produce a two chain insulin analog. Any peptide cleavage enzyme can be used provided the recognition peptide is not located within the insulin B or A chain sequences. In one embodiment the linking moiety comprises the sequence SSSSRAPPPSLPSPSRLPGPSDTPILPQK (SEQ ID NO: 79) and the expressed single chain insulin analog is cleaved with Lys C to produce a two chain insulin analog. In one embodiment the host cell is a yeast cell that has been modified to only express human glycosylation enzymes. In an alternative embodiment the host cell is a mammalian cell line including for example CHO cells.

Pegylation of Insulin Analogs

Covalently linkage of a hydrophilic moiety to the insulin analogs disclosed herein may further enhance the properties of the CTP containing insulin analogs to provide analogs having slower onset, extended duration and exhibit a basal profile of activity. In one embodiment, the insulin analogs disclosed herein (i.e., modified to contain a glycosylation site) are further modified to comprise a hydrophilic moiety covalently linked to the side chain of an amino acid at a position selected from the group consisting of A9, A14 and A15 of the A chain or positions B0, B1, B10, B22, B28 or B29 of the B chain or at any position of the linking moiety that links the A chain and B chain. In exemplary embodiments, this hydrophilic moiety is covalently linked to a Lys, Cys, Orn, homocysteine, or acetyl-phenylalanine residue at any of these positions. In one embodiment the hydrophilic moiety is covalently linked to the side chain of an amino acid of the linking moiety.

Exemplary hydrophilic moieties include polyethylene glycol (PEG), for example, of a molecular weight of about 1,000 Daltons to about 40,000 Daltons, or about 20,000 Daltons to about 40,000 Daltons. Additional suitable hydrophilic moieties include, polypropylene glycol, polyoxyethylated polyols (e.g., POG), polyoxyethylated sorbitol, polyoxyethylated glucose, polyoxyethylated glycerol (POG), polyoxyalkylenes, polyethylene glycol propionaldehyde, copolymers of ethylene glycol/propylene glycol, monomethoxy-polyethylene glycol, mono-(C1-C10) alkoxy- or aryloxy-polyethylene glycol, carboxymethylcellulose, polyacetals, polyvinyl alcohol (PVA), polyvinyl pyrrolidone, poly-1,3-dioxolane, poly-1,3,6-trioxane, ethylene/maleic anhydride copolymer, poly (beta-amino acids) (either homopolymers or random copolymers), poly(n-vinyl pyrrolidone)polyethylene glycol, propropylene glycol homopolymers (PPG) and other polyakylene oxides, polypropylene oxide/ethylene oxide copolymers, colonic acids or other polysaccharide polymers, Ficoll or dextran and mixtures thereof.

The hydrophilic moiety, e.g., polyethylene glycol chain in accordance with some embodiments has a molecular weight selected from the range of about 500 to about 40,000 Daltons. In one embodiment the hydrophilic moiety, e.g. PEG, has a molecular weight selected from the range of about 500 to about 5,000 Daltons, or about 1,000 to about 5,000 Daltons. In another embodiment the hydrophilic moiety, e.g., PEG, has a molecular weight of about 10,000 to about 20,000 Daltons. In yet other exemplary embodiment the hydrophilic moiety, e.g., PEG, has a molecular weight of about 20,000 to about 40,000 Daltons. In one embodiment the hydrophilic moiety, e.g. PEG, has a molecular weight of about 20,000 Daltons. In one embodiment a single chain insulin analog is provided wherein one or more amino acids of the analog are pegylated, and the combined molecular weight of the covalently linked PEG chains is about 20,000 Daltons.

In one embodiment dextrans are used as the hydrophilic moiety. Dextrans are polysaccharide polymers of glucose subunits, predominantly linked by cd-6 linkages. Dextran is available in many molecular weight ranges, e.g., about 1 kD to about 100 kD, or from about 5, 10, 15 or 20 kD to about 20, 30, 40, 50, 60, 70, 80 or 90 kD.

Linear or branched polymers are contemplated. Resulting preparations of conjugates may be essentially monodisperse or polydisperse, and may have about 0.5, 0.7, 1, 1.2, 1.5 or 2 polymer moieties per peptide.

In one embodiment the hydrophilic moiety is a polyethylene glycol (PEG) chain, optionally linked to the side chain of an amino acid at a position selected from the group consisting of A9, A14 and A15 of the A chain, at the amino terminal amino acid of the B chain, at positions B10, B22, B28 or B29 of the B chain or at any position of the linking moiety that links the A chain and B chain. In one embodiment the single chain insulin analog comprises a peptide linking moiety, wherein one of the amino acids of the linking moiety has a polyethylene chain covalently bound to its side chain. In one embodiment the single chain insulin analog comprises a peptide linking moiety, wherein an amino acid of the linking moiety is pegylated, and one or more amino acid at a position selected from the group consisting of A9, A14 and A15 of the A chain, at the amino terminal amino acid of the B chain and at positions B10, B22, B28 or B29 of the B chain is also pegylated. In one embodiment the total molecular weight of the covalently linked PEG chain(s) is about 20,000 Daltons.

In one embodiment a single chain insulin analog is provided, wherein one of the amino acids of the linking moiety has a 20,000 Dalton polyethylene chain covalently bound to its side chain. In another embodiment a single chain insulin analog comprises a polyethylene chain covalently bound to one of the amino acids of the linking moiety and a second PEG chain linked to an amino terminal amino acids or at B29 of the B chain. In one embodiment when two PEG chains are linked to the single chain insulin analog, each PEG chain has a molecular weight of about 10,000 Daltons.

Hydrophilic moieties such as polyethylene glycol can be attached to the insulin analog under any suitable conditions used to react a protein with an activated polymer molecule. Any means known in the art can be used, including via acylation, reductive alkylation, Michael addition, thiol alkylation or other chemoselective conjugation/ligation methods through a reactive group on the PEG moiety (e.g., an aldehyde, amino, ester, thiol, α-haloacetyl, maleimido or hydrazino group) to a reactive group on the target compound (e.g., an aldehyde, amino, ester, thiol, α-haloacetyl, maleimido or hydrazino group). Activating groups which can be used to link the water soluble polymer to one or more proteins include without limitation sulfone, maleimide, sulfhydryl, thiol, triflate, tresylate, azidirine, oxirane and 5-pyridyl. If attached to the peptide by reductive alkylation, the polymer selected should have a single reactive aldehyde so that the degree of polymerization is controlled. See, for example, Kinstler et al., *Adv. Drug. Delivery Rev.* 54: 477-485 (2002); Roberts et al., *Adv. Drug Delivery Rev.* 54: 459-476 (2002); and Zalipsky et al., *Adv. Drug Delivery Rev.* 16: 157-182 (1995).

In a specific aspect of the invention, an amino acid residue on the insulin analog having a thiol is modified with a hydrophilic moiety such as PEG. In some embodiments, the thiol is modified with maleimide-activated PEG in a Michael addition reaction to result in a PEGylated peptide comprising the thioether linkage shown below:

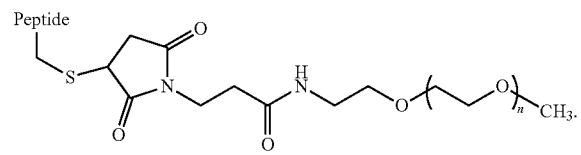

In some embodiments, the thiol is modified with a haloacetyl-activated PEG in a nucleophilic substitution reaction to result in a PEGylated peptide comprising the thioether linkage shown below:

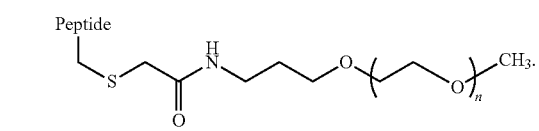

Acylation of Insulin Analogs

In some embodiments, the insulin analog is modified to comprise an acyl group. The acyl group can be covalently linked directly to an amino acid of the insulin analog, or indirectly to an amino acid of the insulin analog via a spacer, wherein the spacer is positioned between the amino acid of the insulin analog and the acyl group. The insulin analog may be acylated at the same amino acid position where a hydrophilic moiety is linked, or at a different amino acid position. For example, acylation may occur at any position including any of amino acid of the A or B chains as well as a position within the linking moiety, provided that the activity exhibited by the non-acylated insulin analog is retained upon acylation. Nonlimiting examples include acylation at positions A14 and A15 of the A chain, positions the amino terminal amino acid (B1 for insulin based B chains or B2 for IGF based B chains), B10, B22, B28 or B29 of the B chain or at any position of the linking moiety.

In one specific aspect of the invention, the insulin analog (or derivative or conjugate thereof) is modified to comprise an acyl group by direct acylation of an amine, hydroxyl, or thiol of a side chain of an amino acid of the insulin analog. In some embodiments, the insulin analog is directly acylated through the side chain amine, hydroxyl, or thiol of an amino acid. In some embodiments, acylation is at position B28 or B29 (according to the amino acid numbering of the native insulin A and B chain sequences). In this regard, an insulin analog can be provided that has been modified by one or more amino acid substitutions in the A or B chain sequence, including for example at positions A14, A15, B1/B2, B10, B22, B28 or B29 (according to the amino acid numbering of the native insulin A and B chain sequences) or at any position of the linking moiety with an amino acid comprising a side chain amine, hydroxyl, or thiol. In some specific embodiments of the invention, the direct acylation of the insulin analog occurs through the side chain amine, hydroxyl, or thiol of the amino acid at position B28 or B29 (according to the amino acid numbering of the native insulin A and B chain sequences).

In one embodiment, the insulin analog comprises an amino acid of Formula I:

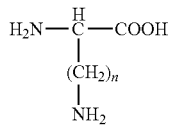

wherein n=1 to 4
[Formula I]
In some exemplary embodiments, the amino acid of Formula I, is the amino acid wherein n is 4 (Lys) or n is 3 (Orn).

In another embodiment, the insulin analog comprises an amino acid of Formula II:

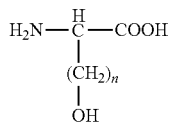

wherein n=1 to 4
[Formula II]
In some exemplary embodiments, the amino acid of Formula II is the amino acid wherein n is 1 (Ser).

In yet another embodiment, the insulin analog comprises a side chain thiol is an amino acid of Formula III:

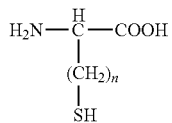

wherein n=1 to 4
[Formula III]
In some exemplary embodiments, the amino acid of Formula III is the amino acid wherein n is 1 (Cys).

In yet another embodiment, the insulin analog comprises a disubstituted amino acid comprising the same structure of Formula I, Formula II, or Formula III, except that the hydrogen bonded to the alpha carbon of the amino acid of Formula I, Formula II, or Formula III is replaced with a second side chain.

In accordance with one embodiment, the acylated insulin analogs comprise a spacer between the peptide and the acyl group. In some embodiments, the insulin analog is covalently bound to the spacer, which is covalently bound to the acyl group. In some exemplary embodiments, the insulin analog is modified to comprise an acyl group by acylation of an amine, hydroxyl, or thiol of a spacer, which spacer is attached to a side chain of an amino acid at position B28 or B29 (according to the amino acid numbering of the A or B chain of native insulin), or at any position of the spacer moiety. The amino acid of the insulin analog to which the spacer is attached can be any amino acid comprising a moiety which permits linkage to the spacer. For example, an amino acid comprising a side chain —NH$_2$, —OH, or —COOH (e.g., Lys, Orn, Ser, Asp, or Glu) is suitable.

In some embodiments, the spacer between the insulin analog and the acyl group is an amino acid comprising a side chain amine, hydroxyl, or thiol (or a dipeptide or tripeptide comprising an amino acid comprising a side chain amine, hydroxyl, or thiol). In some embodiments, the spacer comprises a hydrophilic bifunctional spacer. In a specific embodiment, the spacer comprises an amino poly(alkyloxy) carboxylate. In this regard, the spacer can comprise, for example, NH$_2$(CH$_2$CH$_2$O)$_n$(CH$_2$)$_m$COOH, wherein m is any integer from 1 to 6 and n is any integer from 2 to 12, such as, e.g., 8-amino-3,6-dioxaoctanoic acid, which is commercially available from Peptides International, Inc. (Louisville, Ky.). In one embodiment, the hydrophilic bifunctional spacer comprises two or more reactive groups, e.g., an amine, a hydroxyl, a thiol, and a carboxyl group or any combinations thereof. In certain embodiments, the hydrophilic bifunctional spacer comprises a hydroxyl group and a carboxylate. In other embodiments, the hydrophilic bifunctional spacer comprises an amine group and a carboxylate. In other embodiments, the hydrophilic bifunctional spacer comprises a thiol group and a carboxylate.

In some embodiments, the spacer between peptide the insulin analog and the acyl group is a hydrophobic bifunctional spacer. Hydrophobic bifunctional spacers are known in the art. See, e.g., Bioconjugate Techniques, G. T. Hermanson (Academic Press, San Diego, Calif., 1996), which is incorporated by reference in its entirety. In certain embodiments, the hydrophobic bifunctional spacer comprises two or more reactive groups, e.g., an amine, a hydroxyl, a thiol, and a carboxyl group or any combinations thereof. In certain embodiments, the hydrophobic bifunctional spacer comprises a hydroxyl group and a carboxylate. In other embodiments, the hydrophobic bifunctional spacer comprises an amine group and a carboxylate. In other embodiments, the hydrophobic bifunctional spacer comprises a thiol group and a carboxylate. Suitable hydrophobic bifunctional spacers comprising a carboxylate and a hydroxyl group or a thiol group are known in the art and include, for example, 8-hydroxyoctanoic acid and 8-mercaptooctanoic acid.

In accordance with certain embodiments the bifunctional spacer can be a synthetic or naturally occurring amino acid comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. Each amino acid of the dipeptide or tripeptide spacer attached to the insulin analog can be independently selected from the group consisting of: naturally-occurring and/or non-naturally occurring amino acids, including, for example, any of the D or L isomers of the naturally-occurring amino acids (Ala, Cys, Asp, Glu, Phe, Gly, His, Ile, Lys, Leu, Met, Asn, Pro, Arg, Ser, Thr, Val, Trp, Tyr), or any D or L isomers of the non-naturally occurring amino acids selected from the group consisting of: β-alanine (β-Ala), N-α-methyl-alanine (Me-Ala), aminobutyric acid (Abu), α-aminobutyric acid (γ-Abu), aminohexanoic acid (ε-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), β-Cyclohexylalanine (Cha), acetamidomethylcysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met(O2)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe(4-Cl)), 4-fluorophenylalanine (Phe(4-F)), 4-nitrophenylalanine (Phe(4-NO2)), 4-cyanophenylalanine ((Phe (4-CN)), phenylglycine (Phg), piperidinylalanine, piperidinylglycine, 3,4-dehydroproline, pyrrolidinylalanine, sarcosine (Sar), selenocysteine (Sec), U-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2,3,4,-tetrahydro-isoquinoline-3-carboxylic acid (Tic), tetrahydropyranglycine, thienylalanine (Thi), U-Benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (Me-Val), 1-amino-1-cyclohexane carboxylic acid (Acx), aminovaleric acid, beta-cyclopropyl-alanine (Cpa), propargylglycine (Prg), allylglycine (Alg), 2-amino-2-cyclohexyl-propanoic acid (2-Cha), tertbutylglycine (Tbg), vinylglycine (Vg), 1-amino-1-cyclopropane carboxylic acid (Acp), 1-amino-1-cyclopentane carboxylic acid (Acpe), alkylated 3-mercaptopropionic acid, 1-amino-1-cyclobutane carboxylic acid (Acb). In some embodiments the dipeptide spacer is selected from the group consisting of: Ala-Ala, β-Ala-β-Ala, Leu-Leu, Pro-Pro, γ-aminobutyric acid-γ-aminobutyric acid, and γ-Glu-γ-Glu.

The peptide the insulin analog can be modified to comprise an acyl group by acylation of a long chain alkane. In specific aspects, the long chain alkane comprises an amine, hydroxyl, or thiol group (e.g. octadecylamine, tetradecanol, and hexadecanethiol) which reacts with a carboxyl group, or activated form thereof, of the insulin analog. The carboxyl group, or activated form thereof, of the insulin analog can be part of a side chain of an amino acid (e.g., glutamic acid, aspartic acid) of the insulin analog or can be part of the peptide backbone.

In certain embodiments, the insulin analog is modified to comprise an acyl group by acylation of the long chain alkane by a spacer which is attached to the insulin analog. In specific aspects, the long chain alkane comprises an amine, hydroxyl, or thiol group which reacts with a carboxyl group, or activated form thereof, of the spacer. Suitable spacers comprising a carboxyl group, or activated form thereof, are described herein and include, for example, bifunctional spacers, e.g., amino acids, dipeptides, tripeptides, hydrophilic bifunctional spacers and hydrophobic bifunctional spacers. As used herein, the term "activated form of a carboxyl group" refers to a carboxyl group with the general formula R(C=O)X, wherein X is a leaving group and R is the insulin analog or the spacer. For example, activated forms of a carboxyl groups may include, but are not limited to, acyl chlorides, anhydrides, and esters. In some embodiments, the activated carboxyl group is an ester with a N-hydroxysuccinimide (NHS) leaving group.

With regard to these aspects of the invention, in which a long chain alkane is acylated by the peptide the insulin analog or the spacer, the long chain alkane may be of any size and can comprise any length of carbon chain. The long chain alkane can be linear or branched. In certain aspects, the long chain alkane is a $C_4$ to $C_{30}$ alkane. For example, the long chain alkane can be any of a $C_4$ alkane, $C_6$ alkane, $C_8$ alkane, $C_{10}$ alkane, $C_{12}$ alkane, $C_{14}$ alkane, $C_{16}$ alkane, $C_{18}$ alkane, $C_{20}$ alkane, $C_{22}$ alkane, $C_{24}$ alkane, $C_{26}$ alkane, $C_{28}$ alkane, or a $C_{30}$ alkane. In some embodiments, the long chain alkane comprises a $C_8$ to $C_{20}$ alkane, e.g., a $C_{14}$ alkane, $C_{16}$ alkane, or a $C_{18}$ alkane.

In some embodiments, an amine, hydroxyl, or thiol group of the insulin analog is acylated with a cholesterol acid. In a specific embodiment, the peptide is linked to the cholesterol acid through an alkylated des-amino Cys spacer, i.e., an alkylated 3-mercaptopropionic acid spacer. Suitable methods of peptide acylation via amines, hydroxyls, and thiols are known in the art. See, for example, Miller, Biochem Biophys Res Commun 218: 377-382 (1996); Shimohigashi and Stammer, Int J Pept Protein Res 19: 54-62 (1982); and Previero et al., Biochim Biophys Acta 263: 7-13 (1972) (for methods of acylating through a hydroxyl); and San and Silvius, J Pept Res 66: 169-180 (2005) (for methods of acylating through a thiol); Bioconjugate Chem. "Chemical Modifications of Proteins: History and Applications" pages 1, 2-12 (1990); Hashimoto et al., Pharmacuetical Res. "Synthesis of Palmitoyl Derivatives of Insulin and their Biological Activity" Vol. 6, No: 2 pp. 171-176 (1989).

The acyl group of the acylated peptide the insulin analog can be of any size, e.g., any length carbon chain, and can be linear or branched. In some specific embodiments of the invention, the acyl group is a $C_4$ to $C_{30}$ fatty acid. For example, the acyl group can be any of a $C_4$ fatty acid, $C_6$ fatty acid, $C_8$ fatty acid, $C_{10}$ fatty acid, $C_{12}$ fatty acid, $C_{14}$ fatty acid, $C_{16}$ fatty acid, $C_{18}$ fatty acid, $C_{20}$ fatty acid, $C_{22}$ fatty acid, $C_{24}$ fatty acid, $C_{26}$ fatty acid, $C_{28}$ fatty acid, or a $C_{30}$ fatty acid. In some embodiments, the acyl group is a $C_8$ to $C_{20}$ fatty acid, e.g., a $C_{14}$ fatty acid or a $C_{16}$ fatty acid.

In an alternative embodiment, the acyl group is a bile acid. The bile acid can be any suitable bile acid, including, but not limited to, cholic acid, chenodeoxycholic acid, deoxycholic acid, lithocholic acid, taurocholic acid, glycocholic acid, and cholesterol acid.

The acylated insulin analog described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. In some embodiments the acylated analog comprises an amino acid selected from the group consisting of a Cys, Lys, Orn, homo-Cys, or Ac-Phe, and the side chain of the amino acid is covalently bonded to a hydrophilic moiety (e.g., PEG). In one embodiment, the acyl group is attached to position A14, A15, B0, B1, B10, B22, B28 or B29 (according to the amino acid numbering of the A and B chains of native insulin), optionally via a spacer comprising Cys, Lys, Orn, homo-Cys, or Ac-Phe.

Alternatively, the acylated insulin analog comprises a spacer, wherein the spacer is both acylated and modified to comprise the hydrophilic moiety. Nonlimiting examples of suitable spacers include a spacer comprising one or more amino acids selected from the group consisting of Cys, Lys, Orn, homo-Cys, and Ac-Phe.

Alkylation of the Insulin Analog

In some embodiments, the insulin analog modified to comprise a glycosylation site is further modified to comprise an alkyl group. The alkyl group can be covalently linked directly to an amino acid of the insulin analog, or indirectly to an amino acid of the insulin analog via a spacer, wherein the spacer is positioned between the amino acid of the insulin analog and the alkyl group. The alkyl group can be attached to the insulin analog via an ether, thioether, or amino linkage. For example, the insulin analog may be alkylated at the same amino acid position where a hydrophilic moiety is linked, or at a different amino acid position.

Alkylation can be carried out at any position within the insulin analog, including for example in the C-terminal region of the B chain or at a position in the linking moiety, provided that insulin activity is retained. In a specific aspect of the invention, the insulin analog is modified to comprise an alkyl group by direct alkylation of an amine, hydroxyl, or thiol of a side chain of an amino acid of the insulin analog. In some embodiments, the insulin analog is directly alkylated through the side chain amine, hydroxyl, or thiol of an amino acid. In some specific embodiments of the invention, the direct alkylation of the insulin analog occurs through the side chain amine, hydroxyl, or thiol of the amino acid at position A14, A15, B0, B1, B10, B22, B28 or B29 (according to the amino acid numbering of the A and B chain of native insulin).

In some embodiments, the amino acid of the insulin analog comprises an amino acid selected from Formula I, Formula II, and Formula III, and the alkyl group is linked through the amino, hydroxyl or thiol group contained in Formula I, Formula II, and Formula III, respectively. In some exemplary embodiments, the amino acid of Formula I, is the amino acid wherein n is 4 (Lys) or n is 3 (Orn). In some exemplary embodiments, the amino acid of Formula II is the amino acid wherein n is 1 (Ser). In some exemplary embodiments, the amino acid of Formula II is the amino acid wherein n is 1 (Cys). In yet other embodiments, the amino acid of peptide the insulin analog comprising a side chain amine, hydroxyl, or thiol is a disubstituted amino acid comprising the same structure of Formula I, Formula II, or Formula III, except that the hydrogen bonded to the alpha carbon of the amino acid of Formula I, Formula II, or Formula III is replaced with a second side chain.

In some embodiments of the invention, the insulin analog comprises a spacer between the peptide and the alkyl group. In some embodiments, the insulin analog is covalently bound to the spacer, which is covalently bound to the alkyl group. In some exemplary embodiments, the insulin analog is modified to comprise an alkyl group by alkylation of an amine, hydroxyl, or thiol of a spacer, wherein the spacer is attached to a side chain of an amino acid at position A14, A15, B0, B1, B10, B22, B28 or B29 (according to the amino acid numbering of the A and B chains of native insulin). The amino acid of the insulin analog to which the spacer is attached can be any amino acid (e.g., a singly α-substituted amino acid or an α,α-disubstituted amino acid) comprising a moiety which permits linkage to the spacer. An amino acid of the insulin analog comprising a side chain —NH$_2$, —OH, or —COOH (e.g., Lys, Orn, Ser, Asp, or Glu) is suitable. In some embodiments, the spacer between the peptide the insulin analog and the alkyl group is an amino acid comprising a side chain amine, hydroxyl, or thiol or a dipeptide or tripeptide comprising an amino acid comprising a side chain amine, hydroxyl, or thiol.

In the instance in which the alpha amine is alkylated, the spacer amino acid can be any amino acid. For example, the spacer amino acid can be a hydrophobic amino acid, e.g., Gly, Ala, Val, Leu, Ile, Trp, Met, Phe, Tyr. Alternatively, the spacer amino acid can be an acidic residue, e.g., Asp and Glu. In exemplary embodiments, the spacer amino acid can be a hydrophobic amino acid, e.g., Gly, Ala, Val, Leu, Ile, Trp, Met, Phe, Tyr, 6-amino hexanoic acid, 5-aminovaleric acid, 7-aminoheptanoic acid, 8-aminooctanoic acid. Alternatively, the spacer amino acid can be an acidic residue, e.g., Asp and Glu, provided that the alkylation occurs on the alpha amine of the acidic residue. In the instance in which the side chain amine of the spacer amino acid is alkylated, the spacer amino acid is an amino acid comprising a side chain amine, e.g., an amino acid of Formula I (e.g., Lys or Orn). In this instance, it is possible for both the alpha amine and the side chain amine of the spacer amino acid to be alkylated, such that the peptide is dialkylated. Embodiments of the invention include such dialkylated molecules.

When alkylation occurs through a hydroxyl group of the amino acid of the spacer, the amino acid or one of the amino acids of the spacer can be an amino acid of Formula II. In a specific exemplary embodiment, the amino acid is Ser. When alkylation occurs through a thiol group of the amino acid of the spacer, the amino acid or one of the amino acids of the spacer can be an amino acid of Formula III. In a specific exemplary embodiment, the amino acid is Cys.

In some embodiments, the spacer comprises a hydrophilic bifunctional spacer. In a specific embodiment, the spacer comprises an amino poly(alkyloxy)carboxylate. In this regard, the spacer can comprise, for example, NH$_2$(CH$_2$CH$_2$O)$_n$(CH$_2$)$_m$COOH, wherein m is any integer from 1 to 6 and n is any integer from 2 to 12, such as, e.g., 8-amino-3,6-dioxaoctanoic acid, which is commercially available from Peptides International, Inc. (Louisville, Ky.). In some embodiments, the spacer between peptide the insulin analog and the alkyl group is a hydrophilic bifunctional spacer. In certain embodiments, the hydrophilic bifunctional spacer comprises two or more reactive groups, e.g., an amine, a hydroxyl, a thiol, and a carboxyl group or any combinations thereof. In certain embodiments, the hydrophilic bifunctional spacer comprises a hydroxyl group and a carboxylate. In other embodiments, the hydrophilic bifunctional spacer comprises an amine group and a carboxylate. In other embodiments, the hydrophilic bifunctional spacer comprises a thiol group and a carboxylate.

In some embodiments, the spacer between peptide the insulin analog and the alkyl group is a hydrophobic bifunctional spacer. In certain embodiments, the hydrophobic bifunctional spacer comprises two or more reactive groups, e.g., an amine, a hydroxyl, a thiol, and a carboxyl group or any combinations thereof. In certain embodiments, the hydrophobic bifunctional spacer comprises a hydroxyl group and a carboxylate. In other embodiments, the hydrophobic bifunctional spacer comprises an amine group and a carboxylate. In other embodiments, the hydrophobic bifunctional spacer comprises a thiol group and a carboxylate. Suitable hydrophobic bifunctional spacers comprising a carboxylate and a hydroxyl group or a thiol group are known in the art and include, for example, 8-hydroxyoctanoic acid and 8-mercaptooctanoic acid.

The spacer (e.g., amino acid, dipeptide, tripeptide, hydrophilic bifunctional spacer, or hydrophobic bifunctional spacer) is 3 to 10 atoms (e.g., 6 to 10 atoms, (e.g., 6, 7, 8, 9, or 10 atoms)) in length. In more specific embodiments, the spacer is about 3 to 10 atoms (e.g., 6 to 10 atoms) in length and the alkyl is a $C_{12}$ to $C_{18}$ alkyl group, e.g., $C_{14}$ alkyl group, $C_{16}$ alkyl group, such that the total length of the spacer and alkyl group is 14 to 28 atoms, e.g., about 14, 15, 16, 17, 18, 19, 20, 21, 22, 23, 24, 25, 26, 27, or 28 atoms. In some embodiments the length of the spacer and alkyl is 17 to 28 (e.g., 19 to 26, 19 to 21) atoms.

In accordance with one embodiment the bifunctional spacer is a synthetic or non-naturally occurring amino acid comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. The dipeptide or tripeptide spacer attached to the insulin analog can be composed of naturally-occurring and/or non-naturally occurring amino acids, including, for example, any of the amino acids taught herein. In some embodiments the spacer comprises an overall negative charge, e.g., comprises one or two negatively charged amino acids. In some embodiments the dipeptide spacer is selected from the group consisting of: Ala-Ala, β-Ala-β-Ala, Leu-Leu, Pro-Pro, γ-aminobutyric acid-γ-aminobutyric acid, and γ-Glu-γ-Glu. In one embodiment the dipeptide spacer is γ-Glu-γ-Glu.

Suitable methods of peptide alkylation via amines, hydroxyls, and thiols are known in the art. For example, a Williamson ether synthesis can be used to form an ether linkage between the insulin peptide and the alkyl group. Also, a nucleophilic substitution reaction of the peptide with an alkyl halide can result in any of an ether, thioether, or amino linkage. The alkyl group of the alkylated peptide the insulin analog can be of any size, e.g., any length carbon chain, and can be linear or branched. In some embodiments of the invention, the alkyl group is a $C_4$ to $C_{30}$ alkyl. For example, the alkyl group can be any of a $C_4$ alkyl, $C_6$ alkyl, $C_8$ alkyl, $C_{10}$ alkyl, $C_{12}$ alkyl, $C_{14}$ alkyl, $C_{16}$ alkyl, $C_{18}$ alkyl, $C_{20}$ alkyl, $C_{22}$ alkyl, $C_{24}$ alkyl, $C_{26}$ alkyl, $C_{28}$ alkyl, or a $C_{30}$ alkyl. In some embodiments, the alkyl group is a $C_8$ to $C_{20}$ alkyl, e.g., a $C_{14}$ alkyl or a $C_{16}$ alkyl.

In some specific embodiments, the alkyl group comprises a steroid moiety of a bile acid, e.g., cholic acid, chenodeoxycholic acid, deoxycholic acid, lithocholic acid, taurocholic acid, glycocholic acid, and cholesterol acid.

In some embodiments the insulin analog is modified to comprise an alkyl group by reacting a nucleophilic, long chain alkane with the insulin analog, wherein the insulin analog comprises a leaving group suitable for nucleophilic substitution. In specific aspects, the nucleophilic group of the long chain alkane comprises an amine, hydroxyl, or thiol group (e.g. octadecylamine, tetradecanol, and hexadecanethiol).

The leaving group of the insulin analog can be part of a side chain of an amino acid or can be part of the peptide backbone. Suitable leaving groups include, for example, N-hydroxysuccinimide, halogens, and sulfonate esters.

In certain embodiments, the insulin analog is modified to comprise an alkyl group by reacting the nucleophilic, long chain alkane with a spacer, which is attached to the insulin analog, wherein the spacer comprises the leaving group. In specific aspects, the long chain alkane comprises an amine, hydroxyl, or thiol group. In certain embodiments, the spacer comprising the leaving group can be any spacer discussed herein, e.g., amino acids, dipeptides, tripeptides, hydrophilic bifunctional spacers and hydrophobic bifunctional spacers further comprising a suitable leaving group.

When a long chain alkane is alkylated by the insulin analog or the spacer, the long chain alkane may be of any size and can comprise any length of carbon chain. The long chain alkane can be linear or branched. In certain aspects, the long chain alkane is a $C_4$ to $C_{30}$ alkane. For example, the long chain alkane can be any of a $C_4$ alkane, $C_6$ alkane, $C_8$ alkane, $C_{10}$ alkane, $C_{12}$ alkane, $C_{14}$ alkane, $C_{16}$ alkane, $C_{18}$ alkane, $C_{20}$ alkane, $C_{22}$ alkane, $C_{24}$ alkane, $C_{26}$ alkane, $C_{28}$ alkane, or a $C_{30}$ alkane. In some embodiments the long chain alkane comprises a $C_8$ to $C_{20}$ alkane, e.g., a $C_{14}$ alkane, $C_{16}$ alkane, or a $C_{18}$ alkane.

Also, in some embodiments alkylation can occur between the insulin analog and a cholesterol moiety. For example, the hydroxyl group of cholesterol can displace a leaving group on the long chain alkane to form a cholesterol-insulin peptide product. The alkylated insulin analogs described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. In some embodiments the insulin analog can comprise an amino acid selected from Cys, Lys, Orn, homo-Cys, or Ac-Phe, wherein the side chain of the amino acid is covalently bonded to a hydrophilic moiety (e.g., PEG). In some embodiments the alkyl group is attached to position A14, A15, B0, B1, B10, B22, B28 or B29 (according to the amino acid numbering of the A or B chain of native insulin), optionally via a spacer comprising Cys, Lys, Orn, homo-Cys, or Ac-Phe, and optionally further comprising a hydrophilic moiety linked to the side chain of another amino acid. Alternatively, the alkylated insulin analog can comprise a spacer, wherein the spacer is both alkylated and modified to comprise the hydrophilic moiety. Nonlimiting examples of suitable spacers include a spacer comprising one or more amino acids selected from the group consisting of Cys, Lys, Orn, homo-Cys, and Ac-Phe.

Conjugates

In some embodiments, the insulin analogs disclosed herein as being modified to comprise a glycosylation site are further amidated, carboxylated, phosphorylated, esterified, N-acylated, cyclized via, e.g., a disulfide bridge, or converted into a salt (e.g., an acid addition salt, a basic addition salt), and/or optionally dimerized, multimerized, or polymerized, or conjugated. The present disclosure also encompasses conjugates in which the insulin analog is linked to a heterologous moiety. The conjugation between the insulin analog and the heterologous moiety can be through covalent bonding, non-covalent bonding (e.g. electrostatic interactions, hydrogen bonds, van der Waals interactions, salt bridges, hydrophobic interactions, and the like), or both types of bonding. A variety of non-covalent coupling systems may be used, including biotin-avidin, ligand/receptor, enzyme/substrate, nucleic acid/nucleic acid binding protein, lipid/lipid binding protein, cellular adhesion molecule partners; or any binding partners or fragments thereof which have affinity for each other. In some aspects, the covalent bonds are peptide bonds. The conjugation of the insulin analog to the heterologous moiety may be indirect or direct conjugation, the former of which may involve a linker or spacer. Suitable linkers and spacers are known in the art and include, but not limited to, any of the linkers or spacers described.

As used herein, the term "heterologous moiety" is synonymous with the term "conjugate moiety" and refers to any molecule (chemical or biochemical, naturally-occurring or non-coded) which is different from the insulin analog to which it is attached. Exemplary conjugate moieties that can be linked to the insulin analog include but are not limited to a heterologous peptide or polypeptide (including for example, a plasma protein), a targeting agent, an immunoglobulin or portion thereof (e.g., variable region, CDR, or Fc region), a diagnostic label such as a radioisotope, fluorophore or enzymatic label, a polymer including water soluble polymers, or other therapeutic or diagnostic agents. In some embodiments a conjugate is provided comprising the insulin analog and a plasma protein, wherein the plasma protein is selected from the group consisting of albumin, transferin, fibrinogen and globulins. In some embodiments the plasma protein moiety of the conjugate is albumin or transferin. In one embodiment the heterologous moiety is albumin, including for example, albumins such as human serum albumin (HSA) and recombinant human albumin (rHA). The conjugate in some embodiments comprises the insulin analog and one or more of a polypeptide, a nucleic acid molecule, an antibody or fragment thereof, a polymer, a the insulin analoguantum dot, a small molecule, a toxin, a diagnostic agent, a carbohydrate, an amino acid.

Polymer Heterologous Moiety

In some embodiments, the heterologous moiety conjugated to the insulin analog is a polymer. In some embodiments, the polymer is selected from the group consisting of: polyamides, polycarbonates, polyalkylenes and derivatives thereof including, polyalkylene glycols, polyalkylene oxides, polyalkylene terepthalates, polymers of acrylic and methacrylic esters, including poly(methyl methacrylate), poly(ethyl methacrylate), poly(butylmethacrylate), poly (isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly (ethylene oxide), and poly(ethylene terephthalate), and polystyrene.

In some aspects, the polymer is a biodegradable polymer, including a synthetic biodegradable polymer (e.g., polymers of lactic acid and glycolic acid, polyanhydrides, poly(ortho) esters, polyurethanes, poly(butic acid), poly(valeric acid), and poly(lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion.

In some aspects, the polymer is a bioadhesive polymer, such as a bioerodible hydrogel described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly (octadecyl acrylate).

In some embodiments, the polymer is a water-soluble polymer or a hydrophilic polymer. Hydrophilic polymers are further described herein under "Hydrophilic Heterologous Moieties." Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene glycol, and derivatives, salts, and combinations thereof.

In one embodiment, the polymer is a polyalkylene glycol, including, for example, polyethylene glycol (PEG). In some embodiments, the heterologous moiety is a carbohydrate. In some embodiments, the carbohydrate is a monosaccharide (e.g., glucose, galactose, fructose), a disaccharide (e.g., sucrose, lactose, maltose), an oligosaccharide (e.g., raffinose, stachyose), a polysaccharide (a starch, amylase, amylopectin, cellulose, chitin, callose, laminarin, xylan, mannan, fucoidan, galactomannan.

In some embodiments, the heterologous moiety is a lipid. The lipid, in some embodiments, is a fatty acid, eicosanoid, prostaglandin, leukotriene, thromboxane, N-acyl ethanolamine), glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide, oil, wax, cholesterol, sterol, fat-soluble vitamin, monoglyceride, diglyceride, triglyceride, a phospholipid.

Fc Fusion Heterologous Moiety

As noted above, in some embodiments the insulin analog is conjugated, e.g., fused to an immunoglobulin or portion thereof (e.g. variable region, CDR, or Fc region). Known types of immunoglobulins (Ig) include IgG, IgA, IgE, IgD or IgM. The Fc region is a C-terminal region of an Ig heavy chain, which is responsible for binding to Fc receptors that carry out activities such as recycling (which results in prolonged half-life), antibody dependent cell-mediated cytotoxicity (ADCC), and complement dependent cytotoxicity (CDC).

For example, according to some definitions the human IgG heavy chain Fc region stretches from Cys226 to the C-terminus of the heavy chain. The "hinge region" generally extends from Glu216 to Pro230 of human IgG1 (hinge regions of other IgG isotypes may be aligned with the IgG1 sequence by aligning the cysteines involved in cysteine bonding). The Fc region of an IgG includes two constant domains, CH2 and CH3. The CH2 domain of a human IgG Fc region usually extends from amino acids 231 to amino acid 341. The CH3 domain of a human IgG Fc region usually extends from amino acids 342 to 447. References made to amino acid numbering of immunoglobulins or immunoglobulin fragments, or regions, are all based on Kabat et al. 1991, Sequences of Proteins of Immunological Interest, U.S. Department of Public Health, Bethesda, Md. In a related embodiment, the Fc region may comprise one or more native or modified constant regions from an immunoglobulin heavy chain, other than CH1, for example, the CH2 and CH3 regions of IgG and IgA, or the CH3 and CH4 regions of IgE.

Suitable conjugate moieties include portions of immunoglobulin sequence that include the FcRn binding site. FcRn, a salvage receptor, is responsible for recycling immunoglobulins and returning them to circulation in blood. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The major contact sites include amino acid residues 248, 250-257, 272, 285, 288, 290-291, 308-311, and 314 of the CH2 domain and amino acid residues 385-387, 428, and 433-436 of the CH3 domain.

Some conjugate moieties may or may not include FcγR binding site(s). FcγR are responsible for ADCC and CDC. Examples of positions within the Fc region that make a direct contact with FcγR are amino acids 234-239 (lower hinge region), amino acids 265-269 (B/C loop), amino acids 297-299 (C'/E loop), and amino acids 327-332 (F/G) loop (Sondermann et al., Nature 406: 267-273, 2000). The lower hinge region of IgE has also been implicated in the FcRI binding (Henry, et al., Biochemistry 36, 15568-15578, 1997). Residues involved in IgA receptor binding are described in Lewis et al., (J Immunol. 175:6694-701, 2005). Amino acid residues involved in IgE receptor binding are described in Sayers et al. (J Biol Chem. 279(34):35320-5, 2004). Amino acid modifications may be made to the Fc region of an immunoglobulin. Such variant Fc regions comprise at least one amino acid modification in the CH3 domain of the Fc region (residues 342-447) and/or at least one amino acid modification in the CH2 domain of the Fc region (residues 231-341). Mutations believed to impart an increased affinity for FcRn include T256A, T307A, E380A, and N434A (Shields et al. 2001, J. Biol. Chem. 276:6591). Other mutations may reduce binding of the Fc region to FcγRI, FcγRIIA, FcγRIIB, and/or FcγRIIIA without significantly reducing affinity for FcRn. For example, substitution of the Asn at position 297 of the Fc region with Ala or another amino acid removes a highly conserved N-glycosylation site and may result in reduced immunogenicity with concomitant prolonged half-life of the Fc region, as well as reduced binding to FcγRs (Routledge et al. 1995, Transplantation 60:847; Friend et al. 1999, Transplantation 68:1632; Shields et al. 1995, J. Biol. Chem. 276:6591). Amino acid modifications at positions 233-236 of IgG1 have been made that reduce binding to FcγRs (Ward and Ghetie 1995, Therapeutic Immunology 2:77 and Armour et al. 1999, Eur. J. Immunol. 29:2613). Some exemplary amino acid substitutions are described in U.S. Pat. Nos. 7,355,008 and 7,381,408, each incorporated by reference herein in its entirety.

Hydrophilic Heterologous Moiety

In some embodiments, the insulin analog described herein is covalently bonded to a hydrophilic moiety. Hydrophilic moieties can be attached to the insulin analog under any suitable conditions used to react a protein with an activated polymer molecule. Any means known in the art can be used, including via acylation, reductive alkylation, Michael addition, thiol alkylation or other chemoselective conjugation/ligation methods through a reactive group on the hydrophilic moiety (e.g., an aldehyde, amino, ester, thiol, α-haloacetyl, maleimido or hydrazino group) to a reactive group on the target compound (e.g., an aldehyde, amino, ester, thiol, α-haloacetyl, maleimido or hydrazino group). Activating groups which can be used to link the water soluble polymer to one or more proteins include without limitation sulfone, maleimide, sulfhydryl, thiol, triflate, tresylate, azidirine, oxirane, 5-pyridyl, and alpha-halogenated acyl group (e.g., alpha-iodo acetic acid, alpha-bromoacetic acid, alpha-chloroacetic acid). If attached to the peptide by reductive alkylation, the polymer selected should have a single reactive aldehyde so that the degree of polymerization is controlled. See, for example, Kinstler et al., Adv. Drug. Delivery Rev. 54: 477-485 (2002); Roberts et al., Adv. Drug Delivery Rev. 54: 459-476 (2002); and Zalipsky et al., Adv. Drug Delivery Rev. 16: 157-182 (1995). The hydrophilic moiety, e.g., polyethylene glycol chain, in accordance with some embodiments has a molecular weight selected from the range of about 500 to about 40,000 Daltons. In some embodiments the polyethylene glycol chain has a molecular weight selected from the range of about 500 to about 5,000 Daltons, or about 1,000 to about 5,000 Daltons. In another embodiment the hydrophilic moiety, e.g., polyethylene glycol chain, has a molecular weight of about 10,000 to about 20,000 Daltons. In yet other exemplary embodiments the hydrophilic moiety, e.g. polyethylene glycol chain, has a molecular weight of about 20,000 to about 40,000 Daltons. Linear or branched hydrophilic polymers are contemplated. Resulting preparations of conjugates may be essentially monodisperse or polydisperse, and may have about 0.5, 0.7, 1, 1.2, 1.5 or 2 polymer moieties per peptide.

In some embodiments, the native amino acid of the peptide is substituted with an amino acid having a side chain suitable for crosslinking with hydrophilic moieties, to facilitate linkage of the hydrophilic moiety to the peptide. Exemplary amino acids include Cys, Lys, Orn, homo-Cys, or acetyl phenylalanine (Ac-Phe). In other embodiments, an amino acid modified to comprise a hydrophilic group is added to the peptide at the N-terminus or C-terminus. In some embodiments, the peptide of the conjugate is conjugated to a hydrophilic moiety, e.g. PEG, via covalent linkage between a side chain of an amino acid of the peptide and the hydrophilic moiety.

rPEG Heterologous Moiety

In some embodiments, the conjugate comprises a insulin analog fused to an accessory peptide which is capable of forming an extended conformation similar to chemical PEG (e.g., a recombinant PEG (rPEG) molecule), such as those described in International Patent Application Publication No. WO2009/023270 and U.S. Patent Application Publication No. US2008/0286808. The rPEG molecule is not polyethylene glycol. The rPEG molecule in some aspects is a polypeptide comprising one or more of glycine, serine, glutamic acid, aspartic acid, alanine, or proline. In some aspects, the rPEG is a homopolymer, e.g., poly-glycine, poly-serine, poly-glutamic acid, poly-aspartic acid, poly-alanine, or poly-proline. In other embodiments, the rPEG comprises two types of amino acids repeated, e.g., poly(Gly-Ser), poly(Gly-Glu), poly(Gly-Ala), poly(Gly-Asp), poly(Gly-Pro), poly(Ser-Glu), etc. In some aspects, the rPEG comprises three different types of amino acids, e.g., poly(Gly-Ser-Glu). In specific aspects, the rPEG increases the half-life of the insulin analog. In some aspects, the rPEG comprises a net positive or net negative charge. The rPEG in some aspects lacks secondary structure. In some embodiments, the rPEG is greater than or equal to 10 amino acids in length and in some embodiments is about 40 to about 50 amino acids in length. The accessory peptide in some aspects is fused to the N- or C-terminus of the peptide of the invention through a peptide bond or a proteinase cleavage site. The rPEG in some aspects comprises an affinity tag or is linked to a PEG that is greater than 5 kDa. In some embodiments, the rPEG confers the conjugate of the invention with an increased hydrodynamic radius, serum half-life, protease resistance, or solubility and in some aspects confers the conjugate with decreased immunogenicity.

The conjugate moieties can be linked to the insulin analog via direct covalent linkage by reacting targeted amino acid residues of the peptide with an organic derivatizing agent that is capable of reacting with selected side chains or the N- or C-terminal residues of these targeted amino acids. Reactive groups on the peptide or conjugate moiety include, e.g., an aldehyde, amino, ester, thiol, α-haloacetyl, maleimido or hydrazino group. Derivatizing agents include, for example, maleimidobenzoyl sulfosuccinimide ester (conjugation through cysteine residues), N-hydroxysuccinimide (through lysine residues), glutaraldehyde, succinic anhydride or other agents known in the art. Alternatively, the conjugate moieties can be linked to the peptide indirectly through intermediate carriers, such as polysaccharide or polypeptide carriers. Examples of polysaccharide carriers include aminodextran. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier.

Multimers

The insulin analog may be part of a dimer, trimer or higher order multimer comprising at least two, three, or more peptides bound via a linker, wherein at least one or both peptides is a insulin analog. In one embodiment a single chain insulin analog is linked to either the A chain or the B chain of a second insulin polypeptide that is either a heteroduplex comprising the A and B chain or a second single chain insulin analog. The dimer may be a homodimer or heterodimer. In some embodiments, the linker is selected from the group consisting of a bifunctional thiol crosslinker and a bi-functional amine crosslinker. In certain embodiments, the linker is PEG, e.g., a 5 kDa PEG, 20 kDa PEG. In some embodiments, the linker is a disulfide bond. For example, each monomer of the dimer may comprise a Cys residue (e.g., a terminal or internally positioned Cys) and the sulfur atom of each Cys residue participates in the formation of the disulfide bond. In some aspects of the invention, the monomers are connected via terminal amino acids (e.g., N-terminal or C-terminal), via internal amino acids, or via a terminal amino acid of at least one monomer and an internal amino acid of at least one other monomer. In specific aspects, the monomers are not connected via an N-terminal amino acid. In some aspects, the monomers of the multimer are attached together in a "tail-to-tail" orientation in which the C-terminal amino acids of each monomer are attached together. In one embodiment the dimer comprises two single chain insulin analogs wherein the two insulin analogs are linked to one another via the amino acid side chains of an amino acid present in the linking moiety of each single chain insulin analog. A conjugate moiety may be covalently linked to any of the single chain insulin analogs described herein, including a dimer, trimer or higher order multimer.

In accordance with one embodiment a multimer is provided that comprises an IGF YL B chain analog disclosed herein (including prodrug and depot derivatives thereof). The multimer (e.g., a dimer) may be a homodimer or heterodimer, comprising peptides selected from the group consisting of native insulin, native IGF-1, native IGF-II, an insulin analog peptide and IGF analog peptides. In some embodiments, the linker is selected from the group consisting of a bifunctional thiol crosslinker and a bi-functional amine crosslinker. In certain embodiments, the linker is PEG, e.g., a 5 kDa PEG, 20 kDa PEG. In some embodiments, the linker is a disulfide bond.

Controlled Release Formulations

Alternatively, the insulin analogs described herein can be modified into a depot form, such that the manner in which the insulin analog of the present disclosure is released into the body to which it is administered is controlled with respect to time and location within the body (see, for example, U.S. Pat. No. 4,450,150). Depot forms of the insulin analogs of the present disclosures can be, for example, an implantable composition comprising the insulin analog of the present disclosure and a porous or non-porous material, such as a polymer, wherein the insulin analog of the present disclosures is encapsulated by or diffused throughout the material and/or degradation of the non-porous material. The depot is then implanted into the desired location within the body and the insulin analog of the present disclosures are released from the implant at a predetermined rate.

Alternatively, a large depot polymer can be linked to a self cleaving dipeptide element that is covalently bound to the insulin analog as described herein. In this embodiment, the depot polymer effectively sequesters the insulin analog at its site of administration until it is subsequently cleaved from the analog via a non-enzymatic reaction at a predetermined rate. Depot formulations of insulin analogs using a self cleaving dipeptide have been described in PCT/US2009/068713, the disclosure of which is incorporated herein. In one embodiment a insulin analog is provided comprising a dipeptide prodrug element wherein the dipeptide prodrug element is linked to a large polymer such as PEG or dextran.

Pharmaceutical compositions can be prepared that comprise the analogs and are formulated to have a desired in vivo release profile. In some aspects, the pharmaceutical composition is an immediate release, controlled release, sustained release, extended release, delayed release, or biphasic release formulation. Methods of formulating peptides or conjugates for controlled release are known in the art. See, for example, J Pharm 374: 46-52 (2009) and International Patent Application Publication Nos. WO 2008/130158, WO2004/033036; WO2000/032218; and WO 1999/040942. The instant compositions may further comprise, for example, micelles or liposomes, or some other encapsulated form, or may be administered in an extended release form to provide a prolonged storage and/or delivery effect. The disclosed pharmaceutical formulations may be administered according to any regime including, for example, daily (1 time per day, 2 times per day, 3 times per day, 4 times per day, 5 times per day, 6 times per day), every two days, every three days, every four days, every five days, every six days, weekly, bi-weekly, every three weeks, monthly, or bi-monthly.

Prodrug Derivatives of Insulin Analogs

The present disclosure also encompasses prodrug analogs of the insulin analog peptides disclosed herein. Advantageously, the prodrug formulations improve the therapeutic index of the underlying peptide and delay onset of action and enhance the half life of the insulin analog peptide. The disclosed prodrug chemistry can be chemically conjugated to active site amines to form amides that revert to the parent amine upon diketopiperazine formation and release of the prodrug element (see International patent application PCT/US2009/068713, the disclosure of which is expressly incorporated herein). This novel biologically friendly prodrug chemistry spontaneously degrades under physiological conditions (e.g. pH of about 7, at 37° C. in an aqueous environment) and is not reliant on enzymatic degradation.

The duration of the prodrug analog is determined by the selection of the dipeptide prodrug sequence, and thus allows for flexibility in prodrug formulation.

In one embodiment a prodrug is provided having a non-enzymatic activation half time (t½) of between 1-100 hrs under physiological conditions. Physiological conditions as disclosed herein are intended to include a temperature of about 35 to 40° C. and a pH of about 7.0 to about 7.4 and more typically include a pH of 7.2 to 7.4 and a temperature of 36 to 38° C. in an aqueous environment. In one embodiment a dipeptide, capable of undergoing diketopiperazine formation under physiological conditions, is covalently linked through an amide or ester linkage to the insulin analog (see International applications WO 2009/099763 and WO 2010/080607 the disclosures of which are incorporated herein).

Advantageously, the rate of cleavage, and thus activation of the prodrug, depends on the structure and stereochemistry of the dipeptide pro-moiety and also on the strength of the nucleophile. The prodrugs disclosed herein will ultimately be chemically converted to structures that can be recognized by the insulin/IGF receptor, wherein the speed of this chemical conversion will determine the time of onset and duration of in vivo biological action. The prodrug chemistry disclosed in this application relies upon an intramolecular chemical reaction that is not dependent upon additional chemical additives, or enzymes. The speed of conversion is controlled by the chemical nature of the dipeptide substituent and its cleavage under physiological conditions. Since physiological pH and temperature are tightly regulated within a highly defined range, the speed of conversion from prodrug to drug will exhibit high intra and interpatient reproducibility. In one embodiment a prodrug derivative of a single chain insulin analog is provided wherein the single chain insulin analog comprises a linking moiety of at least 18 amino acids, optionally comprising a glycoylation site, and/or optionally wherein one of the amino acids of the linking moiety is pegylated. In one embodiment the linking moiety comprises the sequence of SEQ ID NO: 66. Alternatively, or in addition to the pegylation of the amino acid of the linking moiety, one of the two amino acids of the dipeptide prodrug element can be pegylated. Alternatively, or in any combination with the above mentioned pegylated sites, the single chain insulin prodrug derivative can be pegylated at a position selected from the group consisting of A9, A14 and A15 of the A chain, at the amino terminal amino acid of the B chain or at any of positions B10, B22, B28 or B29 of the B chain or at any position of the linking moiety.

As disclosed herein prodrugs are provided wherein the insulin analog peptides have extended half lives of at least 1 hour, and more typically greater than 20 hours but less than 100 hours, and are converted to the active form at physiological conditions through a non-enzymatic reaction driven by inherent chemical instability. In one embodiment the a non-enzymatic activation t½ time of the prodrug is between 1-100 hrs, and more typically between 12 and 72 hours, and in one embodiment the t½ is between 24-48 hrs as measured by incubating the prodrug in a phosphate buffer solution (e.g., PBS) at 37° C. and pH of 7.2. In one embodiment the half life of the prodrugs is about 1, 8, 12, 20, 24, 48 or 72 hours. In one embodiment the half life of the prodrugs is about 100 hours or greater including half lives of up to about 168, 336, 504, 672 or 720 hours, and are converted to the active form at physiological conditions through a non-enzymatic reaction driven by inherent chemical instability. The half lives of the various prodrugs are calculated by using the formula $t_{1/2}=0.693/k$, where 'k' is the first order rate constant for the degradation of the prodrug. In one embodiment, activation of the prodrug occurs after cleavage of an amide bond linked dipeptide, and formation of a diketopiperazine or diketomorpholine, and the active insulin analog peptide.

In another embodiment, the dipeptide prodrug element is covalently bound to the insulin analog peptide via an amide linkage, and the dipeptide further comprises a depot polymer linked to dipeptide. In one embodiment two or more depot polymers are linked to a single dipeptide element. In one embodiment the depot polymer is linked to the side chain of one of the amino acids comprising the dipeptide prodrug element. The depot polymer is selected to be biocompatible and of sufficient size that the insulin analog, modified by covalent attachment of the dipeptide, remains sequestered at an injection site and/or incapable of interacting with its corresponding receptor upon administration to a patient. Subsequent cleavage of the dipeptide releases the insulin analog to interact with its intended target. The depot bearing dipeptide element can be linked to the insulin analog via an amide bond through any convenient amine group of the insulin analog, including an N-terminal amine or an amine bearing side chain of an internal natural or synthetic amino acid of the insulin analog. In one embodiment the depot bearing dipeptide element is linked to the amino group of a 4-amino phenylalanine present at position A19 of the analog.

In accordance with one embodiment the depot polymer is selected from biocompatible polymers known to those skilled in the art. The depot polymers typically have a size selected from a range of about 20,000 to 120,000 Daltons. In one embodiment the depot polymer has a size selected from a range of about 40,000 to 100,000 or about 40,000 to 80,000 Daltons. In one embodiment the depot polymer has a size of about 40,000, 50,000, 60,000, 70,000 or 80,000 Daltons. Suitable depot polymers include but are not limited to dextrans, polylactides, polyglycolides, caprolactone-based polymers, poly(caprolactone), polyanhydrides, polyamines, polyesteramides, polyorthoesters, polydioxanones, polyacetals, polyketals, polycarbonates, polyphosphoesters, polyesters, polybutylene terephthalate, polyorthocarbonates, polyphosphazenes, succinates, poly(malic acid), poly(amino acids), polyvinylpyrrolidone, polyethylene glycol, polyhydroxycellulose, polysaccharides, chitin, chitosan, hyaluronic acid, and copolymers, terpolymers and mixtures thereof, and biodegradable polymers and their copolymers including caprolactone-based polymers, polycaprolactones and copolymers which include polybutylene terephthalate. In one embodiment the depot polymer is selected from the group consisting of polyethylene glycol, dextran, polylactic acid, polyglycolic acid and a copolymer of lactic acid and glycolic acid, and in one specific embodiment the depot polymer is polyethylene glycol. In one embodiment the depot polymer is polyethylene glycol and the combined molecular weight of depot polymer(s) linked to the dipeptide element is about 40,000 to 80,000 Daltons.

Specific dipeptides composed of natural or synthetic amino acids have been identified that facilitate intramolecular decomposition under physiological conditions to release the active insulin analog. The dipeptide can be linked (via an amide bond) to an amino group present on the insulin analog, or an amino group introduced into the insulin analog by modification of the peptide sequence. In one embodiment the dipeptide structure is selected to resist cleavage by peptidases present in mammalian sera. Accordingly, in one embodiment the rate of cleavage of the dipeptide prodrug element from the bioactive peptide is not substantially enhanced (e.g., greater than 2×) when the reaction is conducted using physiological conditions in the presence of serum proteases relative to conducting the reaction in the absence of the proteases. Thus the cleavage half-life of the dipeptide prodrug element from the insulin analog (in PBS under physiological conditions) is not more than two, three, four or five fold the cleavage half-life of the dipeptide prodrug element from the insulin analog in a solution comprising an insulin degrading protease. In one embodiment the solution comprising the insulin degrading protease is serum, more particularly mammalian serum, including human serum.

In accordance with one embodiment the dipeptide prodrug element comprises the structure U-B, wherein U is an amino acid or a hydroxyl acid and B is an N-alkylated amino acid. The structure of U-B is selected, in one embodiment, wherein chemical cleavage of U-B from the insulin analog is at least about 90% complete within about 1 to about 720 hours in PBS under physiological conditions. In one embodiment the chemical cleavage half-life ($t_{1/2}$) of U-B from the insulin analog peptide is at least about 1 hour to about 1 week in PBS under physiological conditions. In one embodiment U, B, or the amino acid of the insulin analog to which U-B is linked is a non-coded amino acid. In some embodiments U and/or B is an amino acid in the D stereoisomer configuration. In some exemplary embodiments, U is an amino acid in the D stereoisomer configuration and B is an amino acid in the L stereoisomer configuration. In some exemplary embodiments, U is an amino acid in the L stereoisomer configuration and B is an amino acid in the D stereoisomer configuration. In some exemplary embodiments, U is an amino acid in the D stereoisomer configuration and B is an amino acid in the D stereoisomer configuration. In one embodiment B is an N-alkylated amino acid but is not proline. In one embodiment the N-alkylated group of amino acid B is a $C_1$-$C_{18}$ alkyl, and in one embodiment the N-alkylated group is $C_1$-$C_6$ alkyl. In one embodiment U is an amino acid having a disubstitution at the alpha carbon.

In one embodiment one or more dipeptide elements are linked to insulin analog through an amide bond formed through one or more amino groups selected from the N-terminal amino group of the B chain, or the side chain amino group of an amino acid present in the insulin analog. In one embodiment the insulin analog comprises two dipeptide elements, wherein the dipeptide elements are optionally pegylated, alkylated, acylated or linked to a depot polymer. In accordance with one embodiment the dipeptide extension is covalently linked to a insulin analog through the side chain amine of a lysine residue that resides at or near the active site. In one embodiment the dipeptide extension is attached through a synthetic amino acid or a modified amino acid, wherein the synthetic amino acid or modified amino acid exhibits a functional group suitable for covalent attachment of the dipeptide extension (e.g., the aromatic amine of an amino-phenylalanine). In accordance with one embodiment one or more dipeptide elements are linked to the insulin analog at an amino group selected from the N-terminal amino group of the B chain, or the side chain amino group of an aromatic amine of a 4-amino-phenylalanine residue present at a position corresponding to position A19, B16 or B25 of native insulin.

The dipeptide prodrug element is designed to spontaneously cleave its amide linkage to the insulin analog under physiological conditions and in the absence of enzymatic activity. In one embodiment the N-terminal amino acid of the dipeptide prodrug element comprises a C-alkylated amino acid (e.g. amino isobutyric acid). In one embodiment the C-terminal amino acid of the dipeptide prodrug element comprises an N-alkylated amino acid (e.g., proline or N-methyl glycine). In one embodiment the dipeptide comprises the sequence of an N-terminal C-alkylated amino acid followed by an N-alkylated amino acid.

Figure 3:
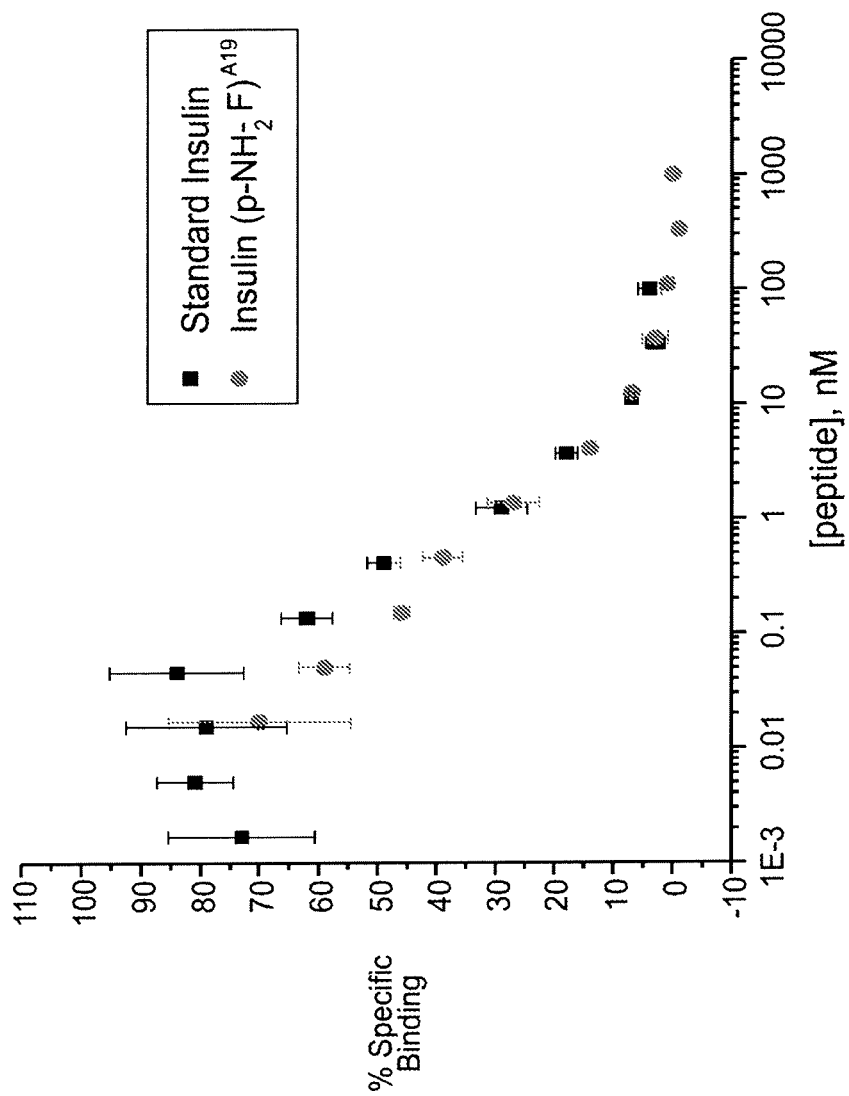
FIG. 3 is a graph comparing relative insulin receptor binding of native insulin and the A19 insulin analog (Insulin (p-NH$_2$—F)$^{19}$). As indicated by the data presented in the graph, the two molecules have similar binding activities.

Applicants have discovered that the selective insertion of a 4-amino phenylalanine amino acid moiety for the native tyrosine at position 19 of the A chain can be accommodated without loss in potency of the insulin peptide (see FIG. 3). Subsequent chemical amidation of this active site amino group with the dipeptide prodrug element disclosed herein dramatically lessens insulin receptor binding activity and thus provides a suitable prodrug of insulin (see FIG. 7-12, data provided for the IGF1Y$^{16}$L$^{17}$ (p-NH$_2$—F)$^{A19}$ analog which has been demonstrated to have comparable activity as insulin (p-NH$_2$—F)$^{A19}$, see FIG. 4). Applicants have discovered that a similar modification can be made to the IGF$^{B16B17}$ analog peptides to provide a suitable attachment site for prodrug chemistry. Accordingly, in one embodiment the dipeptide prodrug element is linked to the aromatic ring of an A19 4-aminophenylalanine of an insulin (p-NH$_2$—F)$^{A19}$ or IGF$^{B16B17}$ insulin analog peptide via an amide bond, wherein the C-terminal amino acid of the dipeptide comprises an N-alkylated amino acid and the N-terminal amino acid of the dipeptide is any amino acid.

The dipeptide prodrug moiety can also be attached to additional sites of an insulin (p-NH$_2$—F)$^{A19}$ or IGF$^{B16B17}$ insulin analog peptide to prepare insulin (p-NH$_2$—F)$^{A19}$ or IGF$^{B16B17}$ insulin analog prodrug derivatives. In accordance with one embodiment an IGF$^{B16B17}$ insulin analog prodrug derivative is provided comprising an IGF$^{B16B17}$ B chain with a dipeptide prodrug element linked via an amide bond to the N-terminal amino group of the B chain, or the side chain amino group of an aromatic amine of a 4-amino-phenylalanine residue present at a position corresponding to A19, B16 or B25 of native insulin or present in the linking moiety. The IGF$^{B16B17}$ insulin analog prodrug derivative may comprise a native insulin A chain or a native IGF-1 A chain or any analogs thereof disclosed herein. In one embodiment the dipeptide comprises an N-terminal C-alkylated amino acid followed by an N-alkylated amino acid. In accordance with one embodiment a single chain insulin analog prodrug derivative is provided wherein the A chain and B chain comprising the analog comprises the sequence of SEQ ID NO: 1 and SEQ ID NO: 2, respectively, or may comprise an analog of SEQ ID NO: 1 and/or SEQ ID NO: 2 wherein the analogs include substitution of the amino acid at position A19, B16 or B25 with a 4-amino phenylalanine and/or one or more amino acid substitutions at positions corresponding to positions A5, A8, A9, A10, A14, A15, A17, A18, A19 and A21, B1, B2, B3, B4, B5, B9, B10, B13, B14, B20, B22, B23, B26, B27, B28, B29 and B30 of native insulin, or deletions of any or all of corresponding positions B1-4 and B26-30, relative to native insulin. In one embodiment the dipeptide is linked to an N-terminal amino group of the B chain of the insulin analog, wherein the C-terminal amino acid of the dipeptide comprises an N-alkylated amino acid and the N-terminal amino acid of the dipeptide is any amino acid, with the proviso that when the C-terminal amino acid of the dipeptide is proline, the N-terminal amino acid of the dipeptide comprises a C-alkylated amino acid.

In one embodiment the dipeptide prodrug element comprises the general structure of Formula X:

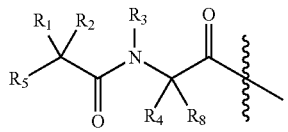

wherein $R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl (W)$C_1$-$C_{12}$ alkyl, wherein W is a heteroatom selected from the group consisting of N, S and O, or $R_1$ and $R_2$ together with the atoms to which they are attached form a $C_3$-$C_{12}$ cycloalkyl or aryl; or $R_4$ and $R_8$ together with the atoms to which they are attached form a $C_3$-$C_6$ cycloalkyl;

$R_3$ is selected from the group consisting of $C_1$-$C_{18}$ alkyl, ($C_1$-$C_{18}$ alkyl)OH, ($C_1$-$C_{18}$ alkyl)NH$_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)$R_7$, and ($C_1$-$C_4$ alkyl)($C_3$-$C_9$ heteroaryl) or $R_4$ and $R_3$ together with the atoms to which they are attached form a 4, 5 or 6 member heterocyclic ring;

$R_5$ is NHR$_6$ or OH;

$R_6$ is H, $C_1$-$C_8$ alkyl or $R_6$ and $R_2$ together with the atoms to which they are attached form a 4, 5 or 6 member heterocyclic ring; and $R_7$ is selected from the group consisting of H and OH. In one embodiment when the prodrug element is linked to the N-terminal amine of the insulin analog and $R_4$ and $R_3$ together with the atoms to which they are attached form a 4, 5 or 6 member heterocyclic ring, then at least one of $R_1$ and $R_2$ are other than H. In one embodiment an amino acid side chain of the dipeptide element is acylated with an acyl group of sufficient size to bind serum albumin. The acyl group can be linear or branched, and in one embodiment is a C16 to C30 fatty acid. For example, the acyl group can be any of a C16 fatty acid, C18 fatty acid, C20 fatty acid, C22 fatty acid, C24 fatty acid, C26 fatty acid, C28 fatty acid, or a C30 fatty acid. In some embodiments, the acyl group is a C16 to C20 fatty acid, e.g., a C18 fatty acid or a C20 fatty acid.

In one embodiment the prodrug element of Formula X is provided wherein $R_1$ is selected from the group consisting of H and $C_1$-$C_8$ alkyl; and $R_2$, $R_8$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$) NH$_2$, ($C_0$-$C_4$ alkyl)($C_3$-$C_6$ cycloalkyl), ($C_0$-$C_4$ alkyl)($C_6$-$C_{10}$ aryl)$R_7$, and CH$_2$($C_5$-$C_9$ heteroaryl), or $R_1$ and $R_2$ together with the atoms to which they are attached form a $C_3$-$C_8$ cycloalkyl ring;

$R_3$ is selected from the group consisting of $C_1$-$C_8$ alkyl, ($C_1$-$C_4$ alkyl)OH, ($C_1$-$C_4$ alkyl)SH, ($C_1$-$C_4$ alkyl)NH$_2$, ($C_3$-$C_6$)cycloalkyl or $R_4$ and $R_3$ together with the atoms to which they are attached form a 5 or 6 member heterocyclic ring;

$R_5$ is NHR$_6$ or OH;

$R_6$ is H, or $R_6$ and $R_2$ together with the atoms to which they are attached form a 5 or 6 member heterocyclic ring; and $R_7$ is selected from the group consisting of H and OH and $R_8$ is H. In one embodiment $R_3$ is $C_1$-$C_8$ alkyl and $R_4$ is selected from the group consisting of H, $C_1$-$C_6$ alkyl, CH$_2$OH, ($C_0$-$C_4$ alkyl)($C_6$-$C_{10}$ aryl)$R_7$, and CH$_2$($C_5$-$C_9$ heteroaryl) or $R_4$ and $R_3$ together with the atoms to which they are attached form a 5 or 6 member heterocyclic ring. In a further embodiment $R_5$ is NHR$_6$ and $R_8$ is H.

In accordance with one embodiment the dipeptide element comprises a compound having the general structure of Formula X:

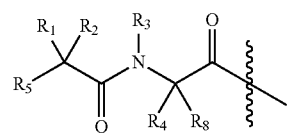

wherein $R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl ($W_1$)$C_1$-$C_{12}$ alkyl, wherein $W_1$ is a heteroatom selected from the group consisting of N, S and O, or $R_1$ and $R_2$ together with the atoms to which they are attached form a $C_3$-$C_{12}$ cycloalkyl; or $R_4$ and $R_8$ together with the atoms to which they are attached form a $C_3$-$C_6$ cycloalkyl;

$R_3$ is selected from the group consisting of $C_1$-$C_{18}$ alkyl, ($C_1$-$C_{18}$ alkyl)OH, ($C_1$-$C_{18}$ alkyl)NH$_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)$R_7$, and ($C_1$-$C_4$ alkyl) ($C_3$-$C_9$ heteroaryl) or $R_4$ and $R_3$ together with the atoms to which they are attached form a 4, 5 or 6 member heterocyclic ring;

$R_5$ is NHR$_6$ or OH;

$R_6$ is H, $C_1$-$C_8$ alkyl or $R_6$ and $R_1$ together with the atoms to which they are attached form a 4, 5 or 6 member heterocyclic ring; and $R_7$ is selected from the group consisting of H, OH, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo.

In another embodiment the dipeptide prodrug element comprises the general structure:

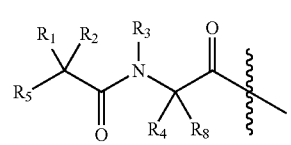

wherein $R_1$ and $R_8$ are independently H or $C_1$-$C_8$ alkyl;

$R_2$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2$+) NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)R$_7$, and CH$_2$($C_3$-$C_9$ heteroaryl), or $R_1$ and $R_2$ together with the atoms to which they are attached form a $C_3$-$C_{12}$ cycloalkyl;

$R_3$ is selected from the group consisting of $C_1$-$C_8$ alkyl, ($C_1$-$C_4$ alkyl)OH, ($C_1$-$C_4$ alkyl)NH$_2$, ($C_1$-$C_4$ alkyl)SH, ($C_3$-$C_6$)cycloalkyl or $R_4$ and $R_3$ together with the atoms to which they are attached form a 5 or 6 member heterocyclic ring;

$R_5$ is NHR$_6$ or OH;

$R_6$ is H, $C_1$-$C_8$ alkyl, or $R_6$ and $R_2$ together with the atoms to which they are attached form a 5 or 6 member heterocyclic ring; and $R_7$ is selected from the group consisting of H, OH, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH and halo, provided that when $R_4$ and $R_3$ together with the atoms to which they are attached form a 5 or 6 member heterocyclic ring, both $R_1$ and $R_2$ are not H. In one embodiment $R_7$ is H or OH. In one embodiment either the first amino acid and/or the second amino acid of the dipeptide prodrug element is an amino acid in the D stereoisomer configuration.

In a further embodiment the prodrug element of Formula X is provided wherein $R_1$ is selected from the group consisting of H and $C_1$-$C_8$ alkyl; and $R_2$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$) NH$_2$, ($C_0$-$C_4$ alkyl)($C_3$-$C_6$ cycloalkyl), ($C_0$-$C_4$ alkyl)($C_6$-$C_{10}$ aryl)R$_7$, and CH$_2$($C_5$-$C_9$ heteroaryl), or $R_1$ and $R_2$ together with the atoms to which they are attached form a $C_3$-$C_8$ cycloalkyl ring;

$R_3$ is selected from the group consisting of $C_1$-$C_8$ alkyl, ($C_1$-$C_4$ alkyl)OH, ($C_1$-$C_4$ alkyl)SH, ($C_1$-$C_4$ alkyl)NH$_2$, ($C_3$-$C_6$)cycloalkyl or $R_4$ and $R_3$ together with the atoms to which they are attached form a 5 or 6 member heterocyclic ring;

$R_5$ is NHR$_6$ or OH;

$R_6$ is H, or $R_6$ and $R_2$ together with the atoms to which they are attached form a 5 or 6 member heterocyclic ring;

$R_7$ is selected from the group consisting of hydrogen, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH and halo, and $R_8$ is H, provided that when the dipeptide element is linked to an N terminal amine and $R_4$ and $R_3$ together with the atoms to which they are attached form a 5 or 6 member heterocyclic ring, both $R_1$ and $R_2$ are not H. In one embodiment either the first amino acid and/or the second amino acid of the dipeptide prodrug element is an amino acid in the D stereoisomer configuration.

In other embodiments the dipeptide prodrug element has the structure of Formula X, wherein $R_1$ and $R_8$ are independently H or $C_1$-$C_8$ alkyl;

$R_2$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2$+) NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)R$_7$, and CH$_2$($C_3$-$C_9$ heteroaryl), or $R_1$ and $R_2$ together with the atoms to which they are attached form a $C_3$-$C_{12}$ cycloalkyl;

$R_3$ is $C_1$-$C_{18}$ alkyl;

$R_5$ is NHR$_6$;

$R_6$ is H or $C_1$-$C_8$ alkyl; and $R_7$ is selected from the group consisting of hydrogen, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo.

In a further embodiment the dipeptide prodrug element has the structure of Formula X, wherein $R_1$ and $R_2$ are independently $C_1$-$C_{18}$ alkyl or ($C_0$-$C_4$ alkyl)($C_6$-$C_{10}$ aryl)R$_7$; or $R_1$ and $R_2$ are linked through —(CH$_2$)$_p$, wherein p is 2-9;

$R_3$ is $C_1$-$C_{18}$ alkyl;

$R_4$ and $R_8$ are each hydrogen;

$R_5$ is NH$_2$; and $R_7$ is selected from the group consisting of hydrogen, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo.

In a further embodiment the dipeptide prodrug element has the structure of Formula X, wherein $R_1$ and $R_2$ are independently selected from the group consisting of hydrogen, $C_1$-$C_{18}$ alkyl, ($C_1$-$C_{18}$ alkyl)OH, ($C_1$-$C_4$ alkyl)NH$_2$, and ($C_0$-$C_4$ alkyl)($C_6$-$C_{10}$ aryl)R$_7$, or $R_1$ and $R_2$ are linked through (CH$_2$)$_p$, wherein p is 2-9;

$R_3$ is $C_1$-$C_{18}$ alkyl or $R_3$ and $R_4$ together with the atoms to which they are attached form a 4-12 heterocyclic ring;

$R_4$ and $R_8$ are independently selected from the group consisting of hydrogen, $C_1$-$C_8$ alkyl and ($C_0$-$C_4$ alkyl)($C_6$-$C_{10}$ aryl)R$_7$;

$R_5$ is NH$_2$; and $R_7$ is selected from the group consisting of H, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo, with the proviso that both $R_1$ and $R_2$ are not hydrogen and provided that at least one of $R_4$ or $R_8$ is hydrogen.

In another embodiment the dipeptide prodrug element has the structure of Formula X, wherein $R_1$ and $R_2$ are independently selected from the group consisting of hydrogen, $C_1$-$C_8$ alkyl and ($C_1$-$C_4$ alkyl)NH$_2$, or $R_1$ and $R_2$ are linked through (CH$_2$)$_p$, wherein p is 2-9;

$R_3$ is $C_1$-$C_8$ alkyl or $R_3$ and $R_4$ together with the atoms to which they are attached form a 4-6 heterocyclic ring;

$R_4$ is selected from the group consisting of hydrogen and $C_1$-$C_8$ alkyl;

$R_8$ is hydrogen; and $R_5$ is NH$_2$, with the proviso that both $R_1$ and $R_2$ are not hydrogen.

In a further embodiment the dipeptide prodrug element has the structure of Formula X, wherein $R_1$ and $R_2$ are independently selected from the group consisting of hydrogen, $C_1$-$C_8$ alkyl and ($C_1$-$C_4$ alkyl)NH$_2$;

$R_3$ is $C_1$-$C_6$ alkyl;

$R_4$ and $R_8$ are each hydrogen; and $R_5$ is $NH_2$, with the proviso that both $R_1$ and $R_2$ are not hydrogen.

In another embodiment the dipeptide prodrug element has the structure of Formula X, wherein $R_1$ and $R_2$ are independently selected from the group consisting of hydrogen and $C_1$-$C_8$ alkyl, ($C_1$-$C_4$ alkyl)$NH_2$, or $R_1$ and $R_2$ are linked through $(CH_2)_p$, wherein p is 2-9;

$R_3$ is $C_1$-$C_8$ alkyl;

$R_4$ is ($C_0$-$C_4$ alkyl)($C_6$-$C_{10}$ aryl)$R_7$;

$R_5$ is $NH_2$;

$R_7$ is selected from the group consisting of hydrogen, $C_1$-$C_8$ alkyl and ($C_0$-$C_4$ alkyl)OH; and $R_8$ is hydrogen, with the proviso that both $R_1$ and $R_2$ are not hydrogen.

In another embodiment the dipeptide prodrug element has the structure of Formula X, wherein $R_1$ is selected from the group consisting of hydrogen, $C_1$-$C_8$ alkyl and ($C_0$-$C_4$ alkyl)($C_6$-$C_{10}$ aryl)$R_7$;

$R_2$ is hydrogen;

$R_3$ is $C_1$-$C_{18}$ alkyl;

$R_4$ and $R_8$ are each hydrogen;

$R_5$ is $NHR_6$ or OH;

$R_6$ is H, $C_1$-$C_8$ alkyl, or $R_6$ and $R_1$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo, with the proviso that, if $R_1$ is alkyl or ($C_0$-$C_4$ alkyl)($C_6$-$C_{10}$ aryl)$R_7$, then $R_1$ and $R_6$ together with the atoms to which they are attached form a 4-11 heterocyclic ring.

In one embodiment a single chain insulin analog is provided comprising an A chain and a B chain wherein the carboxy terminus of the B chain is linked to the amino terminus of said A chain via a linking moiety comprising a CTP peptide. In one embodiment a single chain insulin analog is provided that comprises the structure: IB-LM-IA, wherein IB comprises the sequence $R_{22}$-$X_{25}$LCG$X_{29}$$X_{30}$LV$X_{33}$$X_{34}$LYLVCG$X_{41}$$X_{42}$GF$X_{45}$ (SEQ ID NO: 17), LM is a linking moiety comprising a peptide of SEQ ID NO: 66 or a contiguous 29 amino acid sequence having at least 58% of the amino acids being serine or proline, wherein the linking moiety covalently links IB to IA, and IA comprises the sequence GW$X_4$$X_5$CC$X_8$$X_9$$X_{10}$C$X_{12}$L$X_{14}$$X_{15}$L$X_{17}$$X_{18}$$X_{19}$C$X_{21}$-$R_{13}$ (SEQ ID NO: 18), wherein the amino acid at the designation $X_{45}$ is phenylalanine or tyrosine that is directly bound to the linking moiety, LM. In one embodiment a single chain insulin analog is provided that comprises the structure: IB-LM-IA, wherein IB comprises the sequence J-$R_{23}$-$R_{22}$-$X_{25}$LCG$X_{29}$$X_{30}$LV$X_{33}$$X_{34}$L$X_{36}$LVCG$X_{41}$$X_{42}$GF$X_{45}$ (SEQ ID NO: 16) or a sequence that differs from SEQ ID NO: 16 by 1 to 3 amino acid modifications selected from positions 5, 6, 9, 10, 16, 18, 19 and 21 of SEQ ID NO: 16, LM is a linking moiety comprising a peptide of SEQ ID NO: 66 or a contiguous 29 amino acid sequence having at least 58% of the amino acids being serine or proline, wherein the linking moiety covalently links IB to IA, and IA comprises the sequence GIV$X_4$$X_5$CC$X_8$$X_9$$X_{10}$C$X_{12}$L$X_{14}$$X_{15}$L$X_{17}$$X_{18}$$X_{19}$C$X_{21}$-$R_{13}$ (SEQ ID NO: 18) or a sequence that differs from SEQ ID NO: 15 by 1 to 3 amino acid modifications selected from positions 5, 8, 9, 10, 14, 15, 17, 18 and 21 of SEQ ID NO: 16, wherein J is H or a dipeptide element comprising the general structure of U-B, wherein U is an amino acid or a hydroxyl acid and B is an N-alkylated amino acid linked through an amide bond;

$X_4$ is glutamic acid or aspartic acid;

$X_5$ is glutamine or glutamic acid $X_8$ is histidine, threonine or phenylalanine;

$X_9$ is serine, arginine, ornithine, lysine or alanine;

$X_{10}$ is isoleucine or serine;

$X_{12}$ is serine or aspartic acid $X_{14}$ is tyrosine, arginine, ornithine, lysine or alanine;

$X_{15}$ is glutamine, glutamic acid, arginine, alanine, ornithine, lysine or leucine;

$X_{17}$ is glutamic acid or glutamine;

$X_{18}$ is methionine, asparagine, glutamine, aspartic acid, glutamic acid or threonine;

$X_{19}$ is an amino acid of the general structure:

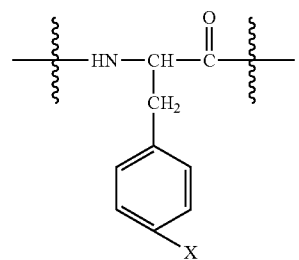

wherein X is selected from the group consisting of OH or $NHR_{10}$, wherein $R_{10}$ is H or a dipeptide element comprising the general structure U-B, wherein U is an amino acid or a hydroxyl acid and B is an N-alkylated amino acid;

$X_{21}$ is selected from the group consisting of alanine, glycine, serine, valine, threonine, isoleucine, leucine, glutamine, glutamic acid, asparagine, aspartic acid, histidine, tryptophan, tyrosine, and methionine;

$X_{25}$ is histidine or threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid, glutamine and glutamic acid;

$X_{34}$ is selected from the group consisting of alanine and threonine;

$X_{36}$ is an amino acid of the general structure

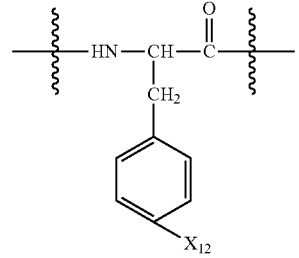

wherein $X_{12}$ is selected from the group consisting of OH and $NHR_{11}$, wherein $R_{11}$ is a dipeptide element comprising the general structure U-B;

$X_{41}$ is selected from the group consisting of glutamic acid, aspartic acid or asparagine;

$X_{42}$ is selected from the group consisting of alanine, ornithine, lysine and arginine;

$X_{45}$ is an amino acid of the general structure

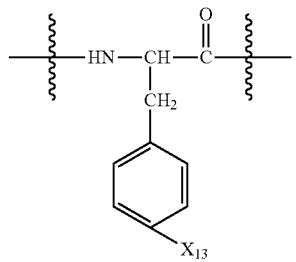

wherein $X_{13}$ is selected from the group consisting of H, OH and $NHR_{12}$, wherein $R_{12}$ is H or dipeptide element comprising the general structure U-B;

$R_{22}$ is selected from the group consisting of AYRPSE (SEQ ID NO: 11), FVNQ (SEQ ID NO: 10), PGPE (SEQ ID NO: 9), a tripeptide glycine-proline-glutamic acid, a tripeptide valine-asparagine-glutamine, a dipeptide proline-glutamic acid, a dipeptide asparagine-glutamine, glutamine, glutamic acid and an N-terminal amine;

$R_{23}$ is a bond or an amino sequence comprising 1 to 6 charged amino acids; and $R_{13}$ is COOH or $CONH_2$. In one embodiment, only one of J, $R_{10}$, $R_{11}$ and $R_{12}$ is U-B. In one embodiment $X_{12}$ is OH and $X_{13}$ is H or OH and J and/or X is U-B. In one embodiment $X_{12}$ is OH and $X_{13}$ is OH, $R_{23}$ is a bond, J is H and X is U-B. In a further embodiment $X_8$, $X_{25}$ and $X_{30}$ are each histidine. In one embodiment the linking moiety comprises the sequence SSSSRAPPPSLPSPSRLPGPSDTPIL-PQK (SEQ ID NO: 79) or SSSSKAPPPSLPSPSRLPGPS-DTPILPQR (SEQ ID NO: 64). In another embodiment the single chain insulin analog peptide comprises an A chain peptide sequence of SEQ ID NO: 15 and a B chain peptide sequence of SEQ ID NO: 16. In one embodiment $R_{23}$ is a bond or comprises an amino sequence $X_{60}X_{61}X_{62}X_{63}X_{64}X_{65}K$ (SEQ ID NO: 19), wherein $X_{60}$ is selected from the group consisting of glycine, glutamic acid and aspartic acid, and $X_{61}$, $X_{62}$, $X_{63}$ $X_{64}$ and $X_{65}$ are independently glutamic acid or aspartic acid. In one embodiment U is a C-alkylated amino acid or C-alkylated hydroxyl acid and B is an N-alkylated amino acid.

In one embodiment a single chain insulin analog is provided that comprises the structure: IB-LM-IA, wherein IB comprises the sequence $J-R_{23}R_{22}-X_{25}LCGX_{29}X_{30}LVEALYLVCG$ ERGFF (SEQ ID NO: 24), LM is a linking moiety comprising a CTP peptide as disclosed herein and IA comprises the sequence $GIVEQCCX_8SICSLYQLX_{17}NX_{19}CX_{23}$ (SEQ ID NO: 23) wherein $X_8$ is selected from the group consisting of threonine and histidine;

$X_{17}$ is glutamic acid or glutamine;

$X_{19}$ is an amino acid of the general structure:

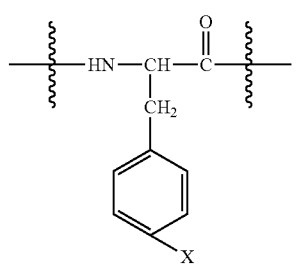

wherein X is selected from the group consisting of OH or $NHR_{10}$, wherein $R_{10}$ is H or a dipeptide element comprising the general structure U-B, wherein U is an amino acid or a hydroxyl acid and B is an N-alkylated amino acid;

$X_{23}$ is asparagine or glycine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$R_{22}$ is selected from the group consisting of FVNQ (SEQ ID NO: 10), a tripeptide valine-asparagine-glutamine, a dipeptide asparagine-glutamine, glutamine, glutamic acid and an N-terminal amine; and $R_{23}$ is a bond or an amino sequence comprising 1 to 6 charged amino acids. In a further embodiment the B chain comprises the sequence $X_{22}VNQX_{25}LCGX_{29}X_{30}LVEALYLVCGERGFFYT-Z_1-B_1$ (SEQ ID NO: 25) wherein $X_{22}$ is selected from the group consisting of phenylalanine and desamino-phenylalanine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$Z_1$ is a dipeptide selected from the group consisting of aspartate-lysine, lysine-proline, and proline-lysine; and $B_1$ is selected from the group consisting of threonine, alanine or a threonine-arginine-arginine tripeptide.

In accordance with one embodiment a single chain insulin analog is provided that comprises the structure: IB-LM-IA, wherein IB comprises the sequence $X_{25}LCGX_{29}X_{30}LVEALYLVCG$ ERGFF (SEQ ID NO: 24), LM is a linking moiety as disclosed herein that covalently links IB to IA, and IA comprises the sequence $GIVEQCCX_8SICSLYQLENX_{19}CX_{21}$ (SEQ ID NO: 26), wherein the C-terminal phenylalanine residue of SEQ ID NO: 24 is directly covalently bound to the linking moiety, LM, in the absence of any intervening amino acids.

In one embodiment a single chain insulin analog is provided that comprises the structure: IB-LM-IA, wherein IB comprises the sequence $J-R_{23}-R_{22}-X_{25}LCGX_{29}X_{30}LVX_{33}X_{34}LYLVCGDX_{42}GFX_{45}$ (SEQ ID NO: 28), LM is a linking moiety as disclosed herein and IA comprises the sequence $GIVX_4ECCX_8X_9SCDLX_{14}X_{15}LX_{17}X_{18}X_{19}CX_{21}-R_{13}$ (SEQ ID NO: 15) wherein J is H or a dipeptide element comprising the general structure of U-B, wherein U is an amino acid or a hydroxyl acid and B is an N-alkylated amino acid linked through an amide bond;

$X_4$ is aspartic acid or glutamic acid;

$X_8$ is histidine or phenylalanine;

$X_9$ and $X_{14}$ are independently selected from arginine, ornithine, lysine or alanine;

$X_{15}$ is arginine, lysine, ornithine or leucine;

$X_{17}$ is glutamic acid or glutamine;

$X_{18}$ is methionine, asparagine or threonine;

$X_{19}$ is an amino acid of the general structure:

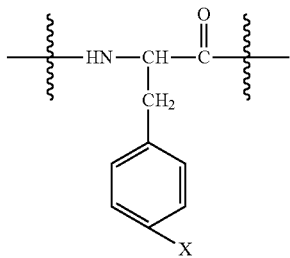

wherein X is selected from the group consisting of OH or $NHR_{10}$, wherein $R_{10}$ is H or a dipeptide element comprising the general structure U-B, wherein U is an amino acid or a hydroxyl acid and B is an N-alkylated amino acid;

$X_{21}$ is alanine, glycine or asparagine;

$R_{22}$ is selected from the group consisting of a covalent bond, AYRPSE (SEQ ID NO: 11), a glycine-proline-glutamic acid tripeptide, a proline-glutamic acid dipeptide and glutamic acid;

$R_{23}$ is a bond or an amino sequence comprising 1 to 6 charged amino acids;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid and glutamic acid;

$X_{34}$ is selected from the group consisting of alanine and threonine;

$X_{42}$ is selected from the group consisting of alanine, lysine ornithine and arginine;

$X_{45}$ is an amino acid of the general structure

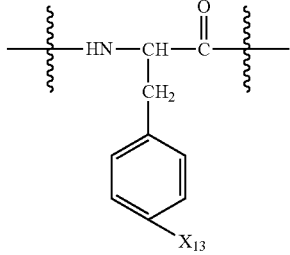

wherein $X_{13}$ is selected from the group consisting of H, OH and $NHR_{12}$, wherein $R_{12}$ is a dipeptide element comprising the general structure U-B;

and $R_{13}$ is COOH or $CONH_2$, with the proviso that one and only one of J, X, and $X_{13}$, comprises U-B. In one embodiment J is H, and $X_{13}$ is OH, and X is NH-U-B.

In one embodiment U and B of the dipeptide prodrug element U-B are selected to inhibit enzymatic cleavage of the U-B dipeptide from an insulin peptide by enzymes found in mammalian serum. In one embodiment U and/or B are selected such that the cleavage half-life of U-B from the insulin peptide, in PBS under physiological conditions, is not more than two fold the cleavage half-life of U-B from the insulin peptide in a solution comprising an insulin degrading protease (i.e., cleavage of U-B from the insulin prodrug does not occur at a rate more than 2× faster in the presence of the protease and physiological conditions relative to identical conditions in the absence of the enzyme). In one embodiment U, B, or the amino acid of the insulin peptide to which U-B is linked is a non-coded amino acid. In one embodiment U and/or B is an amino acid in the D stereoisomer configuration. In some exemplary embodiments, U is an amino acid in the D stereoisomer configuration and B is an amino acid in the L stereoisomer configuration. In some exemplary embodiments, U is an amino acid in the L stereoisomer configuration and B is an amino acid in the D stereoisomer configuration. In some exemplary embodiments, U is an amino acid in the D stereoisomer configuration and B is an amino acid in the D stereoisomer configuration. In one embodiment U-B is a dipeptide comprising the structure of Formula X as defined herein. In one embodiment B is an N-alkylated amino acid but is not proline.

In accordance with one embodiment a single chain insulin agonist polypeptide comprising a B chain and A chain of human insulin, or analogs or derivative thereof is provided, wherein the carboxy terminus of the B chain is linked to the amino terminus of the A chain via a linking moiety. In one embodiment the linking moiety comprises a polyethylene glycol of 6-16 monomer units, and a CTP peptide.

In one embodiment the single chain insulin analog comprises the structure IB-LM-IA, wherein IB comprises the sequence J-$R_{23}R_{22}$-$X_{25}$LCG$X_{29}X_{30}$LV$X_{33}X_{34}$L$X_{36}$LVCG$X_{41}X_{42}$GF$X_{45}$ SEQ ID NO: 16);

LM is a linking moiety comprising a CTP peptide as disclosed herein, and

IA comprises the sequence GIV$X_4X_5$CC$X_8X_9X_{10}$C$X_{12}$L$X_{14}X_{15}$L$X_{17}X_{18}X_{19}$C$X_{21}$-$R_{13}$ (SEQ ID NO: 18) wherein J is H or a dipeptide comprising the general structure of U-B, wherein U is an amino acid or a hydroxyl acid and B is an N-alkylated amino acid linked through an amide bond;

$X_4$ is glutamic acid or aspartic acid;

$X_5$ is glutamine or glutamic acid $X_8$ is histidine, threonine or phenylalanine;

$X_9$ is serine, arginine, lysine, ornithine or alanine;

$X_{10}$ is isoleucine or serine;

$X_{12}$ is serine or aspartic acid $X_{14}$ is tyrosine, arginine, lysine, ornithine or alanine;

$X_{15}$ is glutamine, glutamic acid, arginine, alanine, lysine, ornithine or leucine;

$X_{17}$ is glutamic acid or glutamine;

$X_{18}$ is methionine, asparagine, glutamine, aspartic acid, glutamic acid or threonine;

$X_{19}$ is an amino acid of the general structure:

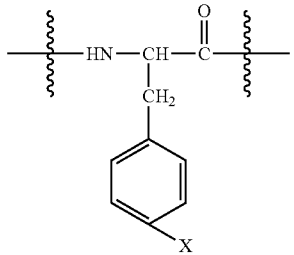

wherein X is selected from the group consisting of OH, OCH$_3$ or NHR$_{10}$, wherein R$_{10}$ is H or a dipeptide element comprising the general structure U-B, wherein U is an amino acid or a hydroxyl acid and B is an N-alkylated amino acid;

X$_{21}$ is selected from the group consisting of alanine, glycine, serine, valine, threonine, isoleucine, leucine, glutamine, glutamic acid, asparagine, aspartic acid, histidine, tryptophan, tyrosine, and methionine;

X$_{25}$ is histidine or threonine;

X$_{29}$ is selected from the group consisting of alanine, glycine and serine;

X$_{30}$ is selected from the group consisting of histidine, aspartic acid, glutamic acid, homocysteic acid and cysteic acid;

X$_{33}$ is selected from the group consisting of aspartic acid, glutamine and glutamic acid;

X$_{34}$ is selected from the group consisting of alanine and threonine;

X$_{36}$ is an amino acid of the general structure

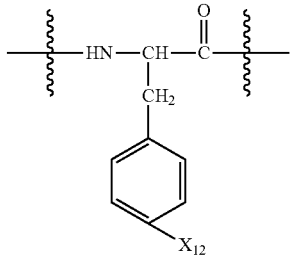

wherein X$_{12}$ is selected from the group consisting of OH and NHR$_{11}$, wherein R$_{11}$ is a dipeptide element comprising the general structure U-B;

X$_{41}$ is selected from the group consisting of glutamic acid, aspartic acid or asparagine;

X$_{42}$ is selected from the group consisting of alanine, lysine, ornithine and arginine;

X$_{45}$ is an amino acid of the general structure

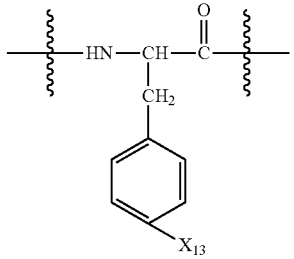

wherein X$_{13}$ is selected from the group consisting of H, OH and NHR$_{12}$, wherein R$_{12}$ is H or dipeptide element comprising the general structure U-B;

R$_{22}$ is selected from the group consisting of AYRPSE (SEQ ID NO: 11), FVNQ (SEQ ID NO: 10), PGPE (SEQ ID NO: 9), a tripeptide glycine-proline-glutamic acid, a tripeptide valine-asparagine-glutamine, a dipeptide proline-glutamic acid, a dipeptide asparagine-glutamine, glutamine, glutamic acid and a bond;

R$_{23}$ is a bond or an amino sequence comprising 1 to 6 charged amino acids; and R$_{13}$ is COOH or CONH$_2$., with the proviso that U, B, or the amino acid of the single chain insulin agonist to which U-B is linked is a non-coded amino acid.

In one embodiment a single chain insulin analog is provided comprising the structure IB-LM-IA, wherein IB comprises the sequence R$_{23}$R$_{22}$-X$_{25}$LCGX$_{29}$X$_{30}$LVX$_{33}$X$_{34}$LYLVCGX$_{41}$X$_{42}$GFX$_{45}$ (SEQ ID NO: 17);

LM is a linking moiety comprising a CTP peptide as disclosed herein; and

IA comprises the sequence GIVX$_4$X$_5$CCX$_8$X$_9$X$_{10}$CX$_{12}$LX$_{14}$X$_{15}$LX$_{17}$X$_{18}$X$_{19}$CX$_{21}$-R$_{13}$ (SEQ ID NO: 18) wherein X$_4$ is glutamic acid or aspartic acid;

X$_5$ is glutamine or glutamic acid

X$_8$ is histidine, threonine or phenylalanine;

X$_9$ is serine, arginine, lysine, ornithine or alanine;

X$_{10}$ is isoleucine or serine;

X$_{12}$ is serine or aspartic acid

X$_{14}$ is tyrosine, arginine, lysine, ornithine or alanine;

X$_{15}$ is glutamine, glutamic acid, arginine, alanine, lysine, ornithine or leucine;

X$_{17}$ is glutamic acid or glutamine;

X$_{18}$ is methionine, asparagine, glutamine, aspartic acid, glutamic acid or threonine;

X$_{19}$ is an amino acid of the general structure:

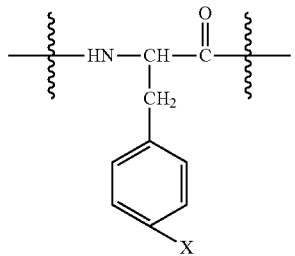

wherein X is selected from the group consisting of OH or NHR$_{10}$, wherein R$_{10}$ is H or a dipeptide element comprising the general structure U-B, wherein U is an amino acid or a hydroxyl acid and B is an N-alkylated amino acid;

X$_{21}$ is selected from the group consisting of alanine, glycine, serine, valine, threonine, isoleucine, leucine, glutamine, glutamic acid, asparagine, aspartic acid, histidine, tryptophan, tyrosine, and methionine;

X$_{25}$ is histidine or threonine;

X$_{29}$ is selected from the group consisting of alanine, glycine and serine;

X$_{30}$ is selected from the group consisting of histidine, aspartic acid, glutamic acid, homocysteic acid and cysteic acid;

X$_{33}$ is selected from the group consisting of aspartic acid, glutamine and glutamic acid;

X$_{34}$ is selected from the group consisting of alanine and threonine;

X$_{45}$ is tyrosine or phenylalanine;

R$_{22}$ is selected from the group consisting of AYRPSE (SEQ ID NO: 11), FVNQ (SEQ ID NO: 10), PGPE (SEQ ID NO: 9), a tripeptide glycine-proline-glutamic acid, a tripeptide valine-asparagine-glutamine, a dipeptide proline-glutamic acid, a dipeptide asparagine-glutamine, glutamine, glutamic acid and a bond;

$R_{23}$ is a H or an amino sequence comprising 1 to 6 charged amino acids; and $R_{13}$ is COOH or $CONH_2$. In one embodiment at least one of n or k is 1. In one embodiment both n and k are 1. In a further embodiment the carboxy terminus of the B chain comprises an additional amino acid extension selected from the group consisting of F, Y, FN, YT, FNK, YTP, FNPK (SEQ ID NO: 47), FNKP (SEQ ID NO: 45), YTPK (SEQ ID NO: 46), YTPKT (SEQ ID NO: 12), YTKPT (SEQ ID NO: 48), FNKPT (SEQ ID NO: 44) and FNPKT (SEQ ID NO: 49). In one embodiment $R_{23}$ is a bond and $R_{22}$ is selected from the group consisting of AYRPSE (SEQ ID NO: 11), PGPE (SEQ ID NO: 9), a tripeptide glycine-proline-glutamic acid, a dipeptide proline-glutamic acid, glutamine, glutamic acid and H.

In one embodiment $R_{23}$ is H or an amino sequence of 4 to 7 amino acids wherein the N-terminal amino acid is selected from the group consisting of glycine, glutamic acid and aspartic acid, the C-terminal amino acid is a lysine and the other amino acids of the sequence are independently selected from the group consisting of glutamic acid and aspartic acid and $R_{22}$ is selected from the group consisting of AYRPSE (SEQ ID NO: 11), PGPE (SEQ ID NO: 9), a tripeptide glycine-proline-glutamic acid, a dipeptide proline-glutamic acid, glutamine, glutamic acid and H.

In one embodiment U-B comprises the structure of Formula X:

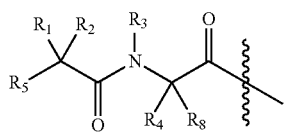

wherein $R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)$SCH_3$, ($C_1$-$C_4$ alkyl)$CONH_2$, ($C_1$-$C_4$ alkyl)COOH, ($C_1$-$C_4$ alkyl)$NH_2$, ($C_1$-$C_4$ alkyl)NHC($NH_2^+$)$NH_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl($W_1$)$C_1$-$C_{12}$ alkyl, wherein $W_1$ is a heteroatom selected from the group consisting of N, S and O, or $R_1$ and $R_2$ together with the atoms to which they are attached form a $C_3$-$C_{12}$ cycloalkyl or aryl; or $R_4$ and $R_8$ together with the atoms to which they are attached form a $C_3$-$C_6$ cycloalkyl;

$R_3$ is selected from the group consisting of $C_1$-$C_{18}$ alkyl, ($C_1$-$C_{18}$ alkyl)OH, ($C_1$-$C_{18}$ alkyl)$NH_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)$R_7$, and ($C_1$-$C_4$ alkyl)($C_3$-$C_9$ heteroaryl) or $R_4$ and $R_3$ together with the atoms to which they are attached form a 4, 5 or 6 member heterocyclic ring;

$R_5$ is $NHR_6$ or OH;

$R_6$ is H, $C_1$-$C_8$ alkyl or $R_6$ and $R_1$ together with the atoms to which they are attached form a 4, 5 or 6 member heterocyclic ring; and $R_7$ is selected from the group consisting of H, OH, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo. In one embodiment either $R_1$ or $R_2$ is other than H.

In another embodiment a single chain insulin analog is provided comprising the structure IB-LM-IA, wherein IB comprises the sequence J-$R_{23}$-$R_{22}$-$X_{25}$LCGX$_{29}$X$_{30}$LVX$_{33}$X$_{34}$LYLVCGX$_{41}$X$_{42}$GFX$_{45}$ (SEQ ID NO: 17);

LM comprises a linking moiety comprising a CTP peptide as disclosed herein; and

IA comprises the sequence GIVX$_4$X$_5$CCX$_8$X$_9$X$_{10}$CX$_{12}$LX$_{14}$X$_{15}$LX$_{17}$X$_{18}$X$_{19}$CX$_{21}$-$R_{13}$ (SEQ ID NO: 18) wherein J is H or a dipeptide comprising the general structure of U-B, wherein U is an amino acid or a hydroxyl acid and B is an N-alkylated amino acid linked through an amide bond;

$X_4$ is glutamic acid or aspartic acid;

$X_5$ is glutamine or glutamic acid $X_8$ is histidine, threonine or phenylalanine;

$X_9$ is serine, arginine, lysine, ornithine or alanine;

$X_{10}$ is isoleucine or serine;

$X_{12}$ is serine or aspartic acid $X_{14}$ is tyrosine, arginine, lysine, ornithine or alanine;

$X_{15}$ is glutamine, glutamic acid, arginine, alanine, lysine, ornithine or leucine;

$X_{17}$ is glutamic acid or glutamine;

$X_{18}$ is methionine, asparagine, glutamine, aspartic acid, glutamic acid or threonine;

$X_{19}$ is an amino acid of the general structure:

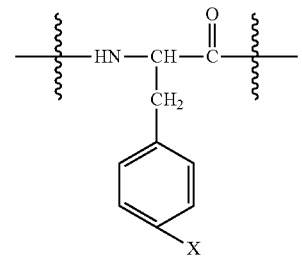

wherein X is selected from the group consisting of OH or $NHR_{10}$, wherein $R_{10}$ is H or a dipeptide element comprising the general structure U-B, wherein U is an amino acid or a hydroxyl acid and B is an N-alkylated amino acid;

$X_{21}$ is selected from the group consisting of alanine, glycine, serine, valine, threonine, isoleucine, leucine, glutamine, glutamic acid, asparagine, aspartic acid, histidine, tryptophan, tyrosine, and methionine;

$X_{25}$ is histidine or threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid, glutamine and glutamic acid;

$X_{34}$ is selected from the group consisting of alanine and threonine;

$X_{41}$ is selected from the group consisting of glutamic acid, aspartic acid or asparagine;

$X_{42}$ is selected from the group consisting of alanine, lysine, ornithine and arginine;

$X_{45}$ is an amino acid of the general structure

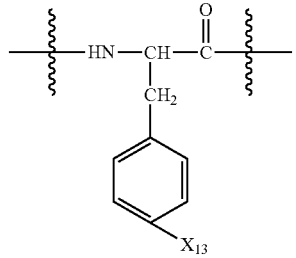

wherein $X_{13}$ is selected from the group consisting of H, OH and $NHR_{12}$, wherein $R_{12}$ is H or dipeptide element comprising the general structure U-B;

$R_{22}$ is selected from the group consisting of AYRPSE (SEQ ID NO: 11), FVNQ (SEQ ID NO: 10), PGPE (SEQ ID NO: 9), a tripeptide glycine-proline-glutamic acid, a tripeptide valine-asparagine-glutamine, a dipeptide proline-glutamic acid, a dipeptide asparagine-glutamine, glutamine, glutamic acid and a bond;

$R_{23}$ is a bond or an amino sequence comprising 1 to 6 charged amino acids; and $R_{13}$ is COOH or $CONH_2$. In a further embodiment the carboxy terminus of the B chain comprises an additional amino acid extension selected from the group consisting of F, Y, FN, YT, FNK, YTP, FNPK (SEQ ID NO: 47), FNKP (SEQ ID NO: 45), YTPK (SEQ ID NO: 46), YTPKT (SEQ ID NO: 12), YTKPT (SEQ ID NO: 48), FNKPT (SEQ ID NO: 44) and FNPKT (SEQ ID NO: 49).

In one embodiment $R_{23}$ is a bond or $X_{60}X_{61}X_{62}X_{63}X_{64}X_{65}K$ (SEQ ID NO: 19), wherein $X_{60}$ is selected from the group consisting of glycine, glutamic acid and aspartic acid, and $X_{61}$, $X_{62}$, $X_{63}$ $X_{64}$ and $X_{65}$ are independently glutamic acid or aspartic acid; and $R_{13}$ is COOH or $CONH_2$.

In one embodiment the single chain insulin analog comprises the structure IB-LM-IA, wherein IB comprises sequence J-$R_{23}$-$R_{22}$-$X_{25}$LCGX$_{29}$X$_{30}$LVX$_{33}$X$_{34}$LX$_{36}$LVCGX$_{41}$X$_{42}$GFX$_{45}$ SEQ ID NO: 16);

LM is a linking moiety comprising a CTP peptide as disclosed herein; and

IA comprises the sequence GIVX$_4$X$_5$CCX$_8$X$_9$X$_{10}$CX$_{12}$LX$_{14}$X$_{15}$LX$_{17}$X$_{18}$X$_{19}$CX$_{21}$-$R_{13}$ (SEQ ID NO: 18). In one embodiment the carboxy terminus of the B chain has an amino acid terminal extension consisting of F, Y, FN, YT, FNK, YTP, FNPK (SEQ ID NO: 47), FNKP (SEQ ID NO: 45), YTPK (SEQ ID NO: 46), YTPKT (SEQ ID NO: 12), YTKPT (SEQ ID NO: 48), FNKPT (SEQ ID NO: 44) and FNPKT (SEQ ID NO: 49).

In one embodiment $R_{23}$ is an N-terminal amine or $X_{60}X_{61}X_{62}X_{63}X_{64}X_{65}K$ (SEQ ID NO: 19), wherein $X_{60}$ is selected from the group consisting of glycine, glutamic acid and aspartic acid, and $X_{61}$, $X_{62}$, $X_{63}$ $X_{64}$ and $X_{65}$ are independently glutamic acid or aspartic acid. In accordance with one embodiment the dipeptide element U-B comprises the structure of Formula X:

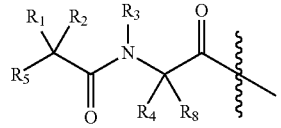

wherein (a) $R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)R$_7$, ($C_1$-$C_4$ alkyl)($C_3$-$C_9$ heteroaryl), and $C_1$-$C_{12}$ alkyl (W1)$C_1$-$C_{12}$ alkyl, wherein W1 is a heteroatom selected from the group consisting of N, S and O, or (ii) $R_1$ and $R_2$ together with the atoms to which they are attached form a C3-C12 cycloalkyl or aryl; or (iii) $R_4$ and $R_8$ together with the atoms to which they are attached form a $C_3$-$C_6$ cycloalkyl;

(b) $R_3$ is selected from the group consisting of $C_1$-$C_{18}$ alkyl, ($C_1$-$C_{18}$ alkyl)OH, ($C_1$-$C_{18}$ alkyl)NH$_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)R$_7$, and ($C_1$-$C_4$ alkyl)($C_3$-$C_9$ heteroaryl) or $R_4$ and $R_3$ together with the atoms to which they are attached form a 4, 5 or 6 member heterocyclic ring;

(c) $R_5$ is NHR$_6$ or OH;

(d) $R_6$ is H, $C_1$-$C_8$ alkyl or $R_6$ and $R_2$ together with the atoms to which they are attached form a 4, 5 or 6 member heterocyclic ring; and (e) $R_7$ is selected from the group consisting of H and OH. In one embodiment either $R_1$ or $R_2$ is other than H.

In accordance with one embodiment the dipeptide element U-B comprises the structure:

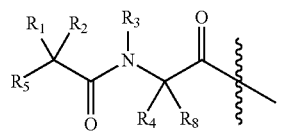

wherein $R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)R$_7$, ($C_1$-$C_4$ alkyl)($C_3$-$C_9$ heteroaryl), and $C_1$-$C_{12}$ alkyl (W$_1$)$C_1$-$C_{12}$ alkyl, wherein W$_1$ is a heteroatom selected from the group consisting of N, S and O, or $R_1$ and $R_2$ together with the atoms to which they are attached form a $C_3$-$C_{12}$ cycloalkyl; or $R_4$ and $R_8$ together with the atoms to which they are attached form a $C_3$-$C_6$ cycloalkyl;

$R_3$ is selected from the group consisting of $C_1$-$C_{18}$ alkyl, ($C_1$-$C_{18}$ alkyl)OH, ($C_1$-$C_{18}$ alkyl)$NH_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)$R_7$, and ($C_1$-$C_4$ alkyl)($C_3$-$C_9$ heteroaryl) or $R_4$ and $R_3$ together with the atoms to which they are attached form a 4, 5 or 6 member heterocyclic ring;

$R_5$ is $NHR_6$ or OH;

$R_6$ is H, $C_1$-$C_8$ alkyl or $R_6$ and $R_1$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo. In one embodiment either $R_1$ or $R_2$ is other than H.

In one specific embodiment the dipeptide element comprises the structure of Formula X wherein $R_1$ and $R_2$ are independently C1-C18 alkyl or aryl;

$R_3$ is $C_1$-$C_{18}$ alkyl or $R_3$ and $R_4$ together with the atoms to which they are attached form a 4-12 heterocyclic ring;

$R_4$ and $R_8$ are independently selected from the group consisting of hydrogen, $C_1$-$C_{18}$ alkyl and aryl; and $R_5$ is an amine or a hydroxyl.

In another specific embodiment the dipeptide element comprises the structure of Formula X wherein $R_1$ is selected from the group consisting of hydrogen, $C_1$-$C_{18}$ alkyl and aryl, or $R_1$ and $R_2$ are linked through —(CH2)p-, wherein p is 2-9;

$R_3$ is $C_1$-$C_{18}$ alkyl or $R_3$ and $R_4$ together with the atoms to which they are attached form a 4-6 heterocyclic ring;

$R_4$ and $R_8$ are independently selected from the group consisting of hydrogen, $C_1$-$C_{18}$ alkyl and aryl; and $R_5$ is an amine or N-substituted amine.

In another specific embodiment the dipeptide element comprises the structure of Formula X wherein $R_1$ and $R_2$ are independently selected from the group consisting of hydrogen, $C_1$-$C_8$ alkyl and aryl;

$R_3$ is $C_1$-$C_{18}$ alkyl or $R_3$ and $R_4$ together with the atoms to which they are attached form a 4-6 heterocyclic ring;

$R_4$ and $R_8$ are each hydrogen; and $R_5$ is selected from the group consisting of amine, N-substituted amine and hydroxyl.

In accordance with one embodiment a prodrug form of a single chain insulin analog comprises the structure IB-LM-IA, wherein IB comprises the sequence $R_{22}$HLCGS$X_{30}$LVEALYLVCG ERGFF (SEQ ID NO: 56) or $X_{22}$VNQ$X_{25}$LCG$X_{29}X_{30}$LVEALYLVCGERGFFYT-$Z_1$-$B_1$ (SEQ ID NO: 25); LM is a linking moiety comprising a CTP peptide as disclosed herein and IA comprises the sequence GIVEQCC$X_8$SICSLYQLENX$_{19}$CX$_{21}$-$R_{13}$ (SEQ ID NO: 26) or GIV$X_4$ECC$X_8X_9$SCDL$X_{14}$ $X_{15}$L$X_{17}X_{18}X_{19}$C$X_{21}$-$R_{13}$ (SEQ ID NO: 15), wherein $X_4$ is glutamic acid or aspartic acid;

$X_8$ is histidine, threonine or phenylalanine;

$X_9$ is arginine, lysine, ornithine or alanine;

$X_{14}$ is arginine, lysine, ornithine or alanine;

$X_{15}$ is glutamine, glutamic acid, arginine, alanine, lysine, ornithine or leucine;

$X_{17}$ is glutamic acid or glutamine;

$X_{18}$ is methionine, asparagine, glutamine, aspartic acid, glutamic acid or threonine;

$X_{19}$ is an amino acid of the general structure

IV

;

wherein $m_1$ is an integer ranging from 1 to 3;

$R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)$SCH_3$, ($C_1$-$C_4$ alkyl)$CONH_2$, ($C_1$-$C_4$ alkyl)COOH, ($C_1$-$C_4$ alkyl)$NH_2$, ($C_1$-$C_4$ alkyl)NHC($NH_2^+$)$NH_2$, ($C_0$-$C_1$ alkyl)($C_3$-$C_6$ cycloalkyl), ($C_0$-$C_4$ alkyl)($C_2$-$C_5$ heterocyclic), ($C_0$-$C_1$ alkyl)($C_6$-$C_{10}$ aryl)$R_7$, ($C_1$-$C_4$ alkyl)($C_3$-$C_9$ heteroaryl), and $C_1$-$C_{12}$ alkyl($W_1$)$C_1$-$C_{12}$ alkyl, wherein $W_1$ is a heteroatom selected from the group consisting of N, S and O, or $R_1$ and $R_2$ together with the atoms to which they are attached form a $C_3$-$C_{12}$ cycloalkyl; or $R_4$ and $R_8$ together with the atoms to which they are attached form a $C_3$-$C_6$ cycloalkyl;

$R_3$ is selected from the group consisting of $C_1$-$C_{18}$ alkyl, ($C_1$-$C_{18}$ alkyl)OH, ($C_1$-$C_{18}$ alkyl)$NH_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)$R_7$, and ($C_1$-$C_4$ alkyl)($C_3$-$C_9$ heteroaryl) or $R_4$ and $R_3$ together with the atoms to which they are attached form a 4, 5 or 6 member heterocyclic ring;

$R_5$ is $NHR_6$ or OH;

$R_6$ is H, $C_1$-$C_8$ alkyl or $R_6$ and $R_1$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo;

$X_{21}$ is selected from the group consisting of alanine, glycine, serine, valine, threonine, isoleucine, leucine, glutamine, glutamic acid, asparagine, aspartic acid, histidine, tryptophan, tyrosine, and methionine;

$X_{22}$ is selected from the group consisting of phenylalanine and desamino-phenylalanine;

$X_{23}$ is asparagine or glycine;

$X_{25}$ is histidine or threonine;

$X_{29}$ is selected from the group consisting of alanine, glycine and serine;

$X_{30}$ is selected from the group consisting of histidine, aspartic acid, glutamic acid, homocysteic acid and cysteic acid;

$Z_1$ is a dipeptide selected from the group consisting of aspartate-lysine, lysine-proline, and proline-lysine; and $B_1$ is selected from the group consisting of threonine, alanine or a threonine-arginine-arginine tripeptide.

$R_{22}$ is selected from the group consisting of $X_{22}$VNQ (SEQ ID NO: 50), a tripeptide valine-asparagine-glutamine, a dipeptide asparagine-glutamine, glutamine, and an N-terminal amine; and $R_{13}$ is COOH or CONH$_2$. In one embodiment $m_1$ is 1. In accordance with one embodiment the single chain insulin analog comprises the structure IB-LM-IA, wherein IB comprises the sequence $X_{22}$VNQX$_{25}$LCGX$_{29}$X$_{30}$LVEALYLVCGERGFFYT-Z$_1$-B$_1$ (SEQ ID NO: 25), LM is a linking moiety comprising a CTP peptide as disclosed herein and IA comprises the sequence GIVX$_4$ECCX$_8$X$_9$SCDLX$_{14}$X$_{15}$LX$_{17}$X$_{18}$X$_{19}$CX$_{21}$-R$_{13}$ (SEQ ID NO: 15).

In one embodiment the single chain insulin analog comprises a compound of the formula: IB-LM-IA, wherein IB represents an IGF YL B chain comprising the sequence GPETLCGAELVDALYLVCGDRGFYFNKPT (SEQ ID NO: 6) or GPETLCGAELVDALYLVCGDRGFYFNPKT (SEQ ID NO: 52), LM represents a linking moiety comprising SEQ ID NO: 66 and IA represents an IGF A chain comprising the sequence GIVDECCHRSCDLRRLEMX$_{19}$CA-R$_{13}$ (SEQ ID NO: 61) or GIVDECCHOSCDLOOLQMX$_{19}$CN-R$_{13}$ (SEQ ID NO: 43) or the native insulin sequence GIVEQCCTSICSLYQLENX$_{19}$CN-R$_{13}$ (SEQ ID NO: 61) wherein $X_8$ is histidine or phenylalanine;

$X_{19}$ is an amino acid of the general structure

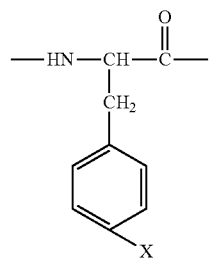

wherein X is selected from the group consisting of OH or NHR$_{10}$, wherein R$_{10}$ is a dipeptide comprising the general structure:

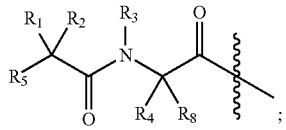

$R_1$ is selected from the group consisting of H and $C_1$-$C_8$ alkyl;

$R_2$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$) NH$_2$, ($C_0$-$C_4$ alkyl)($C_3$-$C_6$ cycloalkyl), ($C_0$-$C_4$ alkyl)($C_6$-$C_{10}$ aryl)R$_7$, and CH$_2$($C_5$-$C_9$ heteroaryl), or $R_1$ and $R_2$ together with the atoms to which they are attached form a $C_3$-$C_6$ cycloalkyl;

$R_3$ is selected from the group consisting of $C_1$-$C_8$ alkyl, ($C_1$-$C_4$ alkyl)OH, ($C_1$-$C_4$ alkyl)NH$_2$, ($C_1$-$C_4$ alkyl)SH, and ($C_3$-$C_6$)cycloalkyl or $R_4$ and $R_3$ together with the atoms to which they are attached form a 5 or 6 member heterocyclic ring;

$R_5$ is NHR$_6$ or OH;

$R_6$ is H, or $R_6$ and $R_2$ together with the atoms to which they are attached form a 5 or 6 member heterocyclic ring;

$R_7$ is selected from the group consisting of H and OH; and $R_8$ is H; and $R_{13}$ and $R_{14}$ are independently COOH or CONH$_2$. In one embodiment either $R_1$ or $R_2$ is other than H. The present invention also encompasses any combination of insulin analog A chain and B chain peptides, as disclosed herein, linked together via a linking moiety as disclosed herein as a single chain insulin analog of the formula IB-LM-IA.

The Dipeptide Prodrug Element

The substituents of the dipeptide prodrug element, and its site of attachment to the insulin analog, can be selected to provide the desired half life of a prodrug analog of the insulin analogs disclosed herein. For example, when a dipeptide prodrug element comprising the structure:

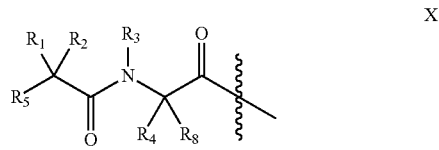

is linked to the alpha amino group of the N-terminal amino acid of the insulin analog B chain, compounds having a $t_{1/2}$ of about 1 hour in PBS under physiological conditions are provided when $R_1$ and $R_2$ are independently $C_1$-$C_8$ alkyl or aryl; or $R_1$ and $R_2$ are linked through —(CH$_2$)$_p$—, wherein p is 2-9;

$R_3$ is $C_1$-$C_{18}$ alkyl;

$R_4$ and $R_8$ are each hydrogen; and $R_5$ is an amine.

In other embodiments, prodrugs linked at the N-terminus and having a $t_{1/2}$ of, e.g., about 1 hour comprise a dipeptide prodrug element with the structure:

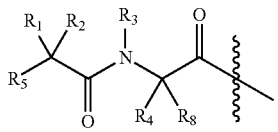

wherein $R_1$ and $R_2$ are independently $C_1$-$C_8$ alkyl or ($C_0$-$C_4$ alkyl)($C_6$-$C_{10}$ aryl)R$_7$; or $R_1$ and $R_2$ are linked through —(CH$_2$)$_p$, wherein p is 2-9;

$R_3$ is $C_1$-$C_{18}$ alkyl;

$R_4$ and $R_8$ are each hydrogen;

$R_5$ is NH$_2$;

$R_7$ is selected from the group consisting of hydrogen, $C_1$-$C_8$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo; and $R_8$ is H.

Alternatively, in one embodiment a insulin analog prodrug derivative is provided wherein the dipeptide prodrug is linked to the alpha amino group of the N-terminal amino acid of the insulin analog B chain, and the prodrug has a $t_{1/2}$ between about 6 to about 24 hours in PBS under physiological conditions. In one embodiment a insulin analog prodrug derivative having a $t_{1/2}$ between about 6 to about 24 hours in PBS under physiological conditions is provided wherein the prodrug element has the structure of Formula X and $R_1$ and $R_2$ are independently selected from the group consisting of hydrogen, $C_1$-$C_{18}$ alkyl and aryl, or $R_1$ and $R_2$ are linked through —$(CH_2)_p$—, wherein p is 2-9;

$R_3$ is $C_1$-$C_{18}$ alkyl or $R_3$ and $R_4$ together with the atoms to which they are attached form a 4-12 heterocyclic ring;

$R_4$ and $R_8$ are independently selected from the group consisting of hydrogen, $C_1$-$C_8$ alkyl and aryl; and $R_5$ is an amine, with the proviso that both $R_1$ and $R_2$ are not hydrogen and provided that one of $R_4$ or $R_8$ is hydrogen.

In a further embodiment a insulin analog prodrug derivative is provided wherein the dipeptide prodrug is linked to the alpha amino group of the N-terminal amino acid of the insulin analog B chain, and the prodrug has a $t_{1/2}$ between about 72 to about 168 hours in PBS under physiological conditions. In one embodiment a insulin analog prodrug derivative having a $t_{1/2}$ between about 72 to about 168 hours in PBS under physiological conditions is provided wherein the prodrug element has the structure of Formula X and $R_1$ is selected from the group consisting of hydrogen, $C_1$-$C_8$ alkyl and aryl;

$R_2$ is H;

$R_3$ is $C_1$-$C_{18}$ alkyl;

$R_4$ and $R_8$ are each hydrogen; and $R_5$ is an amine or N-substituted amine or a hydroxyl;

with the proviso that, if $R_1$ is alkyl or aryl, then $R_1$ and $R_5$ together with the atoms to which they are attached form a 4-11 heterocyclic ring.

In some embodiments, prodrugs having the dipeptide prodrug element linked to the N-terminal alpha amino acid of the insulin analog B chain peptide and having a $t_{1/2}$, e.g., between about 12 to about 72 hours, or in some embodiments between about 12 to about 48 hours, comprise a dipeptide prodrug element with the structure:

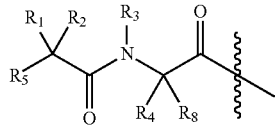

wherein $R_1$ and $R_2$ are independently selected from the group consisting of hydrogen, $C_1$-$C_{18}$ alkyl, ($C_1$-$C_8$ alkyl)OH, ($C_1$-$C_4$ alkyl)$NH_2$, and ($C_0$-$C_4$ alkyl)($C_6$-$C_{10}$ aryl)$R_7$, or $R_1$ and $R_2$ are linked through $(CH_2)_p$, wherein p is 2-9;

$R_3$ is $C_1$-$C_8$ alkyl or $R_3$ and $R_4$ together with the atoms to which they are attached form a 4-12 heterocyclic ring;

$R_4$ and $R_8$ are independently selected from the group consisting of hydrogen, $C_1$-$C_8$ alkyl and ($C_0$-$C_4$ alkyl)($C_6$-$C_{10}$ aryl)$R_7$;

$R_5$ is $NH_2$; and $R_7$ is selected from the group consisting of H, $C_1$-$C_8$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo;

with the proviso that both $R_1$ and $R_2$ are not hydrogen and provided that at least one of $R_4$ or $R_8$ is hydrogen.

In some embodiments, prodrugs having the dipeptide prodrug element linked to the N-terminal amino acid of the insulin analog B chain peptide and having a $t_{1/2}$, e.g., between about 12 to about 72 hours, or in some embodiments between about 12 to about 48 hours, comprise a dipeptide prodrug element with the structure:

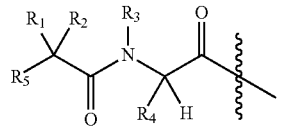

wherein $R_1$ and $R_2$ are independently selected from the group consisting of hydrogen, $C_1$-$C_8$ alkyl and ($C_1$-$C_4$ alkyl)$NH_2$, or $R_1$ and $R_2$ are linked through $(CH_2)_p$, wherein p is 2-9;

$R_3$ is $C_1$-$C_8$ alkyl or $R_3$ and $R_4$ together with the atoms to which they are attached form a 4-6 heterocyclic ring;

$R_4$ is selected from the group consisting of hydrogen and $C_1$-$C_8$ alkyl; and $R_5$ is $NH_2$;

with the proviso that both $R_1$ and $R_2$ are not hydrogen.

In other embodiments, prodrugs having the dipeptide prodrug element linked to the N-terminal amino acid of the insulin analog B chain peptide and having a $t_{1/2}$, e.g., between about 12 to about 72 hours, or in some embodiments between about 12 to about 48 hours, comprise a dipeptide prodrug element with the structure:

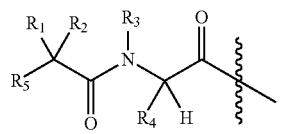

wherein $R_1$ and $R_2$ are independently selected from the group consisting of hydrogen, $C_1$-$C_8$ alkyl and ($C_1$-$C_4$ alkyl)$NH_2$;

$R_3$ is $C_1$-$C_6$ alkyl;

$R_4$ is hydrogen; and $R_5$ is $NH_2$;

with the proviso that both $R_1$ and $R_2$ are not hydrogen.

In some embodiments, prodrugs having the dipeptide prodrug element linked to the N-terminal amino acid of the insulin analog B chain peptide and having a $t_{1/2}$, e.g., between about 12 to about 72 hours, or in some embodiments between about 12 to about 48 hours, comprise a dipeptide prodrug element with the structure:

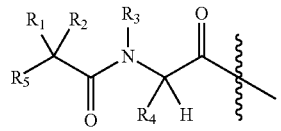

wherein $R_1$ and $R_2$ are independently selected from the group consisting of hydrogen and $C_1$-$C_8$ alkyl, ($C_1$-$C_4$ alkyl)$NH_2$, or $R_1$ and $R_2$ are linked through $(CH_2)_p$, wherein p is 2-9;

$R_3$ is $C_1$-$C_8$ alkyl;

$R_4$ is ($C_0$-$C_4$ alkyl)($C_6$-$C_{10}$ aryl)$R_7$;

$R_5$ is $NH_2$; and $R_7$ is selected from the group consisting of hydrogen, $C_1$-$C_8$ alkyl and ($C_0$-$C_4$ alkyl)OH;

with the proviso that both $R_1$ and $R_2$ are not hydrogen.

In addition a prodrug having the dipeptide prodrug element linked to the N-terminal alpha amino acid of the insulin analog and having a $t_{1/2}$, e.g., of about 72 to about 168 hours is provided wherein the dipeptide prodrug element has the structure:

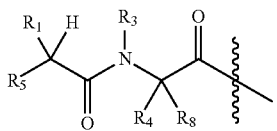

X wherein $R_1$ is selected from the group consisting of hydrogen, $C_1$-$C_8$ alkyl and ($C_0$-$C_4$ alkyl)($C_6$-$C_{10}$ aryl)$R_7$;

$R_3$ is $C_1$-$C_8$ alkyl;

$R_4$ and $R_8$ are each hydrogen;

$R_5$ is $NHR_6$ or OH;

$R_6$ is H, $C_1$-$C_8$ alkyl, or $R_6$ and $R_1$ together with the atoms to which they are attached form a 4, 5 or 6 member heterocyclic ring; and $R_7$ is selected from the group consisting of hydrogen, $C_1$-$C_8$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo;

with the proviso that, if $R_1$ is alkyl or ($C_0$-$C_4$ alkyl)($C_6$-$C_{10}$ aryl)$R_7$, then $R_1$ and $R_5$ together with the atoms to which they are attached form a 4-11 heterocyclic ring.

In some embodiments the dipeptide prodrug element is linked to a side chain amine of an internal amino acid of the insulin analog. In this embodiment prodrugs having a $t_{1/2}$, e.g., of about 1 hour have the structure:

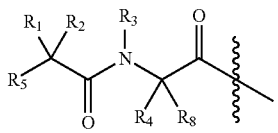

wherein $R_1$ and $R_2$ are independently $C_1$-$C_8$ alkyl or ($C_0$-$C_4$ alkyl)($C_6$-$C_{10}$ aryl)$R_7$; or $R_1$ and $R_2$ are linked through —$(CH_2)_p$—, wherein p is 2-9;

$R_3$ is $C_1$-$C_{18}$ alkyl;

$R_4$ and $R_8$ are each hydrogen;

$R_5$ is $NH_2$; and $R_7$ is selected from the group consisting of hydrogen, $C_1$-$C_8$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo.

Furthermore, prodrugs having a $t_{1/2}$, e.g., between about 6 to about 24 hours and having the dipeptide prodrug element linked to an internal amino acid side chain are provided wherein the prodrug comprises a dipeptide prodrug element with the structure:

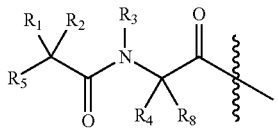

wherein $R_1$ and $R_2$ are independently selected from the group consisting of hydrogen, $C_1$-$C_8$ alkyl, and ($C_0$-$C_4$ alkyl)($C_6$-$C_{10}$ aryl)$R_7$, or $R_1$ and $R_2$ are linked through —$(CH_2)_p$—, wherein p is 2-9;

$R_3$ is $C_1$-$C_{18}$ alkyl or $R_3$ and $R_4$ together with the atoms to which they are attached form a 4-12 heterocyclic ring;

$R_4$ and $R_8$ are independently hydrogen, $C_1$-$C_{18}$ alkyl or ($C_0$-$C_4$ alkyl)($C_6$-$C_{10}$ aryl)$R_7$;

$R_5$ is $NHR_6$;

$R_6$ is H or $C_1$-$C_8$ alkyl, or $R_6$ and $R_2$ together with the atoms to which they are attached form a 4, 5 or 6 member heterocyclic ring; and $R_7$ is selected from the group consisting of hydrogen, $C_1$-$C_8$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo;

with the proviso that both $R_1$ and $R_2$ are not hydrogen and provided that at least one of $R_4$ or $R_8$ is hydrogen.

In addition a prodrug having a $t_{1/2}$, e.g., of about 72 to about 168 hours and having the dipeptide prodrug element linked to a internal amino acid side chain of the insulin analog is provided wherein the dipeptide prodrug element has the structure:

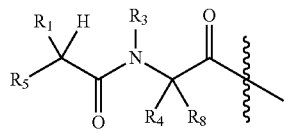

wherein $R_1$ is selected from the group consisting of hydrogen, $C_1$-$C_{18}$ alkyl and ($C_0$-$C_4$ alkyl)($C_6$-$C_{10}$ aryl)$R_7$;

$R_3$ is $C_1$-$C_{18}$ alkyl;

$R_4$ and $R_8$ are each hydrogen;

$R_5$ is $NHR_6$ or OH;

$R_6$ is H or $C_1$-$C_8$ alkyl, or $R_6$ and $R_1$ together with the atoms to which they are attached form a 4, 5 or 6 member heterocyclic ring; and $R_7$ is selected from the group consisting of hydrogen, $C_1$-$C_8$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo; with the proviso that, if $R_1$ and $R_2$ are both independently an alkyl or ($C_0$-$C_4$ alkyl)($C_6$-$C_{10}$ aryl)$R_7$, either $R_1$ or $R_2$ is linked through $(CH_2)_p$ to $R_5$, wherein p is 2-9.

In some embodiments the dipeptide prodrug element is linked to a side chain amine of an internal amino acid of the insulin analog wherein the internal amino acid comprises the structure of Formula V

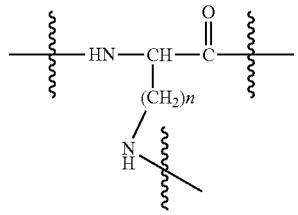

wherein n is an integer selected from 1 to 4. In some embodiments n is 3 or 4 and in some embodiments the internal amino acid is lysine. In some embodiments the dipeptide prodrug element is linked to a primary amine on a side chain of an amino acid located at position 28, or 29 of the B-chain of the insulin analog.

In embodiments where the dipeptide prodrug element of formula X is linked to an amino substituent of an aryl group of an aromatic amino acid, prodrug, the substituents of the prodrug element can be selected to provide the desired time of activation. For example, the half life of a prodrug analog of any of the insulin analogs disclosed herein comprising an amino acid of the structure of Formula IV:

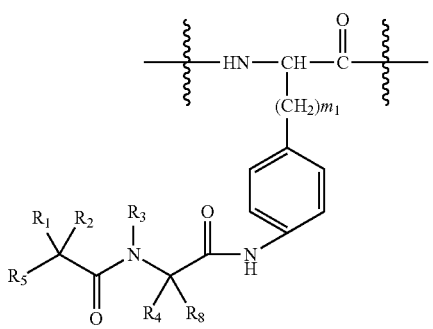

wherein $m_1$ is an integer from 0 to 3, can be selected by altering the substituents of $R_1$, $R_2$, $R_3$, $R_4$, $R_5$, and $R_8$. In one embodiment the amino acid of formula V is present at an amino acid corresponding to position A19, B16 or B25 of native insulin, and in one specific example the amino acid of formula V is located at position A19 of the insulin analog, and $m_1$ is 1. In one embodiment a insulin analog prodrug derivative comprising the structure of Formula IV and having a t½ of about 1 hour in PBS under physiological conditions is provided. In one embodiment the insulin analog prodrug derivative having a t½ of about 1 hour in PBS under physiological conditions comprises the structure of formula IV wherein, $R_1$ and $R_2$ are independently $C_1$-$C_{18}$ alkyl or aryl;

$R_3$ is $C_1$-$C_{18}$ alkyl or $R_3$ and $R_4$ together with the atoms to which they are attached form a 4-12 heterocyclic ring;

$R_4$ and $R_8$ are independently selected from the group consisting of hydrogen, $C_1$-$C_{18}$ alkyl and aryl; and $R_5$ is an amine or a hydroxyl. In one embodiment $m_1$ is 1.

In one embodiment, the dipeptide prodrug element is linked to the insulin analog via an amine present on an aryl group of an aromatic amino acid of the insulin analog, wherein the prodrug has a $t_{1/2}$, e.g., of about 1 hour has a dipeptide structure of:

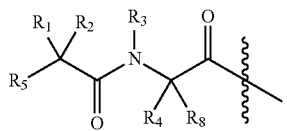

wherein $R_1$ and $R_2$ are independently $C_1$-$C_8$ alkyl or $(C_0$-$C_4$ alkyl$)(C_6$-$C_{10}$ aryl$)R_7$;

$R_3$ is $C_1$-$C_{18}$ alkyl or $R_3$ and $R_4$ together with the atoms to which they are attached form a 4-12 heterocyclic ring;

$R_4$ and $R_8$ are independently selected from the group consisting of hydrogen, $C_1$-$C_{18}$ alkyl and $(C_0$-$C_4$ alkyl$)(C_6$-$C_{10}$ aryl$)R_7$;

$R_5$ is $NH_2$ or OH; and $R_7$ is selected from the group consisting of hydrogen, $C_1$-$C_8$ alkyl, $C_2$-$C_{18}$ alkenyl, $(C_0$-$C_4$ alkyl$)CONH_2$, $(C_0$-$C_4$ alkyl$)COOH$, $(C_0$-$C_4$ alkyl$)NH_2$, $(C_0$-$C_4$ alkyl$)OH$, and halo.

In another embodiment a insulin analog prodrug derivative comprising the structure of Formula IV, wherein $m_1$ is an integer from 0 to 3 and having a t½ of about 6 to about 24 hours in PBS under physiological conditions, is provided. In one embodiment where the insulin analog prodrug having a t½ of about 6 to about 24 hours in PBS under physiological conditions comprises the structure of formula IV wherein, $R_1$ is selected from the group consisting of hydrogen, $C_1$-$C_8$ alkyl and aryl, or $R_1$ and $R_2$ are linked through —$(CH_2)_p$—, wherein p is 2-9;

$R_3$ is $C_1$-$C_{18}$ alkyl or $R_3$ and $R_4$ together with the atoms to which they are attached form a 4-6 heterocyclic ring;

$R_4$ and $R_8$ are independently selected from the group consisting of hydrogen, $C_1$-$C_{18}$ alkyl and aryl; and $R_5$ is an amine or N-substituted amine. In one embodiment $m_1$ is 1.

In one embodiment, prodrugs having the dipeptide prodrug element linked via an aromatic amino acid and having a $t_{1/2}$, e.g., of about 6 to about 24 hours are provided wherein the dipeptide comprises a structure of:

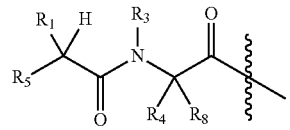

wherein $R_1$ is selected from the group consisting of hydrogen, $C_1$-$C_8$ alkyl, $(C_1$-$C_{18}$ alkyl$)OH$, $(C_1$-$C_4$ alkyl$)NH_2$, and $(C_0$-$C_4$ alkyl$)(C_6$-$C_{10}$ aryl$)R_7$;

$R_3$ is $C_1$-$C_{18}$ alkyl or $R_3$ and $R_4$ together with the atoms to which they are attached form a 4-6 heterocyclic ring;

$R_4$ and $R_8$ are independently selected from the group consisting of hydrogen, $C_1$-$C_{18}$ alkyl and $(C_0$-$C_4$ alkyl$)(C_6$-$C_{10}$ aryl$)R_7$;

$R_5$ is $NHR_6$;

$R_6$ is H, $C_1$-$C_8$ alkyl, or $R_6$ and $R_1$ together with the atoms to which they are attached form a 4, 5 or 6 member heterocyclic ring; and $R_7$ is selected from the group consisting of hydrogen, $C_1$-$C_8$ alkyl, $C_2$-$C_{18}$ alkenyl, $(C_0$-$C_4$ alkyl$)CONH_2$, $(C_0$-$C_4$ alkyl$)COOH$, $(C_0$-$C_4$ alkyl$)NH_2$, $(C_0$-$C_4$ alkyl$)OH$, and halo.

In another embodiment an insulin analog prodrug derivative comprising the structure of Formula IV, wherein $m_1$ is an integer from 0 to 3 and having a t½ of about 72 to about 168 hours in PBS under physiological conditions, is provided. In one embodiment where the insulin analog prodrug derivative having a t½ of about 72 to about 168 hours in PBS under physiological conditions comprises the structure of formula IV wherein, $R_1$ and $R_2$ are independently selected from the group consisting of hydrogen, $C_1$-$C_8$ alkyl and aryl;

$R_3$ is $C_1$-$C_{18}$ alkyl or $R_3$ and $R_4$ together with the atoms to which they are attached form a 4-6 heterocyclic ring;

$R_4$ and $R_8$ are each hydrogen; and $R_5$ is selected from the group consisting of amine, N-substituted amine and hydroxyl. In one embodiment $m_1$ is 1.

In one embodiment, prodrugs having the dipeptide prodrug element linked via an aromatic amino acid and having a $t_{1/2}$, e.g., of about 72 to about 168 hours are provided wherein the dipeptide comprises a structure of:

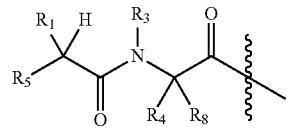

wherein $R_1$ and $R_2$ are independently selected from the group consisting of hydrogen, $C_1$-$C_8$ alkyl, ($C_1$-$C_4$ alkyl)COOH, and ($C_0$-$C_4$ alkyl)($C_6$-$C_{10}$ aryl)$R_7$, or $R_1$ and $R_5$ together with the atoms to which they are attached form a 4-11 heterocyclic ring;

$R_3$ is $C_1$-$C_8$ alkyl or $R_3$ and $R_4$ together with the atoms to which they are attached form a 4-6 heterocyclic ring;

$R_4$ is hydrogen or forms a 4-6 heterocyclic ring with $R_3$;

$R_8$ is hydrogen;

$R_5$ is $NHR_6$ or OH;

$R_6$ is H or $C_1$-$C_8$ alkyl, or $R_6$ and $R_1$ together with the atoms to which they are attached form a 4, 5 or 6 member heterocyclic ring; and $R_7$ is selected from the group consisting of hydrogen, $C_1$-$C_8$ alkyl, $C_2$-$C_{1s}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo.

In accordance with one embodiment the dipeptide of Formula X is further modified to comprise a large polymer that interferes with the insulin analog's ability to interact with the insulin or IGF-1 receptor. Subsequent cleavage of the dipeptide releases the insulin analog from the dipeptide complex wherein the released insulin analog is fully active. In accordance with one embodiment the dipeptide of Formula X is further modified to comprises a large polymer that interferes with the bound insulin analog's ability to interact with the insulin or IGF-1 receptor. In accordance with one embodiment the insulin analog comprises a dipeptide of the general structure of Formula X:

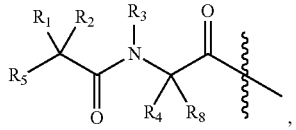

wherein one of the amino acid side chains of the dipept

The insulin analogs and prodrug derivative thereof disclosed herein can be further modified to improve the peptide's solubility in aqueous solutions at physiological pH, while enhancing the effective duration of the peptide by preventing renal clearance of the peptide. Peptides are easily cleared because of their relatively small molecular size when compared to plasma proteins. Increasing the molecular weight of a peptide above 40 kDa exceeds the renal threshold and significantly extends duration in the plasma. Accordingly, in one embodiment the peptide prodrugs are further modified to comprise a covalently linked hydrophilic moiety.

In one embodiment the hydrophilic moiety is a plasma protein, polyethylene glycol chain or the Fc portion of an immunoglobin. Therefore, in one embodiment the presently disclosed insulin analogs are further modified to comprise one or more hydrophilic groups covalently linked to the side chains of amino acids.

In accordance with one embodiment the insulin prodrugs disclosed herein are further modified by linking a hydrophilic moiety to either the N-terminal amino acid of the B chain or to the side chain of a lysine amino acid (or other suitable amino acid) located at the carboxy terminus of the B chain, including for example, at position 28 of SEQ ID NO: 9. In one embodiment a single-chain insulin prodrug derivative is provided wherein one of the amino acids of the linking moiety is modified by linking a hydrophilic moiety to the side chain of the peptide linker. In one embodiment the modified amino acid is cysteine, lysine or acetyl phenylalanine.

In accordance with one embodiment a prodrug derivative of the insulin analog is provided wherein the dipeptide element of Formula X further comprises an polyethylene glycol, alkyl or acyl group. In one embodiment one or more polyethylene glycol chains are linked to the dipeptide of Formula X wherein the combined molecular weight of the polyethylene glycol chains ranges from about 20,000 to about 80,000 Daltons, or 40,000 to 80,000 Daltons or 40,000 to 60,000 Daltons. In one embodiment at least one polyethylene glycol chain having a molecular weight of about 40,000 Daltons is linked to the dipeptide of Formula X. In another embodiment the dipeptide of Formula X is acylated with an acyl group of sufficient size to bind serum albumin and thus inactivate the IGF$^{B16B17}$ analog peptide upon administration. The acyl group can be linear or branched, and in one embodiment is a C16 to C30 fatty acid. For example, the acyl group can be any of a C16 fatty acid, C18 fatty acid, C20 fatty acid, C22 fatty acid, C24 fatty acid, C26 fatty acid, C28 fatty acid, or a C30 fatty acid. In some embodiments, the acyl group is a C16 to C20 fatty acid, e.g., a C18 fatty acid or a C20 fatty acid.

In another embodiment the insulin analog peptides, and their prodrug analogs, disclosed herein are further modified by the addition of a modified amino acid to the carboxy or amino terminus of the A chain or the amino terminus of the B chain of the insulin analog peptide, wherein the added amino acid is modified to comprise a hydrophilic moiety linked to the amino acid. In one embodiment the amino acid added to the C-terminus is a modified cysteine, lysine or acetyl phenylalanine. In one embodiment the hydrophilic moiety is selected from the group consisting of a plasma protein, polyethylene glycol chain and an Fc portion of an immunoglobin.

In one embodiment the hydrophilic group is a polyethylene glycol chain, and in one embodiment two or more polyethylene glycol chains are covalently attached to two or more amino acid side chains of the insulin analog. In accordance with one embodiment the hydrophilic moiety is covalently attached to an amino acid side chain of a insulin analog disclosed herein at a position corresponding to A10, B28, B29, the C-terminus of the A chain or the N-terminus of the B chain (positions relative to native insulin). For insulin analogs and their prodrug derivatives having multiple polyethylene glycol chains, the polyethylene glycol chains can be attached at the N-terminal amino acid of the B chain or to the side chain of a lysine amino acid located at the carboxy terminus of the B chain, or by the addition of a single amino acid at the C-terminus of the peptide wherein the added amino acid has a polyethylene glycol chain linked to its side chain. In accordance with one embodiment a prodrug derivative is provided wherein the polyethylene glycol chain or other hydrophilic moiety is linked to the side chain of one of the two amino acids comprising the dipeptide prodrug element. In one embodiment the dipeptide prodrug element comprises a lysine (in the D or L stereoisomer configuration) with a polyethylene glycol chain attached to the side chain amine of the lysine.

In accordance with one embodiment, the insulin analog peptides, or prodrug derivatives thereof, disclosed herein are further modified by amino acid substitutions, wherein the substituting amino acid comprises a side chain suitable for crosslinking with hydrophilic moieties, including for example, polyethylene glycol. For example, in one embodiment a native amino acid at a position corresponding to A5, A8, A9, A10, A12, A14, A15, A17, A18, B1, B2, B3, B4, B5, B13, B14, B17, B21, B22, B26, B27, B28, B29 and B30 of native insulin is substituted with a lysine, cysteine or acetyl phenylalanine residue (or a lysine, cysteine or acetyl phenylalanine residue is added to the C-terminus) to allow for the covalent attachment of a polyethylene glycol chain.

In one embodiment the insulin analog, or prodrug derivative thereof, has a single cysteine substitution or a single cysteine residue added to the amino or carboxy terminus of the insulin analog, or an amino acid within the linking moiety or the dipeptide element of an insulin prodrug derivative is substituted with at least one cysteine residue, wherein the side chain of the cysteine residue is further modified with a thiol reactive reagent, including for example, maleimido, vinyl sulfone, 2-pyridylthio, haloalkyl, and haloacyl. These thiol reactive reagents may contain carboxy, keto, hydroxyl, and ether groups as well as other hydrophilic moieties such as polyethylene glycol units. In an alternative embodiment, the insulin analog, or prodrug derivative thereof, has a single lysine substitution or a single lysine residue added to the amino or carboxy terminus of the insulin analog, or an amino acid within the linking moiety or the dipeptide element of an insulin prodrug derivative is substituted with lysine, and the side chain of the substituting lysine residue is further modified using amine reactive reagents such as active esters (succinimido, anhydride, etc) of carboxylic acids or aldehydes of hydrophilic moieties such as polyethylene glycol.

In accordance with one embodiment a pharmaceutical composition is provided comprising any of the novel insulin analogs disclosed herein, preferably at a purity level of at least 90%, 91%, 92%, 93%, 94%, 95%, 96%, 97%, 98% or 99%, and a pharmaceutically acceptable diluent, carrier or excipient. Such compositions may contain a insulin analog as disclosed herein at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored contained within various package containers. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

In one embodiment, a composition is provided comprising a mixture of a first and second insulin analog prodrug derivative, wherein the first and second insulin analog prodrug derivatives differ from one another based on the structure of the prodrug element. More particularly, the first insulin analog prodrug derivative may comprise a dipeptide prodrug element that has a half life substantially different from the dipeptide prodrug element of the second insulin analog prodrug derivative. Accordingly, selection of different combinations of substituents on the dipeptide element will allow for the preparation of compositions that comprise a mixture of insulin analog prodrug derivatives that are activated in a controlled manner over a desired time frame and at specific time intervals. For example, the compositions can be formulated to release active insulin analog peptide at mealtimes followed by a subsequent activation insulin analog peptide during nighttime with suitable dosages being released based on time of activation.

In another embodiment the pharmaceutical composition comprises a mixture of a insulin analog prodrug derivative disclosed herein and native insulin, or a known bioactive analog of insulin. The mixture in one embodiment can be in the form of a heteroduplex linking an insulin analog and a native insulin, or a known bioactive analog of insulin. The dimers may comprise a insulin analog peptide linked to another insulin analog or to a disulfide linked A chain to B chain insulin heteroduplex. The mixtures may comprise one or more of the insulin analogs, native insulin, or a known bioactive analog of insulin, in prodrug derivatives thereof or depot derivative thereof or other conjugate forms, and any combination thereof, as disclosed herein.

The disclosed insulin analogs, and their corresponding prodrug derivatives, are believed to be suitable for any use that has previously been described for insulin peptides. Accordingly, the insulin analogs, and their corresponding prodrug derivatives, described herein can be used to treat hyperglycemia, or treat other metabolic diseases that result from high blood glucose levels. Accordingly, the present invention encompasses pharmaceutical compositions comprising a insulin analog as disclosed herein, or a prodrug derivative thereof, and a pharmaceutically acceptable carrier for use in treating a patient suffering from high blood glucose levels. In accordance with one embodiment the patient to be treated using a insulin analog disclosed herein is a domesticated animal, and in another embodiment the patient to be treated is a human.

One method of treating hyperglycemia in accordance with the present disclosure comprises the steps of administering the presently disclosed insulin analog, or depot or prodrug derivative thereof, to a patient using any standard route of administration, including parenterally, such as intravenously, intraperitoneally, subcutaneously or intramuscularly, intrathecally, transdermally, rectally, orally, nasally or by inhalation. In one embodiment the composition is administered subcutaneously or intramuscularly. In one embodiment, the composition is administered parenterally and the insulin analog, or prodrug derivative thereof, is prepackaged in a syringe.

The insulin analog disclosed herein, and depot or prodrug derivative thereof, may be administered alone or in combination with other anti-diabetic agents. Anti-diabetic agents known in the art or under investigation include native insulin, native glucagon and functional analogs thereof, sulfonylureas, such as tolbutamide (Orinase), acetohexamide (Dymelor), tolazamide (Tolinase), chlorpropamide (Diabinese), glipizide (Glucotrol), glyburide (Diabeta, Micronase, Glynase), glimepiride (Amaryl), or gliclazide (Diamicron); meglitinides, such as repaglinide (Prandin) or nateglinide (Starlix); biguanides such as metformin (Glucophage) or phenformin; thiazolidinediones such as rosiglitazone (Avandia), pioglitazone (Actos), or troglitazone (Rezulin), or other PPARy inhibitors; alpha glucosidase inhibitors that inhibit carbohydrate digestion, such as miglitol (Glyset), acarbose (Precose/Glucobay); exenatide (Byetta) or pramlintide; Dipeptidyl peptidase-4 (DPP-4) inhibitors such as vildagliptin or sitagliptin; SGLT (sodium-dependent glucose transporter 1) inhibitors; or FBPase (fructose 1,6-bisphosphatase) inhibitors.

Pharmaceutical compositions comprising the insulin analogs disclosed herein, or depot or prodrug derivatives thereof, can be formulated and administered to patients using standard pharmaceutically acceptable carriers and routes of administration known to those skilled in the art. Accordingly, the present disclosure also encompasses pharmaceutical compositions comprising one or more of the insulin analogs disclosed herein (or prodrug derivative thereof), or a pharmaceutically acceptable salt thereof, in combination with a pharmaceutically acceptable carrier. In one embodiment the pharmaceutical composition comprises a 1 mg/ml concentration of the insulin analog at a pH of about 4.0 to about 7.0 in a phosphate buffer system. The pharmaceutical compositions may comprise the insulin analog as the sole pharmaceutically active component, or the insulin analog peptide can be combined with one or more additional active agents.

All therapeutic methods, pharmaceutical compositions, kits and other similar embodiments described herein contemplate that insulin analog peptides, or prodrug derivatives thereof, include all pharmaceutically acceptable salts thereof.

In one embodiment the kit is provided with a device for administering the insulin analog composition to a patient. The kit may further include a variety of containers, e.g., vials, tubes, bottles, and the like. Preferably, the kits will also include instructions for use. In accordance with one embodiment the device of the kit is an aerosol dispensing device, wherein the composition is prepackaged within the aerosol device. In another embodiment the kit comprises a syringe and a needle, and in one embodiment the insulin analog composition is prepackaged within the syringe.

The compounds of this invention may be prepared by standard synthetic methods, recombinant DNA techniques, or any other methods of preparing peptides and fusion proteins. Although certain non-natural amino acids cannot be expressed by standard recombinant DNA techniques, techniques for their preparation are known in the art. Compounds of this invention that encompass non-peptide portions may be synthesized by standard organic chemistry reactions, in addition to standard peptide chemistry reactions when applicable.

In accordance with the present disclosure the following exemplary embodiments are provided:
1. A single chain insulin analog comprising an A chain, a B chain and a linking moiety, wherein said linking moiety comprises a peptide of 18 amino acids that covalently links the carboxy terminus of the B chain to the amino terminus of the A chain to form a contiguous amino acid chain, with the proviso that the linking moiety does not comprise an 18 amino acid sequence that is identical to an 18 amino acid sequence of SEQ ID NO: 53 directly linked to the carboxy terminus of the B chain.

2. The single chain insulin analog of embodiment 1 wherein said linking moiety comprises a total of 18 to 158 amino acids residues.

3. The single chain insulin analog of embodiment 1 wherein said linking moiety comprises a total of 28 to 56 amino acids.

4. The single chain insulin analog of embodiment 2 or 3 wherein said linking moiety comprises a 29 contiguous amino acid sequence, directly linked to the carboxy terminal amino acid of the B chain, wherein said 29 contiguous amino acid sequence has greater than 90% sequence identity to SSSS$X_{50}$APPPSLPSPSRLPGPSDTPILPQ$X_{51}$ (SEQ ID NO: 66), wherein $X_{50}$ and $X_{51}$ are independently selected from arginine and lysine.

5. The single chain insulin analog of embodiment 2 or 3 wherein said linking moiety comprises a 29 contiguous amino acid sequence, directly linked to the carboxy terminal amino acid of the B chain, wherein at least 58% of the amino acids comprising said 29 contiguous amino acid sequence are selected from the group consisting of serine and proline.

6. The single chain insulin analog of embodiment 2, 3, 4 or 5 wherein said insulin analog further comprises a non-native glycosylation site.

7. The single chain insulin analog of embodiment 2, 3, 4 or 5 wherein said linking moiety comprises a glycosylation site.

8. The single chain insulin analog of embodiment 7 wherein said linking moiety comprises an N-linked glycosylation site.

9. The single chain insulin analog of embodiment 7 or 8 wherein said linking moiety comprises an O-linked glycosylation site.

10. The insulin analog of any of embodiments 6-8 wherein said linking moiety is glycosylated.

11. The single chain insulin analog of embodiment 2 or 3 wherein said linking moiety comprises an analog of (SEQ ID NO: 64), wherein said analog differs from (SEQ ID NO: 64) by 1 to 6 amino acid substitutions.

12. The single chain insulin analog of embodiment 4 wherein said linking moiety comprises (SEQ ID NO: 66).

13. The single chain insulin analog of any of embodiments 1-12 wherein the sequence SSSS$X_{50}$APPPSLPSPSRLPGPSDTPILPQ$X_{51}$ (SEQ ID NO: 66), SSSS$X_{50}$APPPSLPSPSRLPGPSDTPILPQ (SEQ ID NO; 92) or MGSSSS$X_{50}$APPPSLPSPSRLPGPSDTPILPQ (SEQ ID NO; 93) is linked to the amino terminus of the B chain, optionally with an intervening sequence consisting of 1 to 5 acidic amino acids followed by an arginine or lysine.

14. The single chain insulin analog of any of embodiments 1-13 wherein said linking moiety comprises the sequence SSSSRAPPPSLPSPSRLPGPSDTPILPQK (SEQ ID NO: 79) or SSSSKAPPPSLPSPSRLPGPSDTPILPQR (SEQ ID NO: 64).

15. The single chain insulin analog of any of embodiments 1-14 wherein said A chain comprises the sequence GIV$X_4X_5$CC$X_8X_9X_{10}$C$X_{12}$L$X_{14}X_{15}$L$X_{17}X_{18}X_{19}$C$X_{21}$-$R_{13}$ (SEQ ID NO: 18); and said B chain comprises the sequence $R_{22}$-$X_{25}$LCG$X_{29}X_{30}$LV$X_{33}X_{34}$LYLVCG$X_{41}X_{42}$GF$X_{45}$ (SEQ ID NO: 17) wherein $X_4$ is glutamic acid or aspartic acid; $X_5$ is glutamine or glutamic acid; $X_8$ is histidine, threonine or phenylalanine; $X_9$ is serine, arginine, lysine, ornithine or alanine; $X_{10}$ is isoleucine or serine; $X_{12}$ is serine or aspartic acid; $X_{14}$ is tyrosine, arginine, lysine, ornithine or alanine; $X_{15}$ is glutamine, glutamic acid, arginine, alanine, lysine, ornithine or leucine; $X_{17}$ is glutamine, glutamic acid, arginine, aspartic acid, ornithine or lysine; $X_{18}$ is methionine, asparagine, glutamine, aspartic acid, glutamic acid or threonine; $X_{19}$ is tyrosine, 4-methoxy-phenylalanine or 4-amino phenylalanine; $X_{21}$ is selected from the group consisting of alanine, glycine, serine, valine, threonine, isoleucine, leucine, glutamine, glutamic acid, asparagine, aspartic acid, histidine, tryptophan, tyrosine, and methionine; $X_{25}$ is histidine or threonine; $X_{29}$ is selected from the group consisting of alanine, glycine and serine; $X_{30}$ is selected from the group consisting of histidine, aspartic acid, glutamic acid, homocysteic acid and cysteic acid; $X_{33}$ is selected from the group consisting of aspartic acid, glutamine and glutamic acid; $X_{34}$ is selected from the group consisting of alanine and threonine; $X_{41}$ is selected from the group consisting of glutamic acid, aspartic acid or asparagine; $X_{42}$ is selected from the group consisting of alanine, lysine, ornithine and arginine; $X_{45}$ is tyrosine or phenylalanine; $R_{22}$ is selected from the group consisting of AYRPSE (SEQ ID NO: 11), FVNQ (SEQ ID NO: 10), PGPE (SEQ ID NO: 9), a tripeptide glycine-proline-glutamic acid, a tripeptide valine-asparagine-glutamine, a dipeptide proline-glutamic acid, a dipeptide asparagine-glutamine, glutamine, glutamic acid and a bond; and $R_{13}$ is COOH or $CONH_2$.

16. The single chain insulin analog of embodiment 15 wherein said A chain comprises the sequence GIV$X_4X_5$CC$X_8X_9X_{10}$C$X_{12}$L$X_{14}X_{15}$LE$X_{18}X_{19}$C$X_{21}$-$R_{13}$ (SEQ ID NO: 55);

said B chain comprises the sequence $X_{25}$LCG$X_{29}X_{30}$LV$X_{33}X_{34}$LYLVCG$X_{41}X_{42}$GF$X_{45}$ (SEQ ID NO: 17); further wherein $X_4$ is glutamic acid or aspartic acid; $X_5$ is glutamic acid or glutamine; $X_8$ is threonine, histidine or phenylalanine; $X_9$ is serine, arginine, ornithine or alanine; $X_{10}$ is serine or isoleucine; $X_{12}$ is serine or aspartic acid; $X_{14}$ is arginine, tyrosine, ornithine or alanine; $X_{15}$ is glutamine, arginine, alanine, ornithine or leucine; $X_{18}$ is methionine, asparagine or threonine; $X_{19}$ is tyrosine, 4-methoxy-phenylalanine or 4-amino phenylalanine; $X_{21}$ is alanine, glycine or asparagine; $X_{25}$ is histidine or threonine; $X_{29}$ is alanine, glycine or serine; $X_{30}$ is histidine, aspartic acid, glutamic acid, homocysteic acid or cysteic acid; $X_{33}$ is aspartic acid or glutamic acid; $X_{34}$ is alanine or threonine; $X_{41}$ is aspartic acid or glutamic acid; $X_{42}$ is alanine, ornithine or arginine; $X_{45}$ is tyrosine or phenylalanine; and $R_{13}$ is COOH or $CONH_2$.

17. The single chain insulin analog of any of embodiments 15-16 wherein the B chain further comprises an amino terminal extension comprising 1 to 6 charged amino acids.

18. The single chain insulin analog of any of embodiments 1-17 wherein the B chain comprises the sequence $R_{22}$-HLCGS$X_{30}$LVEALYLVCGERGFF (SEQ ID NO: 56) or $R_{24}$-$X_{25}$LCG$X_{29}X_{30}$LV$X_{33}X_{34}$LYLVCG$X_{41}X_{42}$GF$X_{45}$ (SEQ ID NO: 17) and the A chain comprises the sequence GIVEQCC$X_8$SICSLYQLEN$X_{19}$C$X_{21}$-$R_{13}$ (SEQ ID NO: 26) or GIV$X_4$ECC$X_8X_9$SCDL$X_{14}X_{15}$L$X_{17}X_{18}X_{19}$C$X_{21}$-$R_{13}$ (SEQ ID NO: 15)

wherein $X_4$ is glutamic acid or aspartic acid; $X_8$ is histidine, threonine or phenylalanine; $X_9$ is arginine, lysine, ornithine or alanine; $X_{14}$ is arginine, lysine, ornithine or alanine; $X_{15}$ is glutamine, glutamic acid, arginine, alanine, lysine, ornithine or leucine; $X_{17}$ is glutamine or glutamic acid; $X_{18}$ is methionine, asparagine, glutamine, aspartic acid, glutamic acid or threonine; $X_{19}$ is tyrosine, 4-methoxyphenylalanine or 4-amino phenylalanine; $X_{21}$ is selected from the group consisting of alanine, glycine, serine, valine, threonine, isoleucine, leucine, glutamine, glutamic acid, asparagine, aspartic acid, histidine, tryptophan, tyrosine, and methionine; $X_{22}$ is selected from the group consisting of phenylalanine and desamino-phenylalanine; $X_{23}$ is asparagine or glycine; $X_{25}$ is histidine or threonine; $X_{29}$ is selected from the group consisting of alanine and glycine; $X_{30}$ is selected from the group consisting of histidine, aspartic acid, glutamic acid, homocysteic acid and cysteic acid; $X_{33}$ is selected from the group consisting of aspartic acid, glutamine and glutamic acid; $X_{34}$ is selected from the group consisting of alanine and threonine; $X_{41}$ is selected from the group consisting of glutamic acid, aspartic acid or asparagine; $X_{42}$ is selected from the group consisting of alanine, lysine, ornithine and arginine; $X_{45}$ is tyrosine or phenylalanine; $R_{22}$ is selected from the group consisting of $X_{22}$VNQ (SEQ ID NO: 50), a tripeptide valine-asparagine-glutamine, a dipeptide asparagine-glutamine, glutamine, and a bond; $R_{24}$ is selected from the group consisting of AYRPSE (SEQ ID NO: 11), PGPE (SEQ ID NO: 9), a tripeptide glycine-proline-glutamic acid, a dipeptide proline-glutamic acid, glutamine, glutamic acid and a bond; and $R_{13}$ is COOH or $CONH_2$.

19. The single chain insulin agonist of embodiment 18 wherein $X_8$, $X_{25}$ and $X_{30}$ are each histidine.

20. The single chain insulin agonist of any of embodiments 15-19 wherein
$X_4$ is aspartic acid;
$X_9$ is arginine, lysine, ornithine or alanine,
$X_{21}$ is alanine, glycine or asparagine;
$X_{29}$ is alanine;
$X_{33}$ is aspartic acid;
$X_{34}$ is alanine;
$X_{41}$ is aspartic acid; and
$R_{22}$ is a glycine-proline-glutamic acid tripeptide.

21. The single chain insulin analog of any of embodiments 1-20 further comprising a hydrophilic moiety linked to said analog.

22. The single chain insulin analog of embodiment 21 wherein the hydrophilic moiety is a plasma protein, polyethylene glycol chain or the Fc portion of an immunoglobin.

23. The single chain insulin analog of embodiment 21 wherein the hydrophilic moiety is a polyethylene glycol linked to the N-terminal amino acid of the B chain or to an amino acid side chain of the linking moiety.

24. The single chain insulin agonist of any of the embodiments 1-23, wherein an amino acid side chain of said single chain insulin agonist is covalently attached to an acyl group or an alkyl group via an alkyl amine, amide, ether, ester, thioether, or thioester linkage.

25. An insulin analog comprising an A chain, a B chain and a CTP peptide, wherein
said A chain comprises the sequence $GIVX_4X_5CCX_8X_9X_{10}CX_{12}LX_{14}X_{15}LEX_{18}X_{19}CX_{21}$-$R_{13}$ (SEQ ID NO: 55);
said B chain comprises the sequence $X_{25}LCGX_{29}X_{30}LVX_{33}X_{34}LYLVCGX_{41}X_{42}GFX_{45}$ (SEQ ID NO: 17); and
said CTP peptide comprises the sequence $(SSSSX_{50}APPPSLPSPSRLPGPSDTPILPQX_{51})_n$ (SEQ ID NO: 66) or $MGSSSSX_{50}APPPSLPSPSRLPGPSDTPILPQEEEEEX_{51}$ (SEQ ID NO; 93), wherein said A and B chain are linked to one another via disulfide bonds and said CTP peptide is covalently bound to the amino or carboxy terminus of the B chain, further wherein n is an integer selected from 1 to 3; $X_4$ is glutamic acid or aspartic acid; $X_5$ is glutamic acid or glutamine; $X_8$ is threonine, histidine or phenylalanine; $X_9$ is serine, arginine, ornithine or alanine; $X_{10}$ is serine or isoleucine; $X_{12}$ is serine or aspartic acid; $X_{14}$ is arginine, tyrosine, ornithine or alanine; $X_{15}$ is glutamine, arginine, alanine, ornithine or leucine; $X_{18}$ is methionine, asparagine or threonine; $X_{19}$ is tyrosine, 4-methoxy-phenylalanine or 4-amino phenylalanine; $X_{21}$ is alanine, glycine or asparagine; $X_{25}$ is histidine or threonine; $X_{29}$ is alanine, glycine or serine; $X_{30}$ is histidine, aspartic acid, glutamic acid, homocysteic acid or cysteic acid; $X_{33}$ is aspartic acid or glutamic acid; $X_{34}$ is alanine or threonine; $X_{41}$ is aspartic acid or glutamic acid; $X_{42}$ is alanine, ornithine or arginine; $X_{45}$ is tyrosine or phenylalanine; $X_{50}$ and $X_{51}$ are independently selected from arginine and lysine; and $R_{13}$ is COOH or $CONH_2$.

26. The insulin analog of embodiment 25 wherein said CTP peptide is covalently bound to the amino terminus of the B chain to provide an N-terminal CTP peptide.

27. The insulin analog of embodiment 25 wherein said CTP peptide is covalently bound to the carboxyl terminus of the B chain to provide a C-terminal CTP peptide.

28. The insulin analog of embodiment 25 or 27 wherein the carboxy terminus of said B chain is covalently linked to the amino terminus of the A chain via a peptide linker to form a contiguous amino acid chain, wherein said peptide linker comprises said CTP peptide, providing a linker CTP peptide.

29. The insulin analog of embodiment 25, 26, 27 or 28 wherein the C-terminal CTP peptide, N-terminal CTP peptide and linker CTP peptide comprise a sequence independently selected from the group consisting of $(SSSSX_{50}APPPSLPSPSRLPGPSDTPILPQ)_n$ (SEQ ID NO: 92), $(SSSSRAPPPSLPSPSRLPGPSDTPILPQK)_n$ (SEQ ID NO: 79), and $(SSSSKAPPPSLPSPSRLPGPSDTPILPQR)_n$ (SEQ ID NO: 64), further wherein n is 1 or 2.

30. The insulin analog of embodiment 29 wherein n is 1 and the linker CTP peptide comprises the sequence SSSSRAPPPSLPSPSRLPGPSDTPILPQK (SEQ ID NO: 79).

31. The insulin analog of any of embodiments 25-30 wherein the B chain comprises the sequence $SSSSX_{50}APPPSLPSPSRLPGPSDTPILPQX_{51}$ SEQ ID NO: 66) linked to carboxy terminus of the B chain and the sequence $MGSSSSX_{50}APPPSLPSPSRLPGPSDTPILPQEEEEEX_{51}$ (SEQ ID NO; 93) linked to the amino terminus of the B chain.

32. The insulin analog of any of embodiments 25-31 wherein the CTP peptide is glycosylated.

33. The insulin analog of any of embodiments 25-32 wherein the B chain comprises the sequence $R_{22}$-$HLCGSX_{30}LVEALYLVCGERGFF$ (SEQ ID NO: 56) or $R_{24}$-$X_{25}LCGX_{29}X_{30}LVX_{33}X_{34}LYLVCGX_{41}X_{42}GFX_{45}$ (SEQ ID NO: 17) and the A chain comprises the sequence $GIVEQCCX_8SICSLYQLENX_{19}CX_{21}$-$R_{13}$ (SEQ ID NO: 26) or $GIVX_4ECCX_8X_9SCDLX_{14}X_{15}LX_{17}X_{18}X_{19}CX_{21}$-$R_{13}$ (SEQ ID NO: 15)
wherein $X_4$ is glutamic acid or aspartic acid; $X_8$ is histidine, threonine or phenylalanine; $X_9$ is arginine, lysine, ornithine or alanine; $X_{14}$ is arginine, lysine, ornithine or alanine; $X_{15}$ is glutamine, glutamic acid, arginine, alanine, lysine, ornithine or leucine; $X_{17}$ is glutamine or glutamic acid; $X_{18}$ is methionine, asparagine, glutamine, aspartic acid, glutamic acid or threonine; $X_{19}$ is tyrosine, 4-methoxy-phenylalanine or 4-amino phenylalanine; $X_{21}$ is selected from the group consisting of alanine, glycine, serine, valine, threonine, isoleucine, leucine, glutamine, glutamic acid, asparagine, aspartic acid, histidine, tryptophan, tyrosine, and methionine; $X_{22}$ is selected from the group consisting of phenylalanine and desamino-phenylalanine; $X_{23}$ is asparagine or glycine; $X_{25}$ is histidine or threonine; $X_{29}$ is selected from the group consisting of alanine and glycine; $X_{30}$ is selected from the group consisting of histidine, aspartic acid, glutamic acid, homocysteic acid and cysteic acid; $X_{33}$ is selected from the group consisting of aspartic acid, glutamine and glutamic acid; $X_{34}$ is selected from the group consisting of alanine and threonine; $X_{41}$ is selected from the group consisting of glutamic acid, aspartic acid or asparagine; $X_{42}$ is selected from the group consisting of alanine, lysine, ornithine and arginine; $X_{45}$ is tyrosine or phenylalanine; $R_{22}$ is selected from the group consisting of $X_{22}$VNQ (SEQ ID NO: 50), a tripeptide valine-asparagine-glutamine, a dipeptide asparagine-glutamine, glutamine, and a bond; $R_{24}$ is selected from the group consisting of AYRPSE (SEQ ID NO: 11), PGPE (SEQ ID NO: 9), a tripeptide glycine-proline-glutamic acid, a dipeptide proline-glutamic acid, glutamine, glutamic acid and a bond; and $R_{13}$ is COOH or $CONH_2$.

34. The insulin analog of embodiment 33 wherein $X_8$, $X_{25}$ and $X_{30}$ are each histidine.

35. The insulin analog of embodiment 33 or 34 wherein $X_4$ is aspartic acid; $X_9$ is arginine, lysine, ornithine or alanine; $X_{21}$ is alanine, glycine or asparagine; $X_{29}$ is alanine; $X_{33}$ is aspartic acid; $X_{34}$ is alanine; $X_{41}$ is aspartic acid; and $R_{22}$ is a glycine-proline-glutamic acid tripeptide.

36. The insulin analog of any of embodiments 25-35 wherein the B chain comprises the sequence $R_{25}$-HLCGSX$_{30}$LVEALYLVCGERGFF (SEQ ID NO: 56), the CTP peptide comprises the sequence of SEQ ID NO 66 and the A chain comprises the sequence of GIVEQCCX$_8$SICSLYQLENX$_{19}$CX$_{21}$-R$_{13}$ (SEQ ID NO: 26), wherein $X_{30}$ is selected from the group consisting of histidine, aspartic acid, glutamic acid, homocysteic acid and cysteic acid; $X_8$ is histidine, threonine or phenylalanine; $X_{19}$ is tyrosine, 4-methoxy-phenylalanine or 4-amino phenylalanine; $X_{21}$ is alanine, glycine or asparagine; $X_{22}$ is selected from the group consisting of phenylalanine and desamino-phenylalanine; and $R_{25}$ is selected from the group consisting of $X_{22}$VNQ (SEQ ID NO: 50), a tripeptide valine-asparagine-glutamine, a dipeptide asparagine-glutamine, glutamine, AYRPSE (SEQ ID NO: 11), PGPE (SEQ ID NO: 9), a tripeptide glycine-proline-glutamic acid, a dipeptide proline-glutamic acid, glutamic acid.

37. The insulin analog of embodiment 36 further comprising a CTP peptide linked to the N-terminus of the B chain.

38. The insulin analog of any of embodiments 25-37 further comprising a hydrophilic moiety linked to said analog.

39. The insulin analog of embodiment 38 wherein the hydrophilic moiety is a polyethylene glycol linked to the N-terminal amino acid of the B chain or an amino acid side chain of the linking moiety.

40. The insulin agonist of any of embodiments 25-39, wherein an amino acid side chain of said insulin agonist is covalently attached to an acyl group or an alkyl group via an alkyl amine, amide, ether, ester, thioether, or thioester linkage.

41. A nucleic acid sequence encoding the insulin analog of any of embodiments 1-37.

42. A eukaryotic host cell comprising a nucleic acid sequence that encodes the insulin analog of embodiment 41.

43. The host cell of embodiment 42 wherein the cell is a mammalian host cell.

44. The host cell of embodiment 42 wherein the cell is a *Pichia* or CHO cell.

45. A method of producing a hyperglycosylated insulin analog, said method comprising culturing a cells of embodiment 42 under conditions wherein said protein is produced; and recovering said protein from the culture.

46. The method of embodiment 45, wherein the insulin analog is expressed as a single chain analog, said method further comprising the step of cleaving the recovered protein to produce a two chain insulin analog.

47. The method of any of embodiment 1-46 wherein the linking moiety comprises the sequence SSSSRAP-PPSLPSPSRLPGPSDTPILPQK (SEQ ID NO: 79).

48. A derivative of the insulin analog of any of embodiments 1-47 further comprising the structure U-B, wherein U is an amino acid or a hydroxy acid; B is an N-alkylated amino acid linked to said single chain insulin analog through an amide bond between a carboxyl moiety of B and an amine of the single chain insulin analog, wherein U, B, or the amino acid of the single chain insulin analog to which U-B is linked is a non-coded amino acid, further wherein the chemical cleavage half-life ($t_{1/2}$) of U-B from the single chain insulin analog is at least about 1 hour to about 1 week in PBS under physiological conditions.

49. The derivative of embodiment 48 wherein said insulin analog comprises an A chain sequence of GIVX$_4$X$_5$CCX$_8$X$_9$X$_{10}$CX$_{12}$LX$_{14}$X$_{15}$LX$_{17}$X$_{18}$X$_{19}$CX$_{21}$-R$_{13}$ (SEQ ID NO: 18) wherein $X_4$ is glutamic acid or aspartic acid; $X_5$ is glutamine or glutamic acid; $X_8$ is histidine, threonine or phenylalanine; $X_9$ is serine, arginine, lysine, ornithine or alanine; $X_{10}$ is isoleucine or serine; $X_{12}$ is serine or aspartic acid; $X_{14}$ is tyrosine, arginine, lysine, ornithine or alanine; $X_{15}$ is glutamine, glutamic acid, arginine, alanine, lysine, ornithine or leucine; $X_{17}$ is glutamine, glutamic acid, arginine, aspartic acid, ornithine or lysine; $X_{18}$ is methionine, asparagine, glutamine, aspartic acid, glutamic acid or threonine; $X_{19}$ is 4-amino phenylalanine; $X_{21}$ is selected from the group consisting of alanine, glycine, serine, valine, threonine, isoleucine, leucine, glutamine, glutamic acid, asparagine, aspartic acid, histidine, tryptophan, tyrosine, and methionine; further wherein U-B is linked to single chain insulin agonist through an amide bond between a carboxyl moiety of B and the para amine of 4-amino phenylalanine at position A19.

50. The derivative of embodiment 48 or 49, wherein $X_4$ is aspartic acid; $X_5$ is glutamic acid; $X_8$ is histidine or phenylalanine; $X_9$ is arginine, lysine or ornithine; $X_{10}$ is serine; $X_{12}$ is aspartic acid; $X_{14}$ and $X_{15}$ are independently arginine, lysine or ornithine; $X_{17}$ is glutamine, glutamic acid, arginine, aspartic acid, ornithine or lysine; $X_{18}$ is methionine; and $X_{21}$ is alanine or asparagine.

51. The derivative of any of embodiments 47-49, wherein the first amino acid and/or the second amino acid of the structure U-B is an amino acid in the D stereoisomer configuration.

52 The derivative of embodiment 49, wherein U-B comprises the structure of Formula X:

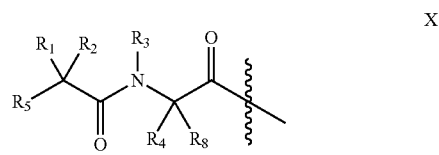

wherein
$R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, (C$_1$-C$_4$ alkyl)COOH, (C$_1$-C$_4$ alkyl)NH$_2$, (C$_1$-C$_4$ alkyl)NHC(NH$_2$$^+$)NH$_2$, (C$_0$-C$_4$ alkyl)(C$_3$-C$_6$ cycloalkyl), (C$_0$-C$_4$ alkyl)(C$_2$-C$_5$ heterocyclic), (C$_0$-C$_4$ alkyl)(C$_6$-C$_{10}$ aryl)R$_7$, (C$_1$-C$_4$ alkyl)(C$_3$-C$_9$ heteroaryl), and C$_1$-C$_{12}$ alkyl (W$_1$)C$_1$-C$_{12}$ alkyl, wherein W$_1$ is a heteroatom selected from the group consisting of N, S and O, or R$_1$ and R$_2$ together with the atoms to which they are attached form a C$_3$-C$_{12}$ cycloalkyl or aryl; or R$_4$ and R$_8$ together with the atoms to which they are attached form a C$_3$-C$_6$ cycloalkyl;

R$_3$ is selected from the group consisting of C$_1$-C$_{18}$ alkyl, (C$_1$-C$_{18}$ alkyl)OH, (C$_1$-C$_{18}$ alkyl)NH$_2$, (C$_1$-C$_{18}$ alkyl)SH, (C$_0$-C$_4$ alkyl)(C$_3$-C$_6$)cycloalkyl, (C$_0$-C$_4$ alkyl)(C$_2$-C$_5$ heterocyclic), (C$_0$-C$_4$ alkyl)(C$_6$-C$_{10}$ aryl)R$_7$, and (C$_1$-C$_4$ alkyl)(C$_3$-C$_9$ heteroaryl) or R$_4$ and R$_3$ together with the atoms to which they are attached form a 4, 5 or 6 member heterocyclic ring;

R$_5$ is NHR$_6$ or OH;

R$_6$ is H, C$_1$-C$_8$ alkyl or R$_6$ and R$_1$ together with the atoms to which they are attached form a 4, 5 or 6 member heterocyclic ring; and R$_7$ is selected from the group consisting of H, OH, C$_1$-C$_{18}$ alkyl, C$_2$-C$_{18}$ alkenyl, (C$_0$-C$_4$ alkyl)CONH$_2$, (C$_0$-C$_4$ alkyl)COOH, (C$_0$-C$_4$ alkyl)NH$_2$, (C$_0$-C$_4$ alkyl)OH, and halo.

53. The derivative of embodiment 52 wherein

R$_1$ and R$_2$ are independently C$_1$-C$_{18}$ alkyl or aryl;

R$_3$ is C$_1$-C$_{18}$ alkyl or R$_3$ and R$_4$ together with the atoms to which they are attached form a 4-12 heterocyclic ring;

R$_4$ and R$_8$ are independently selected from the group consisting of hydrogen, C$_1$-C$_{18}$ alkyl and aryl; and R$_5$ is an amine or a hydroxyl.

54. The derivative of embodiment 52, wherein

R$_1$ is selected from the group consisting of hydrogen, C$_1$-C$_{18}$ alkyl and aryl, or R$_1$ and R$_2$ are linked through —(CH2)p-, wherein p is 2-9;

R$_3$ is C$_1$-C$_{18}$ alkyl or R$_3$ and R$_4$ together with the atoms to which they are attached form a 4-6 heterocyclic ring;

R$_4$ and R$_8$ are independently selected from the group consisting of hydrogen, C$_1$-C$_{18}$ alkyl and aryl; and R$_5$ is an amine or N-substituted amine.

55. The derivative of embodiment 52, wherein

R$_1$ and R$_2$ are independently selected from the group consisting of hydrogen, C$_1$-C$_8$ alkyl and aryl;

R$_3$ is C$_1$-C$_{18}$ alkyl or R$_3$ and R$_4$ together with the atoms to which they are attached form a 4-6 heterocyclic ring;

R$_4$ and R$_8$ are each hydrogen; and

R$_5$ is selected from the group consisting of amine, N-substituted amine and hydroxyl.

56. The derivative of any of embodiments 48-55 further comprising a hydrophilic moiety linked to an amino acid of the structure U-B or the linking moiety.

57. The derivative of embodiment 56 wherein the hydrophilic moiety is polyethylene glycol or albumin.

58. A single chain insulin analog comprise the structure IB-LM-IA, wherein

IB comprises the sequence J-R$_{23}$R$_{22}$-X$_{25}$LCGX$_{29}$X$_{30}$LVX$_{33}$X$_{34}$LX$_{36}$LVCGX$_{41}$X$_{42}$GFX$_{45}$ (SEQ ID NO: 16);

LM is a linking moiety comprising an 18 amino acid sequence that covalently links the carboxy terminus of the B chain to the amino terminus of the A chain to form a contiguous amino acid chain, with the proviso that the linking moiety does not comprise an 18 amino acid sequence that is identical to an 18 amino acid sequence of SEQ ID NO: 53 directly linked to the carboxy terminus of the B chain; and IA comprises the sequence GIVX$_4$X$_5$CCX$_8$X$_9$X$_{10}$X$_{11}$X$_{12}$LX$_{14}$X$_{15}$LEX$_{18}$X$_{19}$CX$_{21}$—R$_{13}$ (SEQ ID NO: 55) further wherein J is H or a dipeptide comprising the general structure of U-B, wherein U is an amino acid or a hydroxyl acid and B is an N-alkylated amino acid linked through an amide bond; X$_4$ is glutamic acid or aspartic acid; X$_5$ is glutamine or glutamic acid; X$_8$ is histidine, threonine or phenylalanine; X$_9$ is serine, arginine, lysine, ornithine or alanine; X$_{10}$ is isoleucine or serine; X$_{12}$ is serine or aspartic acid; X$_{14}$ is tyrosine, arginine, lysine, ornithine or alanine; X$_{15}$ is glutamine, glutamic acid, arginine, alanine, lysine, ornithine or leucine; X$_{18}$ is methionine, asparagine, glutamine, aspartic acid, glutamic acid or threonine; X$_{19}$ is an amino acid of the general structure:

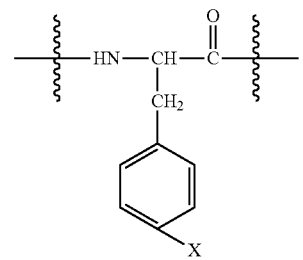

wherein X is selected from the group consisting of OH or NHR$_{10}$, wherein R$_{10}$ is H or a dipeptide element comprising the general structure U-B, wherein U is an amino acid or a hydroxyl acid and B is an N-alkylated amino acid; X$_{21}$ is selected from the group consisting of alanine, glycine, serine, valine, threonine, isoleucine, leucine, glutamine, glutamic acid, asparagine, aspartic acid, histidine, tryptophan, tyrosine, and methionine; X$_{25}$ is histidine or threonine; X$_{29}$ is selected from the group consisting of alanine, glycine and serine; X$_{30}$ is selected from the group consisting of histidine, aspartic acid, glutamic acid, homocysteic acid and cysteic acid; X$_{33}$ is selected from the group consisting of aspartic acid, glutamine and glutamic acid; X$_{34}$ is selected from the group consisting of alanine and threonine; X$_{36}$ is an amino acid of the general structure

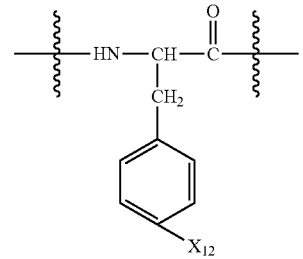

wherein X$_{12}$ is selected from the group consisting of OH and NHR$_{11}$, wherein R$_{11}$ is a dipeptide element comprising the general structure U-B; X$_{41}$ is selected from the group consisting of glutamic acid, aspartic acid or asparagine; X$_{42}$ is selected from the group consisting of alanine, lysine, ornithine and arginine; X$_{45}$ is an amino acid of the general structure

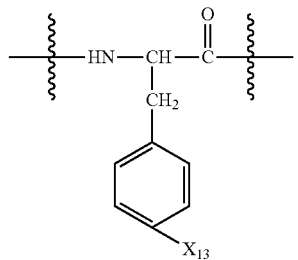

wherein $X_{13}$ is selected from the group consisting of H, OH and $NHR_{12}$, wherein $R_{12}$ is H or dipeptide element comprising the general structure U-B; $R_{22}$ is selected from the group consisting of AYRPSE (SEQ ID NO: 11), FVNQ (SEQ ID NO: 10), PGPE (SEQ ID NO: 9), a tripeptide glycine-proline-glutamic acid, a tripeptide valine-asparagine-glutamine, a dipeptide proline-glutamic acid, a dipeptide asparagine-glutamine, glutamine, glutamic acid and a bond; $R_{23}$ is a bond or an amino sequence comprising 1 to 6 charged amino acids; and $R_{13}$ is COOH or $CONH_2$, with the proviso that U, B, or the amino acid of the single chain insulin agonist to which U-B is linked is a non-coded amino acid.

59. The single chain analog of embodiment 58 wherein $X_{19}$ is an amino acid of the general structure:

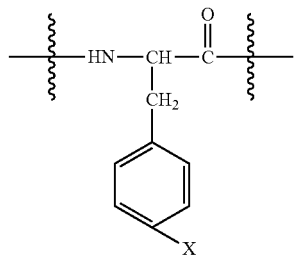

wherein X is selected from the group consisting of OH or $NHR_{10}$, wherein $R_{10}$ is H or a dipeptide element comprising the general structure U-B, wherein U is an amino acid or a hydroxyl acid and B is an N-alkylated amino acid; and $X_{36}$ and $X_{45}$ are both tyrosine.

60. The single chain insulin analog of embodiment 58 or 59 wherein said linking moiety comprises a 29 contiguous amino acid sequence, directly linked to the carboxy terminal amino acid of the B chain, wherein said 28 contiguous amino acid sequence has greater than 95% sequence identity to SEQ ID NO: 64).

61. The single chain insulin analog of embodiment 58 or 59 wherein said linking moiety comprises an analog of (SEQ ID NO: 64), wherein said analog differs from (SEQ ID NO: 64) by 1 to 6 amino acid substitutions.

62. The single chain insulin analog of embodiment 58 or 59 wherein said linking moiety comprises (SEQ ID NO: 66); wherein
$X_{50}$ and $X_{51}$ are independently arginine or lysine.

63. The single chain insulin analog of embodiment 59 wherein said linking moiety comprises SSSSRAPPSLPSPSRLPGPSDTPILPQK (SEQ ID NO: 64).

64. The single chain insulin of any of embodiments 59-63, wherein $X_4$ is aspartic acid; $X_5$ is glutamic acid; $X_8$ is histidine or phenylalanine; $X_9$ is arginine, lysine or ornithine; $X_{10}$ is serine; $X_{12}$ is aspartic acid; $X_{14}$ and $X_{15}$ are independently arginine, lysine or ornithine; $X_{17}$ is glutamine, glutamic acid, arginine, aspartic acid, ornithine or lysine; $X_{18}$ is methionine; and $X_{21}$ is alanine or asparagine.

65. The single chain insulin analog of any of embodiments 59 to 64 wherein
U-B comprises the structure of Formula X:

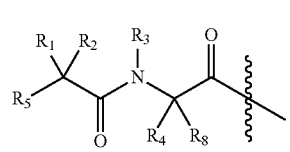

wherein
$R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_1$ alkyl)($C_3$-$C_6$ cycloalkyl), ($C_0$-$C_1$ alkyl)($C_2$-$C_5$ heterocyclic), ($C_0$-$C_4$ alkyl)($C_6$-$C_{10}$ aryl)R$_7$, ($C_1$-$C_4$ alkyl)($C_3$-$C_9$ heteroaryl), and $C_1$-$C_{12}$ alkyl($W_1$)$C_1$-$C_{12}$ alkyl, wherein $W_1$ is a heteroatom selected from the group consisting of N, S and O, or $R_1$ and $R_2$ together with the atoms to which they are attached form a $C_3$-$C_{12}$ cycloalkyl or aryl; or $R_4$ and $R_8$ together with the atoms to which they are attached form a $C_3$-$C_6$ cycloalkyl;
$R_3$ is selected from the group consisting of $C_1$-$C_{18}$ alkyl, ($C_1$-$C_{18}$ alkyl)OH, ($C_1$-$C_{18}$ alkyl)NH$_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)R$_7$, and ($C_1$-$C_4$ alkyl)($C_3$-$C_9$ heteroaryl) or $R_4$ and $R_3$ together with the atoms to which they are attached form a 4, 5 or 6 member heterocyclic ring;
$R_5$ is $NHR_6$ or OH;
$R_6$ is H, $C_1$-$C_8$ alkyl or $R_6$ and $R_1$ together with the atoms to which they are attached form a 4, 5 or 6 member heterocyclic ring; and
$R_7$ is selected from the group consisting of H, OH, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_1$ alkyl)OH, and halo, with the proviso that when $R_4$ and $R_3$ together with the atoms to which they are attached form a 4, 5 or 6 member heterocyclic ring, both $R_1$ and $R_2$ are other than H.

66. The single chain insulin analog of any of embodiments 59-65, further comprising a hydrophilic moiety linked to an amino acid of the structure U-B or the linking moiety.

67. The single chain insulin analog of embodiment 66, wherein the hydrophilic moiety is polyethylene glycol or albumin.

68. The single chain insulin analog of any of embodiments 59-67 wherein IA comprises the sequence GIVEQCCTSICSLYQLENX$_{19}$CX$_{21}$-R$_{13}$ (SEQ ID NO: 95), GIVEQCCHSICSLYQLENX$_{19}$CX$_{21}$-R$_{13}$ (SEQ ID NO: 37) or GIVDECCHRSCDLRRLEMX$_{19}$CX$_{21}$-R$_{13}$ (SEQ ID NO: 51) and IB comprises the sequence FVNQHLCG-SHLVEALYLVCGERGFFYTDRT (SEQ ID NO: 94) FVN-QHLCGSHLVEALYLVCGERGFFYTPKT (SEQ ID NO: 2), GPETLCGAELVDALYLVCGDRGFYFNKPT (SEQ ID NO: 6) or GPETLCGAELVDALYLVCGDRGFYFNPKT (SEQ ID NO: 52); and Xaa at position 21 is alanine, glycine or asparagine.

69. The single chain insulin analog of embodiment 68 wherein the linking moiety comprises the sequence (SSSSX$_{50}$APPPSLPSPSRLPGPSDTPILPQX$_{51}$)$_n$ (SEQ ID NO: 66), wherein n is an integer selected from the group consisting of 1, 2 or 3; and X$_{50}$ and X$_{51}$ are independently arginine or lysine.

70. The single chain insulin agonist of any of embodiments 59-69 wherein said analog is acylated at one or more positions selected from A14, A15, B0, B1, B10, B22, B28, B29, at the side chain of an amino acid side chain of the linking moiety, or the side chain of an amino acid of the dipeptide U-B.

71. The single chain insulin agonist of any of embodiments 59-69 wherein said analog is pegylated at one or more positions selected from A14, A15, B0, B1, B10, B22, B28, B29, at the side chain of an amino acid side chain of the linking moiety, or the side chain of an amino acid of the dipeptide U-B.

72. A dimer or multimer comprising a single chain insulin agonist of any of embodiments 1-71.

73. A pharmaceutical composition comprising a single chain insulin agonist, or prodrug derivative thereof, of any of embodiments 1-72 and a pharmaceutically acceptable carrier.

74. A method of treating diabetes, said method comprising administering an effective amount of a pharmaceutical composition of embodiment 73.

75. The use of a compound any of embodiments 1-72, in the manufacture of a medicament for the treatment of hyperglycemia.

76. The use of a compound of any of embodiments 1-72 to treat diabetes.

Example 1

Synthesis of Insulin A & B Chains

Insulin A & B chains were synthesized on 4-methylbenzhyryl amine (MBHA) resin or 4-Hydroxymethyl-phenylacetamidomethyl (PAM) resin using Boc chemistry. The peptides were cleaved from the resin using HF/p-cresol 95:5 for 1 hour at 0° C. Following HF removal and ether precipitation, peptides were dissolved into 50% aqueous acetic acid and lyophilized. Alternatively, peptides were synthesized using Fmoc chemistry. The peptides were cleaved from the resin using Trifluoroacetic acid (TFA)/Triisopropylsilane (TIS)/H$_2$O (95:2.5:2.5), for 2 hour at room temperature. The peptide was precipitated through the addition of an excessive amount of diethyl ether and the pellet solubilized in aqueous acidic buffer. The quality of peptides were monitored by RP-HPLC and confirmed by Mass Spectrometry (ESI or MALDI).

Insulin A chains were synthesized with a single free cysteine at amino acid 7 and all other cysteines protected as acetamidomethyl A-(SH)$^7$(Acm)$^{6,11,20}$. Insulin B chains were synthesized with a single free cysteine at position 7 and the other cysteine protected as acetamidomethyl B—(SH)$^7$ (Acm)$^{19}$. The crude peptides were purified by conventional RP-HPLC.

The synthesized A and B chains were linked to one another through their native disulfide bond linkage in accordance with the general procedure outlined in FIG. 1. The respective B chain was activated to the Cys$^7$-Npys analog through dissolution in DMF or DMSO and reacted with 2,2'-Dithiobis(5-nitropyridine) (Npys) at a 1:1 molar ratio, at room temperature. The activation was monitored by RP-HPLC and the product was confirmed by ESI-MS.

Figure 2:
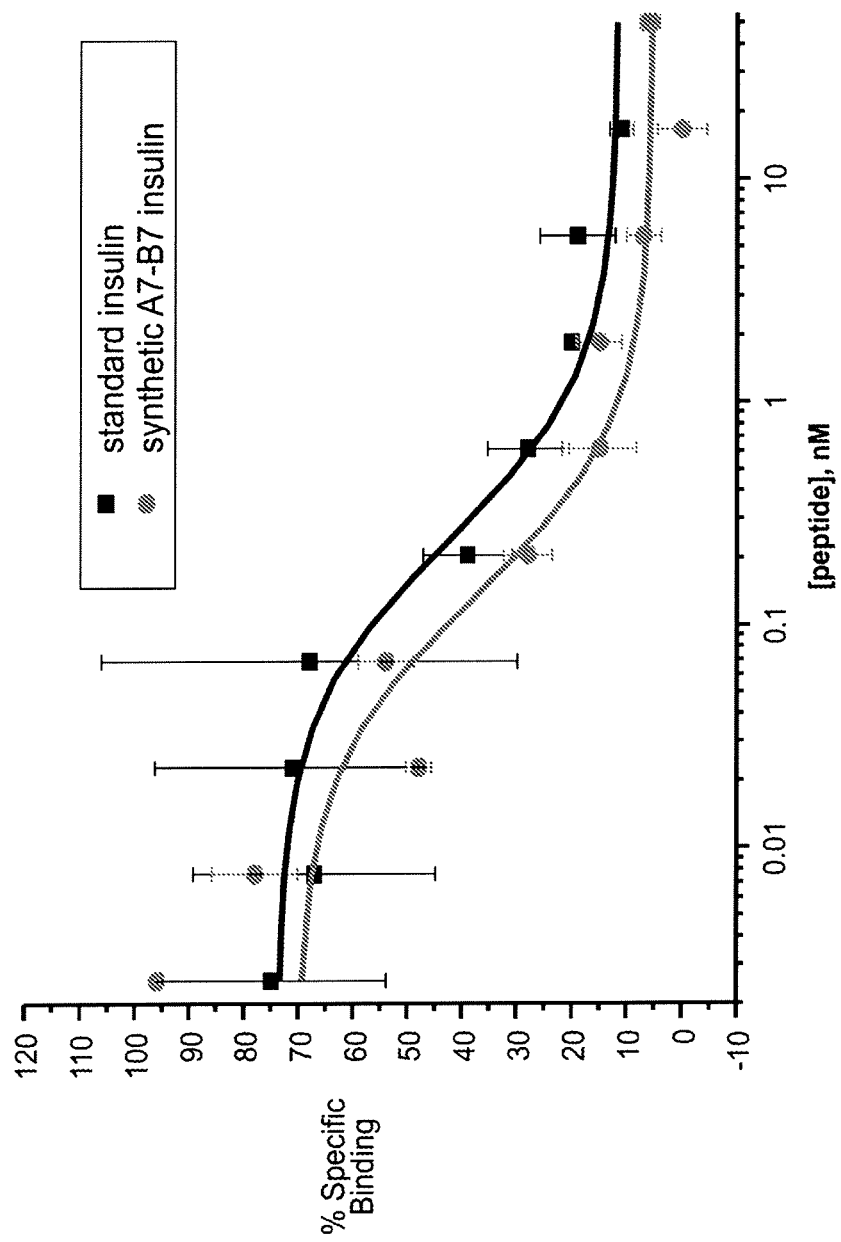
FIG. 2 is a graph comparing insulin receptor specific binding of synthetic human insulin relative to purified native insulin. The synthetic insulin was produced by the approach detailed in FIG. 1 where the $A^7$-$B^7$ bond is the first disulfide formed. As indicated by the data presented in the graph, the two molecules have similar binding activities.

The first B7-A7 disulfide bond was formed by dissolution of the respective A-(SH)$^7$(Acm)$^{6,11,20}$ and B-(Npys)$^7$ (Acm)$^{19}$ at 1:1 molar ratio to a total peptide concentration of 10 mg/ml. When the chain combination reaction was complete the mixture was diluted to a concentration of 50% aqueous acetic acid. The last two disulfide bonds were formed simultaneously through the addition of iodine. A 40 fold molar excess of iodine was added to the solution and the mixture was stirred at room temperature for an additional hour. The reaction was terminated by the addition of an aqueous ascorbic acid solution. The mixture was purified by RP-HPLC and the final compound was confirmed by MALDI-MS. As shown in FIG. 2 and the data in Table 1, the synthetic insulin prepared in accordance with this procedure compares well with purified insulin for insulin receptor binding.

Insulin peptides comprising a modified amino acid (such as 4-amino phenylalanine at position A19) can also be synthesized in vivo using a system that allows for incorporation of non-coded amino acids into proteins, including for example, the system taught in U.S. Pat. Nos. 7,045,337 and 7,083,970.

TABLE 1

Activity of synthesized insulin relative to native insulin

|  | Insulin Standard | | A7-B7 Insulin | |
| --- | --- | --- | --- | --- |
|  | AVER. | STDEV | AVER. | STDEV |
| IC$_{50}$(nM) | 0.24 | 0.07 | 0.13 | 0.08 |
| % of Insulin Activity | 100 | | 176.9 | |

Example 2

Pegylation of Amine Groups (N-Terminus and Lysine) by Reductive Alkylation a. Synthesis Insulin (or an insulin analog), mPEG20k-Aldyhyde, and NaBH$_3$CN, in a molar ratio of 1:2:30, were dissolved in acetic acid buffer at a pH of 4.1-4.4. The reaction solution was composed of 0.1 N NaCl, 0.2 N acetic acid and 0.1 N Na$_2$CO$_3$. The insulin peptide concentration was approximately 0.5 mg/ml. The reaction occurs over six hours at room temperature. The degree of reaction was monitored by RP-HPLC and the yield of the reaction was approximately 50%.

b. Purification

The reaction mixture was diluted 2-5 fold with 0.1% TFA and applied to a preparative RP-HPLC column. HPLC condition: C4 column; flow rate 10 ml/min; A buffer 10% ACN and 0.1% TFA in water; B buffer 0.1% TFA in ACN; A linear gradient B % from 0-40% (0-80 min); PEG-insulin or analogues was eluted at approximately 35% buffer B. The desired compounds were verified by MALDI-TOF, following chemical modification through sulftolysis or trypsin degradation. Pegylation of Amine Groups (N-Terminus and Lysine) by N-Hydroxysuccinimide Acylation.

a. Synthesis

Insulin (or an insulin analog) along with mPEG20k-NHS were dissolved in 0.1 N Bicine buffer (pH 8.0) at a molar ratio of 1:1. The insulin peptide concentration was approximately 0.5 mg/ml. Reaction progress was monitored by HPLC. The yield of the reaction is approximately 90% after 2 hours at room temperature.

b. Purification

The reaction mixture was diluted 2-5 fold and loaded to RP-HPLC. HPLC condition: C4 column; flow rate 10 ml/min; A buffer 10% ACN and 0.1% TFA in water; B buffer 0.1% TFA in ACN; A linear gradient B % from 0-40% (0-80 min); PEG-insulin or analogues was collected at approximately 35% B. The desired compounds were verified by MALDI-TOF, following chemical modification through sulftolysis or trypsin degradation.

Reductive Aminated Pegylation of Acetyl Group on the Aromatic Ring of the Phenylalanine a. Synthesis Insulin (or an insulin analogue), mPEG20k-Hydrazide, and $NaBH_3CN$ in a molar ratio of 1:2:20 were dissolved in acetic acid buffer (pH of 4.1 to 4.4). The reaction solution was composed of 0.1 N NaCl, 0.2 N acetic acid and 0.1 N $Na_2CO_3$. Insulin or insulin analogue concentration was approximately 0.5 mg/ml. at room temperature for 24 h. The reaction process was monitored by HPLC. The conversion of the reaction was approximately 50%. (calculated by HPLC)

b. Purification

The reaction mixture was diluted 2-5 fold and loaded to RP-HPLC. HPLC condition: C4 column; flow rate 10 ml/min; A buffer 10% ACN and 0.1% TFA in water; B buffer 0.1% TFA in ACN; A linear gradient B % from 0-40% (0-80 min); PEG-insulin, or the PEG-insulin analogue was collected at approximately 35% B. The desired compounds were verified by MALDI-TOF, following chemical modification through sulftolysis or trypsin degradation.

Example 3

Insulin Receptor Binding Assay

The affinity of each peptide for the insulin or IGF-1 receptor was measured in a competition binding assay utilizing scintillation proximity technology. Serial 3-fold dilutions of the peptides were made in Tris-Cl buffer (0.05 M Tris-HCl, pH 7.5, 0.15 M NaCl, 0.1% w/v bovine serum albumin) and mixed in 96 well plates (Corning Inc., Acton, Mass.) with 0.05 nM (3-[125I]-iodotyrosyl) A TyrA14 insulin or (3-[125I]-iodotyrosyl) IGF-1 (Amersham Biosciences, Piscataway, N.J.). An aliquot of 1-6 micrograms of plasma membrane fragments prepared from cells over-expressing the human insulin or IGF-1 receptors were present in each well and 0.25 mg/well polyethylene imine-treated wheat germ agglutinin type A scintillation proximity assay beads (Amersham Biosciences, Piscataway, N.J.) were added. After five minutes of shaking at 800 rpm the plate was incubated for 12 h at room temperature and radioactivity was measured with MicroBeta1450 liquid scintillation counter (Perkin-Elmer, Wellesley, Mass.). Non-specifically bound (NSB) radioactivity was measured in the wells with a four-fold concentration excess of "cold" native ligand than the highest concentration in test samples. Total bound radioactivity was detected in the wells with no competitor. Percent specific binding was calculated as following: % Specific Binding=(Bound-NSB/Total bound-NSB)×100. IC50 values were determined by using Origin software (OriginLab, Northampton, Mass.).

Example 4

Insulin Receptor Phosphorylation Assay

To measure receptor phosphorylation by insulin or insulin analogs, receptor transfected HEK293 cells were plated in 96 well tissue culture plates (Costar #3596, Cambridge, Mass.) and cultured in Dulbecco's modified Eagle medium (DMEM) supplemented with 100 IU/ml penicillin, 100 µg/ml streptomycin, 10 mM HEPES and 0.25% bovine growth serum (HyClone SH30541, Logan, Utah) for 16-20 hrs at 37° C., 5% $CO_2$ and 90% humidity. Serial dilutions of insulin or insulin analogs were prepared in DMEM supplemented with 0.5% bovine serum albumin (Roche Applied Science #100350, Indianapolis, Ind.) and added to the wells with adhered cells. After 15 min incubation at 37° C. in humidified atmosphere with 5% $CO_2$ the cells were fixed with 5% paraformaldehyde for 20 min at room temperature, washed twice with phosphate buffered saline pH 7.4 and blocked with 2% bovine serum albumin in PBS for 1 hr. The plate was then washed three times and filled with horseradish peroxidase-conjugated antibody against phosphotyrosine (Upstate biotechnology #16-105, Temecula, Calif.) reconstituted in PBS with 2% bovine serum albumin per manufacturer's recommendation. After 3 hrs incubation at room temperature the plate was washed 4 times and 0.1 ml of TMB single solution substrate (Invitrogen, #00-2023, Carlbad, Calif.) was added to each well. Color development was stopped 5 min later by adding 0.05 ml 1 N HCl. Absorbance at 450 nm was measured on Titertek Multiscan MCC340 (ThermoFisher, Pittsburgh, Pa.). Absorbance vs. peptide concentration dose response curves were plotted and $EC_{50}$ values were determined by using Origin software (OriginLab, Northampton, Mass.).

Example 5

Determination of Rate of Model Dipeptide Cleavage (in PBS)

A specific hexapeptide (HSRGTF-NH$_2$; SEQ ID NO: 57) was used as a model peptide upon which the rate of cleavage of dipeptide N-terminal extensions could be studied. The dipeptide-extended model peptides were prepared Boc-protected sarcosine and lysine were successively added to the model peptide-bound resin to produce peptide A (Lys-Sar-HSRGTF-NH$_2$; SEQ ID NO: 58). Peptide A was cleaved by HF and purified by preparative HPLC.

Preparative Purification Using HPLC:

Purification was performed using HPLC analysis on a silica based 1×25 cm Vydac C18 (5µ particle size, 300 A° pore size) column. The instruments used were: Waters Associates model 600 pump, Injector model 717, and UV detector model 486. A wavelength of 230 nm was used for all samples. Solvent A contained 10% $CH_3CN$/0.1% TFA in distilled water, and solvent B contained 0.1% TFA in $CH_3CN$. A linear gradient was employed (0 to 100% B in 2 hours). The flow rate was 10 ml/min and the fraction size was 4 ml. From ~150 mgs of crude peptide, 30 mgs of the pure peptide was obtained.

Peptide A was dissolved at a concentration of 1 mg/ml in PBS buffer. The solution was incubated at 37° C. Samples were collected for analysis at 5 h, 8 h, 24 h, 31 h, and 47 h. The dipeptide cleavage was quenched by lowering the pH with an equal volume of 0.1% TFA. The rate of cleavage was qualitatively monitored by LC-MS and quantitatively studied by HPLC. The retention time and relative peak area for the prodrug and the parent model peptide were quantified using Peak Simple Chromatography software.

Analysis Using Mass Spectrometry

The mass spectra were obtained using a Sciex API-III electrospray quadrapole mass spectrometer with a standard ESI ion source. Ionization conditions that were used are as follows: ESI in the positive-ion mode; ion spray voltage, 3.9 kV; orifice potential, 60 V. The nebulizing and curtain gas used was nitrogen flow rate of 0.9 L/min. Mass spectra were recorded from 600-1800 Thompsons at 0.5 Th per step and 2 msec dwell time. The sample (about 1 mg/mL) was dissolved in 50% aqueous acetonitrile with 1% acetic acid and introduced by an external syringe pump at the rate of 5 µL/min. Peptides solubilized in PBS were desalted using a ZipTip solid phase extraction tip containing 0.6 µL C4 resin, according to instructions provided by the manufacturer (Millipore Corporation, Billerica, Mass.) prior to analysis.

Analysis Using HPLC

The HPLC analyses were performed using a Beckman System Gold Chromatography system equipped with a UV detector at 214 nm and a 150 mm×4.6 mm C8 Vydac column. The flow rate was 1 ml/min. Solvent A contained 0.1% TFA in distilled water, and solvent B contained 0.1% TFA in 90% CH$_3$CN. A linear gradient was employed (0% to 30% B in 10 minutes). The data were collected and analyzed using Peak Simple Chromatography software.

The rate of cleavage was determined for the respective propeptides. The concentrations of the propeptides and the model parent peptide were determined by their respective peak areas. The first order dissociation rate constants of the prodrugs were determined by plotting the logarithm of the concentration of the prodrug at various time intervals. The slope of this plot provides the rate constant 'k'. The half lives for cleavage of the various prodrugs were calculated by using the formula $t_{1/2}=0.693/k$. The half life of the Lys-Sar extension to this model peptide HSRGTF-NH$_2$ (SEQ ID NO: 57) was determined to be 14.0 h.

Example 6

Rate of Dipeptide Cleavage Half Time in Plasma as Determined with an all d-Isoform Model Peptide An additional model hexapeptide (dHdTdRGdTdF-NH$_2$ SEQ ID NO: 59) was used to determine the rate of dipeptide cleavage in plasma. The d-isomer of each amino acid was used to prevent enzymatic cleavage of the model peptide, with the exception of the prodrug extension. This model d-isomer hexapeptide was synthesized in an analogous fashion to the 1-isomer. The sarcosine and lysine were successively added to the N-terminus as reported previously for peptide A to prepare peptide B (dLys-dSar-dHdTdRGdTdF-NH$_2$ SEQ ID NO: 60)

The rate of cleavage was determined for the respective propeptides. The concentrations of the propeptides and the model parent peptide were determined by their respective peak areas. The first order dissociation rate constants of the prodrugs were determined by plotting the logarithm of the concentration of the prodrug at various time intervals. The slope of this plot provides the rate constant 'k'. The half life of the Lys-Sar extension to this model peptide dHdT-dRGdTdF-NH$_2$ (SEQ ID NO: 59) was determined to be 18.6 h.

Example 7

The rate of cleavage for additional dipeptides linked to the model hexapeptide (HSRGTF-NH$_2$; SEQ ID NO: 57) were determined using the procedures described in Example 5. The results generated in these experiments are presented in Tables 2 and 3.

TABLE 2

Cleavage of the Dipeptide U-B that are linked to the side chain of an N-terminal para-amino-Phe from the Model Hexapeptide (HSRGTF-NH$_2$; SEQ ID NO: 57) in PBS

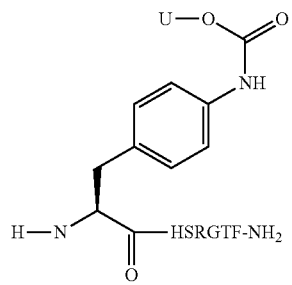

| Compounds | U (amino acid) | O (amino acid) | $t_{1/2}$ |
|---|---|---|---|
| 1 | F | P | 58 h |
| 2 | Hydroxyl-F | P | 327 h |
| 3 | d-F | P | 20 h |
| 4 | d-F | d-P | 39 h |
| 5 | G | P | 72 h |
| 6 | Hydroxyl-G | P | 603 h |
| 7 | L | P | 62 h |
| 8 | tert-L | P | 200 h |
| 9 | S | P | 34 h |
| 10 | P | P | 97 h |
| 11 | K | P | 33 h |
| 12 | dK | P | 11 h |
| 13 | E | P | 85 h |
| 14 | Sar | P | ≈1000 h |
| 15 | Aib | P | 69 min |
| 16 | Hydroxyl-Aib | P | 33 h |
| 17 | cyclohexane | P | 6 min |
| 18 | G | G | No cleavage |
| 19 | Hydroxyl-G | G | No cleavage |
| 20 | S | N-Methyl-Gly | 4.3 h |
| 21 | K | N-Methyl-Gly | 5.2 h |
| 22 | Aib | N-Methyl-Gly | 7.1 min |
| 23 | Hydroxyl-Aib | N-Methyl-Gly | 1.0 h |

TABLE 3

Cleavage of the Dipeptides U—B linked to histidine (or histidine analog) at position 1 (X) from the Model Hexapeptide (XSRGTF—NH$_2$; SEQ ID NO: 61) in PBS
NH$_2$—U—B—XSRGTF—NH$_2$ (SEQ ID NO: 61)

| Cmd. | U (amino acid) | O (amino acid) | X (amino acid) | $t_{1/2}$ |
|---|---|---|---|---|
| 1 | F | P | H | No cleavage |
| 2 | Hydroxyl-F | P | H | No cleavage |
| 3 | G | P | H | No cleavage |
| 4 | Hydroxyl-G | P | H | No cleavage |
| 5 | A | P | H | No cleavage |
| 6 | C | P | H | No cleavage |
| 7 | S | P | H | No cleavage |
| 8 | P | P | H | No cleavage |
| 9 | K | P | H | No cleavage |
| 10 | E | P | H | No cleavage |
| 11 | Dehydro V | P | H | No cleavage |
| 12 | P | d-P | H | No cleavage |
| 13 | d-P | P | H | No cleavage |
| 14 | Aib | P | H | 32 h |
| 15 | Aib | d-P | H | 20 h |
| 16 | Aib | P | d-H | 16 h |
| 17 | Cyclohexyl- | P | H | 5 h |
| 18 | Cyclopropyl- | P | H | 10 h |
| 19 | N-Me-Aib | P | H | >500 h |
| 20 | α,α-diethyl-Gly | P | H | 46 h |

TABLE 3-continued

Cleavage of the Dipeptides U—B linked to histidine (or histidine analog) at position 1 (X) from the Model Hexapeptide (XSRGTF—NH$_2$; SEQ ID NO: 61) in PBS NH$_2$—U—B—XSRGTF—NH$_2$ (SEQ ID NO: 61)

| Cmd. | U (amino acid) | O (amino acid) | X (amino acid) | $t_{1/2}$ |
|------|----------------|----------------|----------------|-----------|
| 21 | Hydroxyl-Aib | P | H | 61 |
| 22 | Aib | P | A | 58 |
| 23 | Aib | P | N-Methyl-His | 30 h |
| 24 | Aib | N-Methyl-Gly | H | 49 min |
| 25 | Aib | N-Hexyl-Gly | H | 10 min |
| 26 | Aib | Azetidine-2-carboxylic acid | H | >500 h |
| 27 | G | N-Methyl-Gly | H | 104 h |
| 28 | Hydroxyl-G | N-Methyl-Gly | H | 149 h |
| 29 | G | N-Hexyl-Gly | H | 70 h |
| 30 | dK | N-Methyl-Gly | H | 27 h |
| 31 | dK | N-Methyl-Ala | H | 14 h |
| 32 | dK | N-Methyl-Phe | H | 57 h |
| 33 | K | N-Methyl-Gly | H | 14 h |
| 34 | F | N-Methyl-Gly | H | 29 h |
| 35 | S | N-Methyl-Gly | H | 17 h |
| 36 | P | N-Methyl-Gly | H | 181 h |

Example 8

Identification of an Insulin Analog with Structure Suitable for Prodrug Construction Position 19 of the A chain is known to be an important site for insulin activity. Modification at this site to allow the attachment of a prodrug element is therefore desirable. Specific analogs of insulin at A19 have been synthesized and characterized for their activity at the insulin receptors. Two highly active structural analogs have been identified at A19, wherein comparable structural changes at a second active site aromatic residue (B24) were not successful in identification of similarly full activity insulin analogs.

Tables 4 and 5 illustrate the high structural conservation at position A19 for full activity at the insulin receptor (receptor binding determined using the assay described in Example 3). Table 4 demonstrates that only two insulin analogs with modifications at A19 have receptor binding activities similar to native insulin. For the 4-amino insulin analog, data from three separate experiments is provided. The column labeled "Activity (in test)" compares the percent binding of the insulin analog relative to native insulin for two separate experiments conducted simultaneously. The column labeled "Activity (0.60 nM)" is the relative percent binding of the insulin analog relative to the historical average value obtained for insulin binding using this assay. Under either analysis, two A19 insulin analogs (4-amino phenylalanine and 4-methoxy phenylalanine) demonstrate receptor binding approximately equivalent to native insulin. FIG. 3 represents a graph demonstrating the respective specific binding of native insulin and the A19 insulin analog to the insulin receptor. Table 5 presents data showing that the two A19 insulin analogs (4-amino and 4-methoxy) that demonstrate equivalent binding activities as native insulin also demonstrate equivalent activity at the insulin receptor (receptor activity determined using the assay described in Example 4).

TABLE 4

Insulin Receptor Binding Activity of A19 Insulin Analogs

| | Insulin Receptor | | | |
|---|---|---|---|---|
| Analogue | IC$_{50}$ | STDev | % native ligand Activity (in test) | % native ligand Activity (0.60 nM) |
| 4-OH (native insulin) | 0.64 | 0.15 | 100.0 | 100.0 |
| 4-COCH$_3$ | 31.9 | 9.47 | 0.6 | 1.9 |
| 4-NH$_2$ | 0.31 | 0.12 | 203.0 | 193.5 |
| | 0.83 | 0.15 | 103.0 | 72.3 |
| | 0.8 | 0.1 | 94.0 | 75.0 |
| 4-NO$_2$ | 215.7 | 108.01 | 0.3 | 1.3 |
| 3,4,5-3F | 123.29 | 31.10 | 0.5 | 0.5 |
| 4-OCH$_3$ | 0.5 | 0.50 | 173.0 | 120.0 |
| 3-OCH$_3$ | 4.74 | 1.09 | 28.0 | 12.7 |
| | 5.16 | 3.88 | 18.0 | 11.6 |
| 4-OH, 3,5-2Br | 1807.17 | 849.72 | 0.0 | 0.0 |
| 4-OH, 3,5-2 NO$_2$ | 2346.2 | 338.93 | 0.0 | 0.0 |

TABLE 5

Insulin Receptor Phosphorylation Activity of A19 Insulin Analogs

| | Insulin Receptor | | |
|---|---|---|---|
| Analogue | EC$_{50}$ | STDev | % native ligand Activity (in test) |
| 4-OH (native insulin) | 1.22 | 0.4 | 100.0 |
| 4-NH$_2$ | 0.31 | 0.14 | 393.5 |
| 4-OCH$_3$ | 0.94 | 0.34 | 129.8 |

Example 9

Insulin Like Growth Factor (IGF) Analog IGF1 ($Y^{B16}L^{B17}$)

Figure 4:
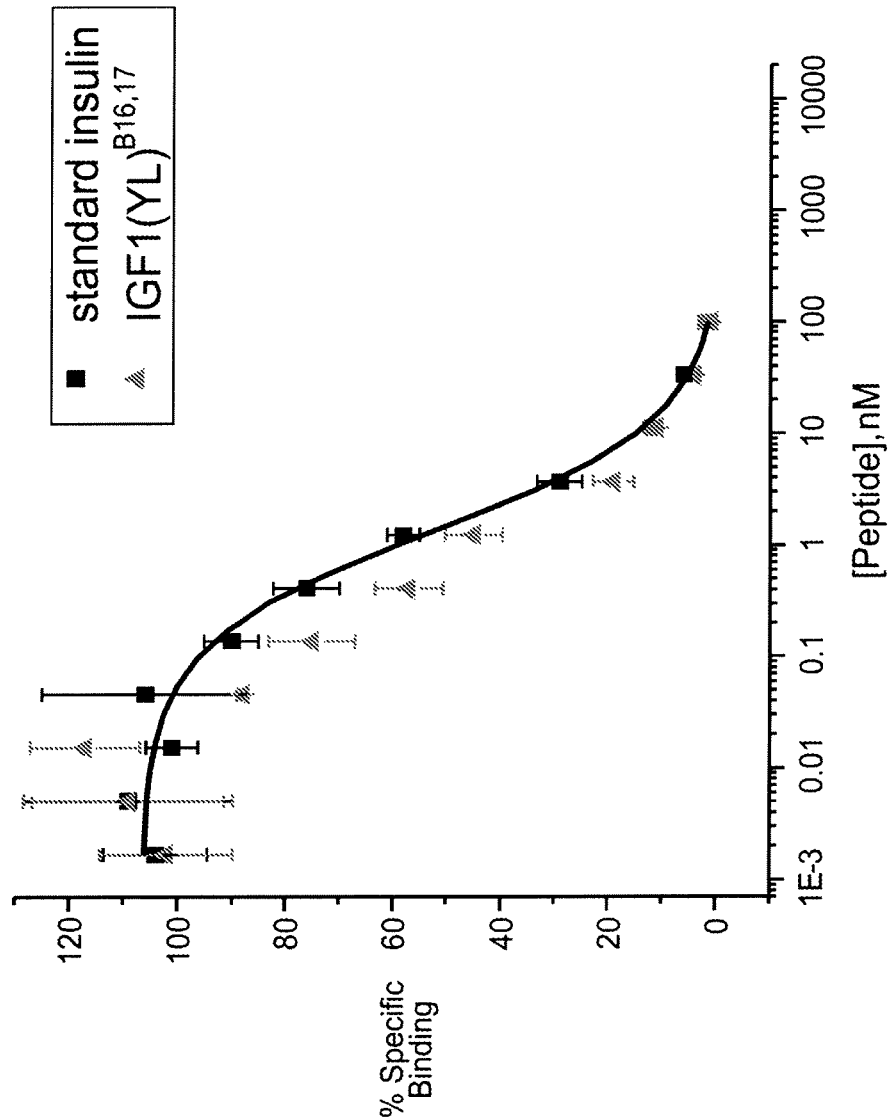
FIG. 4 is a graph comparing relative insulin receptor binding of native insulin and the IGF1($Y^{B16}L^{B17}$) analog. As indicated by the data presented in the graph, the two molecules have similar binding activities.

Applicants have discovered an IGF analog that demonstrates similar activity at the insulin receptor as native insulin. More particularly, the IGF analog (IGF1 ($Y^{B16}L^{B17}$) comprises the native IGF A chain (SEQ ID NO: 5) and the modified B chain (SEQ ID NO: 6), wherein the native glutamine and phenylalanine at positions 15 and 16 of the native IGF B-chain (SEQ ID NO: 3) have been replaced with tyrosine and leucine residues, respectively. As shown in FIG. 4 and Table 6 below the binding activities of IGF1 ($Y^{B16}L^{B17}$) and native insulin demonstrate that each are highly potent agonists of the insulin receptor.

TABLE 6

| | Insulin Standard | | IGF1($Y^{B16}L^{B17}$) | |
|---|---|---|---|---|
| | AVER. | STDEV | AVER. | STDEV |
| IC$_{50}$(nM) | 1.32 | 0.19 | 0.51 | 0.18 |
| % of Insulin Activity | 100 | | 262 | |

Example 10

IGF Prodrug Analogs

Figure 6:
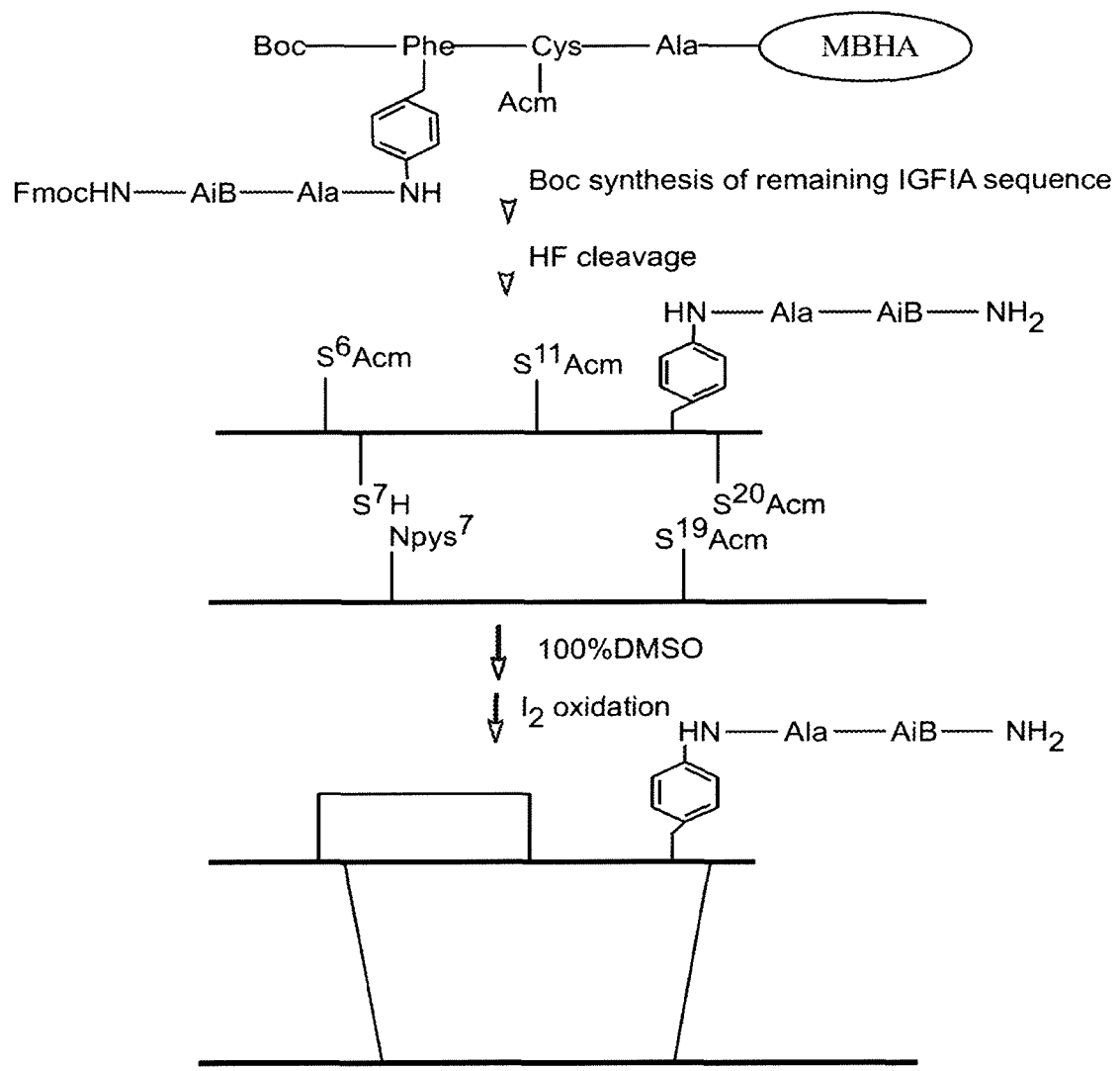
FIG. 6 is a schematic drawing of the synthetic scheme used to prepare the IGF1($Y^{B16}L^{B17}$)(p-NH$_2$—F)$^{A19}$ prodrug derivatives. The specific derivative is p-NH2-F where the aromatic amine is acylated with the dipeptide Aib-Ala, which serves as a negative control since this dipeptide does not cleave under physiological conditions.
Figure 7:
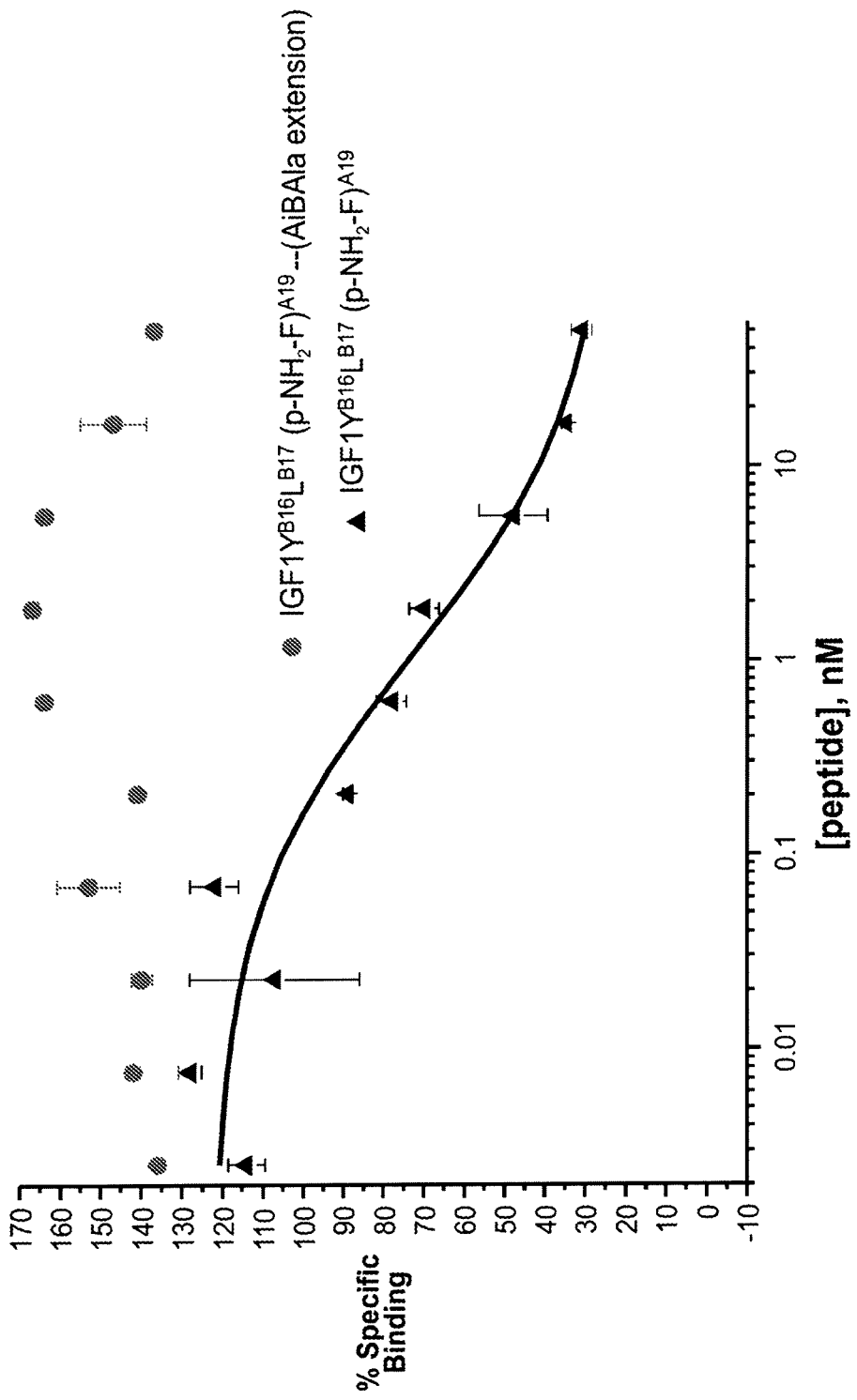
FIG. 7 is a graph comparing relative insulin receptor binding of IGF1($Y^{B16}L^{B17}$)(p-NH$_2$—F)$^{A19}$ and the dipeptide extended form of IGF1($Y^{B16}L^{B17}$)(p-NH$_2$—F)$^{A19}$-AiBAla. The synthesis of this prodrug is shown in FIG. 6 where the dipeptide AiBAla is bound at position A19 (i.e. IGF1 ($Y^{B16}L^{B17}$)(AiBAla). The dipeptide does not readily cleave under physiological conditions and thus the activity is extremely low which demonstrates the ability of acylation at this site with dipeptide to silence bioactivity. This constitutes one of the two central ingredients of a prodrug, low activity in the prodrug form.
Figure 8A:
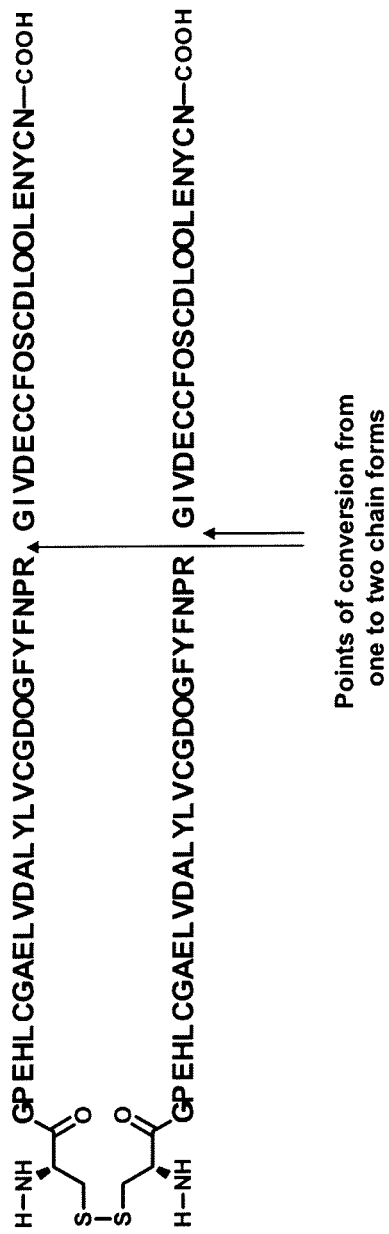
FIG. 8A-8C provides the activity of a dimer prepared in accordance with the present disclosure.
Figure 8B:
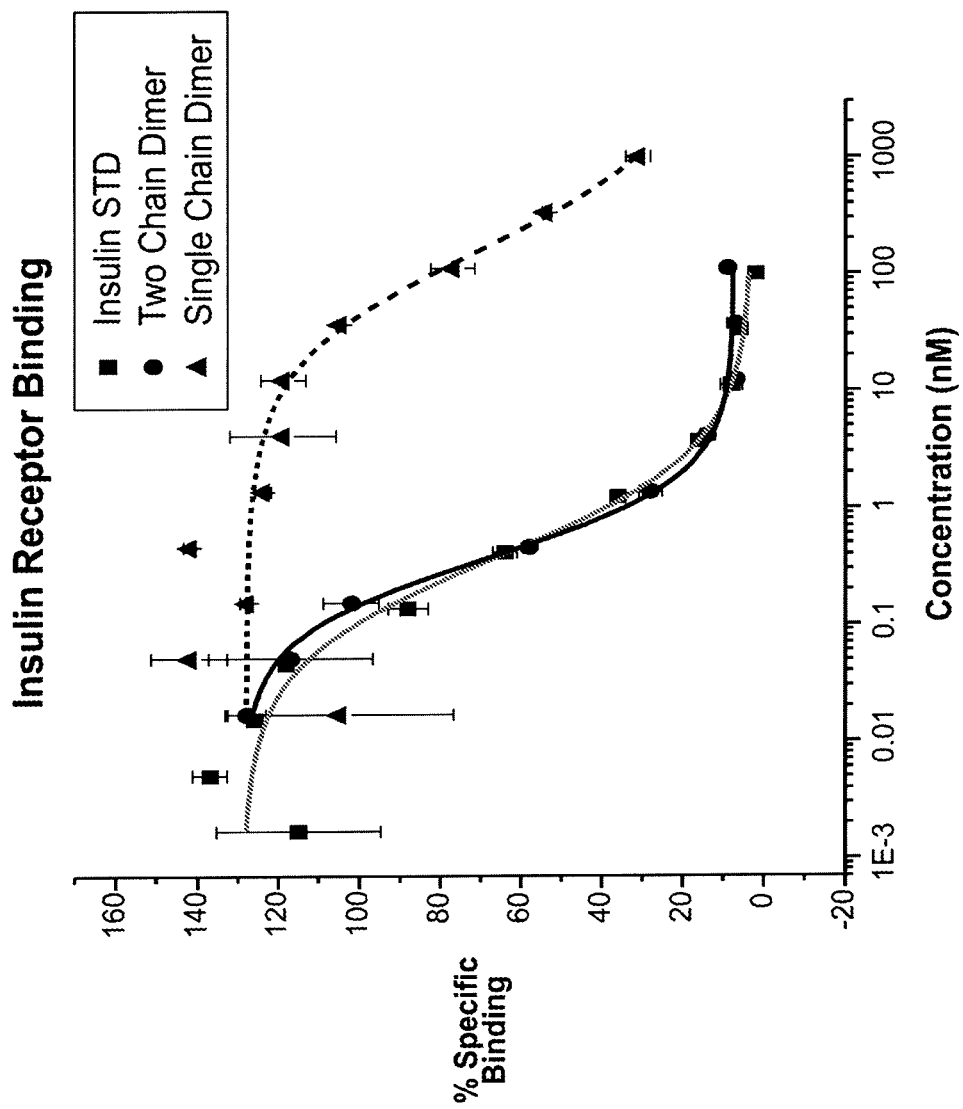
Figure 8C:
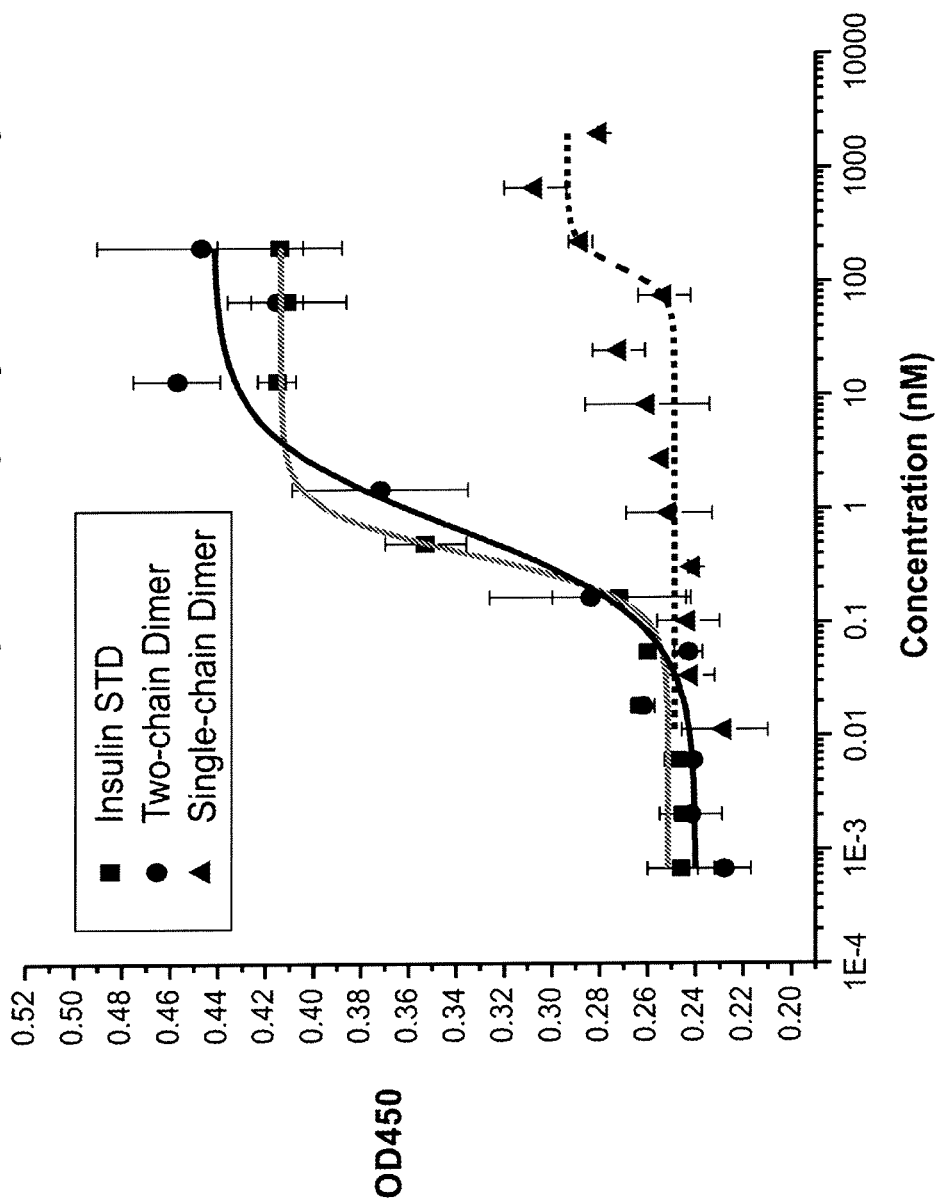

Based on the activity of the A19 insulin analog (see Example 5), a similar modification was made to the IGF1 A:B($Y^{B16}L^{B17}$) analog and its ability to bind and stimulate insulin receptor activity was investigated. FIG. 6 provides the general synthetic scheme for preparing IGF1 A:B($Y^{B16}L^{B17}$) wherein the native tyrosine is replace with a 4-amino phenylalanine [IGF1 A:B($Y^{B16}L^{B17}$)(p-NH$_2$—F)$^{A19}$amide] as well as the preparation of its dipeptide extended analog [IGF1 A:B($Y^{B16}L^{B17}$)$^{A19}$-AiBAla amide], wherein a dipeptide comprising AiB and Ala are linked to the peptide through an amide linkage to the A19 4-amino phenylalanine. As shown in FIG. 7 and Table 7, the IGF analog, IGF1 ($Y^{B16}L^{B17}$) A(p-NH$_2$—F)$^{19}$ specifically binds to the insulin receptor wherein the dipeptide extended analog of that analog fails to specifically bind the insulin receptor. Note the dipeptide extension lacks the proper structure to allow for spontaneous cleavage of the dipeptide (absence of an N-alkylated amino acid at the second position of the dipeptide) and therefore there is no restoration of insulin receptor binding.

IGF A:B($Y^{B16}L^{B17}$) insulin analog peptides comprising a modified amino acid (such as 4-amino phenylalanine at position A19) can also be synthesized in vivo using a system that allows for incorporation of non-coded amino acids into proteins, including for example, the system taught in U.S. Pat. Nos. 7,045,337 and 7,083,970.

TABLE 7

|  | Insulin Standard | | IGF1($Y^{B16}L^{B17}$) (p-NH$_2$—F)$^{A19}$amide | | IGF1($Y^{B16}L^{B17}$) (AiBAla)$^{A19}$amide | |
| --- | --- | --- | --- | --- | --- | --- |
|  | AVER. | STDEV. | AVER. | STDEV. | AVER. | STDEV. |
| IC$_{50}$(nM) | 0.24 | 0.07 | 1.08 | .075 | No Activity | |
| % of Insulin Activity | 100 | | 22 | | | |

A further prodrug analog of an IGF$^{B16B17}$ analog peptide was prepared wherein the dipeptide prodrug element (alanine-proline) was linked via an amide bond to the amino terminus of the A chain (IGF1($Y^{B16}L^{B17}$) (AlaPro)$^{A-1,0}$). As shown in Table 8, the IGF1($Y^{B16}L^{B17}$)(AlaPro)$^{A-1,0}$ has reduced affinity for the insulin receptor. Note, based on the data of Table 3, the dipeptide prodrug element lacks the proper structure to allow for spontaneous cleavage of the dipeptide prodrug element, and therefore the detected insulin receptor binding is not the result of cleavage of the prodrug element.

TABLE 8

|  | Insulin Standard | | IGF1($Y^{B16}L^{B17}$)(AlaPro)$^{A-1, 0}$ | |
| --- | --- | --- | --- | --- |
|  | AVER. | STDEV. | AVER. | STDEV. |
| IC$_{50}$(nM) | 0.72 | 0.09 | 1.93 | .96 |
| % of Insulin Activity | 100 | | 37.12 | |

Example 11

Additional IGF Insulin Analogs

Further modifications of the IGF1 ($Y^{B16}L^{B17}$) peptide sequence reveal additional IGF insulin analogs that vary in their potency at the insulin and IGF-1 receptor. Binding data is presented in Table 9 for each of these analogs (using the assay of Example 3), wherein the position of the modification is designated based on the corresponding position in the native insulin peptide (DPI=des B26-30). For example, a reference herein to "position B28" absent any further elaboration would mean the corresponding position B27 of the B chain of an insulin analog in which the first amino acid of SEQ ID NO: 2 has been deleted. Thus a generic reference to "B(Y16)" refers to a substitution of a tyrosine residue at position 15 of the B chain of the native IGF-1 sequence (SEQ ID NO: 3). Data regarding the relative receptor binding of insulin and IGF analogs is provided in Table 9, and data regarding IGF analog stimulated phosphorylation (using the assay of Example 4) is provided in Table 10.

TABLE 9

Receptor Binding Affinity of Insulin and IGF Analogues

| | Insulin Receptor | | | | | IGF-1 Receptor | | | | | |
| --- | --- | --- | --- | --- | --- | --- | --- | --- | --- | --- | --- |
| Analogue | nM IC$_{50}$: | STDev | Date | % insulin (in test) | % native insulin activity (0.6 nM) | IC$_{50}$: | STDev | Date | % IGF-1 (in test) | % native IGF-1 activity (0.55 nM) | Ratio |
| IGF-1 A:B | 10.41 | 1.65 | Sep. 4, 2007 | 5.8 | 5.8 | | | | | | |
| IGF-1 A:B(E10Y16L17) | 0.66 | 0.36 | May 22, 2007 | 58.7 | 90.9 | 7.85 | 1.98 | Jun. 4, 2007 | 6.8 | 7.0 | 11.9 |
| | 0.51 | 0.18 | May 29, 2007 | 98.8 | 117.6 | 12.19 | 2.17 | Sep. 18, 2007 | 5.0 | 4.5 | |
| IGF-1 A:B(E10 Y16L17)-E31E3 2B-COOH | 1.22 | 0.30 | Mar. 20, 2008 | 36.5 | 50.0 | 17.50 | 2.25 | Apr. 4, 2007 | 3.0 | 3.1 | 14.3 |
| IGF-1 A:B(D10Y16L17) DPI A-COOH | 0.26 | 0.02 | Nov. 9, 2007 | 301.0 | 231.0 | 6.79 | 1.50 | Apr. 4, 2008 | 7.7 | 8.1 | |
| | 0.2 | 0.02 | Dec. 4, 2007 | 380.1 | 300.0 | | | | | | |
| | 0.42 | 0.06 | Jun. 5, 2008 | 174.1 | 144.1 | | | | | | |
| IGF-1 A:B (E10Y16L17) DPI | 0.38 | 0.08 | Aug. 10, 2007 | 51.1 | 157.9 | 22.89 | 5.26 | Sep. 18, 2007 | 3.3 | 2.4 | 60.2 |
| IGF-1 A:B (H5D10Y16L17) DPI | 0.16 | 0.07 | Nov. 9, 2007 | 479.0 | | 4.66 | 0.77 | Apr. 4, 2008 | 11.2 | 11.8 | 29.1 |
| IGF-1 A:B (H5D10Y16L17) (S=O)DPI | 0.25 | 0.04 | Nov. 9, 2007 | 316.0 | | | | | | | |
| IGF-1 A (H8 A9 N21): B(H5D10Y16L17) DPI A-COOH | 0.05 | 0.01 | Dec. 4, 2007 | 1576.7 | | 4.03 | 0.50 | Apr. 4, 2008 | 12.9 | 13.6 | 80.6 |
| | 0.09 | 0.02 | Dec. 14, 2007 | 1667.0 | | | | | | | |

TABLE 9-continued

Receptor Binding Affinity of Insulin and IGF Analogues

| | Insulin Receptor | | | | | IGF-1 Receptor | | | | | |
|---|---|---|---|---|---|---|---|---|---|---|---|
| Analogue | nM IC$_{50}$: | STDev | Date | % insulin (in test) | % native insulin activity (0.6 nM) | IC$_{50}$: | STDev | Date | % IGF-1 (in test) | % native IGF-1 activity (0.55 nM) | Ratio |
| IGF-1 A (H8 A9 N21): B(H5D10Y16L17 A22) DPI A-COOH | 0.12 | 0.02 | Dec. 14, 2007 | 1171.4 | | 22.83 | 3.53 | Apr. 4, 2008 | 2.3 | 2.4 | 190.3 |
| IGF-1 A (H8 A9 N21): B(H5D10Y16L17A22) (S=O) DPI A-COOH | 0.36 | 0.10 | Dec. 14, 2007 | 400.7 | | | | | | | |
| IGF-1 A:IGF-1 B(1-8)-In (9-17)-IGF-1 B(18-30) | 1.59 | 0.62 | May 22, 2007 | 19.1 | 37.7 | 131.30 | 58.05 | Jun. 4, 2007 | 0.3 | 0.4 | 82.6 |
| IGF-1 A:In (1-17)-IGF-1 B (18-30) | 2.77 | 1.19 | May 22, 2007 | 14.0 | 21.7 | 62.50 | 30.28 | Jun. 4, 2007 | 0.9 | 0.9 | 22.6 |
| | 2.67 | 0.67 | May 18, 2007 | 11.3 | 22.5 | | | | | | |
| | 2.48 | 1.35 | May 29, 2007 | 20.1 | 24.2 | | | | | | |
| IGF-1 A:In B(1-5)-IGF-1 B(YL)(6-30) | 0.31 | 0.19 | Aug. 10, 2007 | 62.4 | 193.5 | 27.54 | 6.57 | Sep. 25, 2007 | 3.6 | 2 | 88.8 |
| IGF-2 native | | | | | | 13.33 | 1.85 | Sep. 25, 2007 | 7.5 | 4.5 | |
| IGF-2 AB | | | | | | | | | | | |
| IGF-2 AB(YL) | 6.81 | 3.81 | Oct. 10, 2007 | 8.4 | 8.8 | | | | | | |
| In A:IGF-1 B(YL) | 82.62 | 31.75 | Sep. 4, 2007 | 0.9 | 0.7 | | | | | | |
| | 107.24 | 65.38 | Sep. 4, 2007 | 0.7 | 0.6 | | | | | | |
| In A- IGF-2 D:In B-IGF-2 C | 0.53 | 0.11 | Sep. 4, 2007 | 141.0 | 113.0 | 1.59 | 0.34 | Sep. 18, 2007 | 47.6 | 34.6 | |
| | 0.37 | 0.05 | Oct. 13, 2007 | 179.1 | 162.2 | 14.69 | 3.02 | Sep. 25, 2007 | 6.8 | 3.7 | 39.7 |

**All C terminals are amides (DPI) unless specified otherwise

TABLE 10

Total Phosphorylation by IGF-1 & IGF-2 Analogues

| | Insulin Receptor | | | | IGF-1 Receptor | | | | |
|---|---|---|---|---|---|---|---|---|---|
| Analogue | EC50: | STDev | Date | % Insulin | EC50: | STDev | Date | % IGF | Selective Ratio |
| Insulin | 1.26 | 0.098 | Dec. 14, 2007 | | 114.88 | 46.66 | Jan. 23, 2008 | | 90.89 |
| | 1.43 | 0.72 | Apr. 1, 2008 | | 86.02 | 29.35 | May 20, 2008 | | |
| | 1.12 | 0.11 | Mar. 31, 2008 | | | | | | |
| | 1.53 | 0.13 | Apr. 11, 2008 | | | | | | |
| | 2.70 | 0.71 | Apr. 16, 2008 | | | | | | |
| | 1.22 | 0.40 | May 20, 2008 | | | | | | |
| IGF-1 | 54.39 | 21.102 | Dec. 14, 2007 | 2.3 | 0.87 | 0.16 | Jan. 23, 2008 | 100 | 0.02 |
| | | | | | 0.49 | 0.13 | May 20, 2008 | | |
| | | | | | 0.97 | 0.48 | Jul. 23, 2008 | | |
| IGF-1 AB | | | | | | | | | |
| IGF-1 A:B(E10Y16L17) | 2.57 | 0.59 | Mar. 31, 2008 | 49.2 | 7.42 | 5.59 | Jul. 23, 2008 | 13 | |
| IGF-1 A:B(E10Y16L17)-E31E32 B-COOH | 7.00 | 2.82 | Mar. 31, 2008 | 18.1 | | | | | |
| | 8.52 | 4.34 | Apr. 16, 2008 | 31.7 | | | | | |
| IGF-1 AB(D10Y16L17) DPI A-COOH | 0.08 | 0.006 | Dec. 14, 2007 | 1575 | 0.78 | 0.17 | Jan. 23, 2008 | 111.538 | 9.75 |
| | 4.38 | 2.98 | Apr. 16, 2008 | ?? | | | | | |
| IGF-1 AB (E10Y16L17) DPI | | | | | | | | | |
| IGF-1 AB (H5D10Y16L17) DPI | | | | | 12.22 | 5.46 | Jan. 23, 2008 | 7.1 | |
| IGF-1 AB (H5D10Y16L17) (S=O)DPI | | | | | | | | | |
| IGF-1 A (H8 A9 N21) B(H5D10Y16L17) DPI A-COOH | 0.15 | 0.054 | Dec. 14, 2007 | 840 | 0.43 | 0.44 | Jan. 23, 2008 | 181.395 | 2.81 |
| | 0.25 | 0.2 | Apr. 16, 2008 | 1080 | | | | | |
| IGF-1 A (H8 A9 N21) B(H5D10Y16L17A22) DPI A-COOH | 0.35 | 0.064 | Dec. 14, 2007 | 360 | 11.26 | 2.55 | Jan. 23, 2008 | 7.7 | 32.54 |
| | 0.44 | 0.17 | Apr. 16, 2008 | 614 | | | | | |
| IGF-1 A (H8 A9 N21) B(H5D10Y16L17A22) (S=O) DPI A-COOH | 0.72 | 0.098 | Dec. 14, 2007 | | | | | | |

*All C-terminals are amides unless specified otherwise.

Example 12

Dipeptide Half Life on IGF1 Dipeptide Extended (p-NH$_2$—F)$^{A19}$ Amide Analogs The cleavage of an (pNH2-Phe) amide linked dipeptide AibPro from various IGF-1 peptides was measured to determine the impact of the peptide sequence or heteroduplex on the dipeptide cleavage. Results for the tested peptides is shown in Table 11 and the data reveals that the IGF1-A chain alone represents a good model for the study of prodrug half life for IGF1 B:A (Y$^{B16}$L$^{B17}$) peptides.

TABLE 11

| Parent Peptide | Half Life (hr) |
|---|---|
| IGF1A(Ala)$^{6, 11, 20}$(pNH$_2$-Phe)$^{A19}$ | 2.2 |
| IGF1A(Acm)$^{6, 11, 20}$(pNH$_2$-Phe)$^{A19}$ | 1.8 |
| IGF1 B:A(S-S)$^{A7, B7}$(Acm)$^{A6, 11, 20, B19}$(pNH$_2$-Phe)$^{A19}$ | 1.8 |
| IGF1 B:A(pNH$_2$-Phe)$^{A19}$ | 1.6 |

Comparison of prodrug analogs of the IGF A-chain relative to the disulfide bound A chain and B chain construct (IGF1 A:B(Y$^{B16}$L$^{B17}$)) revealed the two compounds had similar half lives for the prodrug form. The AibAla analog does not cleave and thus is not a prodrug, but serves to show the modification can inactivate the insulin analog IGF1 A:B(Y$^{B16}$L$^{B17}$)(p-NH$_2$—F)$^{A19}$amide. Accordingly, the IGF1A chain alone was determined to be a good model for the study of pro-drug half life on IGF1 B:A (Y$^{B16}$L$^{B17}$) analog peptides. The AibAla analog does not cleave and thus is not a prodrug, but serves to show the modification can inactivate the insulin analog IGF1 A:B(Y$^{B16}$L$^{B17}$)(p-NH$_2$—F)$^{A19}$amide. For simplicity, prodrug half lives were determined using only the IGF1 A chain in the absence of the B chain. The half lives of each propeptide was determined as described in Example 5. The data is presented in Table 12:

TABLE 12

Dipeptide half life on IGF1 dipeptide extended (p-NH$_2$—F)$^{A19}$ amide analogs

| Dipeptide | | Half Life (hr) |
|---|---|---|
| AiB | Pro | 2.2 |
| AiBOH | Pro | 165.0 |
| AiB | dPro | 1.9 |
| AiBOH | Sar | 2.3 |
| dK(acetyl) | Sar | 16.3 |
| K | Sar | 21.8 |
| K(acetyl) | N-methyl Ala | 23.6 |
| dK(acetyl) | N-methyl Ala | 35.3 |

The data shows that by altering the substituents on the dipeptide prodrug element that the half life of prodrug can be varied from 2 hrs to >100 hrs.

Additional prodrug analog peptides were prepared using an IGF1-A(pNH2-F)$^{19}$ base peptide and altering the amino acid composition of the dipeptide prodrug element linked through the 4-amino phenylalanine at position A19. Dipeptide half lives were measured for different constructs both in PBS and in 20% plasma/PBS (i.e. in the presence of serum enzymes. The results are provided in Table 13. The results indicate that three of the four peptides tested were not impacted by serum enzymes.

TABLE 13

Dipeptide half life on IGF1-A(pNH2—F)$^{19}$

| | | Half Life (hr) | |
|---|---|---|---|
| | | PBS | 20% Plasma/PBS |
| AiB | Pro | 2.2 | 2.1 |
| AiB | dPro | 2.1 | 2.2 |
| AiBOH | Sar | 2.3 | |
| dK | N-isobutyl Gly | 4.4 | 4.1 |
| dK | N-hexyl Gly | 10.6 | |
| dK(acetyl) | Sar | 17.2 | |
| K | Sar | 21.8 | 5.9 |
| K(acetyl) | N-methyl Ala | 23.6 | |
| dK(acetyl) | N-methyl Ala | 35.3 | |
| AiBOH | Pro | 165.0 | |
| K(acetyl) | Azetidine-2-carboxylic acid | Not cleavable | |
| dK(acetyl) | Azetidine-2-carboxylic acid | Not cleavable | |

Example 13

Receptor Binding of IGF$^{B16B17}$ Analog Peptides Over Time

Prodrug formulations of IGF$^{B16B17}$ Analog Peptides were prepared and their degradation over time was measured using the insulin receptor binding assay of Example 3. Peptides used in the assay were prepared as follows:

Dipeptide-IGF1A Analogs

If not specified, Boc-chemistry was applied in the synthesis of designed peptide analogs. Selected dipeptide H$_2$N-AA1-AA2-COOH was added to (pNH$_2$-Phe)$^{19}$ on IGF1A (Ala)$^{6,7,11,20}$. The IGF-1 A chain C-terminal tripeptide Boc (Fmoc-pNH-Phe)-Ala-Ala was synthesized on MBHA resin. After removal of Fmoc by the treatment with 20% piperidine/DMF at room temperature for 30 minutes, Fmoc-AA2 was coupled to the p-amino benzyl side chain at A19 by using a threefold excess of amino acid, PyBop, DIEA and catalytic amount of pyridine. The Boc-synthesis of the remaining IGF-1 A chain (Ala)$^{6,7,11,20}$ sequence was completed using an Applied Biosystems 430A Peptide Synthesizer, yielding IGF-1 A chain (Boc)$^0$(Ala)$^{6,7,11,20}$(Fmoc-AA2-pNH-Phe)$^{19}$-MBHA. After the Fmoc group was removed from the N-terminus of AA2, Boc-AA1 was then coupled to the amine using threefold excess of amino acid, DEPBT and DIEA. Removal of the two Boc groups remaining on the A chain by TFA was followed by HF cleavage, yielding IGF-1 A-chain (Ala)$^{6,7,11,20}$(H$_2$N-AA1-AA2-pNH-Phe)$^{19}$amide. In the case of AA1 being d-lysine, acetylation on the ε-amine was performed prior to Boc removal. Dipeptide-IGF-1 A chain analogs were purified by semi-preparative RP-HPLC and characterized by analytical RP-HPLC and MALDI mass spectrometry.

Dipeptide-IGF-1 (YL) Analogs

A selected dipeptide H$_2$N-AA1-AA2-COOH was added to (pNH$_2$-Phe)$^{19}$ on IGF-1 A chain (Acm)$^{6,11,20}$ as described immediately above except PAM resin was used for the synthesis of IGF-1 A chain to yield a C terminal acid upon HF-cleavage. IGF-1 B chain (Y$^{B16}$L$^{B17}$)(Acm)$^{19}$ was synthesized on MBHA resin to yield a C terminal amide. The free thiol on Cys$^{B7}$ was modified by Npys through reaction with DTNP at a 1:1 molar ratio in 100% DMSO. Purified dipeptide-IGF-1 A chain and IGF-1 B chain (Y$^{B16}$L$^{B17}$) analogs were assembled using the "1+2" two step chain combination strategy illustrated in Scheme 1. Intermediate and final purifications were performed on semi-preparative RP-HPLC and characterized by analytical RP-HPLC and MALDI mass spectrometry.

Figures 9A, 9B, 9C:
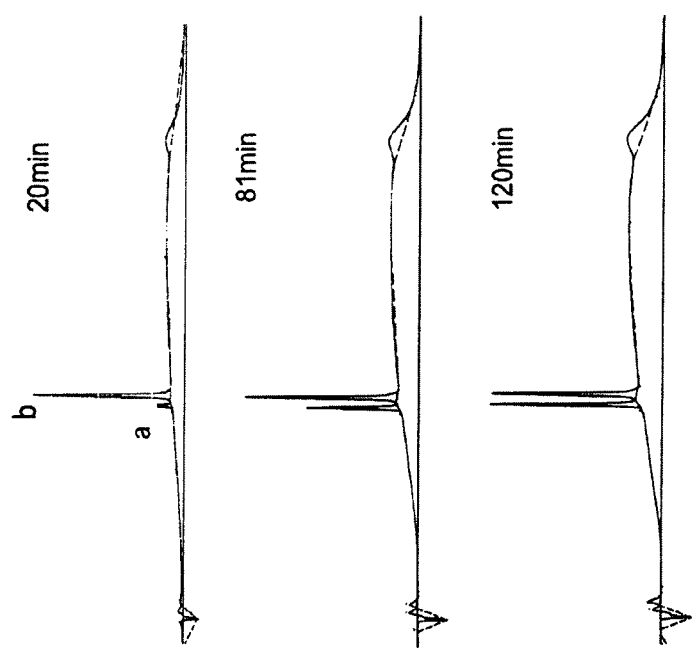
FIG. 9A-9C shows the degradation of a prodrug form of an IGF A chain peptide: (Aib-Pro on (pNH$_2$—F)$^{19}$ of IGF1A (Ala)$^{6,7,11,20}$amide. The dipeptide was incubated in PBS, pH 7.4 at 37° C. for predetermined lengths of time. Aliquots were taken at 20 minutes (FIG. 9A), 81 minutes (FIG. 9B) and 120 minutes (FIG. 9C) after beginning the incubation, were quenched with 0.1% TFA and tested by analytical HPLC. Peak a (IGF1A(Ala)$^{6,7,11,20}$(pNH$_2$—F)$^1$ amide) and b (IGF1A(Ala)$^{6,7,11,20}$(Aib-Pro-pNH-F)$^{19}$amide) were identified with LC-MS and quantified by integration of peak area. The data indicate the spontaneous, non-enzymatic conversion of IGF1A(Ala)$^{6,7,11,20}$(Aib-Pro-pNH-F)$^{19}$amide to IGF1A(Ala)$^{6,7,11,20}$(pNH$_2$—F)$^1$ amide over time.

The IGF$^{B16B17}$ analog peptide prodrugs were incubated in PBS, pH 7.4 at 37° C. and at predetermined time intervals an aliquot was taken and further degradation was quenched with 0.1% TFA and the aliquot was subjected to analytical HPLC analysis. Peaks a and b, representing the prodrug and active forms of the IGF$^{B16B17}$ analog peptide were identified with LC-MS and quantified by integration of peak area an HPLC. FIGS. 9A-9C show the output of an HPLC analysis of the degradation of the IGF$^{B16B17}$ analog peptide prodrug: IGF1A(Ala)$^{6,7,11,20}$(Aib-Pro-pNH-F)$^{19}$. Aliquots were taken at 20 minutes (FIG. 9A), 81 minutes (FIG. 9B) and 120 minutes (FIG. 9C) after beginning the incubation of the prodrug in PBS. The data indicate the spontaneous, non-enzymatic conversion of IGF1A(Ala)$^{6,7,11,20}$(Aib-Pro-pNH-F)$^{19}$amide to IGF1A(Ala)$^{6,7,11,20}$(pNH$_2$—F)$^1$amide over time.

Figure 10A:
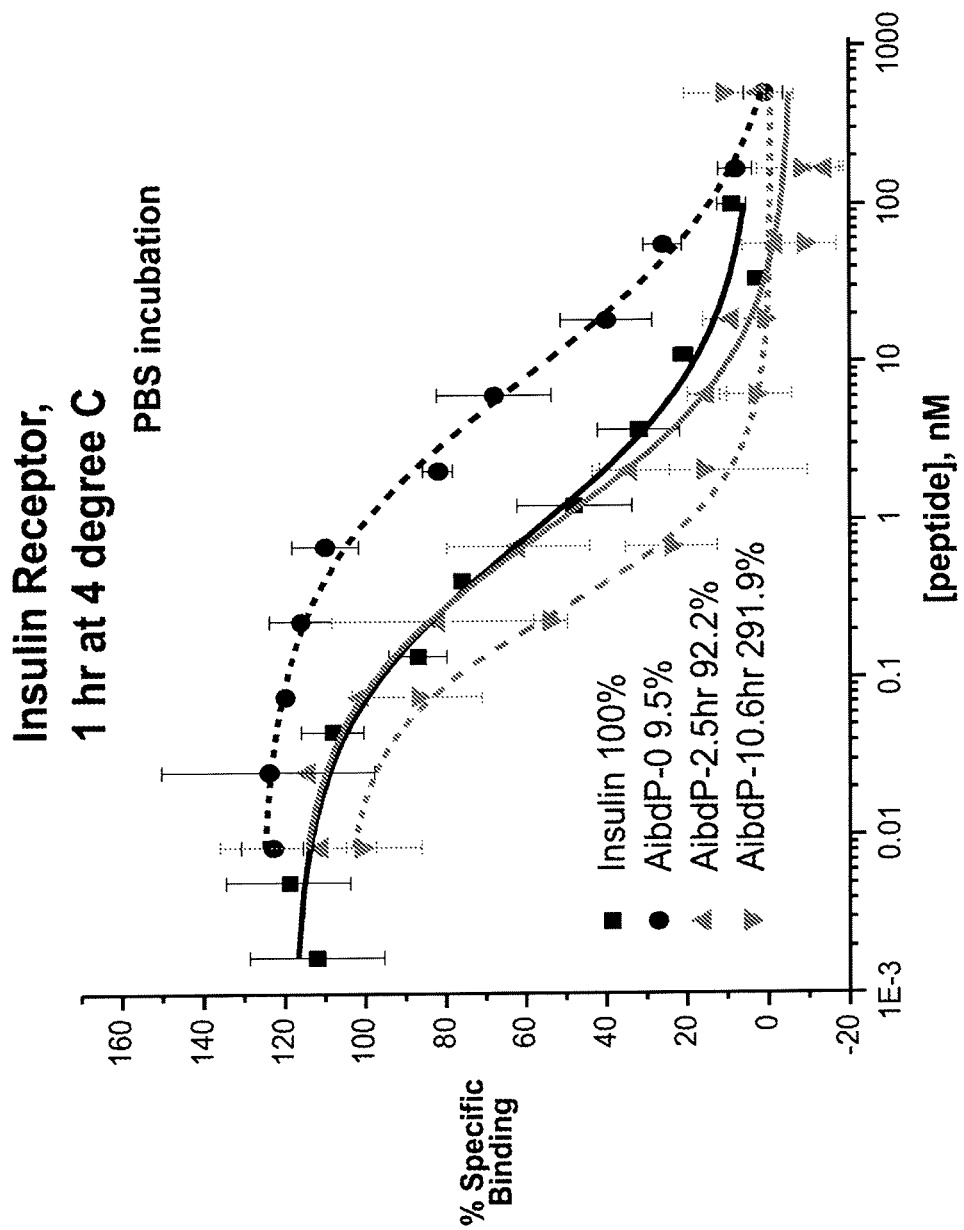
FIGS. 10A & 10B are graphs depicting the in vitro activity of the prodrug Aib,dPro-IGF1YL (dipeptide linked through the A19 4-aminoPhe).
Figure 10B:
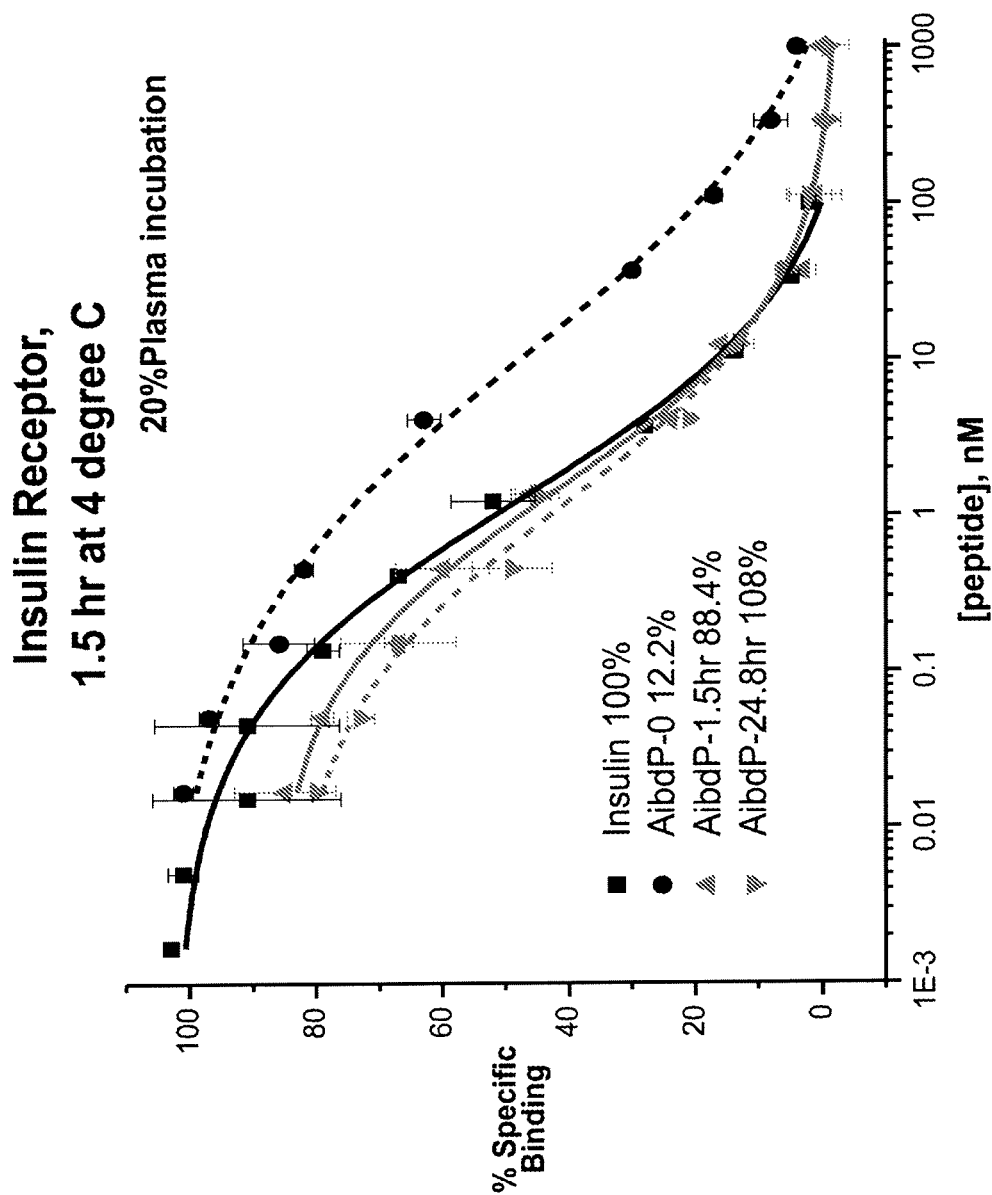

The degradation of the prodrug forms of IGF$^{B16B17}$ analog peptides to their active form was also measured based on the compounds ability to bind to the insulin receptor as measured using the in vitro assay of Example 3. FIGS. 10A & 10B are graphs depicting the in vitro activity of the prodrug Aib,dPro-IGF1YL (dipeptide linked through the A19 4-aminoPhe). FIG. 10A is a graph comparing relative insulin receptor binding of native insulin (measured at 1 hour at 4° C.) and the A19 IGF prodrug derivative (Aib,dPro-IGF1YL) over time (0 hours, 2.5 hours and 10.6 hours) incubated in PBS. FIG. 10B is a graph comparing relative insulin receptor binding of native insulin and the A19 IGF prodrug derivative (Aib,dPro-IGF1YL) over time (0 hours, 1.5 hours and 24.8 hours) incubated in 20% plasma/PBS at 37° C. As indicated by the data presented in the graph, increased activity is recovered form the A19 IGF prodrug derivative sample as the prodrug form is converted to the active IGF1YL peptide. The activity of the IGF$^{B16B17}$ analog peptides was measured relative to insulin receptor binding, and since the underlying IGF$^{B16B17}$ analog peptides have more activity than native insulin, activity of greater than 100% relative to insulin is possible.

Figure 11A:
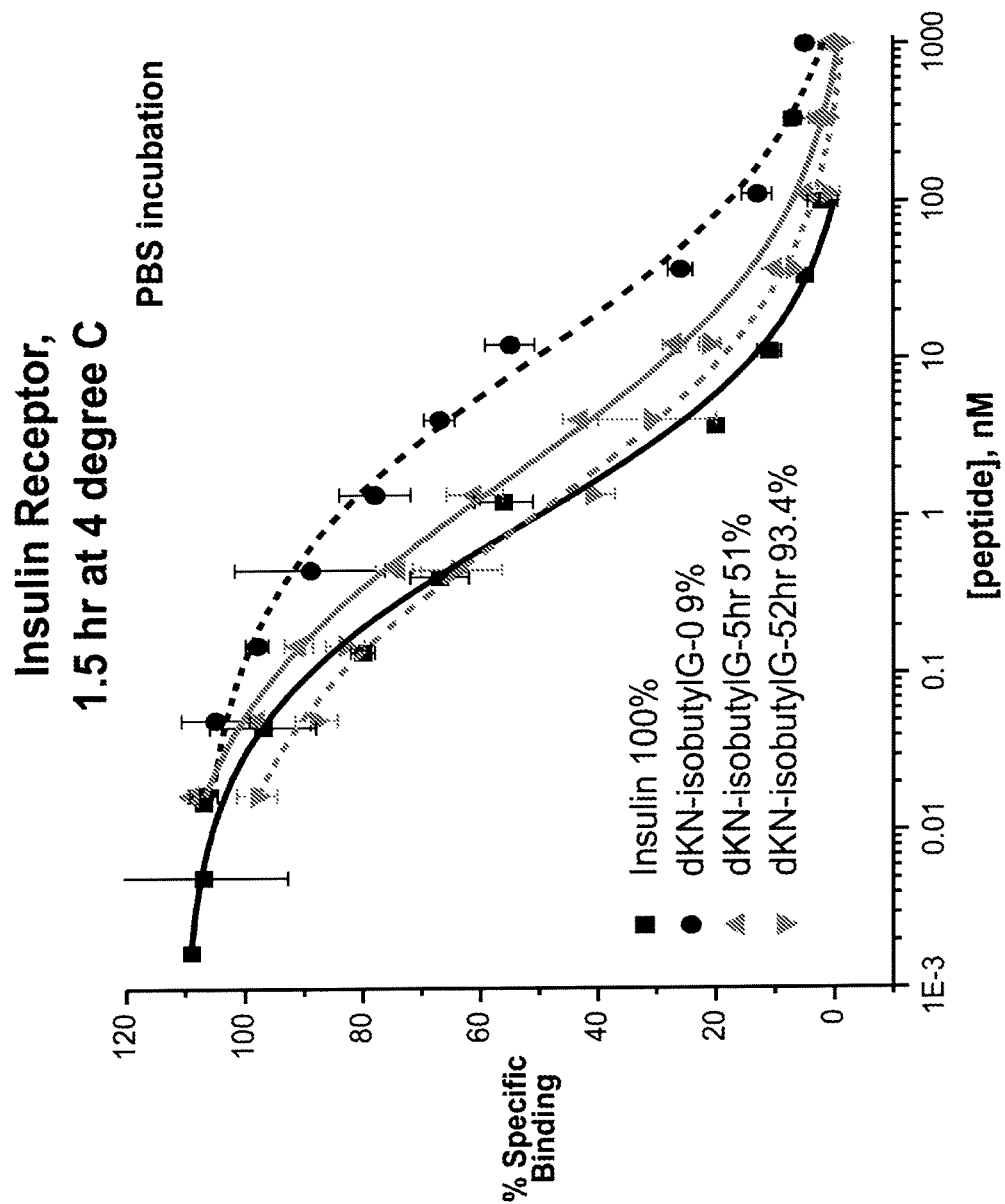
FIGS. 11A & 11B are graphs depicting the in vitro activity of the prodrug dK,(N-isobutylG)-IGF1YL (dipeptide linked through the A19 4-aminoPhe).
Figure 11B:
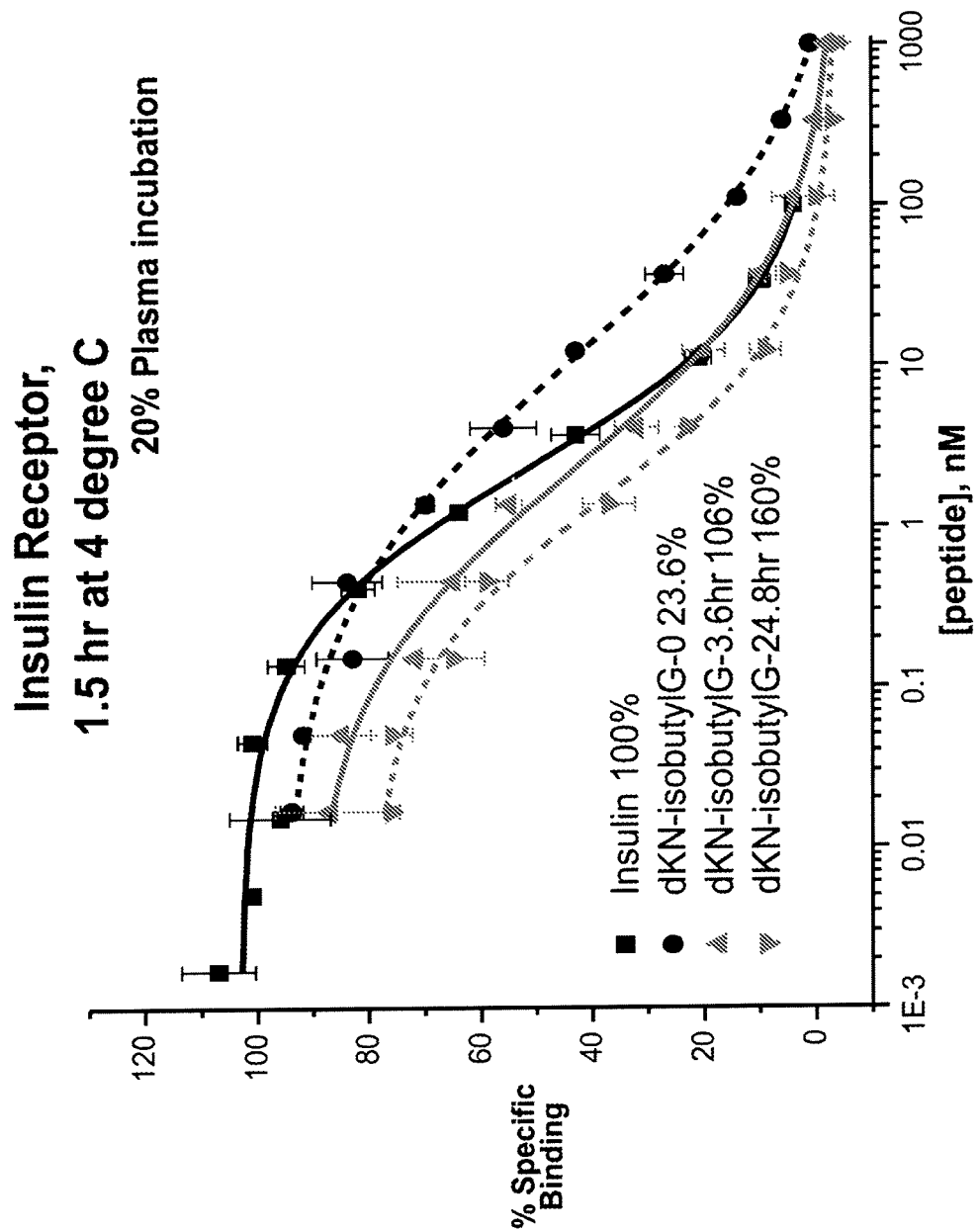

FIGS. 11A & 11B are graphs depicting the in vitro activity of the prodrug dK,(N-isobutylG)-IGF1YL (dipeptide linked through the A19 4-aminoPhe). FIG. 11A is a graph comparing relative insulin receptor binding of native insulin (measured at 1 hour at 4° C.) and the A19 IGF prodrug derivative (IGF1YL: dK,(N-isobutylG) over time (0 hours, 5 hours and 52 hours) incubated in PBS. FIG. 11B is a graph comparing relative insulin receptor binding of native insulin and the A19 IGF prodrug derivative (IGF1YL: dK,(N-isobutylG) over time (0 hours, 3.6 hours and 24.8 hours) incubated in 20% plasma/PBS at 37° C. As indicated by the data presented in the graph, increased activity is recovered form the A19 IGF prodrug derivative sample as the prodrug form is converted to the active IGF1YL peptide.

Figure 12A:
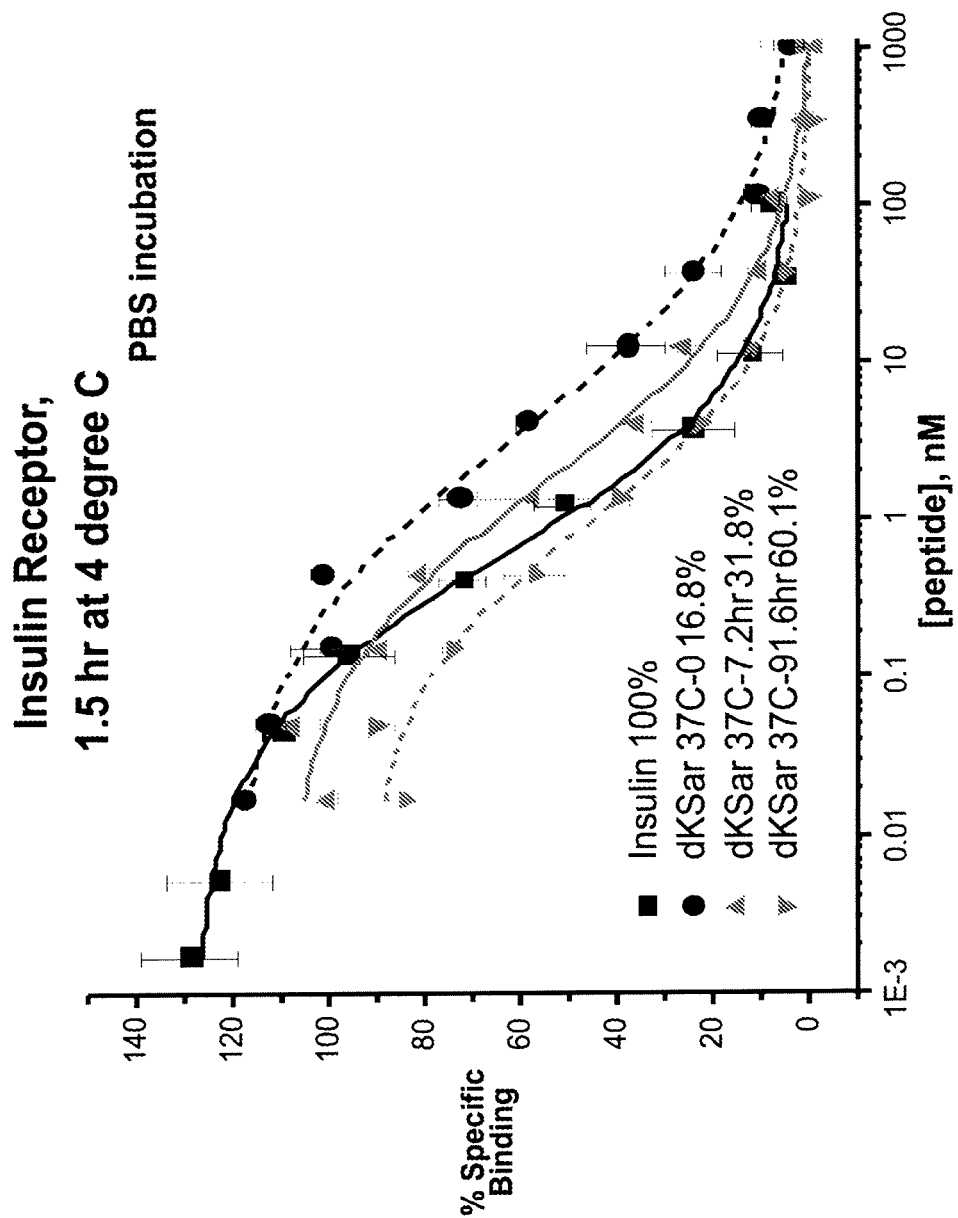
FIGS. 12A & 12B are graphs depicting the in vitro activity of the prodrug dK(e-acetyl),Sar)-IGF1YL (dipeptide linked through the A19 4-aminoPhe).
Figure 12B:
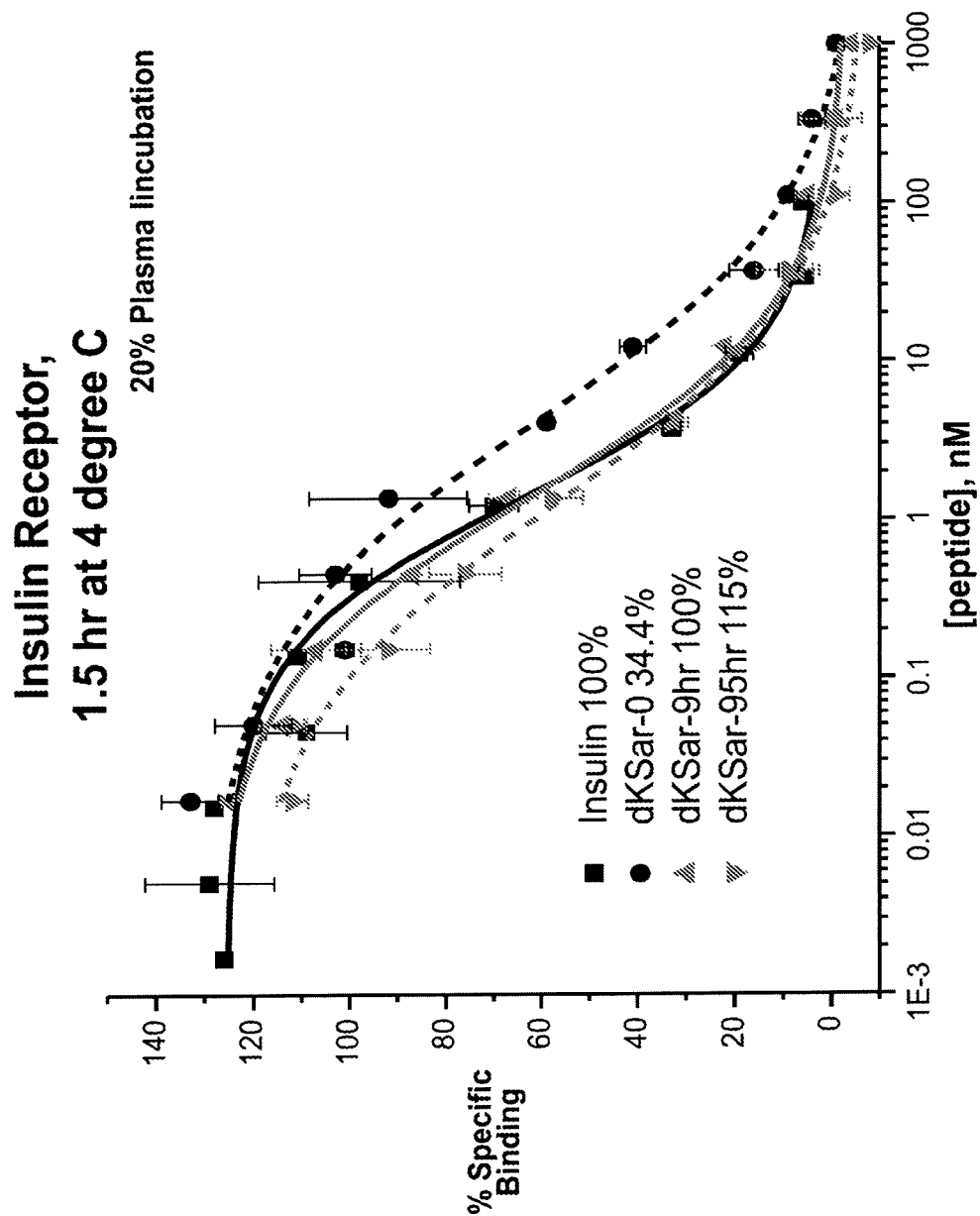
Figure 13:
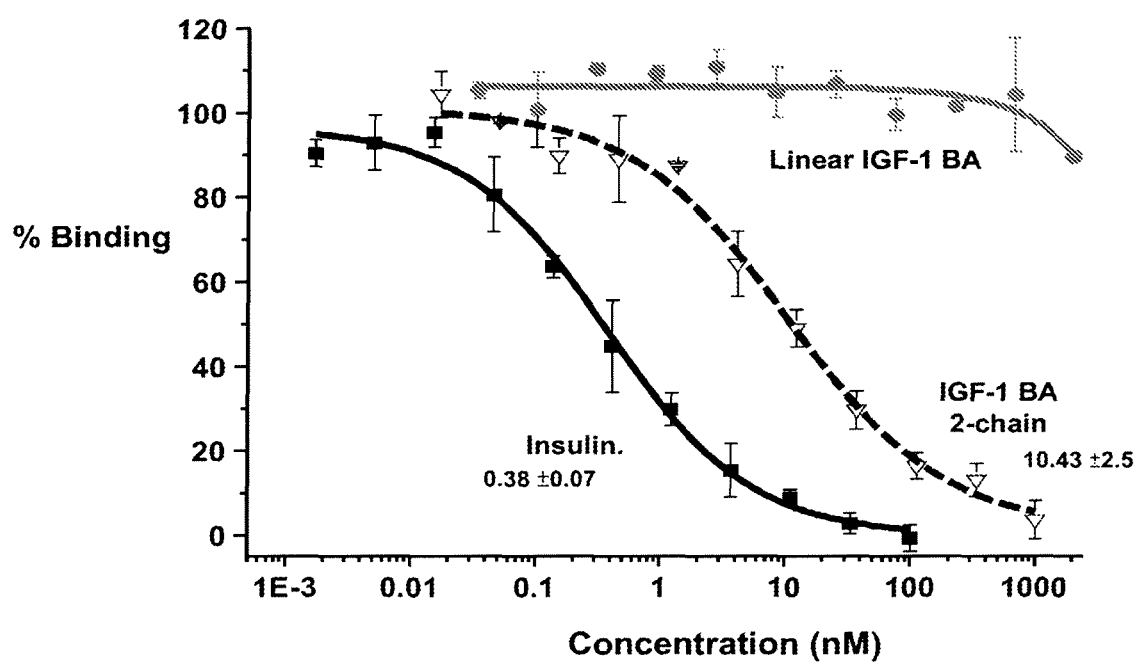
FIG. 13 is a graph comparing relative insulin receptor binding of native insulin heteroduplex and the IGF-1 A and B chain heteroduplex and a single chain IGF-1 analog wherein the carboxy terminus of the B chain is directly linked to the N-terminus of the IGF-1 A chain.
Figure 14:
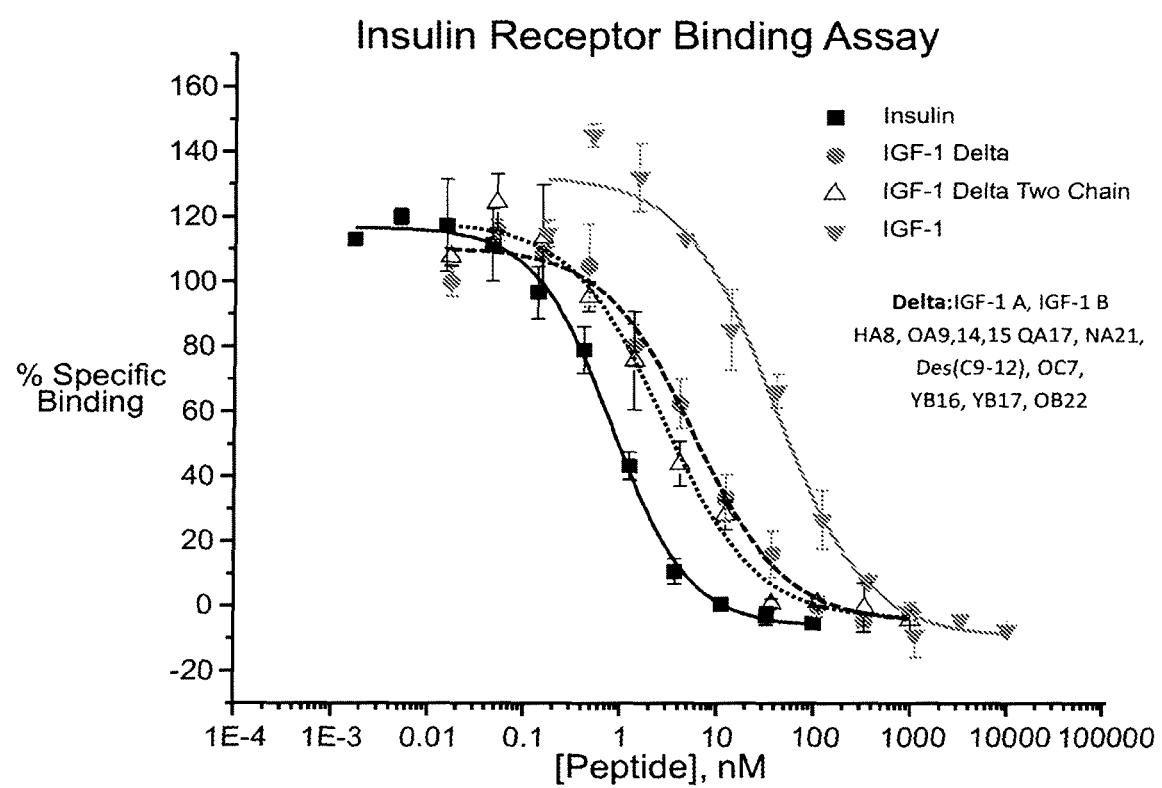
FIG. 14 is a graph comparing relative insulin receptor binding of native insulin heteroduplex, IGF-1, the IGF-1 delta heteroduplex and a single chain IGF-1 delta single chain analog wherein the carboxy terminus of the B chain is linked to the N-terminus of the IGF-1 A chain through a peptide linker consisting of the sequence GYGSSSOR (SEQ ID NO: 35), wherein the IGF-1 delta analog comprises the native IGF-1 sequence with the following amino acid substitutions: HA8, OA9, OA14, OA15, QA17, NA21, YB16, LB17, OB22.

FIGS. 12A & 12B are graphs depicting the in vitro activity of the prodrug dK(e-acetyl),Sar)-IGF1YL (dipeptide linked through the A19 4-aminoPhe). FIG. 12A is a graph comparing relative insulin receptor binding of native insulin (measured at 1 hour at 4° C.) and the A19 IGF prodrug derivative (IGF1YL: dK(e-acetyl),Sar) over time (0 hours, 7.2 hours and 91.6 hours) incubated in PBS. FIG. 12B is a graph comparing relative insulin receptor binding of native insulin and the A19 IGF prodrug derivative (IGF1YL: dK(e-acetyl),Sar) over time (0 hours, 9 hours and 95 hours) incubated in 20% plasma/PBS at 37° C. As indicated by the data presented in the graph, increased activity is recovered form the A19 IGF prodrug derivative sample as the prodrug form is converted to the active IGF1YL peptide.

Example 14

Biosynthesis and Purification of Single Chain Insulin Analogs

An insulin-IGF-I minigene comprising a native insulin B and A chain linked via the IGF-I C chain (B0-C1-A0) was cloned into expression vector pGAPZα A (purchased from Invitrogen) under GAP promoter (promoter of the glyceraldehyde-3-phosphate dehydrogenase (GAPDH)) for constitutive expression and purification of recombinant protein in yeast *Pichia pastoris*. The minigene was fused to an N-terminal peptide encoding *Saccharomyces cerevisiae* α-mating factor leader signal for secretion of the recombinant protein into the medium. A Kex2 cleavage site between the minigene and the leading α-mating factor sequence was used to cleave the leader sequence for secretion of the minigene with native amino termini. Single-site alanine mutations were introduced into C peptide at positions 1 (G1A), 2 (Y2A), 3 (G3A), 4 (S4A), 5 (S5A), 6 (S6A), 7 (R7A), 8 (R8A), 10 (P10A), 11 (Q11A), and 12 (T12A) of the B0C1A0 minigene.

The minigenes including B0C1A0, eleven alanine mutants, and other select derivatives were transformed into yeast *Pichia pastoris* by electroporation. Positive transformants were selected on minimal methanol plates and a genomic preparation of each *Pichia* isolate was performed and integration of the constructs into the yeast genome was confirmed by PCR. An 833 base pair PCR product was visualized on an agarose DNA gel. The insulin analogs were produced by fermentation of a corresponding yeast line. The yeast cells were pelleted by centrifugation at 5 K for 20 minutes in 500 ml Beckman centrifuge tubes and the media was kept for subsequent protein purification.

Growth media supernatants were filtered through 0.2 µm Millipore filter. Acetonitrile (ACN) was added to the supernatant to a final volume of 20%. The supernatant was purified over a Amberlite XAD7HP resin from Sigma, pre-equilibrated with 20% aqueous ACN. The resin was then rinsed twice with 30 ml of 20% aqueous ACN and contaminants were removed with 30% aqueous ACN containing 0.1% TFA. Partially purified insulin analogs were eluted from the column with 54% aqueous ACN containing 0.1% TFA and lyophilizied. Lyophilized samples were re-suspended in 0.025M NH$_3$HCO$_3$ pH 8 and purified on a Luna C18 column (10 µm particle size, 300 A° pore size). Protein was eluted from the column using a linear gradient of 20-60% aqueous ACN. MALDI-MS positive fractions were pooled and transferred to a disposable scintillation vial for subsequent lyophilization. Lyophilized samples were then resuspended in 20% aqueous ACN containing 0.1% TFA, and purified on a Luna C18 column (10 µm particle size, 300 A° pore size). The protein was eluted from the column using a linear gradient of 18-54% aqueous ACN with 0.1% TFA. Protein elution was monitored at an absorbance 280 nm. MALDI-TOF MS positive fractions were analyzed via a C8 analytical column to insure purity.

Figure 15:
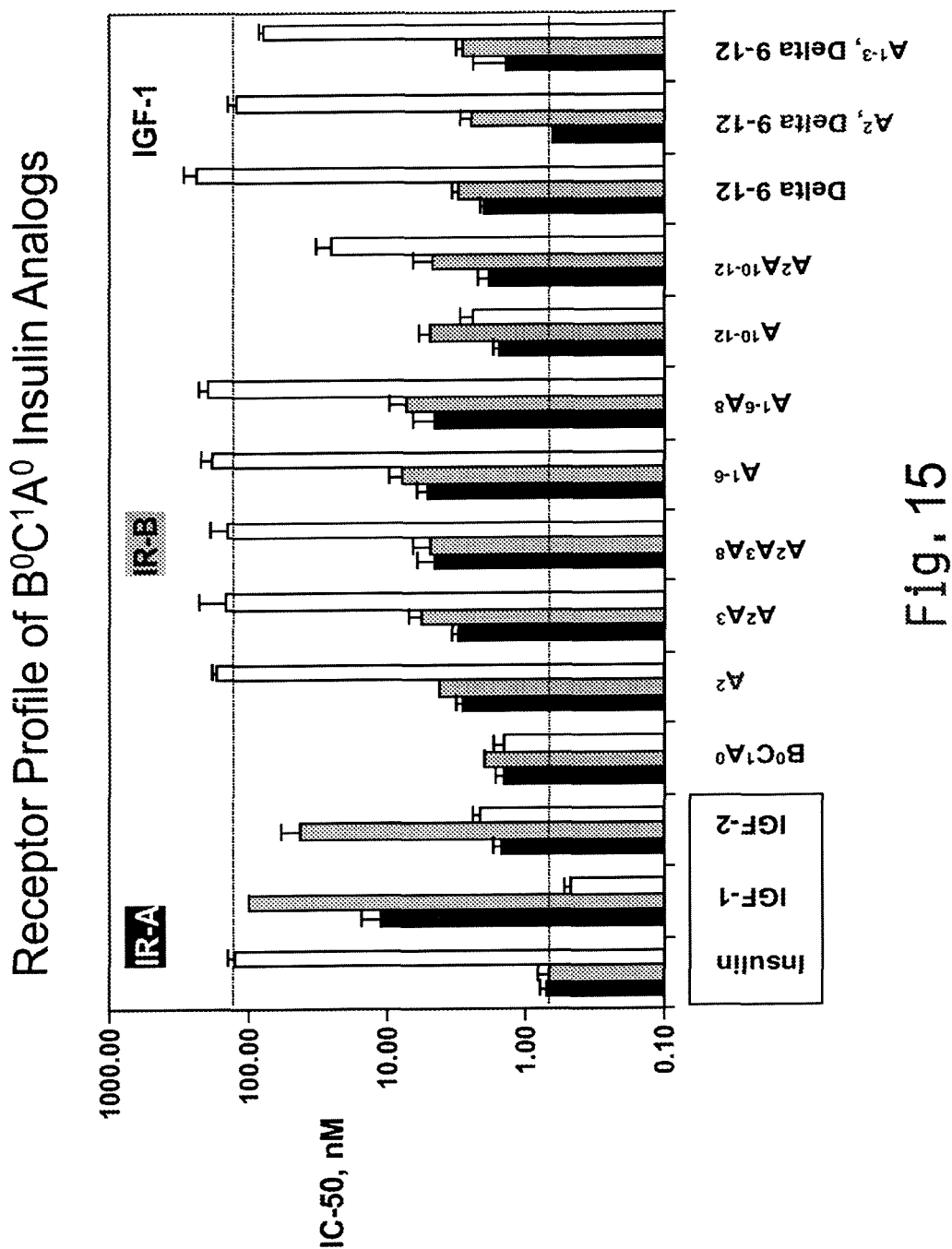
FIG. 15 is a bar graph depicting the relative in vitro binding activity of single chain insulin analogs at the IGF-1 receptor or the A or B subtype insulin receptors wherein the carboxy terminus of the native insulin B chain is linked to the amino terminus of the native insulin A chain via the IGF-1 C peptide or various derivative of the IGF-1 C peptide. In the B⁰C¹A⁰ insulin analog nomenclature, the B⁰ and A⁰ designations refer to the insulin sequences of the A and B chain, while C¹ designates the IGF-1 C peptide. As shown by the data a single chain insulin analog that links the B chain to the A chain via the IGF-1 C peptide is a potent insulin agonist. Furthermore, modifications of position 2 (e.g., substituting alanine for native tyrosine), or alternatively deleting the last four amino acids of the IGF-1 C linking peptide, generates a high potency, insulin selective single chain insulin analog.

FIG. 15 illustrates the potency of the single-chain insulin analogs. The B0-C1-A0 analog demonstrated potency that was equally effective at both insulin receptor isoforms and the IGF-1 receptor. Mutation of the tyrosine at position 2 to alanine or the shortening of the C-peptide to eight amino acids through deletion of C9-12 provided a selective enhancement in the specificity of insulin action by significant reduction in the IGF-1 receptor activity. See also the data provided in Tables 14A and 14B:

TABLE 14A

Insulin Binding & Phosphorylation Analysis
($B^0C^1A^0$)

| Peptide | IR-A Binding | | IR-A Phosphorylation | |
|---|---|---|---|---|
| | IC$_{50}$, nM | n | EC$_{50}$, nM | n |
| Insulin | 0.54 ± 0.02 | 4 | 1.67 ± 0.13 | 1 |
| IGF-1 | 18.81 ± 1.77 | 3 | 29.20 ± 8.41 | 1 |
| 010 ($B^0C^1A^0$) | 2.83 ± 0.52 | 2 | 1.93 ± 0.43 | 1 |
| G1A | 1.21 ± 0.15 | 1 | 2.4 ± 0.24 | 1 |
| Y2A | 1.95 ± 0.28 | 3 | 1.86 ± 0.42 | 1 |
| G3A | 1.41 ± 0.05 | 2 | 2.13 ± 0.02 | 1 |
| S4A | 0.84 ± 0.47 | 2 | 0.76 ± 0.35 | 1 |
| S5A | 0.93 ± 0.44 | 1 | 2.23 ± 1.27 | 1 |
| S6A | 1.15 ± 0.24 | 1 | 2.33 ± 1.65 | 2 |
| R7A | 6.04 ± 0.82 | 1 | 5.21 ± 4.14 | 1 |
| R8A | 0.63 ± 0.09 | 1 | 2.03 ± 0.06 | 2 |
| P10A | 2.86 ± 0.93 | 1 | 2.59 ± 1.2 | 1 |
| Q11A | 1.79 ± 0.47 | 1 | 2.58 ± 0.83 | 1 |
| T12A | 1.2 ± 0.18 | 1 | 2.83 ± 1.31 | 1 |

TABLE 14B

IGF-1 Binding & Phosphorylation Analysis
($B^0C^1A^0$)

| Peptide | IGF-IR Binding | | IGF-IR Phosphorylation | |
|---|---|---|---|---|
| | IC$_{50}$, nM | n | EC$_{50}$, nM | n |
| Insulin | 60.63 ± 4.43 | 1 | 48.66 ± 1.59 | 1 |
| IGF-1 | 0.38 ± 0.07 | 1 | 0.88 ± 0.41 | 1 |
| 010 ($B^0C^1A^0$) | 4.49 ± 1.04 | 1 | 1.29 ± 2.28 | 1 |
| G1A | 42.36 ± 16.24 | 1 | 1.4 ± 0.62 | 1 |
| Y2A | 257.9 ± 29.59 | 1 | 35.6 ± 14.55 | 1 |
| G3A | 34.02 ± 16.09 | 1 | 7.85 ± 0.78 | 1 |
| S4A | 15.30 ± 3.10 | 1 | 1.64 ± 1.65 | 1 |
| S5A | 13.06 ± 3.01 | 1 | 2.63 ± 1.88 | 1 |
| S6A | 2.44 ± 0.79 | 1 | 1.54 ± 0.62 | 2 |
| R7A | 43.86 ± 8.72 | 1 | 1.26 ± 1.55 | 1 |
| R8A | 10.85 ± 1.47 | 1 | 0.50 ± 0.23 | 2 |
| P10A | 6.42 ± 0.47 | 1 | 2.79 ± 1.12 | 1 |
| Q11A | 4.23 ± 0.43 | 1 | 0.41 ± 0.69 | 1 |
| T12A | 9.15 ± 0.83 | 1 | 1.44 ± 1.36 | 1 |

Figure 16:
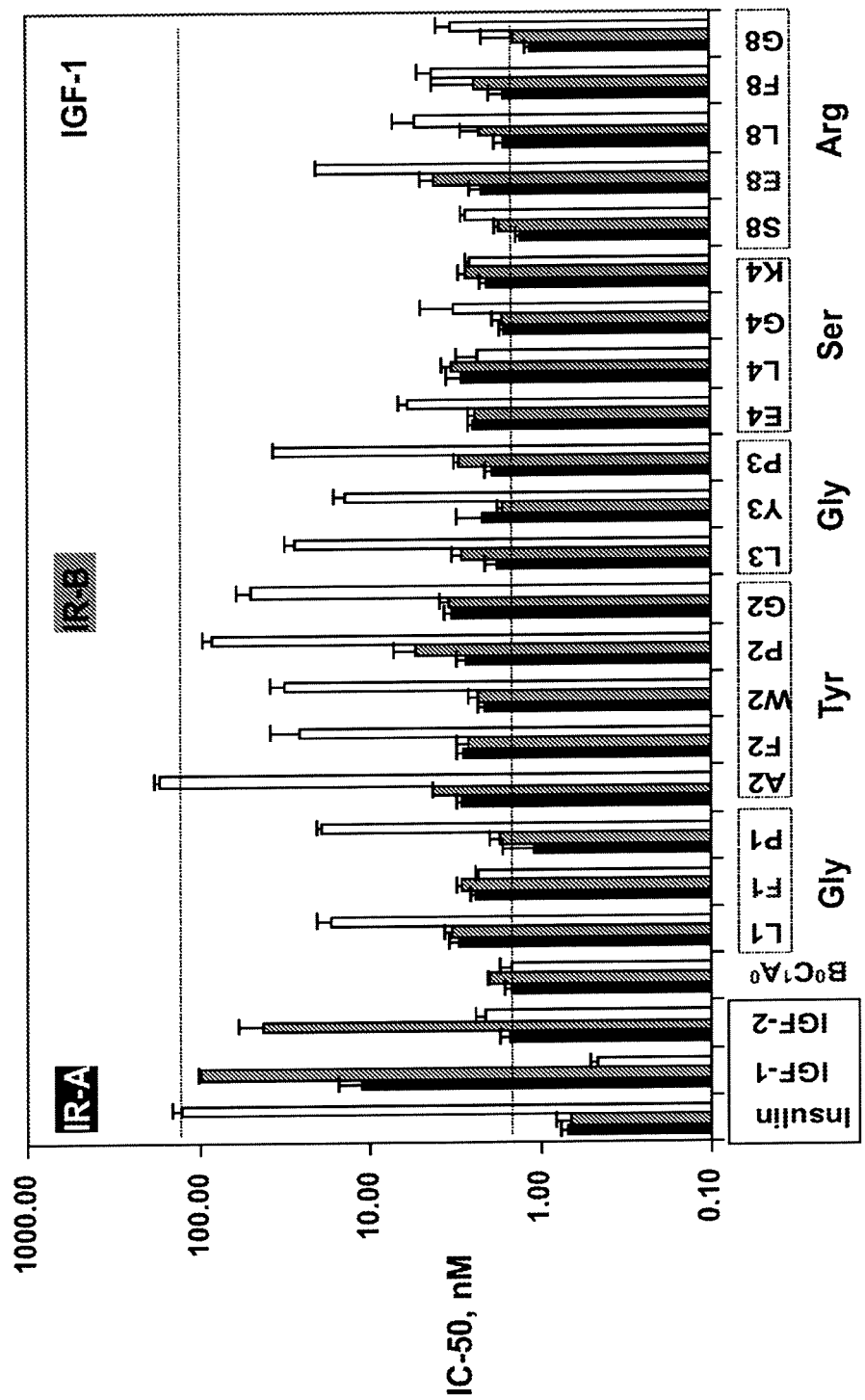
FIG. 16 is a bar graph depicting the relative in vitro binding activity of single chain insulin analogs of the formula B⁰C¹A⁰ at the IGF-1 receptor or the A or B subtype insulin receptors wherein the native sequence of the linking IGF-1 C peptide has been modified by the indicated amino acid substitutions at position 1, 2, 3, 4 or 8. In the B⁰C¹A⁰ insulin analog nomenclature, the B⁰ and A⁰ designations refer to the insulin sequences of the A and B chain, while C¹ designates the IGF-1 C peptide.

FIG. 16 demonstrates that position 2 and 3 in the C-peptide are most sensitive to modification at the IGF-1 receptor with the insulin receptor proving to be relatively immune to modification. Finally, FIGS. 17 and 18 present the in vitro analysis of the single-chain insulin mutants as a ratio of binding affinity (IC50) and biochemical signaling through tyrosine phosphorylation (EC50). The two independent measurements demonstrate great consistency thereby validating this in vitro approach to structure-function analysis. All of the analogs maintained single unit nanomolar activity with certain specific analogs proving to be slightly enhanced in potency (low single unit nanomolar). The most insulin selective analogs were those that we missing the last four residues of the C-peptide, had an alanine mutation at position two of the C-peptide, or a combination of the two changes.

Example 15

Biosynthesis Procedure for Prokaryotic Cells

1. Expression and Purification of DP20 with Native Expression in E. coli

The DP20 gene was codon-optimized, synthesized and cloned into a LIC-SUMO vector. LIC-SUMO is modified from pET22b (Novagen), has a sumo sequence as an N-terminal fusion tag with a TEV protease cleavage site between the SUMO and target protein sequence.

DP20 was expressed in OrigamiB(DE3) (Novagen). Cells were cultured in Luria Broth medium with 50 ug/ml ampicillin, 25 ug/ml kanamycin and 5 ug/ml tetracycline. When the $OD_{600\ nm}$ reached 0.8-1.0 at 37° C. the culture was transferred to 16° C. IPTG was added to the culture at 0.2 mM concentration. The culture was continued overnight and cells were harvested with centrifugation at 5000 rpm for 15 minutes.

Cell pellet was re-suspended in lysis buffer consisting of 50 mM sodium phosphate, 300 mM NaCl, 10 mM imidazole. The cells were lysed by sonication (1 second on, 2 second off, 180 cycles). The lysate was centrifuged at 15000 rpm for 30 minutes. Supernatant was applied to a Ni-NTA (Qiagen) column pre-equilibrated with lysis buffer. The column was washed with a buffer of 50 mM sodium phosphate, 300 mM NaCl, 40 mM imidazole. DP20 was eluted with elution buffer of 50 mM sodium phosphate, 300 mM NaCl, 500 mM imidazole.

The DP20 eluted from the Ni-column was digested with TEV protease at 4° C. overnight. The sample was purified by chromatography on a silica-based C8 HPLC column (Phenomenex) after the pH was adjusted to 2-3. The sample was applied to the column and eluted with a gradient of 15%-25% acetonitrile in 0.15% TFA(aq). Identity of the desired protein was confirmed by analytical HPLC and mass spectrum analysis. Fractions containing DP20 were pooled and lyophilized.

2. Expression and Purification of DP31 Under Denatured Conditions in *E. coli.*

The gene for DP31 was codon-optimized, synthesized and cloned to LIC-SUMO vector. LIC-SUMO is modified from pET22b (Novagen), has a sumo sequence as an N-terminal fusion tag with a TEV protease cleavage site between the SUMO and target protein sequence.

DP31 was expressed in OrigamiB(DE3) (Novagen). Cells were cultured in Luria Broth medium with 50 ug/ml ampicillin, 25 ug/ml kanamycin and 5 ug/ml tetracycline. When the $OD_{600\ nm}$ reached 0.8-1.0 at 37° C., the culture was transferred to 16° C. IPTG was added to the culture at 0.2 mM concentration. The culture was continued overnight and the cells were harvested with centrifugation at 5000 rpm for 15 minutes.

The general scheme for synthesizing single chain analogs under denaturing conditions is shown in FIG. 17. Cell pellet was re-suspended in lysis buffer consisting of 50 mM sodium phosphate, 300 mM NaCl, 10 mM imidazole, 8 M urea. Lysis was performed by sonication (1 second on, 2 second off, 180 cycles). The lysate was centrifuged at 15000 rpm for 30 minutes. Supernatant was loaded to a Ni-NTA (Qiagen) column pre-equilibrated with lysis buffer. The column was washed with 50 mM sodium phosphate, 300 mM NaCl, 40 mM imidazole. DP31 was eluted with 50 mM sodium phosphate, 300 mM NaCl, and 500 mM imidazole.

DP31 purified by Ni-column chromatography was digested with TEV protease at 4° C. overnight. Alternatively, the leader peptide can be cleaved using a tryptophan cleavage site (W), or Lys C cleavage at an inserted lysine residue when no lysines are present within the single chain insulin analog. The pH of the solution was adjusted to 10.5; glycine and cysteine were added to a concentration of 20 mM and 4 mM respectively. The protein was disulfide oxidized and folded over a period of 24-48 hours. The sample was purified by chromatography on a silica C8 HPLC column (Phenomenex) after the pH was adjusted to 2-3. DP-31 was eluted with 15%-25% acetonitrile in 0.15% TFA(aq). Protein Identity was confirmed by analytical HPLC and mass spectrum analysis. Fractions containing DP31 were pooled and lyophilized.

Example 16

Expression and Purification of DP31 in *Pichia pastoris*

Codon-optimized gene of DP31 will be synthesized and cloned into pPICZα (Invitrogen). The construct will include a spacer peptide of EEAEAEAEPK placed between a Kex2 cleavage site and the DP31 gene. The plasmid pPICZα-DP31 will be opened (linearized) with SacI and electroporated into *P. Pastoris* strain X-33 (Invitrogen). The transformed yeast clones will be selected on Zeocin plates which contained increasing concentration of Zeocin. The most viable clones (highest Zeocin concentration) will be selected and used to express the DP31 protein.

The selected *P. Pastoris* cells will be inoculated in 100 ml YPD medium (1% yeast extract, 2% peptone, 2% dextrose) and shaken at 30° C. and 220 rpm for 24 hours. The inoculate will then be placed in 2 L BMGY medium (1% yeast extract, 2% peptone, 100 mM potassium phosphate pH6.0, 1.34% YNB, 4×10$^{-5}$ biotin, 1% glycerol) and shaken at 30° C. and 220 rpm until OD$_{600\,nm}$ reaches between 5-6. The cells will then be collected by centrifugation at 5000 rpm for 5 min at 4° C., re-suspended in 1 L BMMY medium (1% yeast extract, 2% peptone, 100 mM potassium phosphate pH6.0, 1.34% YNB, 4×10$^{-5}$ biotin, 0.5% methanol) to induce production of DP31. Methanol will be supplemented every 24 h to a final concentration of 1.0% (V/V) throughout the induction phase (4-6 days).

Culture medium will be clarified by centrifugation at 5000 rpm for 15 min, loaded to a XAD7HP column (Rohm and Haas). The column will be washed with 5% acetic acid containing 15% ethanol, followed by 5% acetic acid repeatedly to remove impurities. The DP31 will be eluted from the column with 45% ethanol with 5% acetic acid. The eluted protein will then be concentrated by evaporation and further purified by preparative HPLC using the same conditions as provided in Example 15.

Example 17

Expression and Purification of DP31 in Eukaryotic CHO Cells

To express DP31 in CHO cells, a synthetic gene (see diagram below) will be synthesized and ligated to pcDNA3.1 containing NheI and NotI sites.

| hGH | 8xHis- | DP31 |
|---|---|---|

Human growth hormone (hGH) fused to the N-terminal of DP31 can be easily detected by enzyme-linked immunoadsorbent assay (ELISA). It also enhances expression and directs secretion. Eight histidine residues and a TEV protease cleavage site will be placed between the hGH and DP31 to facilitate purification and proteolytic removal of the fusion partner.

CHO cells will be transfected with the pcDND3.1-hGH-DP31 plasmid using a Fugene6 transfection reagent (Roche). Stable cell lines will be screened in medium containing 200 ug/ml Zeocin. Stable cell lines will be amplified and adapted to serum-free medium (EX-cell 301 JRH Biosciences) and expanded to grow in 850-cm$^2$ roller bottles. One hundred milliliters of medium will be maintained in each roller bottle allowing production of 1 liter of conditioned medium every three days from ten roller bottles.

The conditioned serum-free medium will be centrifuged and filtered to remove cell debris. Tris and NaCl will then be added to the medium to a concentration of 20 mM and 300 mM, respectively. The pH will then be adjusted to 8.0 and the media applied to a Ni-NTA column. The column will be washed with five bed-volumes of 20 mM Tris, 20 mM imidazole, 300 mM NaCl at pH 8. The extended DP31 fusion protein will be eluted with 20 mM Tris, 500 mM imidazole, 500 mM NaCl at pH 8. This fusion protein will be digested with TEV protease and further purified by preparative HPLC using the same conditions as disclosed in Example 15.

Example 18

Receptor Binding of CTP Containing Single Chain Insulin Analogs

The affinity of each peptide for the insulin or IGF-1 receptor was measured in a competition binding assay as described in Example 3 and the insulin subtype A and subtype B receptor phosphorylation activity of the insulin analogs was measured using, receptor transfected HEK293 cells as described in Example 4. Each of the compounds were also tested for their ability to induce proliferation of HMEC cells. The results are provided in Table 15. Compounds tested include:

DP19: CTP-E$_5$K-B chain-C peptide-A Chain (SEQ ID NO: 67);

DP20: GE$_5$K-B chain-CTP(K)-A Chain (SEQ ID NO: 68); and

DP22: CTP-E$_5$R-B chain-CTP(K)-A Chain (SEQ ID NO: 91).

TABLE 15

In Vitro Profile of DP19, 20 & 22

| | Receptor Binding | | | | | | Receptor Phosphorylation | | | | | | Proliferation | |
|---|---|---|---|---|---|---|---|---|---|---|---|---|---|---|
| | IR-A | | IR-B | | IGR-1R | | IR-A- | | IR-B | | IGF-IR | | HMEC | |
| Analog | EC$_{50}$ | STDev** | EC$_{50}$ | STDev | EC$_{50}$ | STDev | EC$_{50}$ | STDev | EC$_{50}$ | STDev | EC$_{50}$ | STDev | EC$_{50}$ | STDev |
| Insulin | 0.226 | 0.235 | 0.217 | 0.293 | 171.245 | 1.538 | 0.408 | 0.17 | 0.385 | 0.081 | 77.200 | 60.692 | 23.390 | 2.249 |
| DP19 | 0.524 | 0.263 | 1.214 | 1.253 | 216.270 | #DIV/0! | 0.985 | 0.163 | 4.340 | 3.055 | 26.723 | 17.285 | #DIV/0! | #DIV/0! |
| DP20 | 2.088 | 0.813 | 5.444 | 7.420 | 36.864 | #DIV/0! | 0.720 | 0.072 | 4.827 | 50.23 | 378.673 | 128.061 | 146.500 | 9.192 |
| DP19LysC | 0.434 | 0.136 | 1.832 | 0.096 | 162.257 | #DIV/0! | 0.300 | #DIV/0! | 1.200 | #DIV/0! | 20.720 | #DIV/0! | #DIV/0! | #DIV/0! |
| DP20LysC | 0.231 | 0184 | 0.433 | 0.497 | 50.027 | 22.137 | 0.210 | 0.118 | 1.335 | 1.563 | 13.273 | 4.397 | 8.185 | 0.629 |
| DP22 | 8.418 | #DIV/0! | 16.402 | #DIV/0! | 437.588 | #DIV/0! | 1.245 | 0.389 | 11.335 | 9.850 | 269.025 | 262.938 | 431.000 | 158.392 |
| DP22LysC | 1.062 | #DIV/0! | 3.710 | #DIV/0! | 58.835 | #DIV/0! | 0.385 | 0.007 | 1.410 | 0.665 | 22.985 | 11.575 | 29.700 | 10.607 |
| IGF-1 | 18.809 | 22.813 | 60.697 | 53.193 | 0.493 | 0.204 | 6.480 | 5.996 | 32.175 | 0.318 | 0.617 | 0.144 | 0.310 | #DIV/0! |

**interexperimental

FIG. 18A is a graph showing the ability of DP20 and DP22 relative to native insulin and IGF-1 to induce phosphorylation at the insulin subtype A receptor. The EC50 values (in nM) obtained for each compound in this experiment was:

| Insulin | DP-20 | DP-20Lys | DP22 | DP22Lys random | IGF-1 |
|---|---|---|---|---|---|
| 0.52 ± 0.16 | 0.80 ± 0.20 | 0.34 ± 0.07 | 0.97 ± 0.17 | 0.39 ± 0.06 | 2.24 ± 1.44 |

FIG. 18B is a graph showing the ability of DP19 and DP20 relative to native insulin and IGF-1 to induce phosphorylation at the insulin subtype B receptor. The EC50 values (in nM) obtained for each compound in this experiment was:

| Insulin | DP-20 | DP-20Lys | DP22 | DP22Lys random | IGF-1 |
|---|---|---|---|---|---|
| 0.50 ± 0.10 | 10.6 ± 5.06 | 2.44 ± 1.30 | 18.3 ± 10.3 | 1.88 ± 0.52 | 32.4 ± 14.9 |

FIG. 18C is a graph showing the ability of DP20 and DP22 relative to native insulin and IGF-1 to induce phosphorylation at the IGF-1 receptor. The EC50 values (in nM) for each compound for this experiment was:

| Insulin | DP-20 | DP-20Lys | DP22 | DP22Lys random | IGF-1 |
|---|---|---|---|---|---|
| 22.2 ± 8.21 | 316 ± 152 | 8.23 ± 3.84 | 83.1 ± 11.9 | 14.8 ± 5.07 | 0.45 ± 0.05 |

Figure 19A:
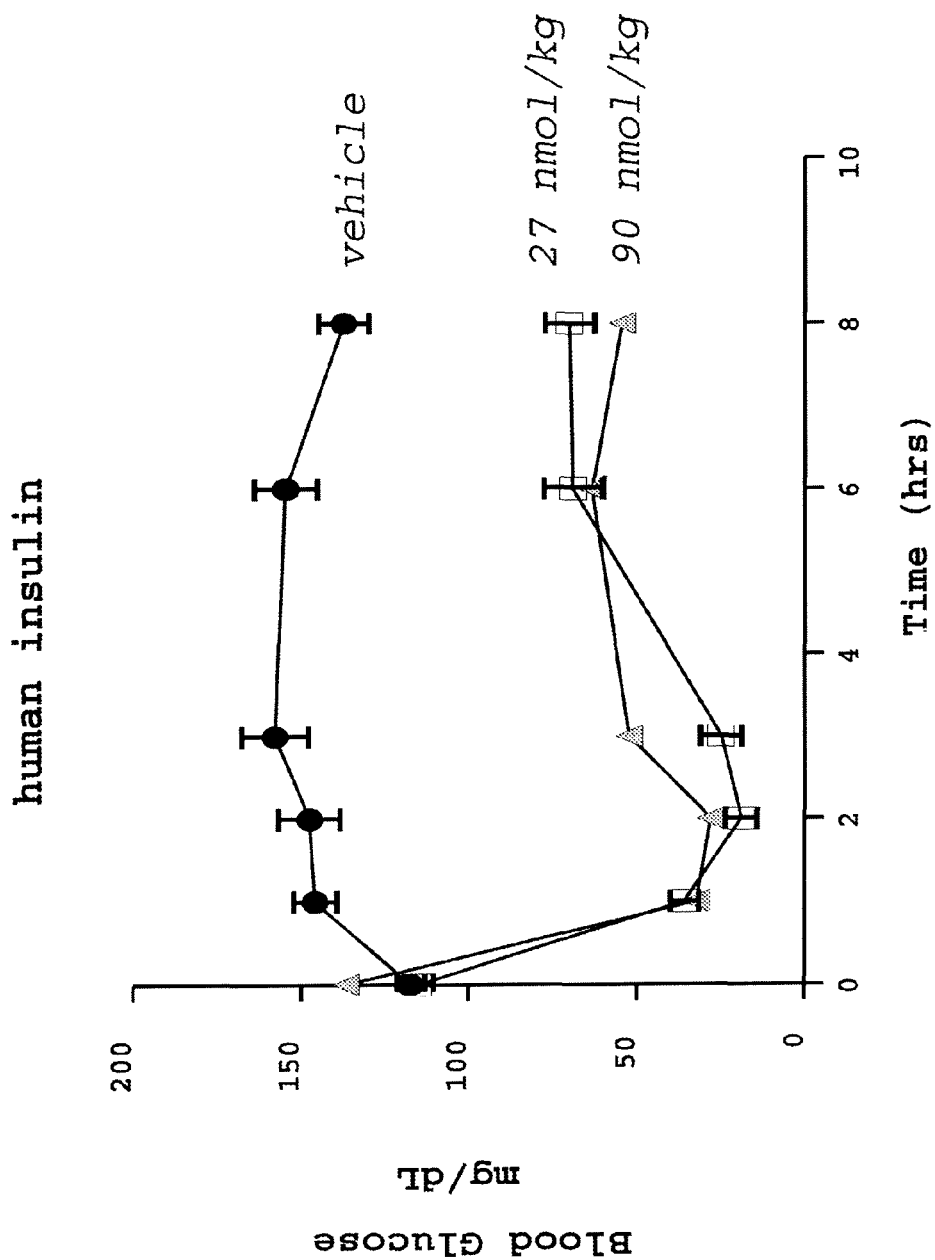
Figure 25A:
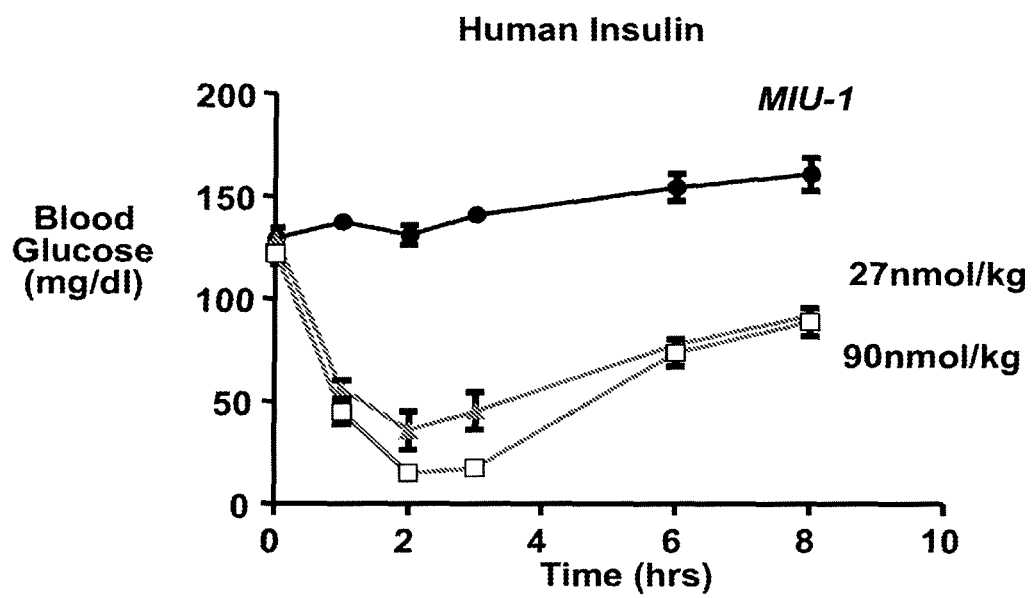
FIGS. 25A-25D are graphs showing the results of comparative insulin tolerance tests conducted on mice comparing the ability of human insulin to reduce and sustain low blood glucose concentration relative to three different acylated insulin analogs. The compounds were tested at two different concentrations (27 nmol/kg and 90 nmol/kg). The acylated insulins included MIU-41, MIU-36 and MIU-37. MIU-41 [B¹(H5,H10,Y16,L17)25a:A¹(H8,rEC16-K14, N18,N21)], is a two chain insulin analog having a C16 acylation via a gamma glutamic acid linker attached to a lysine residue located at position A14. MIU-36 [B¹(C16-K0,H5,H10,Y16,L17)25a:A¹(N18,N21)], is a two chain insulin analog having a C16 acylation linked to the N-terminus of the B chain). MIU-37 [B¹(H5,H10,Y16,L17, C16rE-K22)25a:A¹(N18,N21)], is a two chain insulin analog having a C16 acylation via a gamma glutamic acid linker attached to a lysine residue located at position B22.
Figure 25B:
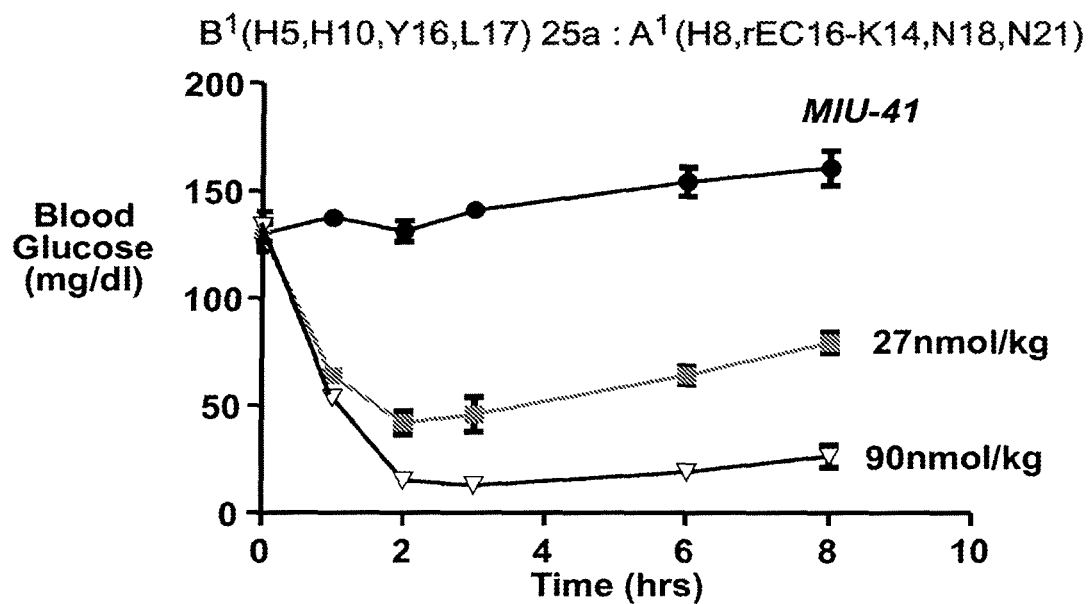
Figure 25C:
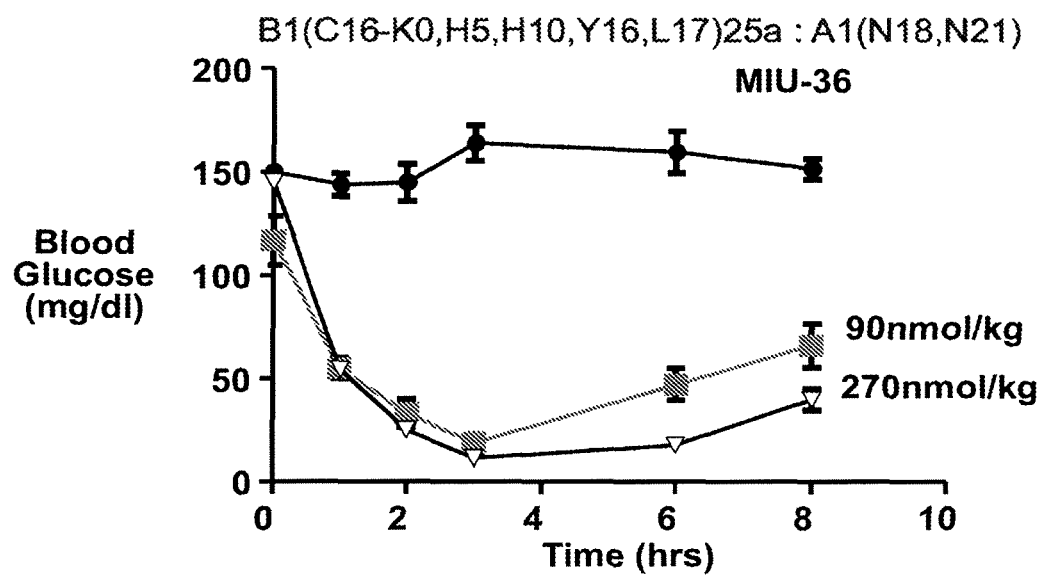
Figure 25D:
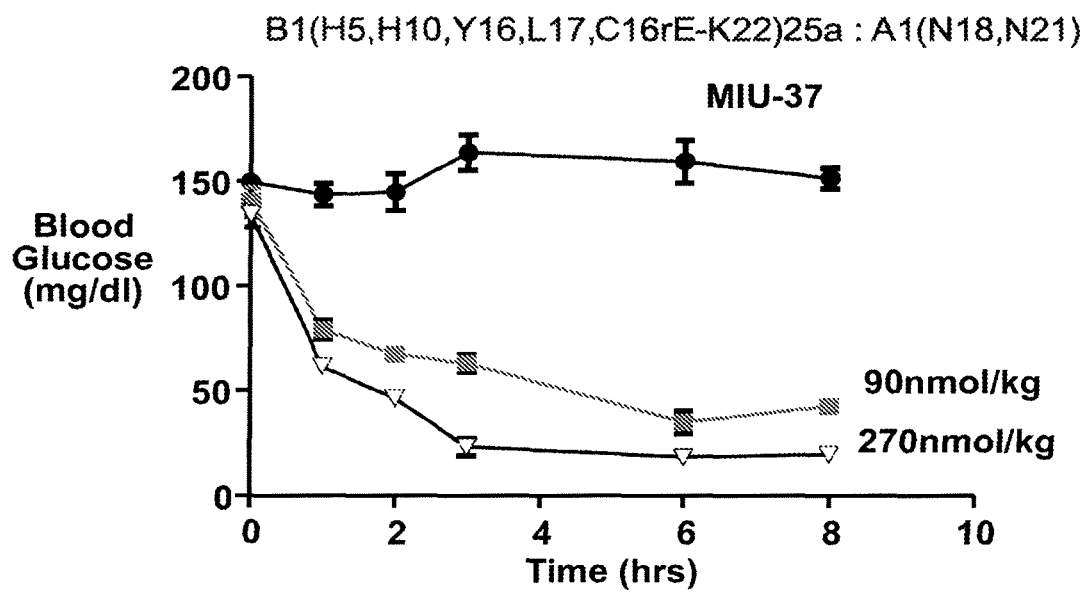

FIGS. 19A-19C show the results of comparative insulin tolerance tests conducted on mice comparing the ability of human insulin relative to two CTP containing single chain insulin analogs. As shown by the data, both the D19 (having a CTP linked to the N-terminus of the B chain) and D20 (having a CTP as the linking moiety) are potent insulin receptor agonists.

The CTP peptide has a high content of serine and proline residues. To determine if the serine residues function to give CTP its surprising activities, the serines of the CTP linking peptide were substituted with alanines and the ability of the analogs to induce phosphorylation by the insulin subtype A and B receptors was measured. In addition, single chin insulin analogs were prepared having the CTP peptide serve as the linking moiety between the B and A chains wherein the amino acid comprising the CTP peptide remain the same, but the sequence of the CTP peptide has been randomized (DP20RCTP). A further analog was prepared based on the DP20 structure, wherein the linking peptide comprises the native proinsulin C peptide. FIGS. 20 A & B are graphs showing the activities of the insulin analogs to induce phosphorylation by the insulin subtype B and A receptors, respectively. The IC$_{50}$ of each analog is provided in Tables 16A and 17B.

TABLE 16A

Phosphorylation at Insulin Receptor Subtype A

| Insulin | DP-20 | DP-20, C$^0$ | DP20, S2A | DP20 random | IGF-1 |
|---|---|---|---|---|---|
| 0.15 | 3.12 | 84.32 | 11.84 | 8.08 | 145.6 |

TABLE 16B

Phosphorylation at Insulin Receptor Subtype B

| Insulin | DP-20 | DP-20, C⁰ | DP20, S2A | DP20 ransom | IGF-1 |
|---------|-------|-----------|-----------|-------------|-------|
| 0.91    | 1.05  | 35.37     | 7.44      | 2.46        | 19.68 |

The data reveal that single chain insulin analogs comprising a CTP peptide as the linking moiety, even when the serines have been substituted with alanines or when the sequence has been randomized, still retain potency at both insulin receptors relative to the native proinsulin or IGF peptides at both insulin receptor subtypes relative to the native proinsulin or IGF peptides.

To further investigate the CTP peptides functionality as an insulin single chain linking moiety, additional single chain analogs were prepared. A single chain analog comprised a CTP peptide as the linking peptide wherein the prolines have been replaced with alanine (DP20 P to A (SEQ ID NO: 70)) and its activity was compared to DP20 modified to either have the native proinsulin C peptide, the native IGF_1 C peptide or the CTP peptide cleaved at the carboxy terminus of the CTP peptide. The activity of these compounds at the insulin subtype A receptor is shown in FIG. 21. A single chain analog comprising a CTP peptide linking moiety wherein the prolines of the CTP peptide have been substituted with alanine still has appreciable activity at the insulin receptor, equivalent to that of native IGF-1. Furthermore, when a single chain insulin analog comprising the CTP peptide as the linking moiety is cleaved at the junction between the CTP and the insulin A chain, the resulting two chain analog is at least as potent as native two chain insulin.

To investigate whether the native proinsulin C peptide interferes with insulin's ability to activate the insulin receptor, single chain insulin analogs were constructed comprising a linking moiety that includes both a CTP peptide and the native proinsulin C peptide. The native C peptide was inserted either between the B chain and the CTP peptide (DP20 C⁰CTP (SEQ ID NO: 74)), or between the CTP peptide and the A chain (DP20 CTPC⁰ (SEQ ID NO: 73)). An additional analog was prepared comprising two CTP peptides linked head to tail as the linking moiety (DP20 2CTP (SEQ ID NO: 75)). FIGS. 22A and 22B are graphs demonstrating the in vitro phosphorylation activity of these single chain insulin analogs. As shown by the data all insulin analogs appear to have activity at the insulin receptor although DP20 CTPC⁰ appears more potent than DP20 C⁰CTP. Furthermore, a single chain analog comprising two CTP peptides as the linking peptide also appears to be active as an insulin agonist.

To investigate whether removing a segment of the native proinsulin C peptide would allow that sequence to be used as a linking moiety in single chain analogs, a series of 6 amino acid deletions were made in the native proinsulin C peptide sequence. Six amino acids were removed to adjust the native proinsulin C peptide to the same size as the CTP peptide. Accordingly single chain analog were prepared using the native proinsulin C peptide as the linking moiety wherein either the first 6 amino acids were removed, DP20 C0 (desC1-6) (SEQ ID NO: 76), amino acids 15-21 were removed, DP20 C0 (desC15-21) (SEQ ID NO: 77), or amino acids 27-33 were removed, DP20 C0 (desC27-33) (SEQ ID NO: 78). FIG. 23 is a graph demonstrating the in vitro phosphorylation activity at the insulin subtype A receptor of single chain insulin analogs relative to a two chain native insulin and an insulin analog having CTP as the linking peptide. Each of the single chain insulin analogs comprising a truncated native proinsulin C peptide demonstrated poor activity at the insulin subtype A receptor, while DP20 was nearly equivalent to native hormone.

Example 19

Single Chain Insulin Based CTP Analogs

To investigate the activity of native insulin sequences in a single chain insulin analog comprising a CTP peptide as the linking moiety, the DP25M peptide was constructed: GEEEEEKFVNQHLCGSHLVEALYLVCGERGFFYT-DRTSSSSRAPPPSLPSPSRL PGPSDTPILPQRGIVEQC-CTSICSLYQLENYCN (SEQ ID NO: 81). This compound was tested for activity at the insulin subtype A (IRA-DP25M) and subtype B (IRB-D25M), see FIG. 24, and was found to be active but about 3 to 4 fold less active than the corresponding DP20 analog. Accordingly, a series of insulin derivatives of DP25 M were prepared wherein the carboxy terminal 5 amino acids have been removed from the B chain:

```
                                         (SEQ ID NO: 83)
DP30: GEEEEEKFVNQHLCGSHLVEALYLVCGERGFF-----SS

SSRAPPPSLPSPSRLPGPSDTPILPQRGIVEQCCTSICSLYQLENYCN;

(SEQ ID NO: 84)
DP31: GEEEEEKFVNQHLCGSHLVEALYLVCGERGFF-----SS

SSRAPPPSLPSPSRLPGPSDTPILPQKGIVEQCCTSICSLYQLENYCN;
and (SEQ ID NO: 85)
DP32: GEEEEEKGPEHLCGSHLVEALYLVCGERGFF-----SS

SSRAPPPSLPSPSRLPGPSDTPILPQKGIVEQCCTSICSLYQLENYCN.
```

The activity of these compounds was tested at the insulin subtype A and B receptors as well as the IGF-1 receptors and are compared to the activity of single chain analogs using the IGF-1 C peptide as the linking moiety:

```
DR3:
                                         (SEQ ID NO: 86)
GEEEEEKFVNQHLCGSHLVEALYLVCGERGFFYTDRTGYGSSSRRAPQTG

IVEQCCTSICSLYQLENYCN

DR4
                                         (SEQ ID NO: 87)
GEEEEEKFVNQHLCGSHLVEALYLVCGERGFFYTDRTGAGSSSRRAPQTG

IVEQCCTSICSLYQLENYCN
```

Results are provided in Tables 17A and 17B. As the data shows DP30 and DP31 are very potent insulin agonists approaching the potency of native insulin, yet having a higher selectivity for both insulin receptors over the IGF-1 receptor relative to DR3 and DR4 (Table 17A). Furthermore comparison of DP30 and DP31 to DP25 reveals that DP25 is not as potent as DP30 and DP31, indicating the last 5 amino acids of the insulin B chain are not desirable in single chain insulin agonists (see Table 17B). when the single analog DP31 was cleaved between the CTP peptide and the A chain (DP31 LysC), the potency of the resulting two chain analog is increased slightly at the insulin receptor, but its activity at the IGF-1 receptor is substantially increased. Consistent with these results DR3 and DR4 were found to have more activity in stimulating cell growth of HMEC cells than DP30 and DP 31. DP30 and DP 31 were found to have similar activity as native insulin in stimulating cell growth of HMEC cells.

TABLE 17A

Insulin Analogs DR 3, 4, 30 & 31 Bioactivity in vitro phosphorylation ($EC_{50}$ nM)

| | Insulin | STD | N | DR3 | STD | N | DR4 | STD | N | DP30 | STD | N | DP31 | STD | N |
|---|---|---|---|---|---|---|---|---|---|---|---|---|---|---|---|
| Average $EC_{50}$ at IRA | 0.81 | 0.45 | 6 | 0.55 | 0.19 | 4 | 0.79 | 0.23 | 3 | 1.41 | 0.89 | 3 | 0.83 | 0.41 | 4 |
| Average $EC_{50}$ at IRB | 0.56 | 0.28 | 7 | 0.56 | 0.23 | 5 | 0.68 | 0.31 | 3 | 1.12 | 0.52 | 3 | 0.91 | 0.20 | 4 |
| Average $EC_{50}$ at IGF-1 R | 55.8 | 9.7 | 2 | 2.24 | 0.42 | 3 | 20.3 | 16.35 | 3 | ~DP31 | – | – | 194 | 87 | 3 |

TABLE 17B

Insulin Analogs DR25, 30 & 31 Bioactivity in vitro phosphorylation ($EC_{50}$ nM)

| | Insulin | STD | N | DP25M | STD | N | DP30 | STD | N | DP31 | STD | N | DP31 LysC | STD | N |
|---|---|---|---|---|---|---|---|---|---|---|---|---|---|---|---|
| Average $EC_{50}$ at IRA | 0.81 | 0.45 | 6 | 4.11 | 1.3 | 2 | 1.41 | .089 | 3 | 0.83 | 0.41 | 4 | 0.40 | 0.11 | 2 |
| Average $EC_{50}$ at IRB | 0.56 | 0.28 | 7 | 5.49 | 1.5 | 2 | 1.12 | 0.52 | 3 | 0.91 | 0.20 | 4 | 0.45 | 0.28 | 2 |
| Average $EC_{50}$ at IGF-1 R | 55.8 | 9.7 | 2 | — | — | – | ~DP31 | – | – | 194 | 87 | 3 | 10.06 | – | 1 |

Example 20

Acylated Insulin Analogs

Comparative insulin tolerance tests were conducted on mice comparing the ability of human insulin relative to three different acylated insulin analogs to reduce and sustain low blood glucose concentration. The compounds were tested at two different concentrations (27 nmol/kg and 90 nmol/kg). The acylated insulins included MIU-41 (a two chain insulin analog having a C16 acylation via a gamma glutamic acid linker attached to a lysine residue located at position A14), MIU-36 (a two chain insulin analog having a C16 acylation linked to the N-terminus of the B chain) and MIU-37 (a two chain insulin analog having a C16 acylation via a gamma glutamic acid linker attached to a lysine residue located at position B22). All three acylated insulin analogs provided a more basal and sustained lowered glucose levels relative to native insulin, even after 8 hours (See FIG. 25A-25D).

Figure 26A:
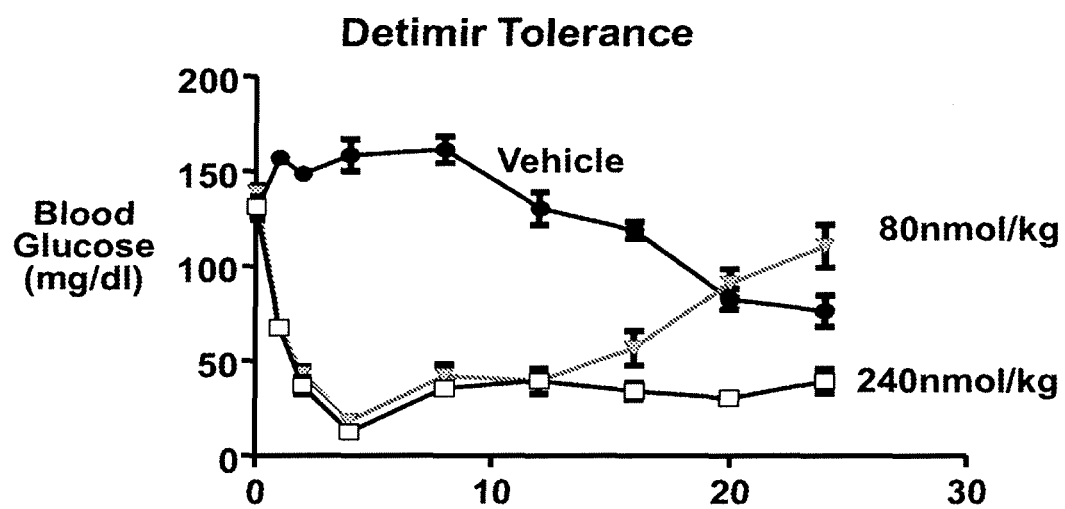
FIGS. 26A-26D show the results of comparative insulin tolerance tests conducted on mice comparing the activity of the commercially available acylated insulin analog (Detemir) relative to the acylated two chain insulin analog MIU-55. MIU-55 [B¹(H5,10,Y16,L17,C16rE-K22)25a:A¹ (N18,N21)] has the C-terminal 5 amino acids of the B chain deleted and terminates as a B chain amide. It is acylated with a C16 fatty acid through a gamma Glu linker at the 8-amino group of Lys B22. The results indicate that MIU-55 is about one third as potent as Detemir (see FIGS. 26A and 26B). The data also indicate that the acylated forms of insulin are longer acting than the non-acylated forms and that MIU-55 while less potent than Detemir, exhibits a similar profile as Detemir.
Figure 26B:
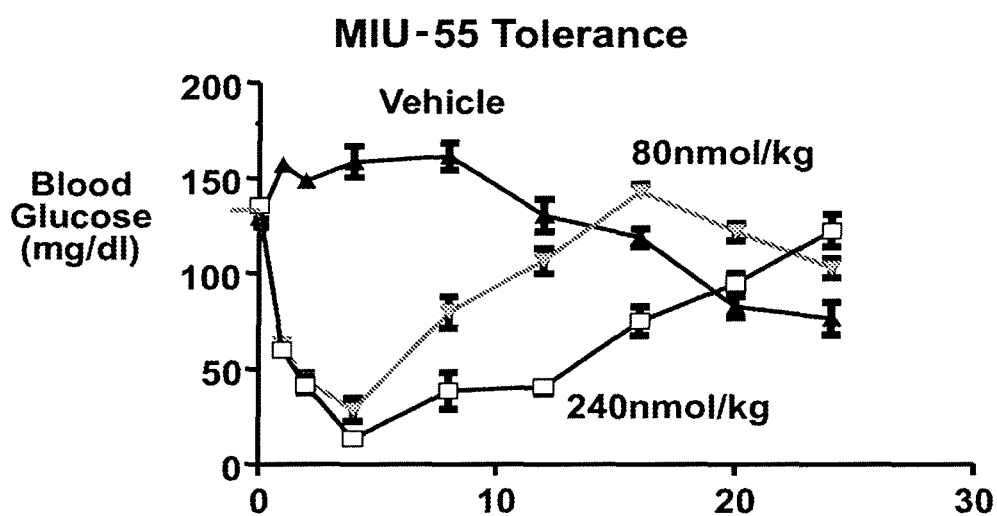
Figure 26C:
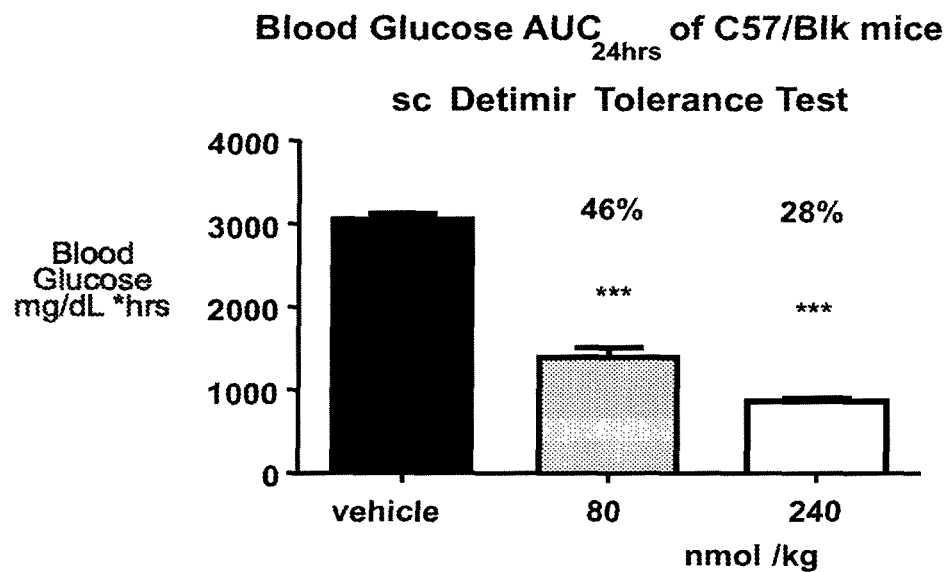
Figure 26D:
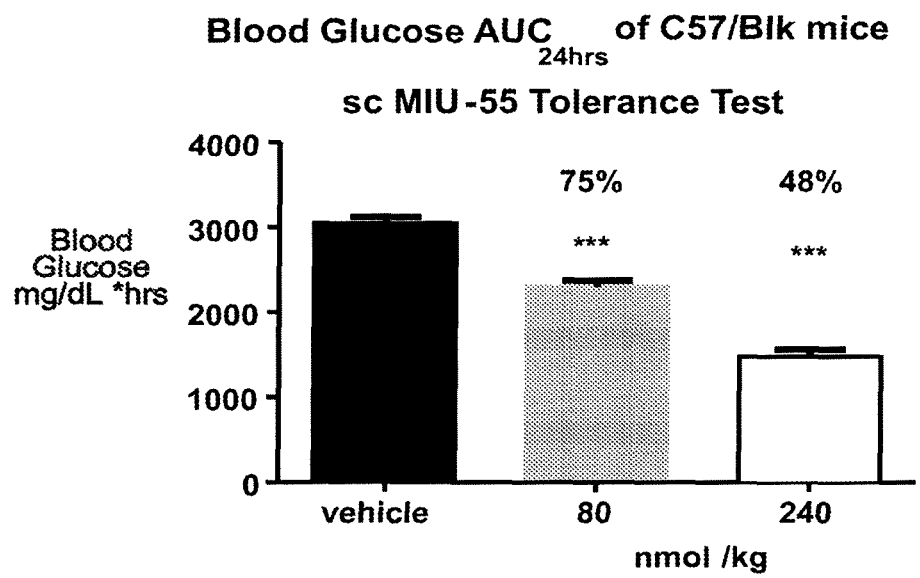
Figure 27A:
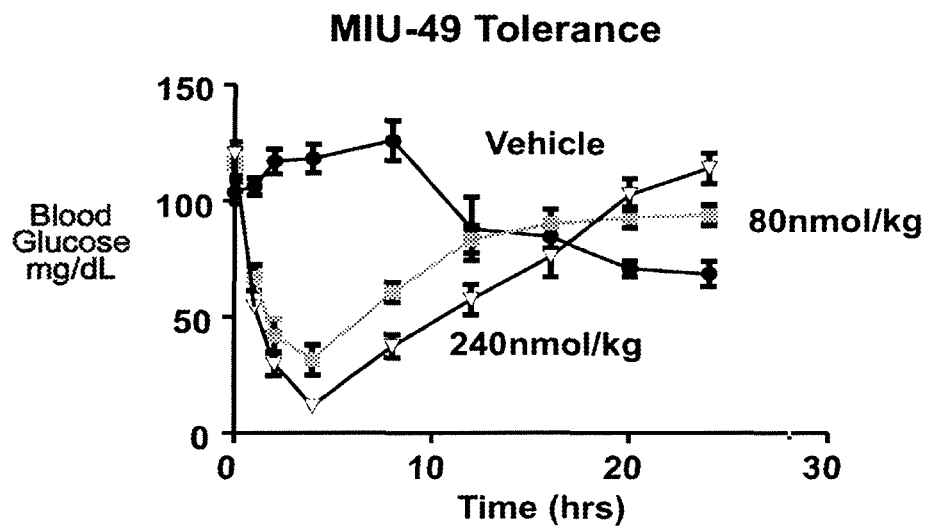
FIGS. 27A-27D show the results of comparative insulin tolerance tests conducted on mice comparing the activity of the commercially available acylated insulin analog (Detemir) relative to the acylated two chain insulin analog MIU-49. MIU-49 [B¹(C16-rE,H5,Aib9,H10,E13-K17,Y16) 25a:A¹(N18,N21)] is a two chain insulin agonist having the C-terminal 5 amino acids of the B chain deleted and acylated with a C16 fatty acid through a gamma Glu linker at the α-amino group of Gly B2). The results indicate that MIU-49 is about one third as potent as Detemir (see FIGS. 27A and 27B). The data also indicate that the acylated forms of insulin are longer acting than the non-acylated forms and that MIU-49 while less potent than Detemir, exhibits a similar profile as Detemir.
Figure 27C:
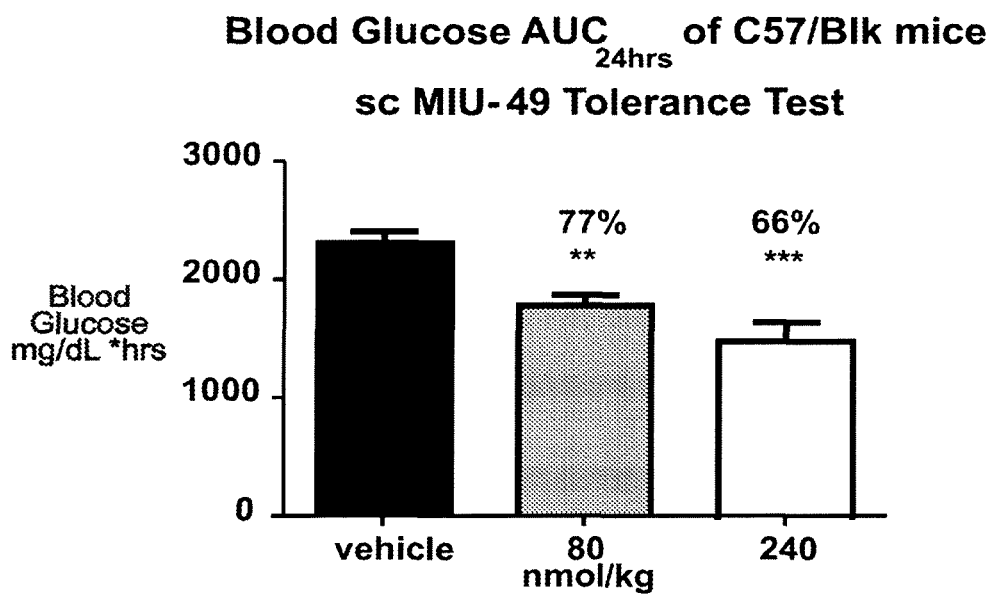
Figure 27B:
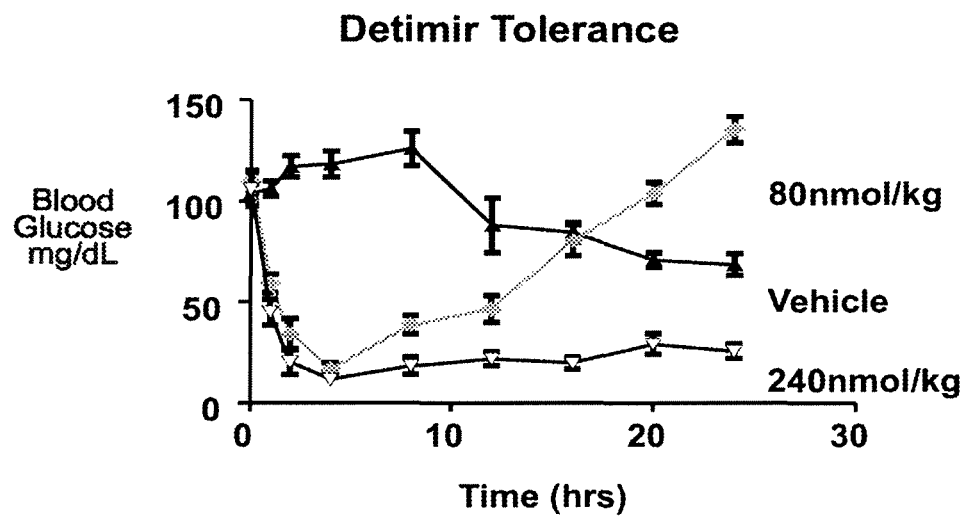
Figure 27D:
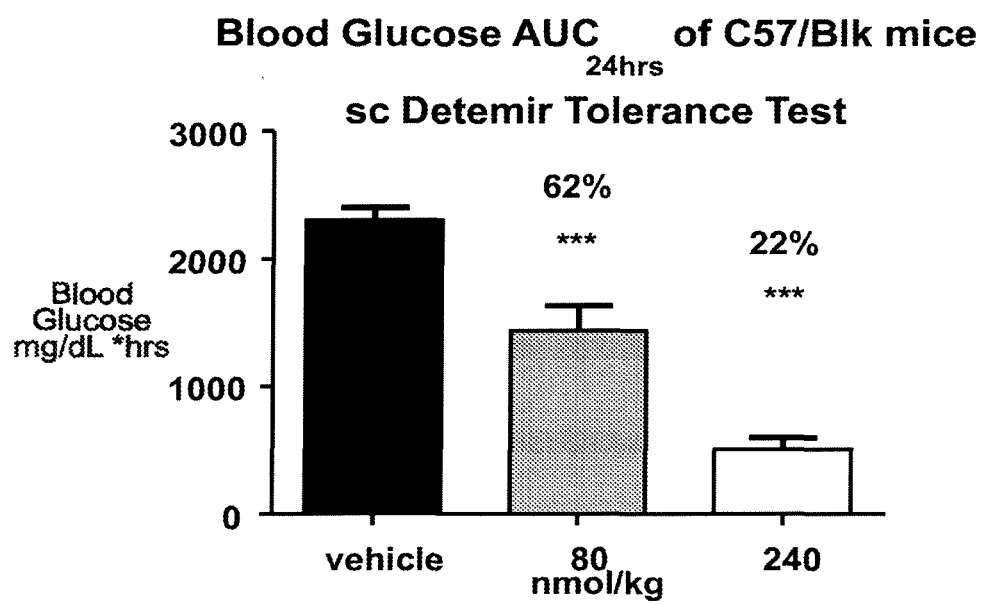
Figure 32A:
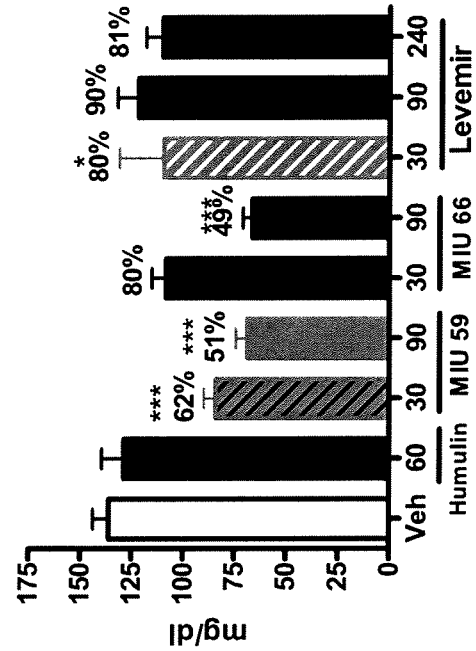
FIGS. 32A & 32B Diabetic mice (db/db mice) were administered pegylated insulin analogs to compare their relative activity in relation to commercially available insulin analogs. The x-axis indicates the concentration of the administered compound (i.e., vehicle control, 30 or 90 nmol/kg or 60 nmol/kg for Humulin and 30, 90 and 240 for Levemir). In particular, insulin analogs Levemir and Humulin were compared to the pegylated insulin analogs MIU-59 (native insulin analog having a single 20 kDa PEG linked to its N-terminus) and MIU-66 (native insulin analog having a single 20 kDa PEG linked to its N-terminus and the amino terminus of the A and B chain carbamylated. Both MIU-59 and MIU-66 have improved activity relative to Levemir and Humulin (see FIGS. 32A at 12 hrs and 32B at 24 hours).
Figure 32B:
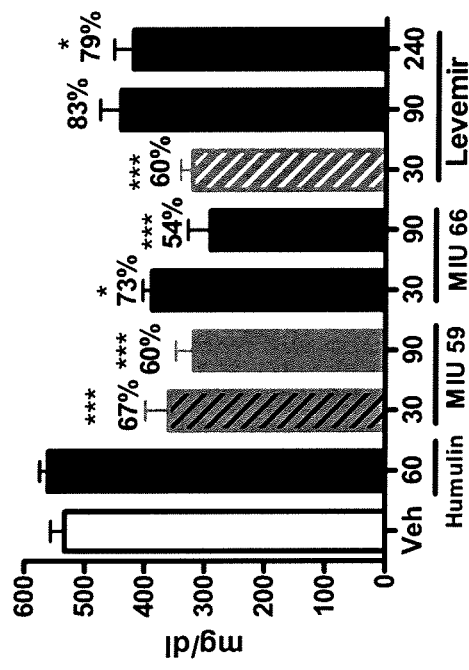

FIGS. 26A-26D show the results of comparative insulin tolerance tests conducted on mice comparing the ability of the commercially available acylated insulin analog (Detimer) to the acylated two chain insulin agonist MIU-55. MIU-55 [B1(H5,10,Y16,L17,C16rE-K22)25a:A1(N18, N21)] has the C-terminal 5 amino acids of the B chain deleted and is acylated with a C14 fatty acid (myristoylic acid) through a gamma Glu linker at the 8-amino group of Lys B29. The results indicate that MIU-55 is about one third as potent as Detimer (See FIGS. 26A and 26B). The data indicate that the acylated forms of insulin are longer acting than the non-acylated forms and that MIU-55 while less potent than Detimir, exhibits a similar profile as Detimir. FIGS. 26C and 26D provide data on blood glucose AUC values after administration of the listed analogs. A comparison of Detimir and MIU-49 in insulin tolerance tests revealed similar results (see FIGS. 27A-27D). MIU-49 [B1(C16-rEO,H5,Aib9,H10,E13-K17,Y16)25a:A1(N18,N21)] is a two chain insulin agonist having the C-terminal 5 amino acids of the B chain deleted and acylated with a C16 fatty acid at the through a gamma Glu linker at the α-amino group of Gly B2. Again, the data shows that MIU-49 is about one third as potent as Detimer (See FIGS. 27A and 32B that MIU-49 while less potent than Detimir, exhibits a similar profile as Detimir.

Example 21

Pegylated Insulin Analogs

Various pegylated insulin analogs were prepared and tested in vitro. Table 18 shows the percent activity of each analog relative to native insulin.

TABLE 18

Pegylated IGF-1 and Insulin Analogs

| | | | % Insulin Activity | | |
|---|---|---|---|---|---|
| MIU # | Name | | IR-B | IR-A | IGF-1 R |
| MIU-35 | $B^1$(H5, H10, Y16, L17)25-$C^1$-$A^1$ (H8, N18, N21) | | 17.4 | 61.4 | 3.2 |
| MIU-56 | C8-PEG20K | | | 14.8 | |
| MIU-57 | $B^1$(H5, Y16, L17)25-PEG8-K-PEG4-$A^1$(N18, N21) B1-PEG20K | MIU-35 | 1.1 | 3.1 | 1.2 |
| MIU-58 | B1-PEG20K-B1- Dimer | MIU-35 | 5.8 | 19.7 | 2.6 |
| MIU-59 | B1-PEG20K | insulin | 11.7 | 17.3 | 0.3 |
| MIU-60 | B29-PEG20K, B1, A1-$NH_2$CO | insulin | 2.7 | 2.4 | <<0.3 |
| MIU-61 | B1, B29, A1-tri-PEG5K | insulin | <0.1 | 0.2 | <<<0.3 |

TABLE 18-continued

Pegylated IGF-1 and Insulin Analogs

| | | | % Insulin Activity | | |
|---|---|---|---|---|---|
| MIU # | Name | | IR-B | IR-A | IGF-1 R |
| MIU-66 | B1-PEG20K, A1-NH$_2$CO | insulin | 2.9 | 3.0 | <0.3 |
| MIU-67 | B0, C8-PEG10K di-PEGylated | MIU-35 | 0.1 | 0.2 | <0.1 |
| MIU-68 | B0, B22-PEG10K di-PEGylated | MIU-35 | 0.1 | 0.4 | <0.1 |
| MIU-69 | B0, A14-PEG10K di-PEGylated | MIU-35 | 0.5 | 1.0 | <0.1 |

Figure 28A:
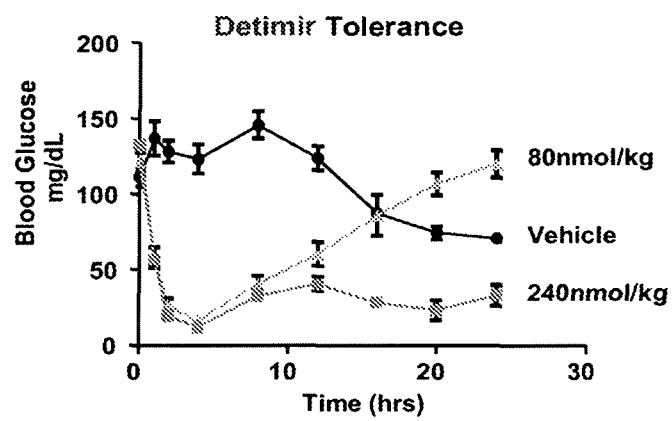
FIGS. 28A-28D represents the results obtained from a comparative insulin tolerance test for Detemir and MIU-56 using C57/Blk mice. MIU-56 is an insulin single chain analog B¹(H5,Y16,L17)25a-PEG8-K-PEG4-A¹(N18,21) comprising a 20 kDa PEG linked to the side chain of the single lysine residue in the linking moiety (PEG8-K-PEG4) that joins the A chain and the B chain.
Figure 28B:
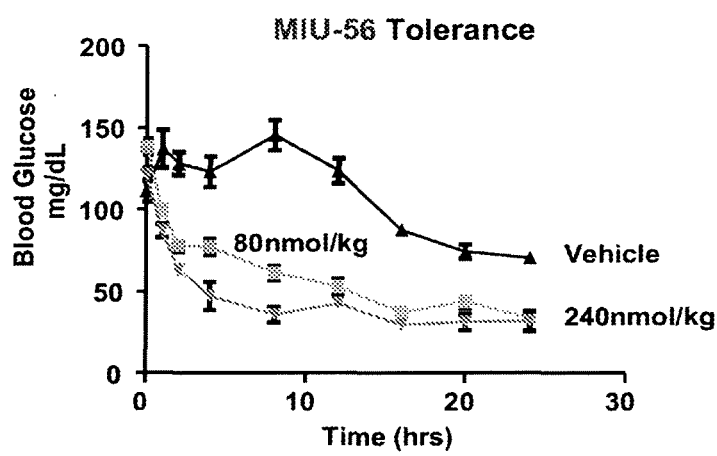
Figure 28C:
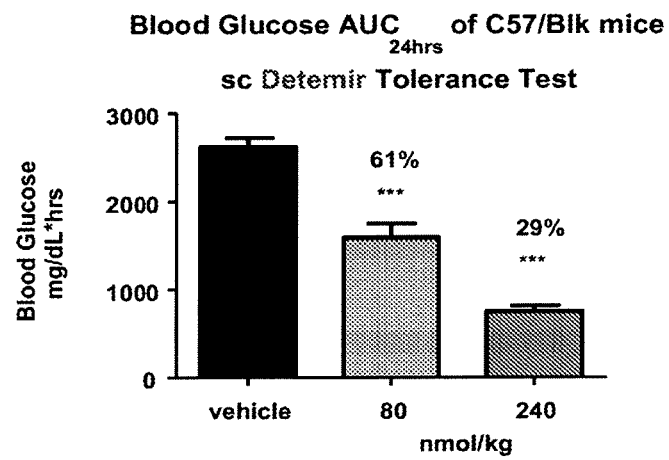
Figure 28D:
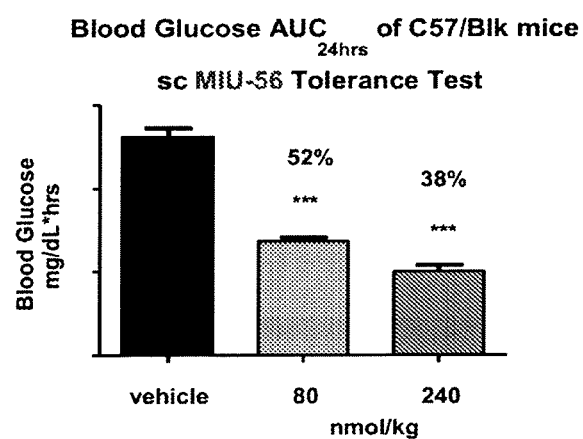
Figure 29A:
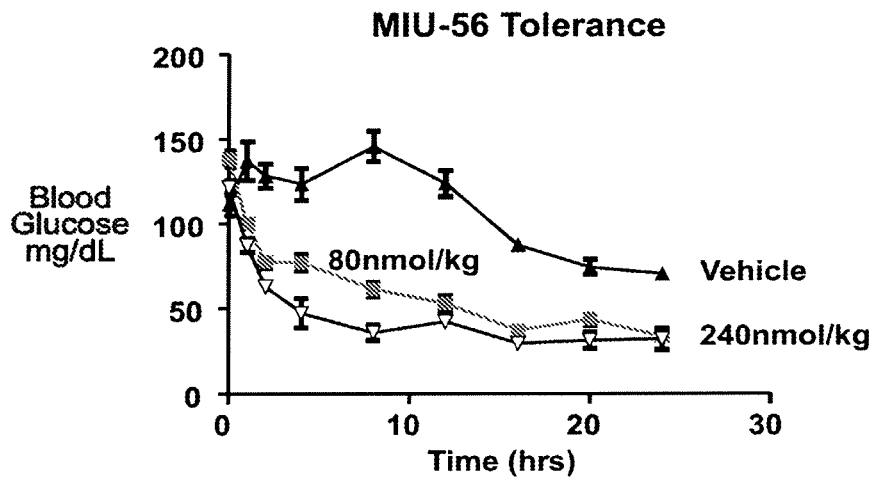
FIGS. 29A-29F represents the results obtained from a comparative insulin tolerance test for MIU-56 and MIU-57 using C57/Blk mice. MIU-57 is an insulin single chain analog (B¹(H5,Y16,L17)25-C¹-A¹(N18,21) comprising a 20 kDa PEG linked to the N-terminus of the B chain.
Figure 29B:
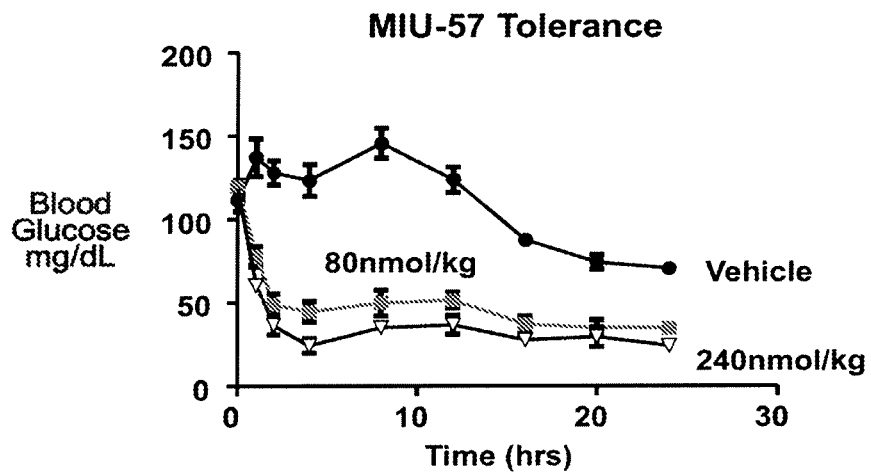
Figure 29C:
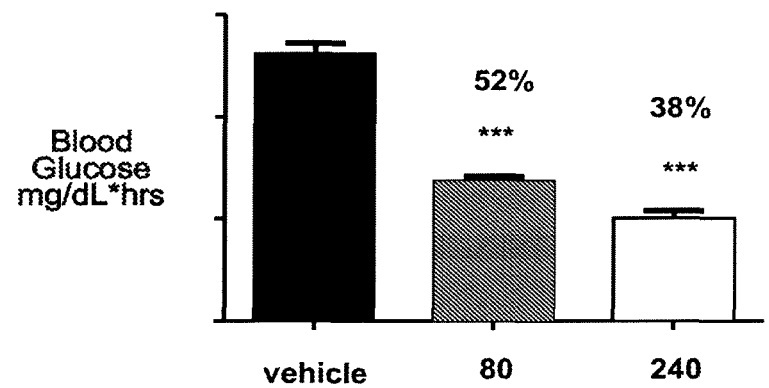
Figure 29D:
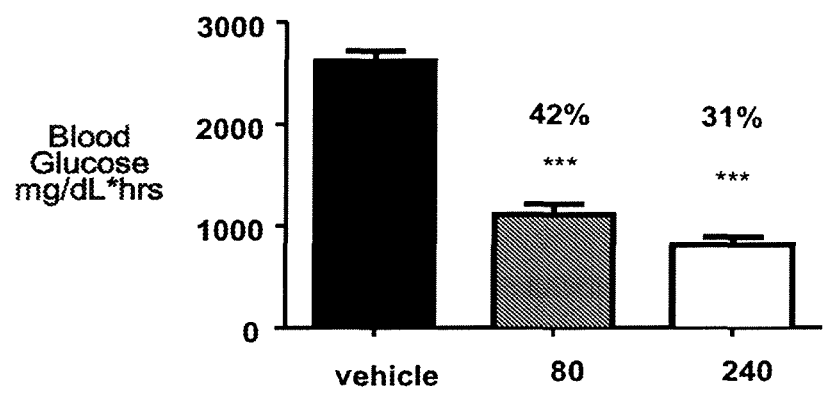
Figure 29E:
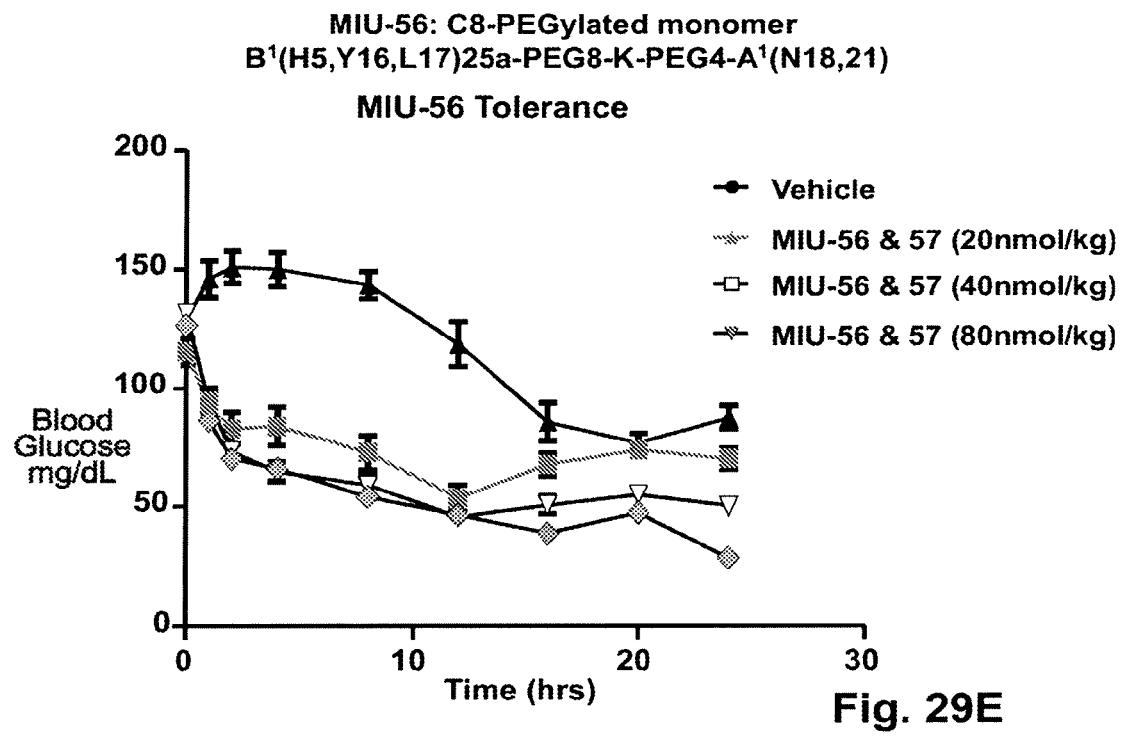
Figure 29F:
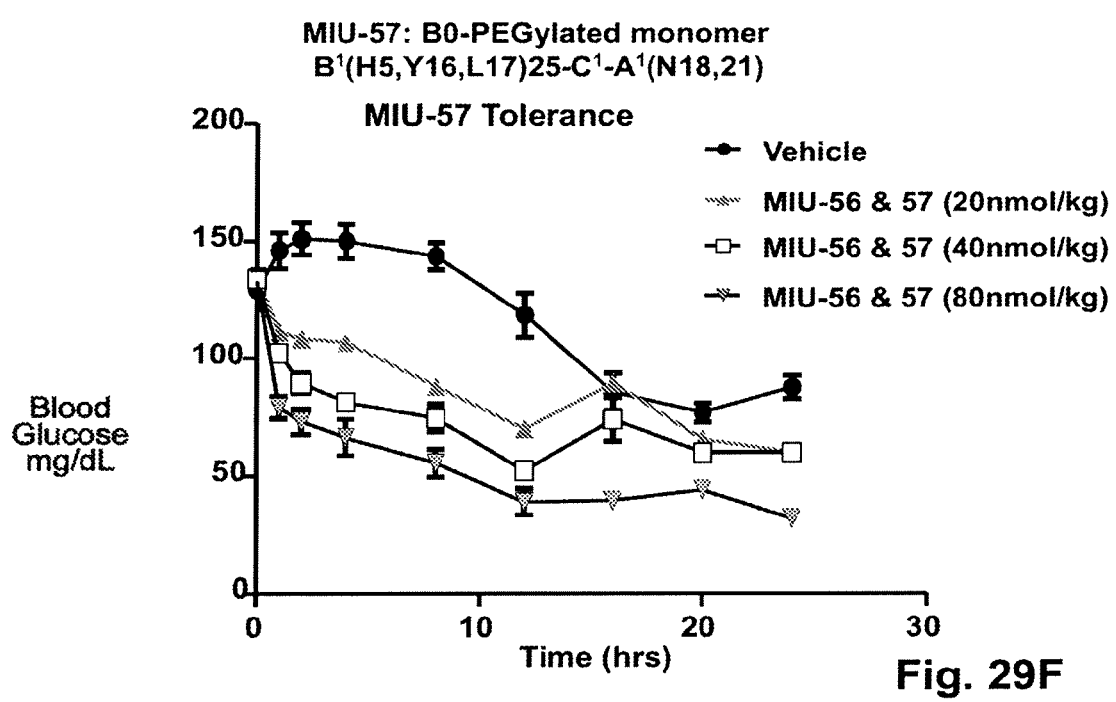

Comparative insulin tolerance tests were conducted on mice comparing the ability of the acylated insulin analog Detimir relative to the pegylated single chain insulin analog MIU-56: B$^1$(H5,Y16,L17)25α-PEG8-K-PEG4-A$^1$(N18,21). This single chain analog comprises a 20 kDa PEG linked to the side chain of the single lysine residue in the linking moiety (PEG8-K-PEG4) that joins the A chain and the B chain. As shown in FIG. 28A-28D, the pegylated analog has a sustained duration of action for 24 hours and its onset is gradual enough to avoid sedation of animals at the dosage required for sustained action through 24 hours. FIGS. 28C and 28D show the blood glucose AUC$_{24\ hrs}$ in mice administered Detimir and MIU-56, respectively. Similar results were obtained for another pegylated single chain insulin analog MIU-57 (see FIGS. 29A-29D). MIU-57 is an insulin single chain analog (B$^1$(H5,Y16,L17)25-C$^1$-A$^1$(N18,21) comprising a 20 kDa PEG linked to the side chain of the N-terminus of the B chain. FIGS. 29A and 29B show the results of a comparative insulin dose titration of single chain insulin analogs pegylated at the linking moiety (MIU-56) or pegylated at the N-terminus of the B chain (MIU-57), respectively. FIGS. 29C and 29D show the blood glucose AUC$_{24\ hrs}$ in mice administered MIU-56 and MIU-57, respectively. The data shows these analogs remain potent and have an improved therapeutic index relative to native insulin. Results from comparative insulin dose titrations of MIU-56 and MIU-57 reveal that a similar profile is obtained in mice for dosages ranging from 20 nmol/kg through 80 nmol/kg (see FIGS. 29E and 29F)

A dimer (MIU 58) was prepared comprising two insulin single chain analogs (B$^1$(H5,Y16,L17)25-C$^1$-A$^1$(N18,21) linked head to head via a 20 kDa PEG chain. FIGS. 29G-29J represents the results obtained from a comparative insulin tolerance test for MIU-57 and MIU-58 using C57/Blk mice. FIGS. 29G and 29H are graphs showing the results of insulin tolerance tests comparing MIU-57 and MIU-58. FIGS. 29I and 29J show the blood glucose AUC$_{24\ hrs}$ in mice administered MIU-57 and MIU-58, respectively. The dimer is less potent than the parent compound, but is still active.

FIGS. 30A and 30B provide data from a comparative insulin dose titration of two pegylated native insulin heterodimers. The analogs comprise two native insulin A and B chain sequences linked via the native disulfide linkages, and modified to have either a 20 kDa PEG linked at the N-terminus of the B chain or at position B29 (with the amino terminus of the A and B chain carbamylated). The data shows that while these compounds differ slightly in their in vitro activities (See Table 18), they behave similarly in vivo in mice. Both compounds remain potent and have an improved therapeutic index relative to non-pegylated native insulin (slow onset, sustained activity for 24 hours and relative flatness of the response).

Insulin analogs were also constructed having two or more covalently linked polyethylene glycol chains and compared to a native insulin analog having a single 20 kDa PEG linked to its N-terminus. More particularly, the activities of a single chain insulin analog (B$^1$(H5,Y16,L17)25-C$^1$(K8)-A$^1$(N18, 21)) having two PEG chains (10K each) linked at the N-terminus and at amino acid 8 of the linking moiety (C8), a single chain insulin analog (B$^1$(H5,Y16,L17, K22)25-C$^1$ (K8)-A$^1$(N18,21)) having two PEG chains (10K each) linked at the N-terminus and at amino acid B22, and a single chain insulin analog (B$^1$(H5,Y16,L17)25-C$^1$(K8)-A$^1$(K14, N18,21)) having two PEG chains (10K each) linked at the N-terminus and at amino acid A14 were compared. FIGS. 31A-31D provide data from a comparative insulin dose titration of the three pegylated insulin analogs relative to the single pegylated native insulin derivative. The activity in vitro is dramatically reduced by at least 10×. However, while the in vivo data shows that some potency is lost, the double pegylated insulin analogs are still effective (particularly for the analog pegylated at the linking moiety). Accordingly, insulin analogs can be prepared having two PEG chains of 10 kDa in length that will provide an improved therapeutic index relative to non-pegylated insulin analogs. In addition pegylation at the linking moiety of single chain analogs appears to be a preferred site of pegylation.

Diabetic mice (db/db mice) were administered pegylated insulin analogs to compare their efficacy to commercially available insulin analogs. In particular, insulin analogs Levemir and Humulin were compared to the pegylated insulin analogs MIU-59 (native insulin analog having a single 20 kDa PEG linked to its N-terminus) and MIU-66 (native insulin analog having a single 20 kDa PEG linked to its N-terminus and the amino terminus of the A and B chain carbamylated). Both MIU-59 and MIU-66 have improved activity relative to Levemir and Humulin (see FIGS. 32A and 32B).

Example 22

Comparative Insulin Tolerance for Insulin Prodrug Analogs

Figure 33:
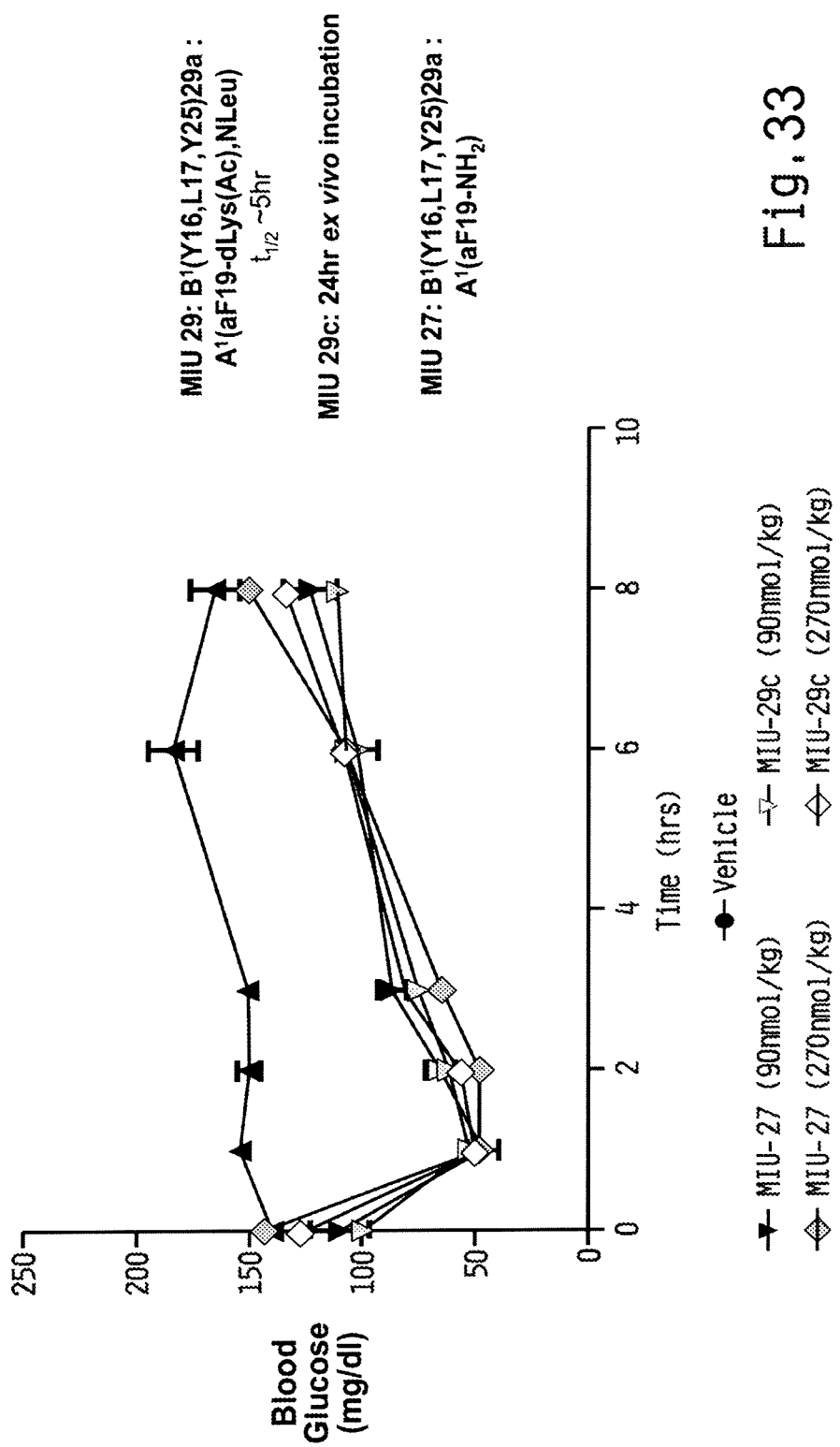
FIG. 33 is a graph showing the results of a comparative insulin tolerance test conducted in normal mice for a prodrug two chain insulin analog acylated at the dipeptide prodrug element (MIU-29: [$B^1$(Y16,L17,Y25)29a:$A^1$(aF19-dLys(Ac),NLeu)] relative to it parent insulin analog (MIU-27: [$B^1$(Y16,L17,Y25)29a:$A^1$(aF19-)]. The prodrug derivative MIU-29 comprises a 4-amino-phenylalanine substitution at position A19 wherein a dipeptide dLys(Ac), NLeu has been covalently linked at the 4-amino position of the A19 residue and the side chain of the lysine of the dipeptide element has been acylated with a C14 fatty acid. This dipeptide will autocleave under physiological conditions with a half life of approximately 5 hours. After incubating MIU-29 for 24 hours ex vivo, the resultant compound (designated "MIU-29c") was administered to mice and its ability to lower blood glucose was compared to parent compound.

Normal mice were administered either an insulin heterodimer analog [B$^1$(Y16,L17,Y25)29a:A$^1$(aF19-NH2)], or a prodrug derivative thereof. The prodrug derivative [B$^1$ (Y16,L17,Y25)29a:A$^1$(aF19-dLys(Ac),NLeu)] comprises a 4-amino-phenylalnine substitution at position A19 wherein a dipeptide dLys(Ac),NLeu have been covalently linked at the 4-amino position of the A19 residue. This dipeptide will autocleave under physiological conditions with a half life of approximately 5 hours. After incubating the prodrug derivative [B$^1$(Y16,L17,Y25)29a:A$^1$(aF19-dLys(Ac),NLeu)] for 24 hours ex vivo, the resultant compound was administered to mice and it ability to lower blood glucose was compared to parent compound. As shown in FIG. 33 the two compounds performed almost identically.

Acylation of the insulin prodrug analogs was investigated to determine if retention times in vivo could be enhanced. The in vitro activity of MIU 42 [B$^1$(Y16,L17,Y25)29a:A$^1$ (dLys(rE-C14),Sar-aF19)], having an acylated dipeptide prodrug element, increases with time incubated ex vivo in 30% ACN/PBS @ pH7.4 37° C. (providing time for prodrug conversion) relative to the non-acylated prodrug. Comparative insulin potency tests conducted using the MIU 42 prodrug (FIG. 34B) administered without a pre-incubation step show that the prodrug is not very potent relative to the non-prodrug parent compound (MIU-27; FIG. 34A). Accordingly, at least in mice the acylation does not produce the desired profile. This was also found to be true for an acylated insulin analog MIU-46 [B$^1$(H5,10 Y16,L17,Y25, K29-C14)28a:A$^1$(N18,21, aF19NH2)] having acylation at the B29 position. The compound did not exhibit sufficient in vivo potency or a basal profile when tested in vivo in mice (data not shown).

Example 23

Comparison of Receptor Binding of CTP Containing Vs. C-Protein Single Chain Insulin Analogs The phosphorylation activity of four single chain insulin analogs (DR3, DR4, DP30 and DP31) at the insulin subtype A and subtype B receptors was measured using receptor transfected HEK293 cells as described in Example 4. DR5 and DR4 represent single chain insulin analogs having the IGF-1 C-peptide as the linking moiety joining the B and A chains. DP30 and DP31 represent single chain insulin analogs having the IGF-1 C-peptide as the linking moiety joining a C-terminal truncated B chain (having the last five carboxy amino acids removed and an A chains. The complete sequence of these constructs is provided:

DR3:
(SEQ ID NO: 96)
GEEEEEKFVNQHLCGSHLVEALYLVCGERGFFYTDRTGYGSSSRRAPQTG

IVEQCCTSICSLYQLENYCN

DR4
(SEQ ID NO: 97)
GEEEEEKFVNQHLCGSHLVEALYLVCGERGFFYTDRTGAGSSSRRAPQTG

IVEQCCTSICSLYQLENYCN

DP30
(SEQ ID NO: 98)
GEEEEEKFVNQHLCGSHLVEALYLVCGERGFFSSSSRAPPPSLPSPSRLP

GPSDTPILPQRGIVEQCCTSICSLYQLENYCN

DP31
(SEQ ID NO: 99)
GEEEEEKFVNQHLCGSHLVEALYLVCGERGFFSSSSRAPPPSLPSPSRLP

GPSDTPILPQKGIVEQCCTSICSLYQLENYCN

DR3 and DR4 differ from each other in the substitution of the native tyrosine in the IGF1 C peptide with alanine in DR4. DP30 and DP31 differ form each other in the substitution of the terminal arginine of the CTP peptide with a lysine, allowing the cleavage of the single chain insulin into a two chain insulin. DR3 and DR4 are high potency analogs that have approximately equivalent activity at the A and B subtype insulin receptors (See Table 19). DR4 is approximately 10 fold less active at the IGF1 receptor due to the substitution YC2A. DP30 and DP31 are also high potency analogs that have approximately equivalent activity at the A and B subtype insulin receptors (See Table 19) with low potency at the IGF1 activity (note that while a value was not determined for the activity of DP30 at IGF1, the activity was similar to that of DP31).

The phosphorylation activity of two additional single chain insulin analogs (DP25M and DP31LysC) relative to DP30 and DP31 at the insulin subtype A and subtype B receptors was measured using receptor transfected HEK293 cells. DP31LysC represents the DP31 construct that has been cleaved at the lysine linking the CTP peptide to the N-terminus of the A chain, thus generating a two chain insulin analog with the CTP peptide remaining bound to the carboxy terminus of the B chain. After cleavage, the insulin activity increases slightly (approximately 2×), but the IGF activity increases almost 20 fold.

DP25M is a single chain insulin analog comprising a CTP peptide as the linking moiety that is similar in structure to DP30 with the exception that a full length B chain is used in the construct. Specifically, DP25M comprises the sequence: GEEEEEKFVNQHLCGSHLVEALYLVCGERGFF YTDRTSSSSRAPPPSLPSPSRL PGPSDTPILPQR-GIVEQCCTSICSLYQLENYCN (SEQ ID NO: 100). This compound has lower activity at the insulin receptors.

The data presented in Tables 19 and 20 represents an assembly of several data points where insulin & the analogs were tested over time, not always side-by-side. Consequently, the averaging may be diminishing the ability to distinguish subtle differences in activity between each analog, but the data is reflective of the overall activities of each individual compound at the respective insulin and IGF receptors and the general relative activities of the compounds tested.

TABLE 19

|  | Insulin | STD | N | DR3 | STD | N | DR4 | STD | N | DP30 | STD | N | DP31 | STD | N |
|---|---|---|---|---|---|---|---|---|---|---|---|---|---|---|---|
| Average EC50 at IRA | 0.81 | 0.45 | 6 | 0.55 | 0.19 | 4 | 0.79 | 0.23 | 3 | 1.41 | 0.89 | 3 | 0.83 | 0.41 | 4 |
| Average EC50 at IRB | 0.56 | 0.28 | 7 | 0.56 | 0.23 | 5 | 0.68 | 0.31 | 3 | 1.12 | 0.52 | 3 | 0.91 | 0.20 | 4 |
| Average EC50 at IGF-1 R | 55.8 | 9.7 | 2 | 2.24 | 0.42 | 3 | 20.3 | 16.35 | 3 | ~DP31 | — | — | 194 | 87 | 3 |

TABLE 20

| | Insulin | STD | N | DP25M | STD | N | DP30 | STD | N | DP31 | STD | N | DP31 LysC | STD | N |
|---|---|---|---|---|---|---|---|---|---|---|---|---|---|---|---|
| Average EC50 at IRA | 0.81 | 0.45 | 6 | 4.11 | 1.3 | 2 | 1.41 | 0.89 | 3 | 0.83 | 0.41 | 4 | 0.40 | 0.11 | 2 |
| Average EC50 at IRB | 0.56 | 0.28 | 7 | 5.49 | 1.5 | 2 | 1.12 | 0.52 | 3 | 0.91 | 0.20 | 4 | 0.45 | 0.28 | 2 |
| Average EC50 at IGF-1 R | 55.8 | 9.7 | 2 | — | — | — | ~DP31 | — | — | 194 | 87 | 3 | 10.06 | — | 1 |

Human Mammary Epithelial Cells Proliferation:

To measure mitogenic potential of insulin analogs, human mammary epithelial cells (HMEC #CC-2551, Cambrex East Rutherford, N.J.) were cultured in complete MEGM (#CC-3051, Cambrex, East Rutherford, N.J.) to 90% confluence. The cells were trypsinized by using TrypLE Express (Invitrogen Grand Island, N.Y.), washed with Dubecco's Modified Eagle Medium (HyClone, Logan, Utah), reconstituted in insulin-deficient MEGM Bullet Kit (#CC-3150, Cambrex East Rutherford, N.J.) and seeded at 40% confluence in Cytostar-T scintillating microplates (#RPNQ0162, Perkin-Elmer, Waltham, Mass.). Serial five-fold dilutions of test analogs, recombinant human insulin, (Eli Lilly & Co Indianapolis, Ind.) and synthetic human insulin-like growth factor I (IGF-1) were prepared from sterile stocks in the insulin-deficient MEGM and transferred to Cytostar-T plate with HMEC. The plate was incubated 4 h at 37° C., 5% $CO_2$ and 90% humidity. The cells were pulsed with 0.1 mCi/well [$^{14}$C]-thymidine (#NEC568050UC, Perkin-Elmer, Waltham, Mass.) and incubated at 37° C. in humidified atmosphere with 5% $CO_2$ for 48 h.

At the end of incubation the signal from each well of the plate was read for 1 min on MicroBeta 1640 scintillation counter (Perkin-Elmer, Waltham, Mass.) and the incubation continued for another 72 h with plate readings at 24 h intervals. The results were plotted as counts per minute (CPM) versus concentration of peptide and $EC_{50}$ values were determined by using Origin software (OriginLab, Northampton, Mass.).

The data presented in Table 21 represents the average measured potency at 24, 48, 72 and 96 hours after contact of the cells with the specific analog. As expected IGF-1 is much more potent than insulin in stimulating proliferation (approximately a 30 fold difference). Lantus, a long-acting basal insulin analogue marketed by Sanofi-Aventis, is a more potent mitogen than native insulin similar in potency to IGF-1. DP3 and DP4 are also potent mitogens, much more potent than native insulin. This is likely due the presence of the IGF-1 C peptide being used as the linking moiety joining the A and B chains. Note substitution of the C2 tyrosine to alanine reduces the mitogenic activity of DP4 relative to DP3. However, DP4 remains 10 fold more potent than native insulin.

The proliferative activity of DP30, DP31 and DP25M is closer to that of native insulin and moreover these analogs exhibit even less proliferative activity than native insulin. Note cleavage of the single chain insulin analog DP31 produces a two chain analog exhibiting a proliferative activity high than IGF-1.

TABLE 21

| Peptide | $EC_{50}$ (nM) |
|---|---|
| IGF-1 | 0.22 |
| Insulin | 6.16 |
| Lantus | 0.37 |
| DR3 | 0.11 |

TABLE 21-continued

| Peptide | $EC_{50}$ (nM) |
|---|---|
| DR4 | 0.70 |
| DP25M | 31.4 |
| DP30 | 12.1 |
| DP31 | 10.9 |
| DP31 LysC | 0.07 |

Example 24

Comparison of Shortened CTP Peptides as Linking Moieties in Single Chain Insulin Analogs To investigate the structure activity relationship of the CTP peptide regarding activity at the insulin and IGF-1 receptors, single chain insulin analogs were prepared using fragments of the CTP peptide. Three constructs were prepared as follows:

DP47:
(SEQ ID NO: 101)
FVNQHLCGSHLVEALYLVCGERGFFSSSSRAPPPSLPGIVEQCCTSICSL

YQLENYCN

DP48:
(SEQ ID NO: 102)
FVNQHLCGSHLVEALYLVCGERGFFSSSSRAPILPQKGIVEQCCTSICSLY

QLENYCN

DP49:
(SEQ ID NO: 103)
FVNQHLCGSHLVEALYLVCGERGFFSSSSRAPPPSLPILPQKGIVEQCCTS

ICSLYQLENYCN

DP47 represents a native insulin A and B chain wherein the 5 C-terminal amino acids have been deleted and the B chain is linked to the A chain by a 12 amino acid linker representing the first 12 amino acids of CTP (DesV, CTP first 12AA). Twelve amino acids were selected because this is the size of the IGF-1 C peptide. DP48 represents a native insulin A and B chain wherein the 5 C-terminal amino acids have been deleted and the B chain is linked to the A chain by a 17 amino acid linker representing the first 12 amino acids of CTP and the last 5 amino acids of CTP. DP49 represents a native insulin A and B chain wherein the 5 C-terminal amino acids have been deleted and the B chain is linked to the A chain by a 12 amino acid linker representing the first 6 amino acids of CTP and the last 6 amino acids of CTP (DesV, CTP First 6AA and Last 6AA) (DesV, CTP first 12AA+last 5AA). The activity of these three compounds, as measure using receptor transfected HEK293 cells as described in Example 4, is shown in Table 22

In this assay native insulin shows equal potency at both the A and B receptors. However, for DP31 the is a selectivity for the insulin subtype B receptor which is the preferred receptor for activation. Furthermore, DP31 is even less potent at the IGF-1 receptor than native insulin. Selectivity for the insulin receptors relative to the IFG-1 receptor appears to decrease as the CTP peptide is reduced in size (see DP49>DP48>DP47)

TABLE 22

| Peptide | $EC_{50}$ | | |
|---|---|---|---|
| | InRec-A | InRec-B | IGF-1 |
| IGF-1 | 10.03 | 16.61 | 0.76 |
| Insulin | 0.50 | 0.50 | 86.7 |

TABLE 22-continued

| Peptide | $EC_{50}$ | | |
|---|---|---|---|
| | InRec-A | InRec-B | IGF-1 |
| DP47 ($CTP^{1-12}$) | 0.69 | 0.83 | 29.7 |
| DR48 ($CTP^{1-6; 23-28}$, K) | 0.29 | 0.47 | 27.1 |
| DP49 ($CTP^{1-12; 24-28}$, K) | 0.72 | 0.37 | 82.6 |
| DP31 ($CTP^{1-28}$, K) | 0.57 | 0.19 | 132.9 |

The invention claimed is:

1. A single chain insulin analog comprising an insulin A chain, an insulin B chain and a linking moiety, wherein said linking moiety covalently links the carboxy terminus of the insulin B chain to the amino terminus of the insulin A chain to form a contiguous amino acid chain, said linking moiety comprising a CTP peptide wherein said CTP peptide is selected from the group consisting of the sequence SSSSKAPPPSLPSPSRLPGPSDTPILPQR (SEQ ID NO: 64),
SSSSX$_{50}$APPPSLPSPSRLPGPSDTPILPQX$_{51}$ (SEQ ID NO: 66), or
SSSSRAPPPSLPSPSRLPGPSDTPILPQK (SEQ ID NO: 79), wherein X$_{50}$ and X$_{51}$ are independently selected from arginine and lysine;

with the proviso that the linking moiety does not comprise an 18 amino acid sequence that is identical to an 18 amino acid sequence of SEQ ID NO: 53 directly linked to the carboxy terminus of the insulin B chain, said single chain analog having activity at the insulin receptor.

2. The single chain insulin analog of claim 1 wherein said insulin B chain comprises the sequence FVNQHLCGSHLVEALYLVCGERGFF (SEQ ID NO: 104), the insulin A chain comprises the sequence GIVEQCCTSICSLYQLENYCN (SEQ ID NO: 1), and the linking moiety comprises the sequence (SSSSX$_{50}$APPPSLPSPSRLPGPSDTPILPQX$_{51}$)$_n$ (SEQ ID NO: 66), wherein X$_{50}$ and X$_{51}$ are independently selected from arginine and lysine; and n is 1 or 2.

3. A derivative of the insulin analog of claim 1 further comprising the structure U-B, wherein U is an amino acid or a hydroxy acid;

B is an N-alkylated amino acid linked to said single chain insulin analog through an amide bond between a carboxyl moiety of B and an amine of the single chain insulin analog, wherein U, B, or the amino acid of the single chain insulin analog to which U-B is linked is a non-coded amino acid, further wherein the chemical cleavage half-life (t$_{1/2}$) of U-B from the single chain insulin analog is at least about 1 hour to about 1 week in PBS under physiological conditions.

4. The derivative of claim 3, wherein U-B comprises the structure of Formula X:

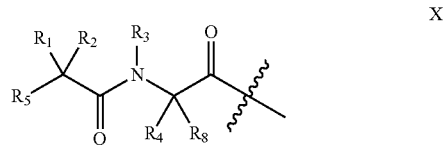

wherein

R$_1$, R$_2$, R$_4$ and R$_8$ are independently selected from the group consisting of H, C$_1$-C$_{18}$ alkyl, C$_2$-C$_{18}$ alkenyl, (C$_1$-C$_{18}$ alkyl)OH, (C$_1$-C$_{18}$ alkyl)SH, (C$_2$-C$_3$ alkyl)SCH$_3$, (C$_1$-C$_4$ alkyl)CONH$_2$, (C$_1$-C$_4$ alkyl)COOH, (C$_1$-C$_4$ alkyl)NH$_2$, (C$_1$-C$_4$ alkyl)NHC(NH$_2$$^+$)NH$_2$, (C$_0$-C$_4$ alkyl)(C$_3$-C$_6$ cycloalkyl), (C$_0$-C$_4$ alkyl)(C$_2$-C$_5$ heterocyclic), (C$_0$-C$_4$ alkyl)(C$_6$-C$_{10}$ aryl)R$_7$, (C$_1$-C$_4$ alkyl)(C$_3$-C$_9$ heteroaryl), and C$_1$-C$_{12}$ alkyl(W$_1$)C$_1$-C$_{12}$ alkyl, wherein W$_1$ is a heteroatom selected from the group consisting of N, S and O, or R$_1$ and R$_2$ together with the atoms to which they are attached form a C$_3$-C$_{12}$ cycloalkyl or aryl; or R$_4$ and R$_8$ together with the atoms to which they are attached form a C$_3$-C$_6$ cycloalkyl;

R$_3$ is selected from the group consisting of C$_1$-C$_{18}$ alkyl, (C$_1$-C$_{18}$ alkyl)OH, (C$_1$-C$_{18}$ alkyl)NH$_2$, (C$_1$-C$_{18}$ alkyl)SH, (C$_0$-C$_4$ alkyl)(C$_3$-C$_6$)cycloalkyl, (C$_0$-C$_4$ alkyl)(C$_2$-C$_5$ heterocyclic), (C$_0$-C$_4$ alkyl)(C$_6$-C$_{10}$ aryl)R$_7$, and (C$_1$-C$_4$ alkyl)(C$_3$-C$_9$ heteroaryl) or R$_4$ and R$_3$ together with the atoms to which they are attached form a 4, 5 or 6 member heterocyclic ring;

$R_5$ is $NHR_6$ or OH;

$R_6$ is H, $C_1$-$C_8$ alkyl or $R_6$ and $R_1$ together with the atoms to which they are attached form a 4, 5 or 6 member heterocyclic ring; and $R_7$ is selected from the group consisting of H, OH, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo.

5. A dimer or multimer comprising a single chain insulin analog of claim 1.

6. A pharmaceutical composition comprising a single chain insulin analog, or prodrug derivative thereof, of claim 1 and a pharmaceutically acceptable carrier.

7. A single chain insulin analog comprising an insulin A chain, an insulin B chain and a linking moiety, wherein said B chain comprises the sequence FVNQHLCGSHLVEALYLVCGERGFF (SEQ ID NO: 104), the A chain comprises the sequence GIVEQCCTSICSLYQLENYCN (SEQ ID NO: 1), and said linking moiety comprises a peptide that covalently links the carboxy terminus of the insulin B chain to the amino terminus of the insulin A chain to form a contiguous amino acid chain, wherein said linking moiety comprises the sequence SSSSRAPPPSLPSPSRLPGPSDTPILPQK (SEQ ID NO: 79);

with the proviso that the linking moiety does not comprise an 18 amino acid sequence that is identical to an 18 amino acid sequence of SEQ ID NO: 53 directly linked to the carboxy terminus of the insulin B chain.

* * * * *

SEQUENCE LISTING

```
<160> NUMBER OF SEQ ID NOS: 104

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 70
<212> TYPE: PRT
<213> ORGANISM: Homo sapiens

<400> SEQUENCE: 3

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70

<210> SEQ ID NO 4
<211> LENGTH: 67
<212> TYPE: PRT
<213> ORGANISM: Homo sapiens

<400> SEQUENCE: 4
```

```
Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
                20                  25                  30

Ser Arg Val Ser Arg Arg Ser Arg Gly Ile Val Glu Glu Cys Cys Phe
                35                  40                  45

Arg Ser Cys Asp Leu Ala Leu Leu Glu Thr Tyr Cys Ala Thr Pro Ala
            50                  55                  60

Lys Ser Glu
65

<210> SEQ ID NO 5
<211> LENGTH: 21
<212> TYPE: PRT
<213> ORGANISM: Homo sapiens

<400> SEQUENCE: 5

Gly Ile Val Asp Glu Cys Cys Phe Arg Ser Cys Asp Leu Arg Arg Leu
1               5                   10                  15

Glu Met Tyr Cys Ala
                20

<210> SEQ ID NO 6
<211> LENGTH: 29
<212> TYPE: PRT
<213> ORGANISM: Homo sapiens

<400> SEQUENCE: 6

Gly Pro Glu Thr Leu Cys Gly Ala Glu Leu Val Asp Ala Leu Tyr Leu
1               5                   10                  15

Val Cys Gly Asp Arg Gly Phe Tyr Phe Asn Lys Pro Thr
                20                  25

<210> SEQ ID NO 7
<211> LENGTH: 21
<212> TYPE: PRT
<213> ORGANISM: Homo sapiens

<400> SEQUENCE: 7

Gly Ile Val Glu Glu Cys Cys Phe Arg Ser Cys Asp Leu Ala Leu Leu
1               5                   10                  15

Glu Thr Tyr Cys Ala
                20

<210> SEQ ID NO 8
<211> LENGTH: 32
<212> TYPE: PRT
<213> ORGANISM: Homo sapiens

<400> SEQUENCE: 8

Ala Tyr Arg Pro Ser Glu Thr Leu Cys Gly Gly Glu Leu Val Asp Thr
1               5                   10                  15

Leu Tyr Leu Val Cys Gly Asp Arg Gly Phe Tyr Phe Ser Arg Pro Ala
                20                  25                  30

<210> SEQ ID NO 9
<211> LENGTH: 4
<212> TYPE: PRT
<213> ORGANISM: Artificial Sequence
<220> FEATURE:
<223> OTHER INFORMATION: spacer sequence
```

```
<400> SEQUENCE: 9

Pro Gly Pro Glu
1

<210> SEQ ID NO 10
<211> LENGTH: 4
<212> TYPE: PRT
<213> ORGANISM: Artificial Sequence
<220> FEATURE:
<223> OTHER INFORMATION: spacer sequence

<400> SEQUENCE: 10

Phe Val Asn Gln
1

<210> SEQ ID NO 11
<211> LENGTH: 6
<212> TYPE: PRT
<213> ORGANISM: Artificial Sequence
<220> FEATURE:
<223> OTHER INFORMATION: spacer sequence

<400> SEQUENCE: 11

Ala Tyr Arg Pro Ser Glu
1               5

<210> SEQ ID NO 12
<211> LENGTH: 5
<212> TYPE: PRT
<213> ORGANISM: Artificial Sequence
<220> FEATURE:
<223> OTHER INFORMATION: spacer sequence

<400> SEQUENCE: 12

Tyr Thr Pro Lys Thr
1               5

<210> SEQ ID NO 13
<211> LENGTH: 12
<212> TYPE: PRT
<213> ORGANISM: Homo sapiens

<400> SEQUENCE: 13

Gly Tyr Gly Ser Ser Ser Arg Arg Ala Pro Gln Thr
1               5                   10

<210> SEQ ID NO 14
<211> LENGTH: 8
<212> TYPE: PRT
<213> ORGANISM: Homo sapiens

<400> SEQUENCE: 14

Gly Tyr Gly Ser Ser Ser Arg Arg
1               5

<210> SEQ ID NO 15
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (4)..(4)
<223> OTHER INFORMATION: Xaa at position 4 is aspartic acid or glutamic
      acid
<220> FEATURE:
```

```
<221> NAME/KEY: MISC_FEATURE
<222> LOCATION: (8)..(8)
<223> OTHER INFORMATION: Xaa at position 8 is histidine, threonine or
      phenylalanine
<220> FEATURE:
<221> NAME/KEY: MISC_FEATURE
<222> LOCATION: (9)..(9)
<223> OTHER INFORMATION: Xaa at position 9 is serine, arginine,
      ornithine, lysine or alanine
<220> FEATURE:
<221> NAME/KEY: MISC_FEATURE
<222> LOCATION: (14)..(14)
<223> OTHER INFORMATION: Xaa at position 14 is tyrosine, arginine,
      ornathine, lysine or alanine
<220> FEATURE:
<221> NAME/KEY: MISC_FEATURE
<222> LOCATION: (15)..(15)
<223> OTHER INFORMATION: Xaa at position 15 is glutamine, glutamic acid,
      arginine, ornithine, alanine, lysine or leucine
<220> FEATURE:
<221> NAME/KEY: MISC_FEATURE
<222> LOCATION: (17)..(17)
<223> OTHER INFORMATION: Xaa at position 17 is glutamine or glutamic
      acid
<220> FEATURE:
<221> NAME/KEY: MISC_FEATURE
<222> LOCATION: (18)..(18)
<223> OTHER INFORMATION: Xaa at position 18 is methionine, asparagine,
      glutamine, glutamic acid, aspartic acid or threonine
<220> FEATURE:
<221> NAME/KEY: MISC_FEATURE
<222> LOCATION: (19)..(19)
<223> OTHER INFORMATION: Xaa at position19 is tyrosine, 4-methoxy
      phenylalanine  or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine, serine,
      valine, threonine, isoleucine, leucine, glutamine, glutamic acid,
      asparagine, aspartic acid, histidine, tryptophan, tyrosine, or
      methionine

<400> SEQUENCE: 15

Gly Ile Val Xaa Glu Cys Cys Xaa Xaa Ser Cys Asp Leu Xaa Xaa Leu
1               5                   10                  15

Xaa Xaa Xaa Cys Xaa
            20

<210> SEQ ID NO 16
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid
<220> FEATURE:
<221> NAME/KEY: MISC_FEATURE
<222> LOCATION: (9)..(9)
<223> OTHER INFORMATION: Xaa at position 9 is aspartic acid, glutamine
      or glutamic acid
<220> FEATURE:
<221> NAME/KEY: MISC_FEATURE
<222> LOCATION: (10)..(10)
<223> OTHER INFORMATION: Xaa at position 10 is alanine or threonine
```

```
<220> FEATURE:
<221> NAME/KEY: MISC_FEATURE
<222> LOCATION: (12)..(12)
<223> OTHER INFORMATION: Xaa at position 12 is tyrosine or 4-amino-
      phenylalanine
<220> FEATURE:
<221> NAME/KEY: MISC_FEATURE
<222> LOCATION: (17)..(17)
<223> OTHER INFORMATION: Xaa at position 12 is glutamic acid, aspartic
      acid or asparagine
<220> FEATURE:
<221> NAME/KEY: MISC_FEATURE
<222> LOCATION: (18)..(18)
<223> OTHER INFORMATION: Xaa at position 18 is alanine, ornithine,
      lysine or arginine
<220> FEATURE:
<221> NAME/KEY: MISC_FEATURE
<222> LOCATION: (21)..(21)
<223> OTHER INFORMATION: Xaa at position 21 is tyrosine, phenylalanine
      or 4-amino-phenylalanine

<400> SEQUENCE: 16

Xaa Leu Cys Gly Xaa Xaa Leu Val Xaa Xaa Leu Xaa Leu Val Cys Gly
1               5                   10                  15

Asp Xaa Gly Phe Xaa
            20

<210> SEQ ID NO 17
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid
<220> FEATURE:
<221> NAME/KEY: MISC_FEATURE
<222> LOCATION: (9)..(9)
<223> OTHER INFORMATION: Xaa at position 9 is aspartic acid, glutamine
      or glutamic acid
<220> FEATURE:
<221> NAME/KEY: MISC_FEATURE
<222> LOCATION: (10)..(10)
<223> OTHER INFORMATION: Xaa at position 10 is alanine or threonine
<220> FEATURE:
<221> NAME/KEY: MISC_FEATURE
<222> LOCATION: (17)..(17)
<223> OTHER INFORMATION: Xaa at position 12 is glutamic acid, aspartic
      acid or asparagine
<220> FEATURE:
<221> NAME/KEY: MISC_FEATURE
<222> LOCATION: (18)..(18)
<223> OTHER INFORMATION: Xaa at position 18 is alanine, ornithine,
      lysine or arginine
<220> FEATURE:
<221> NAME/KEY: MISC_FEATURE
<222> LOCATION: (21)..(21)
<223> OTHER INFORMATION: Xaa at position 21 is tyrosine or 4-amino-
      phenylalanine

<400> SEQUENCE: 17

Xaa Leu Cys Gly Xaa Xaa Leu Val Xaa Xaa Leu Tyr Leu Val Cys Gly
1               5                   10                  15
```

Xaa Xaa Gly Phe Xaa
          20

<210> SEQ ID NO 18
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (4)..(4)
<223> OTHER INFORMATION: Xaa at position 5 is aspartic acid or glutamic
      acid
<220> FEATURE:
<221> NAME/KEY: MISC_FEATURE
<222> LOCATION: (5)..(5)
<223> OTHER INFORMATION: Xaa at position 5 is glutamine or glutamic acid
<220> FEATURE:
<221> NAME/KEY: MISC_FEATURE
<222> LOCATION: (8)..(8)
<223> OTHER INFORMATION: Xaa at position 8 is histidine, threonine or
      phenylalanine
<220> FEATURE:
<221> NAME/KEY: MISC_FEATURE
<222> LOCATION: (9)..(9)
<223> OTHER INFORMATION: Xaa at position 9 is serine, arginine,
      ornithine, lysine or alanine
<220> FEATURE:
<221> NAME/KEY: MISC_FEATURE
<222> LOCATION: (10)..(10)
<223> OTHER INFORMATION: Xaa at position 10 is isoleucine or serine
<220> FEATURE:
<221> NAME/KEY: MISC_FEATURE
<222> LOCATION: (12)..(12)
<223> OTHER INFORMATION: Xaa at position 12 is aspartic acid or serine
<220> FEATURE:
<221> NAME/KEY: MISC_FEATURE
<222> LOCATION: (14)..(14)
<223> OTHER INFORMATION: Xaa at position 14 is tyrosine, arginine,
      ornathine, lysine or alanine
<220> FEATURE:
<221> NAME/KEY: MISC_FEATURE
<222> LOCATION: (15)..(15)
<223> OTHER INFORMATION: Xaa at position 15 is glutamine, glutamic acid,
      arginine, ornithine, alanine, lysine or leucine
<220> FEATURE:
<221> NAME/KEY: MISC_FEATURE
<222> LOCATION: (17)..(17)
<223> OTHER INFORMATION: Xaa at position 17 is glutamine or glutamic
      acid
<220> FEATURE:
<221> NAME/KEY: MISC_FEATURE
<222> LOCATION: (18)..(18)
<223> OTHER INFORMATION: Xaa at position 18 is methionine, asparagine,
      glutamine, glutamic acid, aspartic acid or threonine
<220> FEATURE:
<221> NAME/KEY: MISC_FEATURE
<222> LOCATION: (19)..(19)
<223> OTHER INFORMATION: Xaa at position19 is tyrosine, 4-methoxy
      phenylalanine  or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine, serine,
      valine, threonine, isoleucine, leucine, glutamine, glutamic acid,
      asparagine, aspartic acid, histidine, tryptophan, tyrosine, or
      methionine

<400> SEQUENCE: 18

Gly Ile Val Xaa Xaa Cys Cys Xaa Xaa Xaa Cys Xaa Leu Xaa Xaa Leu
1               5                   10                  15

Xaa Xaa Xaa Cys Xaa
          20

-continued

```
<210> SEQ ID NO 19
<211> LENGTH: 7
<212> TYPE: PRT
<213> ORGANISM: Artificial Sequence
<220> FEATURE:
<223> OTHER INFORMATION: linker peptide
<220> FEATURE:
<221> NAME/KEY: MISC_FEATURE
<222> LOCATION: (1)..(1)
<223> OTHER INFORMATION: the Xaa at position 1 is glycine, glutamic acid
      or aspartic acid
<220> FEATURE:
<221> NAME/KEY: MISC_FEATURE
<222> LOCATION: (2)..(6)
<223> OTHER INFORMATION: the Xaas at positions 2-6 are independently
      glutamic acid or aspartic acid

<400> SEQUENCE: 19

Xaa Xaa Xaa Xaa Xaa Xaa Lys
1               5

<210> SEQ ID NO 20
<211> LENGTH: 7
<212> TYPE: PRT
<213> ORGANISM: Artificial Sequence
<220> FEATURE:
<223> OTHER INFORMATION: linker peptide
<220> FEATURE:
<221> NAME/KEY: MISC_FEATURE
<222> LOCATION: (2)..(6)
<223> OTHER INFORMATION: the Xaas at positions 2-6 are independently
      glutamic acid or aspartic acid

<400> SEQUENCE: 20

Gly Xaa Xaa Xaa Xaa Xaa Lys
1               5

<210> SEQ ID NO 21
<211> LENGTH: 7
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (1)..(5)
<223> OTHER INFORMATION: the Xaas at positions 1-5 are independently
      glutamic acid or aspartic acid

<400> SEQUENCE: 21

Xaa Xaa Xaa Xaa Xaa Arg Lys
1               5

<210> SEQ ID NO 22
<211> LENGTH: 31
<212> TYPE: PRT
<213> ORGANISM: Artificial Sequence
<220> FEATURE:
<223> OTHER INFORMATION: analog of IGF-1 B chain
<220> FEATURE:
<221> NAME/KEY: MISC_FEATURE
<222> LOCATION: (28)..(28)
<223> OTHER INFORMATION: The Xaa at position 28 is alanine lysine,
      ornithine or arginine

<400> SEQUENCE: 22

Gly Glu Glu Glu Glu Glu Lys Gly Pro Glu His Leu Cys Gly Ala His
1               5                   10                  15

Leu Val Asp Ala Leu Tyr Leu Val Cys Gly Asp Xaa Gly Phe Tyr
            20                  25                  30
```

```
<210> SEQ ID NO 23
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is histidine or threonine
<220> FEATURE:
<221> NAME/KEY: MISC_FEATURE
<222> LOCATION: (17)..(17)
<223> OTHER INFORMATION: Xaa at position 17 is glutamine or glutamic
      acid
<220> FEATURE:
<221> NAME/KEY: MISC_FEATURE
<222> LOCATION: (19)..(19)
<223> OTHER INFORMATION: Xaa at position19 is tyrosine, 4-methoxy
      phenylalanine  or 4-amino-phenylalanine
<220> FEATURE:
<221> NAME/KEY: MISC_FEATURE
<222> LOCATION: (21)..(21)
<223> OTHER INFORMATION: Xaa at position 21 is asparagine or glycine

<400> SEQUENCE: 23

Gly Ile Val Glu Gln Cys Cys Xaa Ser Ile Cys Ser Leu Tyr Gln Leu
1               5                   10                  15

Xaa Asn Xaa Cys Xaa
            20

<210> SEQ ID NO 24
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid

<400> SEQUENCE: 24

Xaa Leu Cys Gly Xaa Xaa Leu Val Glu Ala Leu Tyr Leu Val Cys Gly
1               5                   10                  15

Glu Arg Gly Phe Phe
            20

<210> SEQ ID NO 25
<211> LENGTH: 27
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is phenylalanine and
      desamino-phenylalanine
<220> FEATURE:
<221> NAME/KEY: MISC_FEATURE
<222> LOCATION: (5)..(5)
<223> OTHER INFORMATION: Xaa at position 5 is histidine and threonine
```

```
-continued

<220> FEATURE:
<221> NAME/KEY: MISC_FEATURE
<222> LOCATION: (9)..(9)
<223> OTHER INFORMATION: Xaa at position 9 is alanine, glycine or serine
<220> FEATURE:
<221> NAME/KEY: MISC_FEATURE
<222> LOCATION: (10)..(10)
<223> OTHER INFORMATION: Xaa at position 10 is histidine, aspartic acid,
      glutamic acid, homocysteic acid or cysteic acid

<400> SEQUENCE: 25

Xaa Val Asn Gln Xaa Leu Cys Gly Xaa Xaa Leu Val Glu Ala Leu Tyr
1               5                   10                  15

Leu Val Cys Gly Glu Arg Gly Phe Phe Tyr Thr
            20                  25

<210> SEQ ID NO 26
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is histidine or phenylalanine
<220> FEATURE:
<221> NAME/KEY: MISC_FEATURE
<222> LOCATION: (19)..(19)
<223> OTHER INFORMATION: Xaa at position19 is tyrosine or 4-amino-
      phenylalanine
<220> FEATURE:
<221> NAME/KEY: MISC_FEATURE
<222> LOCATION: (21)..(21)
<223> OTHER INFORMATION: Xaa at position 21 is alanine, glycine or
      asparagine

<400> SEQUENCE: 26

Gly Ile Val Glu Gln Cys Cys Xaa Ser Ile Cys Ser Leu Tyr Gln Leu
1               5                   10                  15

Glu Asn Xaa Cys Xaa
            20

<210> SEQ ID NO 27
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is histidine or phenylalnine
<220> FEATURE:
<221> NAME/KEY: MISC_FEATURE
<222> LOCATION: (9)..(9)
<223> OTHER INFORMATION: Xaa at position 9 is arginine, lysine,
      ornithine or alanine
<220> FEATURE:
<221> NAME/KEY: MISC_FEATURE
<222> LOCATION: (14)..(14)
<223> OTHER INFORMATION: Xaa at position 14 is arginine, lysine,
      ornithine or alanine
<220> FEATURE:
<221> NAME/KEY: MISC_FEATURE
<222> LOCATION: (15)..(15)
<223> OTHER INFORMATION: Xaa at position 15 is arginine, lysine,
      ornithine or leucine
<220> FEATURE:
<221> NAME/KEY: MISC_FEATURE
<222> LOCATION: (17)..(17)
<223> OTHER INFORMATION: Xaa at position 17 is glutamine or glutamic
      acid
```

```
<220> FEATURE:
<221> NAME/KEY: MISC_FEATURE
<222> LOCATION: (18)..(18)
<223> OTHER INFORMATION: Xaa at position 18 is methionine, asparagine or
      threonine
<220> FEATURE:
<221> NAME/KEY: MISC_FEATURE
<222> LOCATION: (19)..(19)
<223> OTHER INFORMATION: Xaa at position19 is tyrosine, 4-methoxy
      phenylalanine  or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine or
      asparagine

<400> SEQUENCE: 27

Gly Ile Val Asp Glu Cys Cys Xaa Xaa Ser Cys Asp Leu Xaa Xaa Leu
1               5                   10                  15

Xaa Xaa Xaa Cys Xaa
            20

<210> SEQ ID NO 28
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid
<220> FEATURE:
<221> NAME/KEY: MISC_FEATURE
<222> LOCATION: (9)..(9)
<223> OTHER INFORMATION: Xaa at position 9 is aspartic acid or glutamic
      acid
<220> FEATURE:
<221> NAME/KEY: MISC_FEATURE
<222> LOCATION: (10)..(10)
<223> OTHER INFORMATION: Xaa at position 10 is alanine or threonine
<220> FEATURE:
<221> NAME/KEY: MISC_FEATURE
<222> LOCATION: (18)..(18)
<223> OTHER INFORMATION: Xaa at position 18 is alanine, ornithine,
      lysine or arginine
<220> FEATURE:
<221> NAME/KEY: MISC_FEATURE
<222> LOCATION: (21)..(21)
<223> OTHER INFORMATION: Xaa at position 21 is tyrosine or phenylalanine

<400> SEQUENCE: 28

Xaa Leu Cys Gly Xaa Xaa Leu Val Xaa Xaa Leu Tyr Leu Val Cys Gly
1               5                   10                  15

Asp Xaa Gly Phe Xaa
            20

<210> SEQ ID NO 29
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
```

```
<221> NAME/KEY: MISC_FEATURE
<222> LOCATION: (9)..(9)
<223> OTHER INFORMATION: Xaa at position 9 is arginine, ornithine, or
      lysine
<220> FEATURE:
<221> NAME/KEY: MISC_FEATURE
<222> LOCATION: (14)..(14)
<223> OTHER INFORMATION: Xaa at position 14 is arginine, ornithine, or
      lysine
<220> FEATURE:
<221> NAME/KEY: MISC_FEATURE
<222> LOCATION: (15)..(15)
<223> OTHER INFORMATION: Xaa at position 15 is arginine, ornithine, or
      lysine
<220> FEATURE:
<221> NAME/KEY: MISC_FEATURE
<222> LOCATION: (17)..(17)
<223> OTHER INFORMATION: Xaa at position 17 is glutamine or glutamic
      acid
<220> FEATURE:
<221> NAME/KEY: MISC_FEATURE
<222> LOCATION: (19)..(19)
<223> OTHER INFORMATION: Xaa at position19 is tyrosine, 4-methoxy
      phenylalanine  or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine or
      asparagine

<400> SEQUENCE: 29

Gly Ile Val Asp Glu Cys Cys His Xaa Ser Cys Asp Leu Xaa Xaa Leu
1               5                   10                  15

Xaa Met Xaa Cys Xaa
            20

<210> SEQ ID NO 30
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (6)..(6)
<223> OTHER INFORMATION: Xaa at position 6 is histidine, aspartic acid,
      or glutamic acid
<220> FEATURE:
<221> NAME/KEY: MISC_FEATURE
<222> LOCATION: (18)..(18)
<223> OTHER INFORMATION: Xaa at position 18 is alanine, ornithine,
      lysine or arginine
<220> FEATURE:
<221> NAME/KEY: MISC_FEATURE
<222> LOCATION: (21)..(21)
<223> OTHER INFORMATION: Xaa at position 21 is tyrosine or phenylalanine

<400> SEQUENCE: 30

Xaa Leu Cys Gly Ala Xaa Leu Val Asp Ala Leu Tyr Leu Val Cys Gly
1               5                   10                  15

Asp Xaa Gly Phe Xaa
            20

<210> SEQ ID NO 31
<211> LENGTH: 21
<212> TYPE: PRT
<213> ORGANISM: Artificial Sequence
<220> FEATURE:
<223> OTHER INFORMATION: Analog of IGF-1 B chain
```

```
<220> FEATURE:
<221> NAME/KEY: MISC_FEATURE
<222> LOCATION: (18)..(18)
<223> OTHER INFORMATION: The Xaa at position 18 is ornithine, lysine or
      arginine

<400> SEQUENCE: 31

His Leu Cys Gly Ala Glu Leu Val Asp Ala Leu Tyr Leu Val Cys Gly
1               5                   10                  15

Asp Xaa Gly Phe Tyr
            20

<210> SEQ ID NO 32
<211> LENGTH: 24
<212> TYPE: PRT
<213> ORGANISM: Artificial Sequence
<220> FEATURE:
<223> OTHER INFORMATION: Analog of IGF-1 B chain
<220> FEATURE:
<221> NAME/KEY: MISC_FEATURE
<222> LOCATION: (21)..(21)
<223> OTHER INFORMATION: The Xaa at position 21 is ornithine, lysine or
      arginine

<400> SEQUENCE: 32

Gly Pro Glu His Leu Cys Gly Ala Glu Leu Val Asp Ala Leu Tyr Leu
1               5                   10                  15

Val Cys Gly Asp Xaa Gly Phe Tyr
            20

<210> SEQ ID NO 33
<211> LENGTH: 29
<212> TYPE: PRT
<213> ORGANISM: Artificial Sequence
<220> FEATURE:
<223> OTHER INFORMATION: Analog of IGF-1 B chain
<220> FEATURE:
<221> NAME/KEY: MISC_FEATURE
<222> LOCATION: (21)..(21)
<223> OTHER INFORMATION: The Xaa at position 21 is ornithine, lysine or
      arginine

<400> SEQUENCE: 33

Gly Pro Glu His Leu Cys Gly Ala Glu Leu Val Asp Ala Leu Tyr Leu
1               5                   10                  15

Val Cys Gly Asp Xaa Gly Phe Tyr Phe Asn Pro Lys Thr
            20                  25

<210> SEQ ID NO 34
<211> LENGTH: 29
<212> TYPE: PRT
<213> ORGANISM: Artificial Sequence
<220> FEATURE:
<223> OTHER INFORMATION: Analog of IGF-1 B chain
<220> FEATURE:
<221> NAME/KEY: MISC_FEATURE
<222> LOCATION: (21)..(21)
<223> OTHER INFORMATION: The Xaa at position 21 is ornithine, lysine or
      arginine

<400> SEQUENCE: 34

Gly Pro Glu His Leu Cys Gly Ala Glu Leu Val Asp Ala Leu Tyr Leu
1               5                   10                  15

Val Cys Gly Asp Xaa Gly Phe Tyr Phe Asn Lys Pro Thr
            20                  25

<210> SEQ ID NO 35
```

```
<211> LENGTH: 8
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa at position 7 is ornithine

<400> SEQUENCE: 35

Gly Tyr Gly Ser Ser Ser Xaa Arg
1               5

<210> SEQ ID NO 36
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (9)..(9)
<223> OTHER INFORMATION: Xaa at position 9 is arginine, ornithine, or
      lysine
<220> FEATURE:
<221> NAME/KEY: MISC_FEATURE
<222> LOCATION: (14)..(14)
<223> OTHER INFORMATION: Xaa at position 14 is arginine, ornithine, or
      lysine
<220> FEATURE:
<221> NAME/KEY: MISC_FEATURE
<222> LOCATION: (15)..(15)
<223> OTHER INFORMATION: Xaa at position 15 is arginine, ornithine, or
      lysine

<400> SEQUENCE: 36

Gly Ile Val Asp Glu Cys Cys His Xaa Ser Cys Asp Leu Xaa Xaa Leu
1               5                   10                  15

Gln Met Tyr Cys Asn
            20

<210> SEQ ID NO 37
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (19)..(19)
<223> OTHER INFORMATION: Xaa at position19 is tyrosine, 4-methoxy
      phenylalanine  or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine or
      asparagine

<400> SEQUENCE: 37

Gly Ile Val Glu Gln Cys Cys His Ser Ile Cys Ser Leu Tyr Gln Leu
1               5                   10                  15

Glu Asn Xaa Cys Xaa
            20

<210> SEQ ID NO 38
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
```

```
<222> LOCATION: (8)..(8)
<223> OTHER INFORMATION: Xaa at position 8 is histidine or phenylalnine
<220> FEATURE:
<221> NAME/KEY: MISC_FEATURE
<222> LOCATION: (9)..(9)
<223> OTHER INFORMATION: Xaa at position 9 is arginine, lysine,
      ornithine or alanine
<220> FEATURE:
<221> NAME/KEY: MISC_FEATURE
<222> LOCATION: (14)..(14)
<223> OTHER INFORMATION: Xaa at position 14 is arginine, lysine,
      ornithine or alanine
<220> FEATURE:
<221> NAME/KEY: MISC_FEATURE
<222> LOCATION: (15)..(15)
<223> OTHER INFORMATION: Xaa at position 15 is arginine, lysine,
      ornithine or leucine
<220> FEATURE:
<221> NAME/KEY: MISC_FEATURE
<222> LOCATION: (17)..(17)
<223> OTHER INFORMATION: Xaa at position 17 is glutamine or glutamic
      acid
<220> FEATURE:
<221> NAME/KEY: MISC_FEATURE
<222> LOCATION: (18)..(18)
<223> OTHER INFORMATION: Xaa at position 18 is methionine, asparagine or
      threonine
<220> FEATURE:
<221> NAME/KEY: MISC_FEATURE
<222> LOCATION: (19)..(19)
<223> OTHER INFORMATION: Xaa at position19 is tyrosine, 4-methoxy
      phenylalanine  or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine or
      asparagine

<400> SEQUENCE: 38

Gly Ile Val Asp Glu Cys Cys Xaa Xaa Ser Cys Asp Leu Xaa Xaa Leu
1               5                   10                  15

Xaa Xaa Xaa Cys Xaa
            20

<210> SEQ ID NO 39
<211> LENGTH: 21
<212> TYPE: PRT
<213> ORGANISM: Homo sapiens
<220> FEATURE:
<221> NAME/KEY: MISC_FEATURE
<222> LOCATION: (18)..(18)
<223> OTHER INFORMATION: The Xaa at position 18 is ornithine

<400> SEQUENCE: 39

His Leu Cys Gly Ala Glu Leu Val Asp Ala Leu Tyr Leu Val Cys Gly
1               5                   10                  15

Asp Xaa Gly Phe Tyr
            20

<210> SEQ ID NO 40
<211> LENGTH: 24
<212> TYPE: PRT
<213> ORGANISM: Homo sapiens
<220> FEATURE:
<221> NAME/KEY: MISC_FEATURE
<222> LOCATION: (21)..(21)
<223> OTHER INFORMATION: The Xaa at position 21is ornithine

<400> SEQUENCE: 40

Gly Pro Glu His Leu Cys Gly Ala Glu Leu Val Asp Ala Leu Tyr Leu
1               5                   10                  15
```

```
Val Cys Gly Asp Xaa Gly Phe Tyr
            20

<210> SEQ ID NO 41
<211> LENGTH: 29
<212> TYPE: PRT
<213> ORGANISM: Homo sapiens
<220> FEATURE:
<221> NAME/KEY: MISC_FEATURE
<222> LOCATION: (21)..(21)
<223> OTHER INFORMATION: The Xaa at position 21is ornithine

<400> SEQUENCE: 41

Gly Pro Glu His Leu Cys Gly Ala Glu Leu Val Asp Ala Leu Tyr Leu
1               5                   10                  15

Val Cys Gly Asp Xaa Gly Phe Tyr Phe Asn Pro Lys Thr
            20                  25

<210> SEQ ID NO 42
<211> LENGTH: 29
<212> TYPE: PRT
<213> ORGANISM: Homo sapiens
<220> FEATURE:
<221> NAME/KEY: misc_feature
<222> LOCATION: (21)..(21)
<223> OTHER INFORMATION: Xaa can be any naturally occurring amino acid

<400> SEQUENCE: 42

Gly Pro Glu His Leu Cys Gly Ala Glu Leu Val Asp Ala Leu Tyr Leu
1               5                   10                  15

Val Cys Gly Asp Xaa Gly Phe Tyr Phe Asn Lys Pro Thr
            20                  25

<210> SEQ ID NO 43
<211> LENGTH: 21
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: The Xaa at position 9 is ornithine
<220> FEATURE:
<221> NAME/KEY: MISC_FEATURE
<222> LOCATION: (14)..(15)
<223> OTHER INFORMATION: The Xaas at positions 14 and 15 are both
      ornithine
<220> FEATURE:
<221> NAME/KEY: MISC_FEATURE
<222> LOCATION: (19)..(19)
<223> OTHER INFORMATION: The Xaa at position 19 is tyrosine, 4-methoxy-
      phenylalanine or 4-amino phenylalanine

<400> SEQUENCE: 43

Gly Ile Val Asp Glu Cys Cys His Xaa Ser Cys Asp Leu Xaa Xaa Leu
1               5                   10                  15

Gln Met Xaa Cys Asn
            20

<210> SEQ ID NO 44
<211> LENGTH: 5
<212> TYPE: PRT
<213> ORGANISM: Homo sapiens

<400> SEQUENCE: 44

Phe Asn Lys Pro Thr
1               5
```

```
<210> SEQ ID NO 45
<211> LENGTH: 4
<212> TYPE: PRT
<213> ORGANISM: Homo sapiens

<400> SEQUENCE: 45

Phe Asn Lys Pro
 1

<210> SEQ ID NO 46
<211> LENGTH: 4
<212> TYPE: PRT
<213> ORGANISM: Homo sapiens

<400> SEQUENCE: 46

Tyr Thr Pro Lys
 1

<210> SEQ ID NO 47
<211> LENGTH: 4
<212> TYPE: PRT
<213> ORGANISM: Artificial Sequence
<220> FEATURE:
<223> OTHER INFORMATION: Analog of IGF-1 B chain sequence fragment

<400> SEQUENCE: 47

Phe Asn Pro Lys
 1

<210> SEQ ID NO 48
<211> LENGTH: 5
<212> TYPE: PRT
<213> ORGANISM: Artificial Sequence
<220> FEATURE:
<223> OTHER INFORMATION: Analog of insulin B chain sequence fragment

<400> SEQUENCE: 48

Tyr Thr Lys Pro Thr
 1               5

<210> SEQ ID NO 49
<211> LENGTH: 5
<212> TYPE: PRT
<213> ORGANISM: Artificial Sequence
<220> FEATURE:
<223> OTHER INFORMATION: Analog of IGF-1 B chain sequence fragment

<400> SEQUENCE: 49

Phe Asn Pro Lys Thr
 1               5

<210> SEQ ID NO 50
<211> LENGTH: 5
<212> TYPE: PRT
<213> ORGANISM: Artificial Sequence
<220> FEATURE:
<223> OTHER INFORMATION: linker peptide
<220> FEATURE:
<221> NAME/KEY: MISC_FEATURE
<222> LOCATION: (1)..(1)
<223> OTHER INFORMATION: The Xaa at position 1 is phenylalanine or
      desamino-phenylalanine

<400> SEQUENCE: 50

Xaa Val Asn Gln Thr
 1               5
```

```
<210> SEQ ID NO 51
<211> LENGTH: 21
<212> TYPE: PRT
<213> ORGANISM: Homo sapiens
<220> FEATURE:
<221> NAME/KEY: MISC_FEATURE
<222> LOCATION: (19)..(19)
<223> OTHER INFORMATION: The Xaa at position 19 is tyrosine, 4-methoxy-
      phenylalanine or 4-amino phenylalanine
<220> FEATURE:
<221> NAME/KEY: MISC_FEATURE
<222> LOCATION: (21)..(21)
<223> OTHER INFORMATION: The Xaa at position 21 is alanine, glycine or
      asparagine

<400> SEQUENCE: 51

Gly Ile Val Asp Glu Cys Cys His Arg Ser Cys Asp Leu Arg Arg Leu
1               5                   10                  15

Glu Met Xaa Cys Xaa
            20

<210> SEQ ID NO 52
<211> LENGTH: 29
<212> TYPE: PRT
<213> ORGANISM: Homo sapiens

<400> SEQUENCE: 52

Gly Pro Glu Thr Leu Cys Gly Ala Glu Leu Val Asp Ala Leu Tyr Leu
1               5                   10                  15

Val Cys Gly Asp Arg Gly Phe Tyr Phe Asn Pro Lys Thr
            20                  25

<210> SEQ ID NO 53
<211> LENGTH: 35
<212> TYPE: PRT
<213> ORGANISM: Homo sapiens

<400> SEQUENCE: 53

Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Leu Glu Gly Ser Leu
            20                  25                  30

Gln Lys Arg
        35

<210> SEQ ID NO 54
<211> LENGTH: 51
<212> TYPE: PRT
<213> ORGANISM: Homo sapiens
<220> FEATURE:
<221> NAME/KEY: MISC_FEATURE
<222> LOCATION: (22)..(22)
<223> OTHER INFORMATION: The Xaa at position 22 is ornithine
<220> FEATURE:
<221> NAME/KEY: MISC_FEATURE
<222> LOCATION: (39)..(39)
<223> OTHER INFORMATION: The Xaa at position 39 is ornithine
<220> FEATURE:
<221> NAME/KEY: MISC_FEATURE
<222> LOCATION: (44)..(45)
<223> OTHER INFORMATION: The Xaa at positions 44-45 are ornithine

<400> SEQUENCE: 54

Cys Gly Pro Glu His Leu Cys Gly Ala Glu Leu Val Asp Ala Leu Tyr
1               5                   10                  15

Leu Val Cys Gly Asp Xaa Gly Phe Tyr Phe Asn Lys Pro Thr Gly Ile
            20                  25                  30
```

```
Val Asp Glu Cys Cys Phe Xaa Ser Cys Asp Leu Xaa Xaa Leu Glu Asn
        35                  40                  45

Tyr Cys Asn
    50

<210> SEQ ID NO 55
<211> LENGTH: 21
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa at position 5 is aspartic acid or glutamic
      acid
<220> FEATURE:
<221> NAME/KEY: MISC_FEATURE
<222> LOCATION: (5)..(5)
<223> OTHER INFORMATION: Xaa at position 5 is glutamine or glutamic acid
<220> FEATURE:
<221> NAME/KEY: MISC_FEATURE
<222> LOCATION: (8)..(8)
<223> OTHER INFORMATION: Xaa at position 8 is histidine, threonine or
      phenylalanine
<220> FEATURE:
<221> NAME/KEY: MISC_FEATURE
<222> LOCATION: (9)..(9)
<223> OTHER INFORMATION: Xaa at position 9 is serine, arginine,
      ornithine, lysine or alanine
<220> FEATURE:
<221> NAME/KEY: MISC_FEATURE
<222> LOCATION: (10)..(10)
<223> OTHER INFORMATION: Xaa at position 10 is isoleucine or serine
<220> FEATURE:
<221> NAME/KEY: MISC_FEATURE
<222> LOCATION: (12)..(12)
<223> OTHER INFORMATION: Xaa at position 12 is aspartic acid or serine
<220> FEATURE:
<221> NAME/KEY: MISC_FEATURE
<222> LOCATION: (14)..(14)
<223> OTHER INFORMATION: Xaa at position 14 is tyrosine, arginine,
      ornathine, lysine or alanine
<220> FEATURE:
<221> NAME/KEY: MISC_FEATURE
<222> LOCATION: (15)..(15)
<223> OTHER INFORMATION: Xaa at position 15 is glutamine, glutamic acid,
      arginine, ornithine, alanine, lysine or leucine
<220> FEATURE:
<221> NAME/KEY: MISC_FEATURE
<222> LOCATION: (18)..(18)
<223> OTHER INFORMATION: Xaa at position 18 is methionine, asparagine,
      glutamine, glutamic acid, aspartic acid or threonine
<220> FEATURE:
<221> NAME/KEY: MISC_FEATURE
<222> LOCATION: (19)..(19)
<223> OTHER INFORMATION: Xaa at position19 is tyrosine, 4-methoxy
      phenylalanine  or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine, serine,
      valine, threonine, isoleucine, leucine, glutamine, glutamic acid,
      asparagine, aspartic acid, histidine, tryptophan, tyrosine, or
      methionine

<400> SEQUENCE: 55

Gly Ile Val Xaa Xaa Cys Cys Xaa Xaa Xaa Cys Xaa Leu Xaa Xaa Leu
1               5                   10                  15

Glu Xaa Xaa Cys Xaa
            20

<210> SEQ ID NO 56
<211> LENGTH: 21
<212> TYPE: PRT
```

```
<213> ORGANISM: Homo sapiens
<220> FEATURE:
<221> NAME/KEY: MISC_FEATURE
<222> LOCATION: (6)..(6)
<223> OTHER INFORMATION: The Xaa at position 6 is histidine, aspartic
      acid, glutamic acid, homocysteic acid or cysteic acid

<400> SEQUENCE: 56

His Leu Cys Gly Ser Xaa Leu Val Glu Ala Leu Tyr Leu Val Cys Gly
1               5                   10                  15

Glu Arg Gly Phe Phe
            20

<210> SEQ ID NO 57
<211> LENGTH: 6
<212> TYPE: PRT
<213> ORGANISM: Artificial Sequence
<220> FEATURE:
<223> OTHER INFORMATION: synthetic peptide for testing cleavage of
      dipeptide prodrug element

<400> SEQUENCE: 57

His Ser Arg Gly Thr Phe
1               5

<210> SEQ ID NO 58
<211> LENGTH: 8
<212> TYPE: PRT
<213> ORGANISM: Artificial Sequence
<220> FEATURE:
<223> OTHER INFORMATION: synthetic peptide for testing cleavage of
      dipeptide prodrug element
<220> FEATURE:
<221> NAME/KEY: MISC_FEATURE
<222> LOCATION: (2)..(2)
<223> OTHER INFORMATION: Xaa at position 2 is Sarcosine

<400> SEQUENCE: 58

Lys Xaa His Ser Thr Gly Thr Phe
1               5

<210> SEQ ID NO 59
<211> LENGTH: 6
<212> TYPE: PRT
<213> ORGANISM: Artificial Sequence
<220> FEATURE:
<223> OTHER INFORMATION: glucagon analogue
<220> FEATURE:
<221> NAME/KEY: MOD_RES
<222> LOCATION: (1)..(1)
<223> OTHER INFORMATION: Xaa at position 1 is d-histidine
<220> FEATURE:
<221> NAME/KEY: MOD_RES
<222> LOCATION: (2)..(2)
<223> OTHER INFORMATION: Xaa at position 2 is d-threonine
<220> FEATURE:
<221> NAME/KEY: MOD_RES
<222> LOCATION: (3)..(3)
<223> OTHER INFORMATION: Xaa at position 3 is d-arginine
<220> FEATURE:
<221> NAME/KEY: MOD_RES
<222> LOCATION: (5)..(5)
<223> OTHER INFORMATION: Xaa at position 5 is d-threonine
<220> FEATURE:
<221> NAME/KEY: MOD_RES
<222> LOCATION: (6)..(6)
<223> OTHER INFORMATION: Xaa at position 6 is d-phenylalanine

<400> SEQUENCE: 59

Xaa Xaa Xaa Gly Xaa Xaa
1               5
```

```
<210> SEQ ID NO 60
<211> LENGTH: 8
<212> TYPE: PRT
<213> ORGANISM: Artificial Sequence
<220> FEATURE:
<223> OTHER INFORMATION: glucagon analogue
<220> FEATURE:
<221> NAME/KEY: MOD_RES
<222> LOCATION: (1)..(1)
<223> OTHER INFORMATION: Xaa at position 1 is d-lysine
<220> FEATURE:
<221> NAME/KEY: MOD_RES
<222> LOCATION: (2)..(2)
<223> OTHER INFORMATION: Xaa at position 2 is d-sarcosine
<220> FEATURE:
<221> NAME/KEY: MOD_RES
<222> LOCATION: (3)..(3)
<223> OTHER INFORMATION: Xaa at position 3 is d-histidine
<220> FEATURE:
<221> NAME/KEY: MOD_RES
<222> LOCATION: (4)..(4)
<223> OTHER INFORMATION: Xaa at position 4 is d-threonine
<220> FEATURE:
<221> NAME/KEY: MOD_RES
<222> LOCATION: (5)..(5)
<223> OTHER INFORMATION: Xaa at position 5 is d-arginine
<220> FEATURE:
<221> NAME/KEY: MOD_RES
<222> LOCATION: (7)..(7)
<223> OTHER INFORMATION: Xaa at position 7 is d-threonine
<220> FEATURE:
<221> NAME/KEY: MOD_RES
<222> LOCATION: (8)..(8)
<223> OTHER INFORMATION: Xaa at position 8 is d-phenylalanine

<400> SEQUENCE: 60

Xaa Xaa Xaa Xaa Xaa Gly Xaa Xaa
1               5

<210> SEQ ID NO 61
<211> LENGTH: 6
<212> TYPE: PRT
<213> ORGANISM: Artificial Sequence
<220> FEATURE:
<223> OTHER INFORMATION: synthetic peptide for testing cleavage of
      dipeptide prodrug element
<220> FEATURE:
<221> NAME/KEY: MISC_FEATURE
<222> LOCATION: (1)..(1)
<223> OTHER INFORMATION: The Xaa at position 1 is histidine,
      d-histidine or N-methyl-histdine

<400> SEQUENCE: 61

Xaa Ser Arg Gly Thr Phe
1               5

<210> SEQ ID NO 62
<211> LENGTH: 29
<212> TYPE: PRT
<213> ORGANISM: Homo sapiens

<400> SEQUENCE: 62

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr
            20                  25

<210> SEQ ID NO 63
<211> LENGTH: 21
<212> TYPE: PRT
```

```
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (19)..(19)
<223> OTHER INFORMATION: Xaa at position 19 is tyrosine or 4-amino
      phenylanaline

<400> SEQUENCE: 63

Gly Ile Val Asp Glu Cys Cys His Arg Ser Cys Asp Leu Arg Arg Leu
1               5                   10                  15

Glu Met Xaa Cys Ala
            20

<210> SEQ ID NO 64
<211> LENGTH: 29
<212> TYPE: PRT
<213> ORGANISM: Homo sapiens

<400> SEQUENCE: 64

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln Arg
            20                  25

<210> SEQ ID NO 65
<211> LENGTH: 28
<212> TYPE: PRT
<213> ORGANISM: Homo sapiens

<400> SEQUENCE: 65

Ser Ser Ser Ser Arg Ala Pro Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 66
<211> LENGTH: 29
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa at position 5 is lysine or Arginine
<220> FEATURE:
<221> NAME/KEY: MISC_FEATURE
<222> LOCATION: (29)..(29)
<223> OTHER INFORMATION: Xaa at position 29 is lysine or Arginine

<400> SEQUENCE: 66

Ser Ser Ser Ser Xaa Ala Pro Pro Pro Ser Leu Pro Ser Pro Ser Arg
1               5                   10                  15

Leu Pro Gly Pro Ser Asp Thr Pro Ile Leu Pro Gln Xaa
            20                  25

<210> SEQ ID NO 67
<211> LENGTH: 93
<212> TYPE: PRT
<213> ORGANISM: Homo sapiens

<400> SEQUENCE: 67

Met Gly Ser Ser Ser Ser Lys Ala Pro Pro Pro Ser Leu Pro Ser Pro
1               5                   10                  15

Ser Arg Leu Pro Gly Pro Ser Asp Thr Pro Ile Leu Pro Gln Glu Glu
```

```
            20                  25                  30

Glu Glu Glu Lys Gly Pro Glu His Leu Cys Gly Ala His Leu Val Asp
            35                  40                  45

Ala Leu Tyr Leu Val Cys Gly Asp Arg Gly Phe Tyr Gly Tyr Gly Ser
        50                  55                  60

Ser Ser Arg Arg Ala Pro Gln Thr Gly Ile Val Asp Glu Cys Cys His
65                  70                  75                  80

Arg Ser Cys Asp Leu Arg Arg Leu Glu Asn Tyr Cys Asn
                85                  90

<210> SEQ ID NO 68
<211> LENGTH: 81
<212> TYPE: PRT
<213> ORGANISM: Homo sapiens

<400> SEQUENCE: 68

Gly Glu Glu Glu Glu Lys Gly Pro Glu His Leu Cys Gly Ala His
1               5                   10                  15

Leu Val Asp Ala Leu Tyr Leu Val Cys Gly Asp Arg Gly Phe Tyr Ser
                20                  25                  30

Ser Ser Ser Arg Ala Pro Pro Pro Ser Leu Pro Ser Pro Ser Arg Leu
            35                  40                  45

Pro Gly Pro Ser Asp Thr Pro Ile Leu Pro Gln Lys Gly Ile Val Asp
        50                  55                  60

Glu Cys Cys His Arg Ser Cys Asp Leu Arg Arg Leu Glu Asn Tyr Cys
65                  70                  75                  80

Asn

<210> SEQ ID NO 69
<211> LENGTH: 26
<212> TYPE: PRT
<213> ORGANISM: Homo sapiens

<400> SEQUENCE: 69

Pro Pro Arg Pro Pro Gln Ser Ala Ser Pro Pro Asp Leu Ser Pro Leu
1               5                   10                  15

Ser Gly Thr Pro Ser Arg Pro Ser Leu Ser
                20                  25

<210> SEQ ID NO 70
<211> LENGTH: 81
<212> TYPE: PRT
<213> ORGANISM: Homo sapiens

<400> SEQUENCE: 70

Gly Glu Glu Glu Glu Lys Gly Pro Glu His Leu Cys Gly Ala His
1               5                   10                  15

Leu Val Asp Ala Leu Tyr Leu Val Cys Gly Asp Arg Gly Phe Tyr Ser
                20                  25                  30

Ser Ser Ser Arg Ala Ala Ala Ala Ser Leu Ala Ser Ala Ser Arg Leu
            35                  40                  45

Ala Gly Ala Ser Asp Thr Ala Ile Leu Ala Gln Lys Gly Ile Val Asp
        50                  55                  60

Glu Cys Cys His Arg Ser Cys Asp Leu Arg Arg Leu Glu Asn Tyr Cys
65                  70                  75                  80

Asn
```

-continued

```
<210> SEQ ID NO 71
<211> LENGTH: 87
<212> TYPE: PRT
<213> ORGANISM: Homo sapiens

<400> SEQUENCE: 71

Gly Glu Glu Glu Glu Lys Gly Pro Glu His Leu Cys Gly Ala His
1               5                   10                  15

Leu Val Asp Ala Leu Tyr Leu Val Cys Gly Asp Arg Gly Phe Tyr Arg
            20                  25                  30

Arg Glu Ala Glu Asp Leu Gln Val Gly Gln Val Glu Leu Gly Gly Gly
        35                  40                  45

Pro Gly Ala Gly Ser Leu Gln Pro Leu Ala Leu Glu Gly Ser Leu Gln
    50                  55                  60

Arg Lys Gly Ile Val Asp Glu Cys Cys His Arg Ser Cys Asp Leu Arg
65                  70                  75                  80

Arg Leu Glu Asn Tyr Cys Asn
                85

<210> SEQ ID NO 72
<211> LENGTH: 64
<212> TYPE: PRT
<213> ORGANISM: Homo sapiens

<400> SEQUENCE: 72

Gly Glu Glu Glu Glu Lys Gly Pro Glu His Leu Cys Gly Ala His
1               5                   10                  15

Leu Val Asp Ala Leu Tyr Leu Val Cys Gly Asp Arg Gly Phe Tyr Gly
            20                  25                  30

Tyr Gly Ser Ser Ser Arg Arg Ala Pro Gln Thr Gly Ile Val Asp Glu
        35                  40                  45

Cys Cys His Arg Ser Cys Asp Leu Arg Arg Leu Glu Asn Tyr Cys Asn
    50                  55                  60

<210> SEQ ID NO 73
<211> LENGTH: 116
<212> TYPE: PRT
<213> ORGANISM: Homo sapiens

<400> SEQUENCE: 73

Gly Glu Glu Glu Glu Lys Gly Pro Glu His Leu Cys Gly Ala His
1               5                   10                  15

Leu Val Asp Ala Leu Tyr Leu Val Cys Gly Asp Arg Gly Phe Tyr Ser
            20                  25                  30

Ser Ser Ser Arg Ala Pro Pro Pro Ser Leu Pro Ser Pro Ser Arg Leu
        35                  40                  45

Pro Gly Pro Ser Asp Thr Pro Ile Leu Pro Gln Lys Arg Arg Glu Ala
    50                  55                  60

Glu Asp Leu Gln Val Gly Gln Val Glu Leu Gly Gly Gly Pro Gly Ala
65                  70                  75                  80

Gly Ser Leu Gln Pro Leu Ala Leu Glu Gly Ser Leu Gln Arg Lys Gly
                85                  90                  95

Ile Val Asp Glu Cys Cys His Arg Ser Cys Asp Leu Arg Arg Leu Glu
            100                 105                 110

Asn Tyr Cys Asn
        115

<210> SEQ ID NO 74
```

```
<211> LENGTH: 116
<212> TYPE: PRT
<213> ORGANISM: Homo sapiens

<400> SEQUENCE: 74

Gly Glu Glu Glu Glu Lys Gly Pro Glu His Leu Cys Gly Ala His
1               5                   10                  15

Leu Val Asp Ala Leu Tyr Leu Val Cys Gly Asp Arg Gly Phe Tyr Arg
                20                  25                  30

Arg Glu Ala Glu Asp Leu Gln Val Gly Gln Val Glu Leu Gly Gly Gly
                35                  40                  45

Pro Gly Ala Gly Ser Leu Gln Pro Leu Ala Leu Glu Gly Ser Leu Gln
    50                  55                  60

Arg Lys Ser Ser Ser Arg Ala Pro Pro Ser Leu Pro Ser Pro
65                  70                  75                  80

Ser Arg Leu Pro Gly Pro Ser Asp Thr Pro Ile Leu Pro Gln Lys Gly
                85                  90                  95

Ile Val Asp Glu Cys Cys His Arg Ser Cys Asp Leu Arg Leu Glu
                100                 105                 110

Asn Tyr Cys Asn
        115

<210> SEQ ID NO 75
<211> LENGTH: 110
<212> TYPE: PRT
<213> ORGANISM: Homo sapiens

<400> SEQUENCE: 75

Gly Glu Glu Glu Glu Lys Gly Pro Glu His Leu Cys Gly Ala His
1               5                   10                  15

Leu Val Asp Ala Leu Tyr Leu Val Cys Gly Asp Arg Gly Phe Tyr Ser
                20                  25                  30

Ser Ser Ser Arg Ala Pro Pro Pro Ser Leu Pro Ser Pro Ser Arg Leu
                35                  40                  45

Pro Gly Pro Ser Asp Thr Pro Ile Leu Pro Gln Lys Ser Ser Ser
    50                  55                  60

Arg Ala Pro Pro Pro Ser Leu Pro Ser Pro Ser Arg Leu Pro Gly Pro
65                  70                  75                  80

Ser Asp Thr Pro Ile Leu Pro Gln Lys Gly Ile Val Asp Glu Cys Cys
                85                  90                  95

His Arg Ser Cys Asp Leu Arg Arg Leu Glu Asn Tyr Cys Asn
                100                 105                 110

<210> SEQ ID NO 76
<211> LENGTH: 81
<212> TYPE: PRT
<213> ORGANISM: Homo sapiens

<400> SEQUENCE: 76

Gly Glu Glu Glu Glu Lys Gly Pro Glu His Leu Cys Gly Ala His
1               5                   10                  15

Leu Val Asp Ala Leu Tyr Leu Val Cys Gly Asp Arg Gly Phe Tyr Leu
                20                  25                  30

Gln Val Gly Gln Val Glu Leu Gly Gly Gly Pro Gly Ala Gly Ser Leu
                35                  40                  45

Gln Pro Leu Ala Leu Glu Gly Ser Leu Gln Arg Lys Gly Ile Val Asp
    50                  55                  60
```

```
Glu Cys Cys His Arg Ser Cys Asp Leu Arg Arg Leu Glu Asn Tyr Cys
 65                  70                  75                  80

Asn

<210> SEQ ID NO 77
<211> LENGTH: 80
<212> TYPE: PRT
<213> ORGANISM: Homo sapiens

<400> SEQUENCE: 77

Gly Glu Glu Glu Glu Lys Gly Pro Glu His Leu Cys Gly Ala His
 1               5                  10                  15

Leu Val Asp Ala Leu Tyr Leu Val Cys Gly Asp Arg Gly Phe Tyr Arg
                 20                  25                  30

Arg Glu Ala Glu Asp Leu Gln Val Gly Gln Val Glu Leu Ser Leu Gln
             35                  40                  45

Pro Leu Ala Leu Glu Gly Ser Leu Gln Arg Lys Gly Ile Val Asp Glu
     50                  55                  60

Cys Cys His Arg Ser Cys Asp Leu Arg Arg Leu Glu Asn Tyr Cys Asn
 65                  70                  75                  80

<210> SEQ ID NO 78
<211> LENGTH: 80
<212> TYPE: PRT
<213> ORGANISM: Homo sapiens

<400> SEQUENCE: 78

Gly Glu Glu Glu Glu Lys Gly Pro Glu His Leu Cys Gly Ala His
 1               5                  10                  15

Leu Val Asp Ala Leu Tyr Leu Val Cys Gly Asp Arg Gly Phe Tyr Arg
                 20                  25                  30

Arg Glu Ala Glu Asp Leu Gln Val Gly Gln Val Glu Leu Gly Gly Gly
             35                  40                  45

Pro Gly Ala Gly Ser Leu Gln Pro Leu Arg Lys Gly Ile Val Asp Glu
     50                  55                  60

Cys Cys His Arg Ser Cys Asp Leu Arg Arg Leu Glu Asn Tyr Cys Asn
 65                  70                  75                  80

<210> SEQ ID NO 79
<211> LENGTH: 29
<212> TYPE: PRT
<213> ORGANISM: Homo sapiens

<400> SEQUENCE: 79

Ser Ser Ser Ser Arg Ala Pro Pro Ser Leu Pro Ser Pro Ser Arg
 1               5                  10                  15

Leu Pro Gly Pro Ser Asp Thr Pro Ile Leu Pro Gln Lys
                 20                  25

<210> SEQ ID NO 80
<211> LENGTH: 81
<212> TYPE: PRT
<213> ORGANISM: Homo sapiens

<400> SEQUENCE: 80

Gly Glu Glu Glu Glu Lys Gly Pro Glu His Leu Cys Gly Ala His
 1               5                  10                  15

Leu Val Asp Ala Leu Tyr Leu Val Cys Gly Asp Arg Gly Phe Tyr Ala
                 20                  25                  30
```

-continued

```
Ala Ala Ala Arg Ala Pro Pro Ala Leu Pro Ala Pro Ala Arg Leu
            35                  40                  45
Pro Gly Pro Ala Asp Thr Pro Ile Leu Pro Gln Lys Gly Ile Val Asp
 50                  55                  60
Glu Cys Cys His Arg Ser Cys Asp Leu Arg Arg Leu Glu Asn Tyr Cys
 65                  70                  75                  80
Asn

<210> SEQ ID NO 81
<211> LENGTH: 87
<212> TYPE: PRT
<213> ORGANISM: Artificial Sequence
<220> FEATURE:
<223> OTHER INFORMATION: Insulin analog

<400> SEQUENCE: 81

Gly Glu Glu Glu Glu Lys Phe Val Asn Gln His Leu Cys Gly Ser
 1               5                  10                  15
His Leu Val Glu Ala Leu Tyr Leu Val Cys Gly Glu Arg Gly Phe Phe
            20                  25                  30
Tyr Thr Asp Arg Thr Ser Ser Ser Arg Ala Pro Pro Pro Ser Leu
            35                  40                  45
Pro Ser Pro Ser Arg Leu Pro Gly Pro Ser Asp Thr Pro Ile Leu Pro
 50                  55                  60
Gln Arg Gly Ile Val Glu Gln Cys Cys Thr Ser Ile Cys Ser Leu Tyr
 65                  70                  75                  80
Gln Leu Glu Asn Tyr Cys Asn
            85

<210> SEQ ID NO 82
<211> LENGTH: 109
<212> TYPE: PRT
<213> ORGANISM: Artificial Sequence
<220> FEATURE:
<223> OTHER INFORMATION: Insulin analog

<400> SEQUENCE: 82

Ser Ser Ser Ser Arg Ala Pro Pro Ser Leu Pro Ser Pro Ser Arg
 1               5                  10                  15
Leu Pro Gly Pro Ser Asp Thr Pro Ile Leu Pro Gln Lys Phe Val Asn
            20                  25                  30
Gln His Leu Cys Gly Ser His Leu Val Glu Ala Leu Tyr Leu Val Cys
            35                  40                  45
Gly Glu Arg Gly Phe Phe Tyr Thr Asp Arg Thr Ser Ser Ser Lys
 50                  55                  60
Ala Pro Pro Pro Ser Leu Pro Ser Pro Ser Arg Leu Pro Gly Pro Ser
 65                  70                  75                  80
Asp Thr Pro Ile Leu Pro Gln Arg Gly Ile Val Glu Gln Cys Cys Thr
            85                  90                  95
Ser Ile Cys Ser Leu Tyr Gln Leu Glu Asn Tyr Cys Asn
            100                 105

<210> SEQ ID NO 83
<211> LENGTH: 82
<212> TYPE: PRT
<213> ORGANISM: Artificial Sequence
<220> FEATURE:
<223> OTHER INFORMATION: Insulin analog

<400> SEQUENCE: 83
```

```
Gly Glu Glu Glu Glu Lys Phe Val Asn Gln His Leu Cys Gly Ser
1               5                   10                  15

His Leu Val Glu Ala Leu Tyr Leu Val Cys Gly Glu Arg Gly Phe Phe
            20                  25                  30

Ser Ser Ser Ser Arg Ala Pro Pro Pro Ser Leu Pro Ser Pro Ser Arg
        35                  40                  45

Leu Pro Gly Pro Ser Asp Thr Pro Ile Leu Pro Gln Arg Gly Ile Val
    50                  55                  60

Glu Gln Cys Cys Thr Ser Ile Cys Ser Leu Tyr Gln Leu Glu Asn Tyr
65              70                  75                  80

Cys Asn
```

<210> SEQ ID NO 84
<211> LENGTH: 82
<212> TYPE: PRT
<213> ORGANISM: Artificial Sequence
<220> FEATURE:
<223> OTHER INFORMATION: Insulin analog

<400> SEQUENCE: 84

```
Gly Glu Glu Glu Glu Lys Phe Val Asn Gln His Leu Cys Gly Ser
1               5                   10                  15

His Leu Val Glu Ala Leu Tyr Leu Val Cys Gly Glu Arg Gly Phe Phe
            20                  25                  30

Ser Ser Ser Ser Arg Ala Pro Pro Pro Ser Leu Pro Ser Pro Ser Arg
        35                  40                  45

Leu Pro Gly Pro Ser Asp Thr Pro Ile Leu Pro Gln Lys Gly Ile Val
    50                  55                  60

Glu Gln Cys Cys Thr Ser Ile Cys Ser Leu Tyr Gln Leu Glu Asn Tyr
65              70                  75                  80

Cys Asn
```

<210> SEQ ID NO 85
<211> LENGTH: 81
<212> TYPE: PRT
<213> ORGANISM: Artificial Sequence
<220> FEATURE:
<223> OTHER INFORMATION: Insulin analog

<400> SEQUENCE: 85

```
Gly Glu Glu Glu Glu Lys Gly Pro Glu His Leu Cys Gly Ser His
1               5                   10                  15

Leu Val Glu Ala Leu Tyr Leu Val Cys Gly Glu Arg Gly Phe Phe Ser
            20                  25                  30

Ser Ser Ser Arg Ala Pro Pro Pro Ser Leu Pro Ser Pro Ser Arg Leu
        35                  40                  45

Pro Gly Pro Ser Asp Thr Pro Ile Leu Pro Gln Lys Gly Ile Val Glu
    50                  55                  60

Gln Cys Cys Thr Ser Ile Cys Ser Leu Tyr Gln Leu Glu Asn Tyr Cys
65              70                  75                  80

Asn
```

<210> SEQ ID NO 86
<211> LENGTH: 70
<212> TYPE: PRT
<213> ORGANISM: Artificial Sequence
<220> FEATURE:
<223> OTHER INFORMATION: Insulin analog

<400> SEQUENCE: 86

Gly Glu Glu Glu Glu Lys Phe Val Asn Gln His Leu Cys Gly Ser
1               5                   10                  15

His Leu Val Glu Ala Leu Tyr Leu Val Cys Gly Glu Arg Gly Phe Phe
            20                  25                  30

Tyr Thr Asp Arg Thr Gly Tyr Gly Ser Ser Arg Arg Ala Pro Gln
        35                  40                  45

Thr Gly Ile Val Glu Gln Cys Cys Thr Ser Ile Cys Ser Leu Tyr Gln
    50                  55                  60

Leu Glu Asn Tyr Cys Asn
65                  70

<210> SEQ ID NO 87
<211> LENGTH: 70
<212> TYPE: PRT
<213> ORGANISM: Artificial Sequence
<220> FEATURE:
<223> OTHER INFORMATION: Insulin analog

<400> SEQUENCE: 87

Gly Glu Glu Glu Glu Lys Phe Val Asn Gln His Leu Cys Gly Ser
1               5                   10                  15

His Leu Val Glu Ala Leu Tyr Leu Val Cys Gly Glu Arg Gly Phe Phe
            20                  25                  30

Tyr Thr Asp Arg Thr Gly Ala Gly Ser Ser Arg Arg Ala Pro Gln
        35                  40                  45

Thr Gly Ile Val Glu Gln Cys Cys Thr Ser Ile Cys Ser Leu Tyr Gln
    50                  55                  60

Leu Glu Asn Tyr Cys Asn
65                  70

<210> SEQ ID NO 88
<211> LENGTH: 75
<212> TYPE: PRT
<213> ORGANISM: Artificial Sequence
<220> FEATURE:
<223> OTHER INFORMATION: Insulin analog

<400> SEQUENCE: 88

Phe Val Asn Gln His Leu Cys Gly Ser His Leu Val Glu Ala Leu Tyr
1               5                   10                  15

Leu Val Cys Gly Glu Arg Gly Phe Phe Ser Ser Ser Ser Arg Ala Pro
            20                  25                  30

Pro Pro Ser Leu Pro Ser Pro Ser Arg Leu Pro Gly Pro Ser Asp Thr
        35                  40                  45

Pro Ile Leu Pro Gln Arg Gly Ile Val Glu Gln Cys Cys Thr Ser Ile
    50                  55                  60

Cys Ser Leu Tyr Gln Leu Glu Asn Tyr Cys Asn
65                  70                  75

<210> SEQ ID NO 89
<211> LENGTH: 75
<212> TYPE: PRT
<213> ORGANISM: Artificial Sequence
<220> FEATURE:
<223> OTHER INFORMATION: Insulin analog

<400> SEQUENCE: 89

Phe Val Asn Gln His Leu Cys Gly Ser His Leu Val Glu Ala Leu Tyr

```
                1               5                   10                  15
Leu Val Cys Gly Glu Arg Gly Phe Phe Ser Ser Ser Arg Ala Pro
                20                  25                  30
Pro Pro Ser Leu Pro Ser Pro Ser Arg Leu Pro Gly Pro Ser Asp Thr
            35                  40                  45
Pro Ile Leu Pro Gln Lys Gly Ile Val Glu Gln Cys Cys Thr Ser Ile
        50                  55                  60
Cys Ser Leu Tyr Gln Leu Glu Asn Tyr Cys Asn
65                  70                  75
```

<210> SEQ ID NO 90
<211> LENGTH: 74
<212> TYPE: PRT
<213> ORGANISM: Artificial Sequence
<220> FEATURE:
<223> OTHER INFORMATION: Insulin analog

<400> SEQUENCE: 90

```
Gly Pro Glu His Leu Cys Gly Ser His Leu Val Glu Ala Leu Tyr Leu
1               5                   10                  15
Val Cys Gly Glu Arg Gly Phe Phe Ser Ser Ser Ser Arg Ala Pro Pro
                20                  25                  30
Pro Ser Leu Pro Ser Pro Ser Arg Leu Pro Gly Pro Ser Asp Thr Pro
            35                  40                  45
Ile Leu Pro Gln Lys Gly Ile Val Glu Gln Cys Cys Thr Ser Ile Cys
        50                  55                  60
Ser Leu Tyr Gln Leu Glu Asn Tyr Cys Asn
65                  70
```

<210> SEQ ID NO 91
<211> LENGTH: 110
<212> TYPE: PRT
<213> ORGANISM: Artificial Sequence
<220> FEATURE:
<223> OTHER INFORMATION: single chain insulin analog

<400> SEQUENCE: 91

```
Met Gly Ser Ser Ser Lys Ala Pro Pro Ser Leu Pro Ser Pro Ser Pro
1               5                   10                  15
Ser Arg Leu Pro Gly Pro Ser Asp Thr Pro Ile Leu Pro Gln Glu Glu
                20                  25                  30
Glu Glu Glu Arg Gly Pro Glu His Leu Cys Gly Ala His Leu Val Asp
            35                  40                  45
Ala Leu Tyr Leu Val Cys Gly Asp Arg Gly Phe Tyr Ser Ser Ser Ser
        50                  55                  60
Arg Ala Pro Pro Ser Leu Pro Ser Pro Ser Arg Leu Pro Gly Pro
65                  70                  75                  80
Ser Asp Thr Pro Ile Leu Pro Gln Lys Gly Ile Val Asp Glu Cys Cys
                85                  90                  95
His Arg Ser Cys Asp Leu Arg Arg Leu Glu Asn Tyr Cys Asn
            100                 105                 110
```

<210> SEQ ID NO 92
<211> LENGTH: 28
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa at position 5 is lysine or Arginine

<400> SEQUENCE: 92

Ser Ser Ser Ser Xaa Ala Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 93
<211> LENGTH: 30
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa at position 5 is lysine or Arginine
<220> FEATURE:
<221> NAME/KEY: misc_feature
<222> LOCATION: (7)..(7)
<223> OTHER INFORMATION: Xaa can be any naturally occurring amino acid

<400> SEQUENCE: 93

Met Gly Ser Ser Ser Xaa Ala Pro Pro Ser Leu Pro Ser Pro
1               5                   10
Ser Arg Leu Pro Gly Pro Ser Asp Thr Pro Ile Leu Pro Gln
            20                  25                  30

<210> SEQ ID NO 94
<211> LENGTH: 30
<212> TYPE: PRT
<213> ORGANISM: Homo sapiens

<400> SEQUENCE: 94

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Arg Thr
            20                  25                  30

<210> SEQ ID NO 95
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (19)..(19)
<223> OTHER INFORMATION: Xaa at position19 is tyrosine, 4-methoxy
      phenylalanine  or 4-amino-phenylalanine
<220> FEATURE:
<221> NAME/KEY: MISC_FEATURE
<222> LOCATION: (21)..(21)
<223> OTHER INFORMATION: Xaa at position 21 is alanine, glycine or
      asparagine

<400> SEQUENCE: 95

Gly Ile Val Glu Gln Cys Cys Thr Ser Ile Cys Ser Leu Tyr Gln Leu
1               5                   10                  15

Glu Asn Xaa Cys Xaa
            20

<210> SEQ ID NO 96
<211> LENGTH: 70
<212> TYPE: PRT
<213> ORGANISM: Homo sapiens

<400> SEQUENCE: 96

```
Gly Glu Glu Glu Glu Lys Phe Val Asn Gln His Leu Cys Gly Ser
1               5                   10                  15

His Leu Val Glu Ala Leu Tyr Leu Val Cys Gly Glu Arg Gly Phe Phe
            20                  25                  30

Tyr Thr Asp Arg Thr Gly Tyr Gly Ser Ser Arg Arg Ala Pro Gln
        35                  40                  45

Thr Gly Ile Val Glu Gln Cys Cys Thr Ser Ile Cys Ser Leu Tyr Gln
    50                  55                  60

Leu Glu Asn Tyr Cys Asn
65                  70
```

<210> SEQ ID NO 97
<211> LENGTH: 70
<212> TYPE: PRT
<213> ORGANISM: Homo sapiens

<400> SEQUENCE: 97

```
Gly Glu Glu Glu Glu Lys Phe Val Asn Gln His Leu Cys Gly Ser
1               5                   10                  15

His Leu Val Glu Ala Leu Tyr Leu Val Cys Gly Glu Arg Gly Phe Phe
            20                  25                  30

Tyr Thr Asp Arg Thr Gly Ala Gly Ser Ser Arg Arg Ala Pro Gln
        35                  40                  45

Thr Gly Ile Val Glu Gln Cys Cys Thr Ser Ile Cys Ser Leu Tyr Gln
    50                  55                  60

Leu Glu Asn Tyr Cys Asn
65                  70
```

<210> SEQ ID NO 98
<211> LENGTH: 82
<212> TYPE: PRT
<213> ORGANISM: Homo sapiens

<400> SEQUENCE: 98

```
Gly Glu Glu Glu Glu Lys Phe Val Asn Gln His Leu Cys Gly Ser
1               5                   10                  15

His Leu Val Glu Ala Leu Tyr Leu Val Cys Gly Glu Arg Gly Phe Phe
            20                  25                  30

Ser Ser Ser Ser Arg Ala Pro Pro Ser Leu Pro Ser Pro Ser Arg
            35                  40                  45

Leu Pro Gly Pro Ser Asp Thr Pro Ile Leu Pro Gln Arg Gly Ile Val
    50                  55                  60

Glu Gln Cys Cys Thr Ser Ile Cys Ser Leu Tyr Gln Leu Glu Asn Tyr
65                  70                  75                  80

Cys Asn
```

<210> SEQ ID NO 99
<211> LENGTH: 82
<212> TYPE: PRT
<213> ORGANISM: Homo sapiens

<400> SEQUENCE: 99

```
Gly Glu Glu Glu Glu Lys Phe Val Asn Gln His Leu Cys Gly Ser
1               5                   10                  15

His Leu Val Glu Ala Leu Tyr Leu Val Cys Gly Glu Arg Gly Phe Phe
            20                  25                  30

Ser Ser Ser Ser Arg Ala Pro Pro Ser Leu Pro Ser Pro Ser Arg
            35                  40                  45
```

Leu Pro Gly Pro Ser Asp Thr Pro Ile Leu Pro Gln Lys Gly Ile Val
            50                  55                  60

Glu Gln Cys Cys Thr Ser Ile Cys Ser Leu Tyr Gln Leu Glu Asn Tyr
 65                  70                  75                  80

Cys Asn

<210> SEQ ID NO 100
<211> LENGTH: 87
<212> TYPE: PRT
<213> ORGANISM: Homo sapiens

<400> SEQUENCE: 100

Gly Glu Glu Glu Glu Lys Phe Val Asn Gln His Leu Cys Gly Ser
 1               5                  10                  15

His Leu Val Glu Ala Leu Tyr Leu Val Cys Gly Glu Arg Gly Phe Phe
                20                  25                  30

Tyr Thr Asp Arg Thr Ser Ser Ser Arg Ala Pro Pro Pro Ser Leu
                35                  40                  45

Pro Ser Pro Ser Arg Leu Pro Gly Pro Ser Asp Thr Pro Ile Leu Pro
 50                  55                  60

Gln Arg Gly Ile Val Glu Gln Cys Cys Thr Ser Ile Cys Ser Leu Tyr
 65                  70                  75                  80

Gln Leu Glu Asn Tyr Cys Asn
                85

<210> SEQ ID NO 101
<211> LENGTH: 58
<212> TYPE: PRT
<213> ORGANISM: Homo sapiens

<400> SEQUENCE: 101

Phe Val Asn Gln His Leu Cys Gly Ser His Leu Val Glu Ala Leu Tyr
 1               5                  10                  15

Leu Val Cys Gly Glu Arg Gly Phe Phe Ser Ser Ser Arg Ala Pro
                20                  25                  30

Pro Pro Ser Leu Pro Gly Ile Val Glu Gln Cys Cys Thr Ser Ile Cys
                35                  40                  45

Ser Leu Tyr Gln Leu Glu Asn Tyr Cys Asn
     50                  55

<210> SEQ ID NO 102
<211> LENGTH: 58
<212> TYPE: PRT
<213> ORGANISM: Homo sapiens

<400> SEQUENCE: 102

Phe Val Asn Gln His Leu Cys Gly Ser His Leu Val Glu Ala Leu Tyr
 1               5                  10                  15

Leu Val Cys Gly Glu Arg Gly Phe Phe Ser Ser Ser Arg Ala Pro
                20                  25                  30

Ile Leu Pro Gln Lys Gly Ile Val Glu Gln Cys Cys Thr Ser Ile Cys
                35                  40                  45

Ser Leu Tyr Gln Leu Glu Asn Tyr Cys Asn
     50                  55

<210> SEQ ID NO 103
<211> LENGTH: 63
<212> TYPE: PRT

```
<213> ORGANISM: Homo sapiens

<400> SEQUENCE: 103

Phe Val Asn Gln His Leu Cys Gly Ser His Leu Val Glu Ala Leu Tyr
1               5                   10                  15

Leu Val Cys Gly Glu Arg Gly Phe Phe Ser Ser Ser Ser Arg Ala Pro
            20                  25                  30

Pro Pro Ser Leu Pro Ile Leu Pro Gln Lys Gly Ile Val Glu Gln Cys
        35                  40                  45

Cys Thr Ser Ile Cys Ser Leu Tyr Gln Leu Glu Asn Tyr Cys Asn
    50                  55                  60

<210> SEQ ID NO 104
<211> LENGTH: 25
<212> TYPE: PRT
<213> ORGANISM: Homo sapiens

<400> SEQUENCE: 104

Phe Val Asn Gln His Leu Cys Gly Ser His Leu Val Glu Ala Leu Tyr
1               5                   10                  15

Leu Val Cys Gly Glu Arg Gly Phe Phe
            20                  25
```